US008183353B2

(12) United States Patent
Wang

(10) Patent No.: US 8,183,353 B2
(45) Date of Patent: May 22, 2012

(54) BREAST CANCER PROGNOSTICS

(75) Inventor: Yixin Wang, San Diego, CA (US)

(73) Assignee: Veridex, LLC., Raritan, NJ (US)

( * ) Notice: Subject to any disclaimer, the term of this patent is extended or adjusted under 35 U.S.C. 154(b) by 0 days.

(21) Appl. No.: 11/923,888

(22) Filed: Oct. 25, 2007

(65) Prior Publication Data

US 2010/0009861 A1 Jan. 14, 2010

Related U.S. Application Data

(62) Division of application No. 10/422,522, filed on Apr. 24, 2003, now Pat. No. 7,306,910.

(51) Int. Cl.

| | |
|---|---|
| ***G01N 31/00*** | (2006.01) |
| ***C07H 1/00*** | (2006.01) |
| ***C07H 5/04*** | (2006.01) |
| ***C07H 5/06*** | (2006.01) |
| ***C07H 19/00*** | (2006.01) |
| ***C07H 21/00*** | (2006.01) |
| ***C07H 21/04*** | (2006.01) |
| ***C08B 37/00*** | (2006.01) |
| ***C40B 40/00*** | (2006.01) |
| ***C40B 40/04*** | (2006.01) |
| ***C40B 40/06*** | (2006.01) |
| ***C40B 40/08*** | (2006.01) |

(52) U.S. Cl. .................... 536/23.1; 536/1.11; 536/18.7; 536/22.1; 536/23.5; 435/4; 435/6; 436/64; 506/13; 506/15; 506/16; 506/17

(58) Field of Classification Search ........................ None
See application file for complete search history.

(56) References Cited

OTHER PUBLICATIONS

Stratagene 1991 Product Catalog, p. 66.*

* cited by examiner

*Primary Examiner* — Alana Harris Dent
(74) *Attorney, Agent, or Firm* — Johnson & Johnson; Todd F. Volyn

(57) ABSTRACT

A method of providing a prognosis of breast cancer is conducted by analyzing the expression of a group of genes. Gene expression profiles in a variety of medium such as microarrays are included as are kits that contain them.

3 Claims, 3 Drawing Sheets

BREAST CANCER PROGNOSTICS

This application is a divisional application of Ser. No. 10/422,522 filed Apr. 24, 2003, now issued as U.S. Pat. No. 7,306,910.

BACKGROUND

This invention relates to prognostics for breast cancer based on the gene expression profiles of biological samples.

In breast cancers, prognosis is determined primarily by the presence or absence of metastases in draining axillary lymph nodes. However, in approximately one third of women with breast cancer who have negative lymph nodes, the disease recurs and about one third of patients with positive lymph nodes are free of disease ten years after local or regional therapy. Furthermore, an increasing proportion of breast cancers are being diagnosed at an early stage because of increased awareness and wider use of screening modalities. Universal application of systematic therapy to these patients often leads to over-treatment. According to the St Gallen and NIH consensus, 70-80% of the Stage I and II patients would not have developed distant metastases without adjuvant treatment and may potentially suffer from the side effects. These data highlight the need for more sensitive and specific prognostic assays that could significantly reduce the number of patients that receive unnecessary treatment.

Tumor size and lymphatic or vascular invasion have been found to be of significant prognostic value in several studies. Quantitative pathological features, i.e. nuclear morphology, DNA content and proliferative activity may further demarcate tumors that have a high chance of micrometastases. Known molecular genetic changes that affect patient outcome include Her2/NEU over-expression, DNA amplifications, p53 mutations, ER/PR status, uPA and PAI expression. Because the metastatic cascade is a complex process that includes multiple steps, single factors that contribute to tumor process have limitations for prognostic assessment. The gene expression profiles of this invention will provide increased prognostic power.

SUMMARY OF THE INVENTION

The invention is a method of assessing the likelihood of a recurrence or metastasis of breast cancer in a patient diagnosed with or treated for breast cancer. The method involves the analysis of a gene expression profile.

In one aspect of the invention, the gene expression profile includes 56 genes. In yet other aspects of the invention, the profiles comprise those of at least 45 genes, 26 genes, 13 genes, and 6 genes respectively.

Articles used in practicing the methods are also an aspect of the invention. Such articles include gene expression profiles or representations of them that are fixed in machine-readable media such as computer readable media.

Articles used to identify gene expression profiles can also include substrates or surfaces (such as microarrays) to capture and/or indicate the presence, absence, or degree of gene expression.

In yet another aspect of the invention, kits include reagents for conducting the gene expression analysis prognostic of breast cancer recurrence or metastasis.

DETAILED DESCRIPTION

Figure 1:
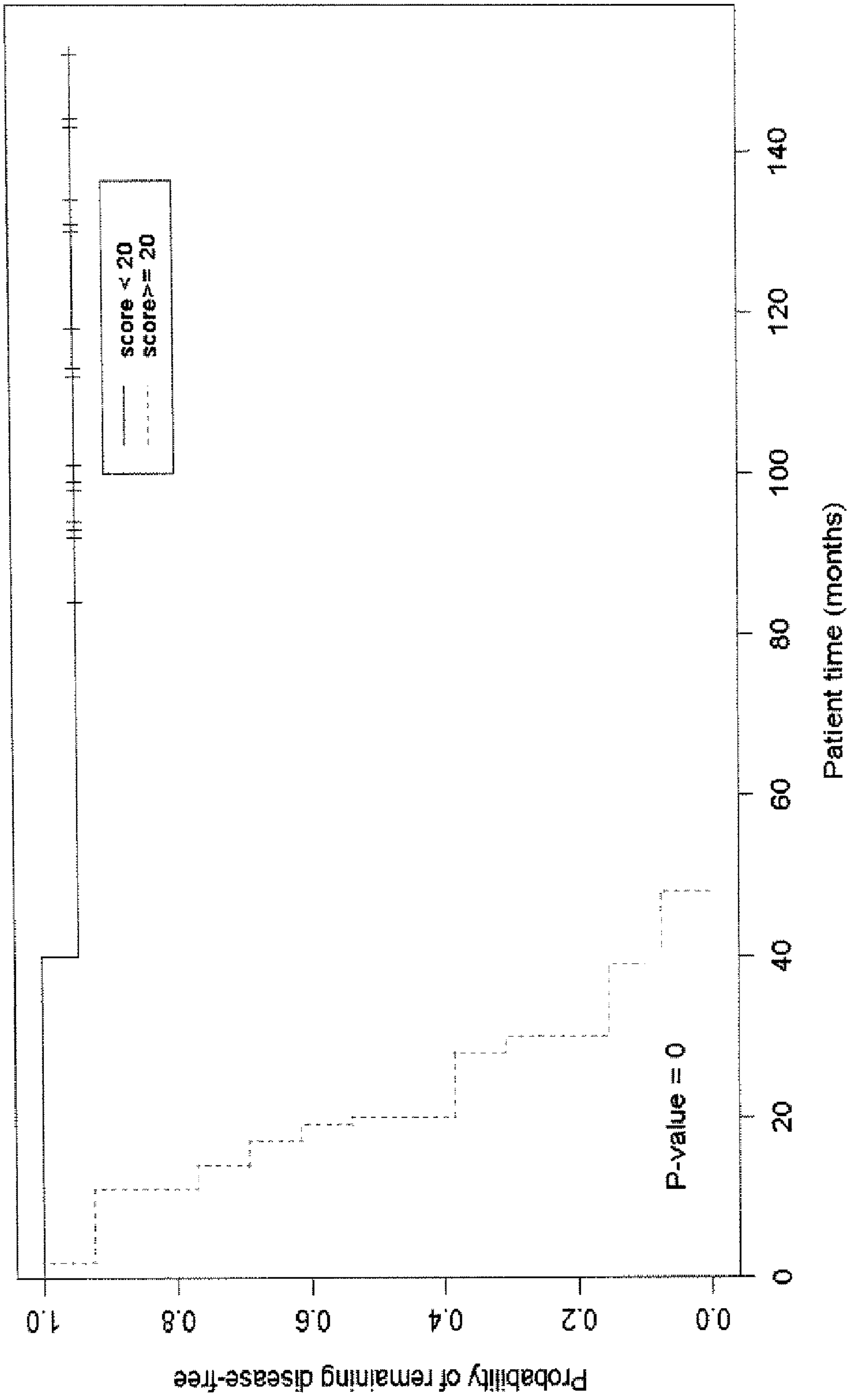
FIG. 1 is a standard Kaplan-Meier Plot constructed from the patient data as a training set as described in the Examples.

The mere presence or absence of particular nucleic acid sequences in a tissue sample has only rarely been found to have diagnostic or prognostic value. Information about the expression of various proteins, peptides or mRNA, on the other hand, is increasingly viewed as important. The mere presence of nucleic acid sequences having the potential to express proteins, peptides, or mRNA (such sequences referred to as "genes") within the genome by itself is not determinative of whether a protein, peptide, or mRNA is expressed in a given cell. Whether or not a given gene capable of expressing proteins, peptides, or mRNA does so and to what extent such expression occurs, if at all, is determined by a variety of complex factors. Irrespective of difficulties in understanding and assessing these factors, assaying gene expression can provide useful information about the occurrence of important events such as tumerogenesis, metastasis, apoptosis, and other clinically relevant phenomena. Relative indications of the degree to which genes are active or inactive can be found in gene expression profiles. The gene expression profiles of this invention are used to provide a prognosis and treat patients for breast cancer.

Sample preparation requires the collection of patient samples. Patient samples used in the inventive method are those that are suspected of containing diseased cells such as epithelial cells taken from a breast or lymph node sample or from surgical margins. One useful technique for obtaining suspect samples is Laser Capture Microdisection (LCM). LCM technology provides a way to select the cells to be studied, minimizing variability caused by cell type heterogeneity. Consequently, moderate or small changes in gene expression between normal and cancerous cells can be readily detected. In a preferred method, the samples comprise circulating epithelial cells extracted from peripheral blood. These can be obtained according to a number of methods but the most preferred method is the magnetic separation technique described in U.S. Pat. No. 6,136,182 assigned to Immunivest Corp which is incorporated herein by reference. Once the sample containing the cells of interest has been obtained, RNA is extracted and amplified and a gene expression profile is obtained, preferably via micro-array, for genes in the appropriate portfolios.

Preferred methods for establishing gene expression profiles include determining the amount of RNA that is produced by a gene that can code for a protein or peptide. This is accomplished by reverse transcriptase PCR (RT-PCR), competitive RT-PCR, real time RT-PCR, differential display RT-PCR, Northern Blot analysis and other related tests. While it is possible to conduct these techniques using individual PCR reactions, it is best to amplify complimentary DNA (cDNA) or complimentary RNA (cRNA) produced from mRNA and analyze it via microarray. A number of different array configurations and methods for their production are known to those of skill in the art and are described in U.S. patents such as: U.S. Pat. Nos. 5,445,934; 5,532,128; 5,556,752; 5,242,974; 5,384,261; 5,405,783; 5,412,087; 5,424,186; 5,429,807;

5,436,327; 5,472,672; 5,527,681; 5,529,756; 5,545,531; 5,554,501; 5,561,071; 5,571,639; 5,593,839; 5,599,695; 5,624,711; to 5,658,734; and 5,700,637; the disclosures of which are incorporated herein by reference.

Microarray technology allows for the measurement of the steady-state mRNA level of thousands of genes simultaneously thereby presenting a powerful tool for identifying effects such as the onset, arrest, or modulation of uncontrolled cell proliferation. Two microarray technologies are currently in wide use. The first are cDNA arrays and the second are oligonucleotide arrays. Although differences exist in the construction of these chips, essentially all downstream data analysis and output are the same. The product of these analyses are typically measurements of the intensity of the signal received from a labeled probe used to detect a cDNA sequence from the sample that hybridizes to a nucleic acid sequence at a known location on the microarray. Typically, the intensity of the signal is proportional to the quantity of cDNA, and thus mRNA, expressed in the sample cells. A large number of such techniques are available and useful. Preferred methods for determining gene expression can be found in U.S. Pat. No. 6,271,002 to Linsley, et al.; U.S. Pat. No. 6,218,122 to Friend, et al.; U.S. Pat. No. 6,218,114 to Peck, et al.; and U.S. Pat. No. 6,004,755 to Wang, et al., the disclosure of each of which is incorporated herein by reference.

Analysis of the expression levels is conducted by comparing such intensities. This is best done by generating a ratio matrix of the expression intensities of genes in a test sample versus those in a control sample. For instance, the gene expression intensities from a diseased tissue can be compared with the expression intensities generated from normal tissue of the same type (e.g., diseased breast tissue sample vs. normal breast tissue sample). A ratio of these expression intensities indicates the fold-change in gene expression between the test and control samples.

Gene expression profiles can also be displayed in a number of ways. The most common method is to arrange a raw fluorescence intensities or ratio matrix into a graphical dendogram where columns indicate test samples and rows indicate genes. The data is arranged so genes that have similar expression profiles are proximal to each other. The expression ratio for each gene is visualized as a color. For example, a ratio less than one (indicating down-regulation) may appear in the blue portion of the spectrum while a ratio greater than one (indicating up-regulation) may appear as a color in the red portion of the spectrum. Commercially available computer software programs are available to display such data including "GENESPRINT" from Silicon Genetics, Inc. and "DISCOVERY" and "INFER" software from Partek, Inc.

Modulated genes used in the methods of the invention are described in the Examples. The genes that are differentially expressed are either up regulated or down regulated in patients with a relapse of breast cancer relative to those without a relapse. Up regulation and down regulation are relative terms meaning that a detectable difference (beyond the contribution of noise in the system used to measure it) is found in the amount of expression of the genes relative to some baseline. In this case, the baseline is the measured gene expression of a non-relapsing patient. The genes of interest in the diseased cells (from the relapsing patients) are then either up regulated or down regulated relative to the baseline level using the same measurement method. Diseased, in this context, refers to an alteration of the state of a body that interrupts or disturbs, or has the potential to disturb, proper performance of bodily functions as occurs with the uncontrolled proliferation of cells. Someone is diagnosed with a disease when some aspect of that person's genotype or phenotype is consistent with the presence of the disease. However, the act of conducting a diagnosis or prognosis includes the determination of disease/status issues such as determining the likelihood of relapse or metastasis and therapy monitoring. In therapy monitoring, clinical judgments are made regarding the effect of a given course of therapy by comparing the expression of genes over time to determine whether the gene expression profiles have changed or are changing to patterns more consistent with normal tissue.

Preferably, levels of up and down regulation are distinguished based on fold changes of the intensity measurements of hybridized microarray probes. A 2.0 fold difference is preferred for making such distinctions or a p-value less than 0.05. That is, before a gene is said to be differentially expressed in diseased/relapsing versus normal/non-relapsing cells, the diseased cell is found to yield at least 2 times more, or 2 times less intensity than the normal cells. The greater the fold difference, the more preferred is use of the gene as a diagnostic or prognostic tool. Genes selected for the gene expression profiles of the instant invention have expression levels that result in the generation of a signal that is distinguishable from those of the normal or non-modulated genes by an amount that exceeds background using clinical laboratory instrumentation.

Statistical values can be used to confidently distinguish modulated from non-modulated genes and noise. Statistical tests find the genes most significantly different between diverse groups of samples. The Student's t-test is an example of a robust statistical test that can be used to find significant differences between two groups. The lower the p-value, the more compelling the evidence that the gene is showing a difference between the different groups. Nevertheless, since microarrays measure more than one gene at a time, tens of thousands of statistical tests may be asked at one time. Because of this, one is unlikely to see small p-values just by chance and adjustments for this using a Sidak correction as well as a randomization/permutation experiment can be made. A p-value less than 0.05 by the t-test is evidence that the gene is significantly different. More compelling evidence is a p-value less then 0.05 after the Sidak correction is factored in. For a large number of samples in each group, a p-value less than 0.05 after the randomization/permutation test is the most compelling evidence of a significant difference.

Another parameter that can be used to select genes that generate a signal that is greater than that of the non-modulated gene or noise is the use of a measurement of absolute signal difference. Preferably, the signal generated by the modulated gene expression is at least 20% different than those of the normal or non-modulated gene (on an absolute basis). It is even more preferred that such genes produce expression patterns that are at least 30% different than those of normal or non-modulated genes.

Genes can be grouped so that information obtained about the set of genes in the group provides a sound basis for making a clinically relevant judgment such as a diagnosis, prognosis, or treatment choice. These sets of genes make up the portfolios of the invention. In this case, the judgments supported by the portfolios involve breast cancer. As with most diagnostic markers, it is often desirable to use the fewest number of markers sufficient to make a correct medical judgment. This prevents a delay in treatment pending further analysis as well inappropriate use of time and resources.

Preferably, portfolios are established such that the combination of genes in the portfolio exhibit improved sensitivity and specificity relative to individual genes or randomly selected combinations of genes. In the context of the instant invention, the sensitivity of the portfolio can be reflected in the fold differences exhibited by a gene's expression in the diseased state relative to the normal state. Specificity can be reflected in statistical measurements of the correlation of the signaling of gene expression with the condition of interest For example, standard deviation can be a used as such a measurement. In considering a group of genes for inclusion in a portfolio, a small standard deviation in expression measurements correlates with greater specificity. Other measurements of variation such as correlation coefficients can also be used in this capacity.

A preferred method of establishing gene expression portfolios is through the use of optimization algorithms such as the mean variance algorithm widely used in establishing stock portfolios. This method is described in detail in the patent application entitled "Selection of Markers" by Tim Jatkoe, et. al., filed on Mar. 21, 2003 (application Ser. No. 10/394,087, incorporated herein by reference). Essentially, the method calls for the establishment of a set of inputs (stocks in financial applications, expression as measured by intensity here) that will optimize the return (e.g., signal that is generated) one receives for using it while minimizing the variability of the return. Many commercial software programs are available to conduct such operations. "Wagner Associates Mean-Variance Optimization Application", referred to as "Wagner Software" throughout this specification, is preferred. This software uses functions from the "Wagner Associates Mean-Variance Optimization Library" to determine an efficient frontier and optimal portfolios.

Use of this type of software requires that microarray data (i.e. intensity measurements) be transformed so that it can be treated as an input in the way stock return and risk measurements are used when the software is used for its intended financial analysis purposes.

The process of portfolio selection and characterization of an unknown is summarized as follows:

1. Choose baseline class
2. Calculate mean, and standard deviation of each gene for baseline class samples
3. Calculate (X*Standard Deviation+Mean) for each gene. This is the baseline reading from which all other samples will be compared. X is a stringency variable with higher values of X being more stringent than lower.
4. Calculate ratio between each Experimental sample versus baseline reading calculated in step 3.
5. Transform ratios such that ratios less than 1 are negative (eg. using Log base 10). (Down regulated genes now correctly have negative values necessary for MV optimization).
6. These transformed ratios are used as inputs in place of the asset returns that are normally used in the software application.
7. The software will plot the efficient frontier and return an optimized portfolio at any point along the efficient frontier.
8. Choose a desired return or variance on the efficient frontier.
9. Calculate the Portfolio's Value for each sample by summing the multiples of each gene's intensity value by the weight generated by the portfolio selection algorithm.
10. Calculate a boundary value by adding the mean Portfolio Value for Baseline groups to the multiple of Y and the Standard Deviation of the Baseline's Portfolio Values. Values greater than this boundary value shall be classified as the Experimental Class.
11. Optionally one can reiterate this process until best prediction accuracy is obtained.

Alternatively, genes can first be pre-selected by identifying those genes whose expression shows some minimal level of differentiation. The pre-selection in this alternative method is preferably based on a threshold given by $$1 \leq \left|\frac{(\mu_t - \mu_n)}{(\sigma_t + \sigma_n)}\right|,$$

where $\mu_t$ is the mean of the subset known to possess the disease or condition, $\mu_n$ is the mean of the subset of normal samples, and $\sigma_t+\sigma_n$ represent the combined standard deviations. A signal to noise cutoff can also be used by pre-selecting the data according to a relationship such as $$0.5 \leq \left|\frac{(\mu_t - \mathrm{MAX}_n)}{(\sigma_t + \sigma_n)}\right|.$$

This ensures that genes that are pre-selected based on their differential modulation are differentiated in a clinically significant way. That is, above the noise level of instrumentation appropriate to the task of measuring the diagnostic parameters. For each marker pre-selected according to these criteria, a matrix is established in which columns represents samples, rows represent markers and each element is a normalized intensity measurement for the expression of that marker according to the relationship $$\left|\frac{(\mu_t - I)}{\mu_t}\right|$$

where I is the intensity measurement.

It is also possible to set additional boundary conditions to define the optimal portfolios. For example, portfolio size can be limited to a fixed range or number of markers. This can be done either by making data pre-selection criteria more stringent $$\left(\text{e.g, } .8 \leq \left|\frac{(\mu_t - \mathrm{MAX}_n)}{(\sigma_t + \sigma_n)}\right| \text{ instead of } 0.5 \leq \left|\frac{(\mu_t - \mathrm{MAX}_n)}{(\sigma_t + \sigma_n)}\right|\right)$$

or by using programming features such as restricting portfolio size. One could, for example, set the boundary condition that the efficient frontier is to be selected from among only the most optimal 10 genes. One could also use all of the genes pre-selected for determining the efficient frontier and then limit the number of genes selected (e.g., no more than 10).

The process of selecting a portfolio can also include the application of heuristic rules. Preferably, such rules are formulated based on biology and an understanding of the technology used to produce clinical results. More preferably, they are applied to output from the optimization method. For example, the mean variance method of portfolio selection can be applied to microarray data for a number of genes differentially expressed in subjects with breast cancer. Output from the method would be an optimized set of genes that could include some genes that are expressed in peripheral blood as well as in diseased tissue. If samples used in the testing method are obtained from peripheral blood and certain genes differentially expressed in instances of breast cancer could also be differentially expressed in peripheral blood, then a heuristic rule can be applied in which a portfolio is selected from the efficient frontier excluding those that are differentially expressed in peripheral blood. Of course, the rule can be applied prior to the formation of the efficient frontier by, for example, applying the rule during data pre-selection.

Other heuristic rules can be applied that are not necessarily related to the biology in question. For example, one can apply the rule that only a given percentage of the portfolio can be represented by a particular gene or genes. Commercially available software such as the Wagner Software readily accommodates these types of heuristics. This can be useful, for example, when factors other than accuracy and precision (e.g., anticipated licensing fees) have an impact on the desirability of including one or more genes.

One method of the invention involves comparing gene expression profiles for various genes (or portfolios) to ascribe prognoses. The gene expression profiles of each of the genes comprising the portfolio are fixed in a medium such as a computer readable medium. This can take a number of forms. For example, a table can be established into which the range of signals (e.g., intensity measurements) indicative of disease/relapse is input. Actual patient data can then be compared to the values in the table to determine whether the patient samples are normal or diseased. In a more sophisticated embodiment, patterns of the expression signals (e.g., flourescent intensity) are recorded digitally or graphically. The gene expression patterns from the gene portfolios used in conjunction with patient samples are then compared to the expression patterns. Pattern comparison software can then be used to determine whether the patient samples have a pattern indicative of recurrence of the disease. Of course, these comparisons can also be used to determine whether the patient is not likely to experience disease recurrence. The expression profiles of the samples are then compared to the portfolio of a control cell. If the sample expression patterns are consistent with the expression pattern for recurrence of a breast cancer then (in the absence of countervailing medical considerations) the patient is treated as one would treat a relapse patient. If the sample expression patterns are consistent with the expression pattern from the normal/control cell then the patient is diagnosed negative for breast cancer.

Numerous well known methods of pattern recognition are available. The following references provide some examples:

Weighted Voting:

Golub, T R., Slonim, D K., Tamaya, P., Huard, C., Gaasenbeek, M., Mesirov, J P., Coller, H., Loh, L., Downing, J R., Caligiuri, M A., Bloomfield, C D., Lander, E S. *Molecular classification of cancer: class discovery and class prediction by gene expression monitoring*. Science 286:531-537, 1999

Support Vector Machines:

Su, A I., Welsh, J B., Sapinoso, L M., Kern, S G., Dimitrov, P., Lapp, H., Schultz, P G., Powell, S M., Moskaluk, C A., Frierson, H F. Jr., Hampton, G M. *Molecular classification of human carcinomas by use of gene expression signatures*. Cancer Research 61:7388-93, 2001

Ramaswamy, S., Tamayo, P., Ritkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. *Multiclass cancer diagnosis using tumor gene expression signatures* Proceedings of the National Academy of Sciences of the USA 98:15149-15154, 2001

K-Nearest Neighbors:

Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. *Multiclass cancer diagnosis using tumor gene expression signatures* Proceedings of the National Academy of Sciences of the USA 98:15149-15154, 2001

Correlation Coefficients:

van't Veer L I, Dai H, van de Vijver M J, He Y D, Hart A A, Mao M, Peterse H L, van der Kooy K, Marton M J, Witeveen A T, Schreiber G J, Kerthoven R M, Roberts C, Linsley P S, Bernards R, Friend S H. Gene expression profiling predicts clinical outcome of breast cancer. Nature, Jan. 31, 2002; 415(6871):530-6.

The gene expression profiles of this invention can also be used in conjunction with other non-genetic diagnostic methods useful in cancer diagnosis, prognosis, or treatment monitoring. For example, in some circumstances it is beneficial to combine the diagnostic power of the gene expression based methods described above with data from conventional markers such as serum protein markers. A range of such markers exists including such analytes as Estrogen Receptor (ER) with ER+ results indicating a greater likelihood of recurrence or metastasis. Other markers such as the protein (or peptides) produced by the estrogen regulated gene sequence pLIV1 can be used in this capacity as described in U.S. Pat. No. 5,693,465 (incorporated by reference in this specification). In one such method, blood is periodically taken from a treated patient and then subjected to an enzyme immunoassay for one or more serum markers. When the concentration of the marker(s) suggests the return of tumors or failure of therapy, a sample source amenable to gene expression analysis is taken. Where a suspicious mass exists, a fine needle aspirate is taken and gene expression profiles of cells taken from the mass are then analyzed as described above. Alternatively, tissue samples may be taken from areas adjacent to the tissue from which a tumor was previously removed. This approach can be particularly useful when other testing produces ambiguous results.

Articles of this invention include representations of the gene expression profiles useful for treating, diagnosing, prognosticating, and otherwise assessing diseases. These profile representations are reduced to a medium that can be automatically read by a machine such as computer readable media (magnetic, optical, and the like). The articles can also include instructions for assessing the gene expression profiles in such media. For example, the articles may comprise a CD ROM having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms such as those incorporated in "DISCOVERY" and "INFER" software from Partek, Inc. mentioned above can best assist in the visualization of such data.

Different types of articles of manufacture according to the invention are media or formatted assays used to reveal gene expression profiles. These can comprise, for example, microarrays in which sequence complements or probes are affixed to a matrix to which the sequences indicative of the genes of interest combine creating a readable determinant of their presence. Alternatively, articles according to the invention can be fashioned into reagent kits for conducting hybridization, amplification, and signal generation indicative or the level of expression or the genes of interest for detecting breast cancer.

Kits made according to the invention include formatted assays for determining the gene expression profiles. These can include all or some of the materials needed to conduct the assays such as reagents and instructions.

The invention is further illustrated by the following non-limiting examples.

EXAMPLES

Genes analyzed according to this invention are typically related to full-length nucleic acid sequences that code for the production of a protein or peptide. One skilled in the art will recognize that identification of full-length sequences is not necessary from an analytical point of view. That is, portions of the sequences or ESTs can be selected according to well-known principles for which probes can be designed to assess gene expression for the corresponding gene.

Example 1

Sample Handling and LCM

Fresh frozen tissue samples were collected from patients who had surgery for breast tumors. The samples that were used were from 149 Stage I and II patients (staged according to standard clinical diagnostics and pathology). Clinical outcome of the patients was known. Seventy four of the patients have remained disease-free for more than seven years while seventy five patients had distant metastases within four years. One hundred and three patients were lymph node negative while forty six were lymph node positive.

The tissues were snap frozen in liquid nitrogen within 20-30 minutes of harvesting, and stored at −80C.° thereafter. For laser capture, the samples were cut (6 μm), and one section was mounted on a glass slide, and the second on film (P.A.L.M.), which had been fixed onto a glass slide (Micro Slides Colorfrost, VWR Scientific, Media, Pa.). The section mounted on a glass slide was after fixed in cold acetone, and stained with Mayer's Haematoxylin (Sigma, St. Louis, Mo.). A pathologist analyzed the samples for diagnosis and grade. The clinical stage was estimated from the accompanying surgical pathology and clinical reports to verify the staging of the tumor. The section mounted on film was after fixed for five minutes in 100% ethanol, counter stained for 1 minute in eosin/100% ethanol (100 μg of Eosin in 100 ml of dehydrated ethanol), quickly soaked once in 100% ethanol to remove the free stain, and air dried for 10 minutes.

Before use in LCM, the membrane (LPC-MEMBRANE PEN FOIL 1.35 μm No 8100, P.A.L.M. GmbH Mikrolaser Technologie, Bernried, Germany) and slides were pretreated to abolish RNases, and to enhance the attachment of the tissue sample onto the film. Briefly, the slides were washed in DEP $H_2O$, and the film was washed in RNase AWAY (Molecular Bioproducts, Inc., San Diego, Calif.) and rinsed in DEP $H_2O$. After attaching the film onto the glass slides, the slides were baked at +120° C. for 8 hours, treated with TI-SAD (Diagnostic Products Corpotation, Los Angeles, Calif., 1:50 in DEP $H_2O$, filtered through cotton wool), and incubated at +37° C. for 30 minutes. Immediately before use, a 10 μl aliquot of RNase inhibitor solution (Rnasin Inhibitor 2500 U=33 U/μl N211A, Promega GmbH, Mannheim, Germany, 0.5 μl in 400 μl of freezing solution, containing 0.15 mol NaCl, 10 mmol Tris pH 8.0, 0.25 mmol dithiothreitol) was spread onto the film, where the tissue sample was to be mounted.

The tissue sections mounted on film were used for LCM. Approximately 2000 epithelial cells/sample were captured using the PALM Robot-Microbeam technology (P.A.L.M. Mikrolaser Technologie, Carl Zeiss, Inc., Thomwood, N.Y.), coupled into Zeiss Axioven 135 microscope (Carl Zeiss Jena GmbH, Jena, Germany). The surrounding stroma in the normal mucosa, and the occasional intervening stromal components in cancer samples, were included. The captured cells were put in tubes in 100% ethanol and preserved at −80° C.

Example 2

RNA Extraction and Amplification

Zymo-Spin Column (Zymo Research, Orange, Calif. 92867) was used to extract total RNA from the LCM captured samples. About 2 ng of total RNA was resuspended in 10 ul of water and 2 rounds of the T7 RNA polymerase based amplification were performed to yield about 50 ug of amplified RNA.

Example 3 cDNA Microarray Hybridization and Quantitation

A set of cDNA microarrays consisting of approximately 23,000 human cDNA clones was used to test the samples by use of the humanU133a chip obtained and commercially available from Affymetrix, Inc. Total RNA obtained and prepared as outlined above and applied to the chips and analyzed by Agilent BioAnalyzer according to the manufacturer's protocol. All 149 samples passed the quality control standards and the data were used for marker selection.

Marker selection was performed by analyzing the 103 lymph node negative patients. Genes that allow the discrimination of distant metastases and survivors were identified using Cox proportional hazard model. Chip intensity data was analyzed using MAS Version 5.0 software commercially available from Affymetrix, Inc. ("MAS 5.0"). An unsupervised analysis was first conducted followed by a supervised analysis.

The chip intensity data obtained as described was the input for the unsupervised clustering software commercially available as PARTEK version 5.1 software. This unsupervised clustering algorithm identified a group of 22 patients with a significant low expression of many genes including estrogen receptor. ER/PR are known prognostic factors for poor outcome in breast cancer so this group of 22 patients were excluded from subsequent analysis to identify additional factors (gene markers) with independent value as prognostic indicators. The remaining 81 patients were further filtered to remove potential effects of the well-characterized prognostic indicators of age and tumor size. Twenty-seven patients older than 55 years or having tumors larger than 5 cm were thus excluded too.

A Cox proportional hazard model was used for gene selection. In each cycle of the total 31 cycles, each of the 31 patients in the training set was held out, the remaining 26 patients were used in the univariate Cox model regression to assess the strength of association of gene expression with the patient survival time. The strength of such association was evaluated by the corresponding estimated standardized parameter estimate and P value returned from the Cox model regression. P value of 0.01 was used as the threshold to select top genes from each cycle of the leave-one-out gene selection. The top genes selected from each cycle were then compared in order to select those genes that showed up at least 28 times in the total of 31 leave-one-out gene selection cycles. A total of 56 genes were

| Gene | Modulation (Standardized Coefficient) | P. value | Sequence I.D. No. |
|---|---|---|---|
| 216516_at | −2.7708 | 0.0056 | Sequence I.D.. No. 32 |
| 211646_at | −2.7853 | 0.0053 | Sequence I.D.. No. 33 |
| 219463_at | −2.7860 | 0.0053 | Serquence I.D. No. 34 |
| 204532_x_at | −2.7921 | 0.0052 | Sequence I.D. No. 35 |
| 210365_at | −2.7931 | 0.0052 | Sequence I.D.. No. 36 |
| 222098_s_at | −2.8121 | 0.0049 | Sequence I.D.. No. 37 |
| 212800_at | −2.8267 | 0.0047 | Sequence I.D.. No. 38 |
| 205582_s_at | −2.8350 | 0.0046 | Sequence I.D.. No. 39: |
| 219096_at | −2.8393 | 0.0045 | Sequence I.D.. No. 40 |
| 216944_s_at | −2.8667 | 0.0041 | Sequence I.D.. No. 41 |
| 208923_at | −2.8766 | 0.0040 | Sequence I.D.. No. 42 |
| 209309_at | −2.9149 | 0.0036 | Sequence I.D.. No. 43 |
| 207981_s_at | −2.9294 | 0.0034 | Sequence I.D.. No. 44 |
| 210160_at | −2.9448 | 0.0032 | Sequence I.D.. No. 45 |
| 206862_at | −2.9676 | 0.0030 | Sequence I.D.. No. 46 |
| 213110_s_at | −2.9857 | 0.0028 | Sequence I.D.. No. 47 |
| 201906_s_at | −3.0124 | 0.0026 | Sequence I.D.. No. 48 |
| 201057_s_at | −3.0133 | 0.0026 | Sequence I.D.. No. 49 |
| 220798_x_at | −3.0270 | 0.0025 | Sequence I.D.. No. 50 |
| 218650_at | −3.0513 | 0.0023 | Sequence I.D.. No. 51 |
| 220986_s_at | −3.2095 | 0.0013 | Sequence I.D.. No. 52 |
| 214451_at | −3.4431 | 0.0006 | Sequence I.D.. No. 53 |
| 203844_at | −3.4965 | 0.0005 | Sequence I.D.. No. 54 |
| 202966_at | −3.5864 | 0.0003 | Sequence I.D.. No. 55 |

Construction of a multiple-gene predictor: The prediction index is defined as the sum of the product of the 56 genes' expression values (log 10 based) and their corresponding cox model parameter estimates. The parameter estimate from the cox models measures the hazard ratio of the patient when the gene expression value increases. Therefore, patients with high scores using the index have poor survival outcomes. This prediction index was applied to the training set to obtain an estimate of the prediction accuracy (FIG. 1).

Cross-validation and evaluation of predictor: Performance of the predictor should be determined on an independent data set because most classification selected. Gene expression for those genes having Seq. ID No 1 to 26 and Seq ID No. 56 were up-regulated at least two fold and genes having Seq. ID No 27 to 55 were down regulated at least two fold.

TABLE 1

Breast Cancer Prognostic Gene Markers.

| Gene | Modulation (Standardized Coefficient) | P. value | Sequence I.D. No. |
|---|---|---|---|
| 202984_s_at | 3.8521 | 0.0001 | Sequence I.D. No.: 1 |
| 208777_s_at | 3.4922 | 0.0005 | Sequence I.D. No. 2. |
| 222133_s_at | 3.1841 | 0.0015 | Sequence I.D. No. 3 |
| 218185_s_at | 3.1379 | 0.0017 | Sequence I.D. No. 4 |
| 219571_s_at | 3.1131 | 0.0019 | Sequence I.D.. No. 5 |
| 201138_s_at | 3.1075 | 0.0019 | Sequence I.D.. No. 6 |
| 209155_s_at | 3.1018 | 0.0019 | Sequence I.D.. No. 7 |
| 212468_at | 0.0019 | 0.0022 | Sequence I.D.. No. 8 |
| 217593_at | 0.0019 | 0.0022 | Sequence I.D.. No. 9 |
| 212973_at | 3.0325 | 0.0024 | Sequence I.D.. No. 10 |
| 202971_s_at | 2.9994 | 0.0027 | Sequence I.D.. No. 11 |
| 204444_at | 2.9926 | 0.0028 | Sequence I.D.. No. 12 |
| 205169_at | 2.9911 | 0.0028 | Sequence I.D.. No. 13 |
| 219751_at | 2.9707 | 0.0030 | Sequence I.D.. No. 14 |
| 217988_at | 2.9649 | 0.0030 | Sequence I.D.. No. 15 |
| 212942_s_at | 2.9460 | 0.0032 | Sequence I.D.. No. 16 |
| 208993_s_at | 2.9423 | 0.0033 | Sequence I.D.. No. 17 |
| 219105_x_at | 2.9324 | 0.0034 | Sequence I.D.. No. 18 |
| 220085_at | 2.9001 | 0.0037 | Sequence I.D.. No. 19 |
| 206640_x_at | 2.8799 | 0.0040 | Sequence I.D. No. 20 |
| 205062_x_at | 2.8663 | 0.0042 | Sequence I.D. No. 21 |
| 209385_s_at | 2.8115 | 0.0049 | Sequence I.D.. No. 22 |

TABLE 1-continued

Breast Cancer Prognostic Gene Markers.

Figure 2:
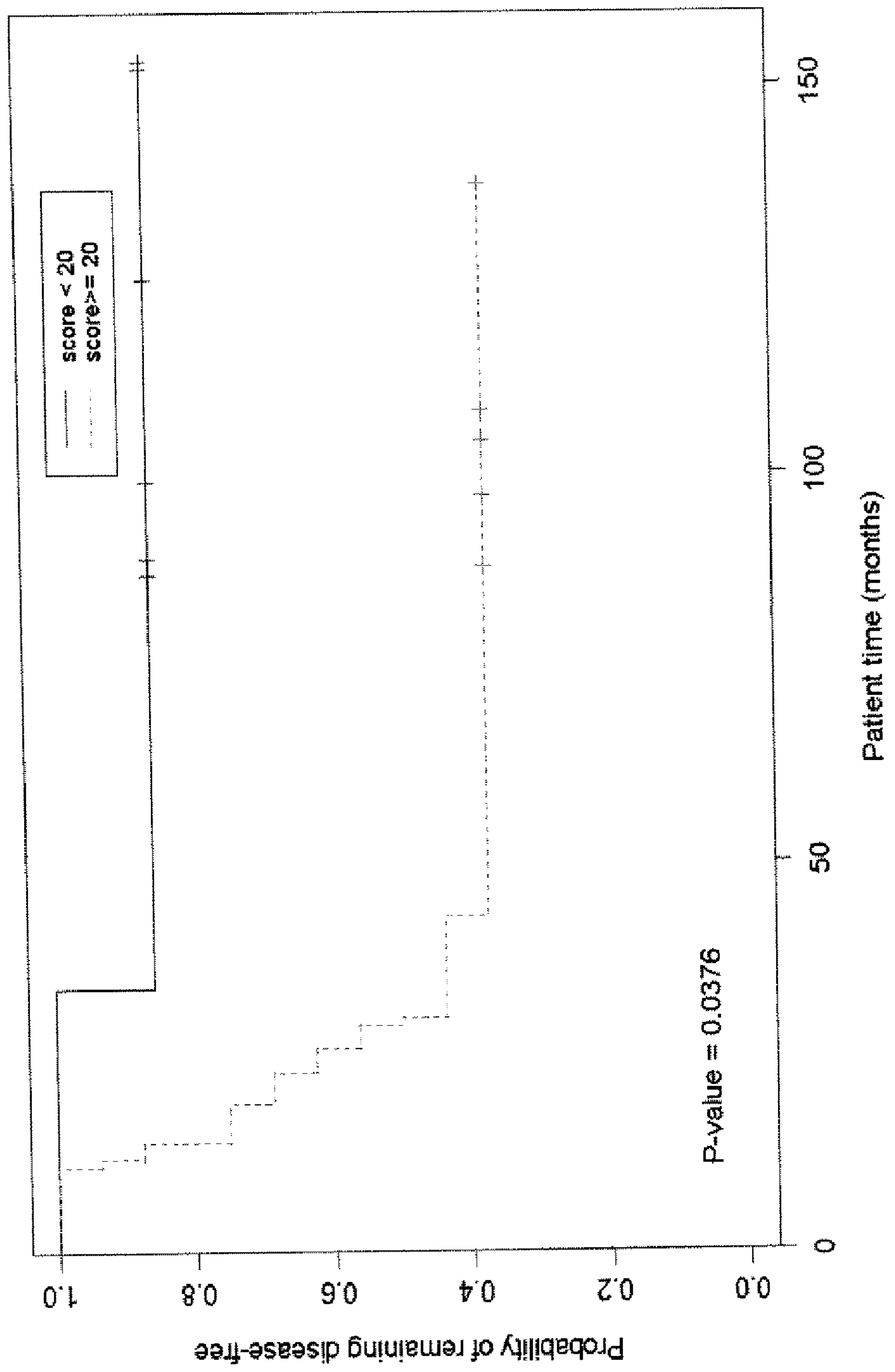
FIG. 2 is a standard Kaplan-Meier Plot constructed from the patient data as a testing set as described in the Examples.

| Gene | Modulation (Standardized Coefficient) | P. value | Sequence I.D. No. |
|---|---|---|---|
| AFFX-M27830_5_at | 2.7868 | 0.0053 | Sequence I.D.. No. 56 |
| 215170_s_at | 2.7814 | 0.0054 | Sequence I.D.. No. 23 |
| 207663_x_at | 2.7634 | 0.0057 | Sequence I.D.. No. 24 |
| 212229_s_at | 2.7422 | 0.0061 | Sequence I.D.. No. 25 |
| 215206_at | 2.7317 | 0.0063 | Sequence I.D.. No. 26 |
| 206241_at | −2.7281 | 0.0064 | Sequence I.D.. No. 27 |
| 219813_at | −2.7406 | 0.0061 | Sequence I.D.. No. 28 |
| 210969_at | −2.7522 | 0.0059 | Sequence I.D.. No. 29 |
| 207865_s_at | −2.7691 | 0.0056 | Sequence I.D.. No. 30 |
| 202520_s_at | −2.7702 | 0.0056 | Sequence I.D.. No. 31 |

methods work well on the examples that were used in their establishment. The 23 patients testing set was used to assess prediction accuracy. The cutoff for the classification is determined using the ROC, curve with 90% sensitivity. With the selected cutoff, the numbers of correct prediction for relapse and survival patients in the test set are summarized in (Table 1). The Kaplan-Meier curve was constructed on the predicted relapsers and survivors (FIG. 2).

Figure 3:
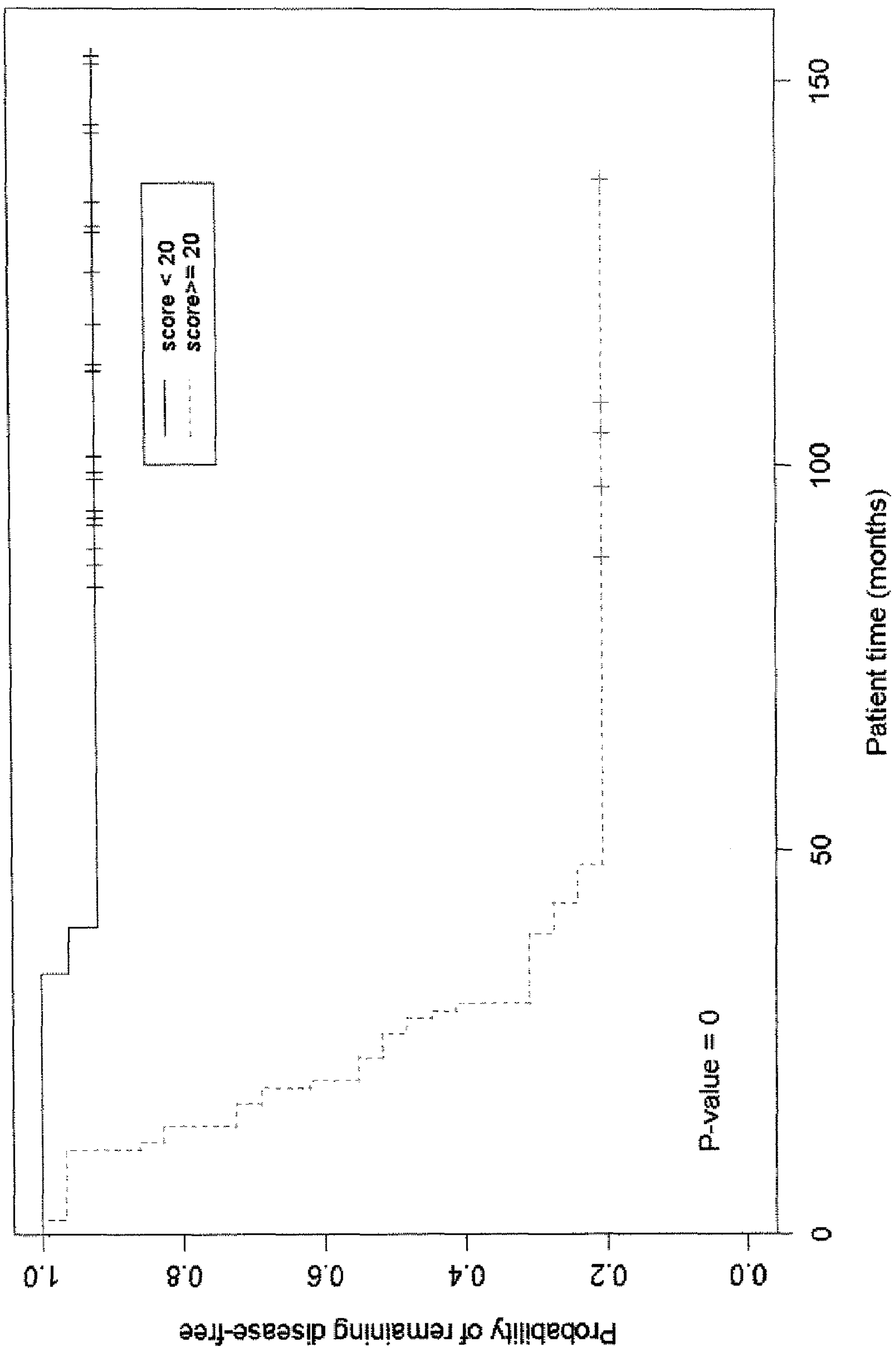
FIG. 3 is a standard Kaplan-Meier Plot constructed from the patient data of 54 patients (training and testing data combined) using a 56-gene expression profile.

Overall prediction: Gene expression profiling of 54 Stage I and II breast cancer patients led to identification of 56 genes that have differential expression in these patients. Thirty-six of the patients have remained disease-free for more than 7 years while 27 patients had distant metasteses within 4 years. Using the 56-gene predictor, 22 of the 27 relapse patients and 27 of 36 disease-free patients were identified correctly. This result represents a sensitivity of 82% and a specificity of 75%. The positive predictive value is 71% and the negative predictive value is 84% (Table 2). The Kaplan-Meier curve was constructed on the predicted distant metastases and survivors (FIG. 3).

An independent study was previously published (Van't Veer et al. *Nature* 415, 530-535. Vijver et al., *NEJM* 347, 1999-2009) in which a 70-gene predictor was constructed to predict patient outcomes in Stage I and II lymph node negative breast cancer. Only one gene overlaps between the 70-gene of the Van't Veer et al. study and the 56-gene predictor of this specification.

TABLE 2

Prediction accuracy based on testing set using 56-gene predictor.

| Study Prediction | Number of Sample | Correct |
|---|---|---|
| Relapse | 11 | 10 |
| Survivor | 12 | 6 |
| Sensitivity | 91% | |
| Specificity | 50% | |

TABLE 3

Prediction accuracy based on all patients using 56-gene predictor.

| Study Prediction | Number of Sample | Correct |
|---|---|---|
| Relapse | 25 | 23 |
| Survivor | 29 | 23 |
| Sensitivity | 92% | |
| Specificity | 79% | |

Example 4

Further Portfolios

The 56 gene portfolio was subjected to different treatments to fashion further portfolios that provide clinically significant benefits with fewer numbers of gene expression signatures for analysis.

a. In a first treatment, correlation coefficients among the 56 genes were calculated by Spearman rank correlation and Pearson's correlation. Using 0.7 as the correlation cutoff, a portfolio of 45 modulated genes was established. The genes are shown in Table 4.

b. In a second treatment, the 56 genes were tested with t-tests using either the training or testing dataset. The genes that displayed significant p values (<0.05) in both training and testing data were selected as a portfolio. A portfolio of 26 modulated genes was thus established. The genes are shown in Table 5.

c. The 26 gene portfolio of (b) and Table 5 were then evaluated based on the known biological functions of the genes in the portfolio. Those having a biological relationship to a metastatic pathway were selected. A portfolio of 13 modulated genes was thus established. The genes are shown in Table 6.

d. A two gene pair exhibiting the best classification performance was selected from the 56 gene portfolio. In serial, one additional gene was added to the portfolio and tested to determine whether the addition of that signature improved the overall classification accuracy in both training set and testing set of the two gene combination. This procedure was repeated until no further improvement was achieved. A portfolio of 6 modulated genes was established. The genes are shown in Table 7.

The sensitivity and specificity for each of the portfolios shown in Tables 4-7 was determined based on predicted versus known outcomes for the samples described above. These values are shown in Tables 8-11.

TABLE 4

45 Gene Set

| Gene | Modulation (Standardized Coefficient) | Sequence I.D. No. |
|---|---|---|
| 220986_s_at | −3.2095 | Seq. I.D. No. 52 |
| 220798_x_at | −3.0270 | Seq. I.D. No. 50 |
| 220085_at | 2.9001 | Seq. I.D. No. 19 |
| 219751_at | 2.9707 | Seq. I.D. No. 14 |
| 219105_x_at | 2.9324 | Seq. I.D. No. 18 |
| 218650_at | −3.0513 | Seq. I.D. No. 51 |
| 214451_at | −3.4431 | Seq. I.D. No. 53 |
| 212973_at | 3.0325 | Seq. I.D. No. 10 |
| 208993_s_at | 2.9423 | Seq. I.D. No. 17 |
| 205582_s_at | −2.8350 | Seq. I.D. No. 39 |
| 205169_at | 2.9911 | Seq. I.D. No. 13 |
| 203844_at | −3.4965 | Seq. I.D. No. 54 |
| 202984_s_at | 3.8521 | Seq. I.D. No. 1 |
| 202966_at | −3.5864 | Seq. I.D. No. 55 |
| 201057_s_at | −3.0133 | Seq. I.D. No. 49 |
| 222133_s_at | 3.1841 | Seq. I.D. No. 3 |
| 219096_at | −2.8393 | Seq. I.D. No. 40 |
| 218185_s_at | 3.1379 | Seq. I.D. No. 4 |
| 212942_s_at | 2.9460 | Seq. I.D. No. 16 |
| 210160_at | −2.9448 | Seq. I.D. No. 45 |
| 209155_s_at | 3.1018 | Seq. I.D. No. 7 |
| 204444_at | 2.9926 | Seq. I.D. No. 12 |
| 202971_s_at | 2.9994 | Seq. I.D. No. 11 |
| 201138_s_at | 3.1075 | Seq. I.D. No. 6 |
| 222098_s_at | −2.8121 | Seq. I.D. No. 37 |

TABLE 4-continued

45 Gene Set

| Gene | Modulation (Standardized Coefficient) | Sequence I.D. No. |
|---|---|---|
| 219813_at | −2.7406 | Seq. I.D. No. 28 |
| 216944_s_at | −2.8667 | Seq. I.D. No. 41 |
| 215206_at | 2.7317 | Seq. I.D. No. 26 |
| 212800_at | −2.8267 | Seq. I.D. No. 38 |
| 212229_s_at | 2.7422 | Seq. I.D. No. 25 |
| 211646_at | −2.7853 | Seq. I.D. No. 33 |
| 210365_at | −2.7931 | Seq. I.D. No. 36 |
| 209385_s_at | 2.8115 | Seq. I.D. No. 22 |
| 209309_at | −2.9149 | Seq. I.D. No. 43 |
| 208923_at | −2.8766 | Seq. I.D. No. 42 |
| 207663_x_at | 2.7634 | Seq. I.D. No. 24 |
| 205062_x_at | 2.8663 | Seq. I.D. No. 21 |
| 202520_s_at | −2.7702 | Seq. I.D. No. 31 |
| AFFX-M27830_5_at | 2.7868 | Seq. I.D. No. 56 |
| 216516_at | −2.7708 | Seq. I.D. No. 32 |
| 215170_s_at | 2.7814 | Seq. I.D. No. 23 |
| 210969_at | −2.7522 | Seq. I.D. No. 29 |
| 207981_s_at | −2.9294 | Seq. I.D. No. 44 |
| 206241_at | −2.7281 | Seq. I.D. No. 27 |
| 204532_x_at | −2.7921 | Seq. I.D. No. 35 |

TABLE 5

26 Gene Set

| Gene | Modulation (Standardized Coefficient) | Sequence I.D. No. |
|---|---|---|
| 205169_at | 2.9911 | Seq. I.D. No. 13 |
| 203844_at | −3.4965 | Seq. I.D. No. 54 |
| 205062_x_at | 2.8663 | Seq. I.D. No. 21 |
| 202971_s_at | 2.9994 | Seq. I.D. No. 11 |
| 201906_s_at | −3.0124 | Seq. I.D. No. 48 |
| 212942_s_at | 2.9460 | Seq. I.D. No. 16 |
| 206862_at | −2.9676 | Seq. I.D. No. 46 |
| 202966_at | −3.5864 | Seq. I.D. No. 55 |
| 201057_s_at | −3.0133 | Seq. I.D. No. 49 |
| 219105_x_at | 2.9324 | Seq. I.D. No. 18 |
| 217593_at | 3.0584 | Seq. I.D. No. 9 |
| 202520_s_at | −2.7702 | Seq. I.D. No. 31 |
| 210365_at | −2.7931 | Seq. I.D. No. 36 |
| 215206_at | 2.7317 | Seq. I.D. No. 26 |
| 212229_s_at | 2.7422 | Seq. I.D. No. 25 |
| 211646_at | −2.7853 | Seq. I.D. No. 33 |
| 219813_at | −2.7406 | Seq. I.D. No. 28 |
| 216944_s_at | −2.8667 | Seq. I.D. No. 41 |
| 219096_at | −2.8393 | Seq. I.D. No. 40 |
| 218185_s_at | 3.1379 | Seq. I.D. No. 4 |
| 213110_s_at | −2.9857 | Seq. I.D. No. 47 |
| 212468_at | 3.0663 | Seq. I.D. No. 8 |
| 208993_s_at | 2.9423 | Seq. I.D. No. 17 |
| 208777_s_at | 3.4922 | Seq. I.D. No. 2 |
| 220085_at | 2.9001 | Seq. I.D. No. 19 |
| 219751_at | 2.9707 | Seq. I.D. No. 14 |

TABLE 6

13 Gene Set

| Gene | Modulation (Standardized Coefficient) | Sequence I.D. No. |
|---|---|---|
| 202971_s_at | 2.9994 | Seq. I.D. No. 11 |
| 201906_s_at | −3.0124 | Seq. I.D. No. 48 |
| 206862_at | −2.9676 | Seq. I.D. No. 46 |
| 202966_at | −3.5864 | Seq. I.D. No. 55 |
| 219105_x_at | 2.9324 | Seq. I.D. No. 18 |

TABLE 6-continued

13 Gene Set

| Gene | Modulation (Standardized Coefficient) | Sequence I.D. No. |
|---|---|---|
| 210365_at | −2.7931 | Seq. I.D. No. 36 |
| 212229_s_at | 2.7422 | Seq. I.D. No. 25 |
| 219813_at | −2.7406 | Seq. I.D. No. 28 |
| 219096_at | −2.8393 | Seq. I.D. No. 40 |
| 218185_s_at | 3.1379 | Seq. I.D. No. 4 |
| 213110_s_at | −2.9857 | Seq. I.D. No. 47 |
| 208777_s_at | 3.4922 | Seq. I.D. No. 2 |
| 220085_at | 2.9001 | Seq. I.D. No. 19 |

TABLE 7

6 Gene Set

| Gene | Modulation (Standardized Coefficient) | Sequence I.D. No. |
|---|---|---|
| 205169_at | 2.9911 | Seq. I.D. No. 13 |
| 202966_at | −3.5864 | Seq. I.D. No. 55 |
| 206862_at | −2.9676 | Seq. I.D. No. 46 |
| 219105_x_at | 2.9324 | Seq. I.D. No. 18 |
| 205062_x_at | 2.8663 | Seq. I.D. No. 21 |
| 201138_s_at | 3.1075 | Seq. I.D. No. 6 |

TABLE 8

45-gene Prognostic Portfolio

| Study Prediction | Number of Sample | Correct |
|---|---|---|
| Relapse | 11 | 10 |
| Survivor | 12 | 6 |
| Sensitivity | 91% | |
| Specificity | 50% | |

TABLE 9

26-gene Prognostic Portfolio

| Study Prediction | Number of Sample | Correct |
|---|---|---|
| Relapse | 11 | 10 |
| Survivor | 12 | 10 |
| Sensitivity | 91% | |
| Specificity | 83% | |

TABLE 10

13-gene Prognostic Portfolio

| Study Prediction | Number of Sample | Correct |
|---|---|---|
| Relapse | 11 | 10 |
| Survivor | 12 | 8 |
| Sensitivity | 91% | |
| Specificity | 67% | |

TABLE 11

6-gene Prognostic Portfolio

| Study Prediction | Number of Sample | Correct |
|---|---|---|
| Relapse | 11 | 10 |
| Survivor | 12 | 8 |
| Sensitivity | 91% | |
| Specificity | 67% | |

The invention claimed is:

1. A kit for determining the prognosis of a breast cancer patient comprising materials for detecting isolated nucleic acid sequences, their complements, or portions thereof comprising a combination of genes including all of Seq. ID. No. 1-56 and wherein said kit further includes materials that indicate up regulation of genes of Seq. ID. No. 1 to 26 and 56 together with down regulation of genes of Seq. ID. No. 27 to 55 such that said patient has a poor prognosis.

2. The kit of claim 1 comprising reagents for conducting a microarray analysis.

3. The kit of claim 1 further comprising a medium through which said nucleic acid sequences, their complements, or portions thereof are assayed.

* * * * *

SEQUENCE LISTING

```
<160> NUMBER OF SEQ ID NOS: 56

<210> SEQ ID NO 1
<211> LENGTH: 533
<212> TYPE: DNA
<213> ORGANISM: Human

<400> SEQUENCE: 1

aaaggcccat taacttaatt taaatgttcc catccttatg aatttactca ctaaggaaaa      60

ctataagctc agattttaca aacaaaagca acttacaagg tattattgct ggtcctttat     120

cccttctctt taatgcaatc tcaaaggttt tttggctatt agttttcata attttcttat     180

gttgcacaca aaaacaagat tcctctctaa aacgtagagg atggggaaaa tgcagatgct     240

gtttttccaa ctaaaaatgt ttacaaaaga acagactgtc tgaacaaaca aaaaaacccc     300

accccgttaa gctgggtagg accaatcagg ccttataagt gaaaaaaaag ccttctatcg     360

agcataatga aacagaacat gtactgcttg tgtttgaacc ttactcttat ttaaccaaaa     420

atttcccctt tctcataatt ttcctagtat tatgtaaggt tatgcctagt tctagattct     480

gaaagacctg cattttaatg cttgcacaac ccatttaaaa tctacaaaag ctg            533
```

<210> SEQ ID NO 2
<211> LENGTH: 1450
<212> TYPE: DNA
<213> ORGANISM: Human

<400> SEQUENCE: 2

```
cgtcggcggc cgcggccggg gacggtgtga gagcggtaag atggcggcgg cggcggtggt     60

ggagttccag agagcccagt ctctactcag caccgaccgg gaggcctcca tcgacatcct    120

ccactccatc gtgaagcgtg acattcagga aaacgatgaa gaggcagtgc aagtcaaaga    180

gcagagcatc ctggaactgg gatctctcct ggcaaagact ggacaagctg cagagcttgg    240

aggactcctg aagtatgtac gacccttctt gaattccatc agcaaggcta aagcagctcg    300

cctggtccga tctcttcttg atctgtttct tgatatggaa gcagctacag ggcaggaggt    360

cgagctgtgt ttagagtcca tcgaatgggc caagtcagag aaaagaactt tcttacgcca    420

agctttggag gcaagactgg tgtctttgta ctttgatacc aagaggtacc aggaagcatt    480

gcatttgggt tctcagctgc tgcgggagtt gaaaaagatg gacgacaaag ctcttttggt    540

ggaagtacag cttttagaaa gcaaaacata ccatgccctg agcaacctgc cgaaagcccg    600

agctgcctta acttctgctc gaaccacagc aaatgccatc tactgccccc ctaaattgca    660

ggccaccttg gacatgcagt cgggtattat ccatgcagca gaagagaagg actggaaaac    720

tgcgtactca tacttctatg aggcatttga gggttatgac tccatcgaca gccccaaggc    780

catcacatct ctgaagtaca tgttgctgtg caaaatcatg ctcaacaccc cagaagatgt    840

ccaggctttg gtgagcggga agcttgcact tcggtatgca gggaggcaga cagaagcatt    900

aaaatgcgtg gctcaggcta gcaagaacag atcactggca gattttgaaa aggctctgac    960

agattaccgg gcagagctcc gggatgaccc aatcatcagc acacacttgg ccaagttgta   1020

tgataactta ctagaacaga atctgatccg agtcattgag ccttttttcca gagtacagat   1080

tgaacacata tctagtctca tcaaactctc caaggccgac gtggaaagga aattatcaca   1140

gatgattctt gacaagaaat ttcatgggat tttggaccag ggggagggtg tcctgattat   1200

tttcgatgaa cccccagtag ataaaactta cgaagctgct ctggaaacaa ttcagaacat   1260

gagcaaagta gtggattccc tctacaacaa agccaagaaa ctgacataga gttggatctg   1320

tagcggtcct ttggagagtg tgtgtggcgg gagagtgaaa ccttggggga aaatgctagg   1380

agattctttt ttctttttgt tctacttttc gctcggaaag tttttaaatc ctcatttggt   1440

gcatctgtat                                                          1450
```

<210> SEQ ID NO 3
<211> LENGTH: 1633
<212> TYPE: DNA
<213> ORGANISM: Human

<400> SEQUENCE: 3

```
ctcaagatga gtaaaaagcc cccaaatcgc cctggaatca cttttgagat tggtgctcgt     60

ttggaggcac tggactactt acaaaaatgg tatccatcac gaattgaaaa aattgactat    120

gaggagggca agatgttggt ccattttgag cgctggagtc atcgttatga tgagtggatt    180

tactgggata gcaatagatt gcgacccctt gagagaccag cactaagaaa agaagggcta    240

aaagatgagg aagatttctt tgattttaaa gctggagaag aagttctggc tcgttggaca    300

gactgtcgct attaccctgc caagattgaa gcaattaaca aagaaggaac atttacagtt    360

cagttttatg atggagtaat tcgttgttta aaaagaatgc acattaaagc catgcccgag    420
```

```
gatgctaagg ggcaggattg gatagcttta gtcaaagcag ctgctgcagc tgcagccaag    480

aacaaaacag ggagtaaacc tcgaaccagc gctaacagca ataaagataa ggataaagat    540

gagagaaagt ggtttaaagt accttcaaag aaggaggaaa cttcaacttg tatagccaca    600

ccagacgtag agaagaagga agatctgcct acatctagtg aaacatttgg acttcatgta    660

gagaacgttc caaagatggt ctttccacag ccagagagca cattatcaaa caagaggaaa    720

aataatcaag gcaactcgtt tcaggcaaag agagctcgac ttaacaagat tactggaaga    780

gaccagctgt gtattttata gctaatatag aatactggaa ggttgtaact ttattggttt    840

gttggcatcc aaagctgttg gggttgatgg tgctgaaaaa aaggaagact acaatgaaac    900

agctccaatg ctggagcagg cgatttcacc taaacctcaa agtcagaaaa aaaatgaagc    960

tgacattagc agttctgcca acactcagaa acctgcactg ttatcctcaa ctttgtcttc   1020

agggaaggct cgcagcaaga aatgcaaaca tgaatctgga gattcttctg ggtgtataaa   1080

acccccctaaa tcaccacttt ccccagaatt aatacaagtc gaggatttga cgcttgtatc   1140

tcagctttct tcttcagtga taaataaaac tatgcctgat gttgcacatt tgccacttga   1200

gaagctggga ccctgtctcc ctcttgactt aagtcgtggt tcagaagtta cagcaccggt   1260

agcctcagat tcctcttacc gtaatgaatg tcccagggca gaaaaagagg atacacagat   1320

gcttccaaat ccttcttcca aagcaatagc tgatggaaga ggagctccag cagcagcagg   1380

aatatcgaaa acagaaaaaa aagtgaaatt ggaagacaaa agctcaacag catttggtat   1440

caggagttgg gatttctcag cactgctaat gaagatcccc tcttatagtc caataagctt   1500

atcaggactt ccagagtcat gacatgaaca gtttaattga acccatccac tctgggcagg   1560

taagagaaaa gaaaaagata aggaaagaag agagaagaga gacaaagatc actacagacc   1620

aaaacagaag aag                                                      1633
```

<210> SEQ ID NO 4
<211> LENGTH: 2666
<212> TYPE: DNA
<213> ORGANISM: Human
<220> FEATURE:
<221> NAME/KEY: misc_feature
<223> OTHER INFORMATION: target:HG-U133A:201042_at; gb`031651; Consensus includes gb:AL031651 /DEF=Human DNA sequence from clone RP5-1054A22 on chromosome 20q11.22-12 Contains two isoforms of the gene for TGM2 (transglutaminase 2 (C polypeptide,

<400> SEQUENCE: 4

```
ggcacgaggg tcacctggga agagtctgca gagcctttgc ccgccagcgc cttcgctctt     60

tggctccctg agttaatccg gttgtttgcg atcgccgcgg ccggggctgc gaaccgaagg    120

gctcgctccg cgccgcctgg gtctctacct catccgtagg tgtggccctg atggtgtggc    180

aggctctgga ctcctaaagc tctggagcga atttaagatt ttattcatgt gcatggcata    240

gaagatgaat tcttccactt ccaccatgag tgaagagcct gacgctctat cggtagttaa    300

ccagttacgg gatctagcag cagatccgtt aaacagaaga gccatcgtcc aggatcaggg    360

atgtctgcct ggccttattt tatttatgga ccatcccaac cctccagtcg tccactccgc    420

tttgcttgct cttcgatact tggcagaatg ccgtgcaaac agagaaaaga tgaaaggaga    480

actgggtatg atgttgagct tacaaaatgt tatacagaaa actacaactc caggagaaac    540

aaaacttctg gcctctgaaa tctatgacat tcttcagtcc tccaatatgg cagatggtga    600

tagttttaat gagatgaatt cacgtcgaag gaaagctcaa ttttttctgg gaactacaaa    660

caaacgtgcc aaaacagtgg ttttgcatat agatggcctt gatgatacgt ctcggagaaa    720
```

tctatgtgaa gaggctttgt taaaaattaa aggtgttatt agctttactt ttcaaatggc 780
tgttcaaagg tgtgtggtgc gaatccgttc agatttgaaa gctgaggctt tggcatcagc 840
aatagcatca accaaggtta tgaaagctca gcaagttgtg aaaagtgaaa gtggagaaga 900
gatgttggtc ccattccaag atactcctgt ggaagttgaa cagaacacag agctacctga 960
ctacctgcct gaggatgaga gtcccacaaa ggaacaggac aaagcggtgt cccgggtcgg 1020
ctcacaccca gaaggtggag ctagctggct tagcacagct gcaaactttt tatccagatc 1080
attttattgg tgacttcact tttgggctca aggactgtgt gaaccaacaa ggggccagtt 1140
ttccattgtt gtggtgaact gtcaagtgca atttgcaata agttatcatg aaaagttttt 1200
agattacacg atcgcatatg ctgcatttca cattttattg gacattttac cccactgagt 1260
ggtaaaaagg acagaggcta cagatggagt tgctttgttt atgaaagtat tttggtttgt 1320
tttctttcat ttaattgcct catatttaaa aaccatgggt ccactgttaa aaccacatgt 1380
gtatgtgcag ctttacattt tattttacgt gaagcatgtg attaggaaaa ctcatttttct 1440 tttcaagcct caggacctac ctgaagagaa gttttcttgt agctcaagtt gtgcatgaat 1500
tactgaatat tttactgtgc ttttcttcat gaagggtaca tgctttgtac tcttcactga 1560
aagctgaaaa catttcttgt taccctcttt tgtgcctttt tattttgcca accgtgttta 1620
tagaaaggac attactaatg acattttgca gattaaaaac attcatttga acacagtagt 1680
cccctagaaa aacaactcta caaaaatttt gcagccttat tcattataat tttgataaaa 1740
ttaacacaaa atcagtcaag aaggaaacat gtatattagt gaagtgtttt tggagactgt 1800
ttgaatgtga ccaaatgtgg ttctagttga cttcttttca ctttggctta tatcaattct 1860
tgagagttaa tgtgatcatg atattgcaaa caactataaa tggtctctag gccttacttt 1920
gtgattatac gttatctccg gctagaaaaa aataatggta gtaaagaaac tgacaaactg 1980
aaaataagaa aacaaaaatc aaatgcctat aataccataa tgccagtttg gtatagagtc 2040
caactttaaa acatgaattg ctcgacagag ttctattcag taggtgtttc tttgtattgt 2100
cttttgtgaa tttattatga aaatgctgcg ttgtgttgaa tgaaaaagac ccaaattact 2160
gcttatgaag aaataaagcc agcattgatc acttaatcct gtttctcatg tccagccaga 2220
aaaaagaact tcagtgaagg taagataaat aaatacatac acatatgttt ttttggtaga 2280
taagtgctaa ttacatatat gtaatgcttt attaaatttc tgaaatattt ggtaactaaa 2340
attttctttt tggaaattaa taaatccaga tacatattaa tgttgatatg agtaaaaaca 2400
aataggaaga aattgaaatt tcttttcatc aacatgtaga gctgctattt tactatttgg 2460
agaatatgat gtgaaaattg gacctcaaag ggtttccttg tgttttcatt gtaaaatacc 2520
atcatcagtg agagtcttga gttcactaac attgtcacct tctggagaga gagttaatgg 2580
ggggcattga ggatgatatt tttttacatg tgtttggttt ctgattcaag tgacacgcac 2640
aaactgaaaa aaaaaaaaaa aaaaaa 2666

<210> SEQ ID NO 5
<211> LENGTH: 2445
<212> TYPE: DNA
<213> ORGANISM: Human

<400> SEQUENCE: 5
tcctgtgcgt ccccaggtca ccgctcgccc tagttcccag gctttggcct ccggtgggcg 60
agaatcgcgg agcctgcggg gctgggcgcc gaagagccgg gccggcaccc aagcgggcgc 120
ggggctgtgc gggccaggcg gaggctcaag cggggatccc cgagcacgac ccccggagcc 180

```
gacggcgctg gggcccaagg ggccggccgg gcggtgacga cggcggaggc gaaggggcgg    240
cgggacccgg gcccggcccg tgtgcgtcct cgacggcccg gccccggctc cgcaggacgg    300
tgagccccag ggagacggat ctgggctccg ggagggacgc cccgtctgga tttgtcccgt    360
aggcccggcc cgggcccctc tggagcagaa cggccttggt gaggtggaca ggaagggacc    420
tcgcgagcag acgcgcgccc gcgacagcaa tcccgccccg gcctgtcggg agcggtgggg    480
cagaggctgc ggagccccag gaggatctgc ctccgctttc acagtcctcc agatttttcc    540
aagagcagca gaaaatgaat aaatccctgg ggccagtgtc attcaaggac gtggctgtgg    600
acttcaccca ggaggaatgg cagcagctgg atcctgagca gaagataact tacagggatg    660
tgatgctgga gaactacagc aatctagttt ctgtggggta tcacattatc aaaccggatg    720
ttatcagcaa gttggagcaa ggagaagagc catggatagt agaaggagaa ttcctacttc    780
agagctatcc agatgaagtc tggcaaactg atgacctaat agagagaatc caggaagagg    840
aaaataaacc ttcaaggcaa actgtgttca ttgagaccct gattgaagag agaggtaatg    900
ttcctggtaa aacttttgat gtagaaacga accctgttcc ttcaagaaaa atagcctata    960
aaaatagcct ctgtgactca tgtgaaaagt gtttaacgtc tgtttcagaa tatattagta   1020
gtgatggaag ctatgcaaga atgaaagctg atgaatgtag tggatgtggg aaatcactcc   1080
tccatattaa gcttgagaaa actcatccag gagatcaagc ttatgaattt aatcaaaatg   1140
gggaacctta tactctaaat gaagaaagtc tttatcagaa aattcgtatt ttggagaaac   1200
cttttgaata tattgaatgc cagaaagcct tccaaaagga cactgttttt gttaatcaca   1260
tggaagaaaa gccctataag tggaatggat ctgaaatagc ctttctccag atgtcggacc   1320
tcactgtaca tcagacatct catatggaaa tgaagcccta tgaatgcagt gaatgtggga   1380
aatccttctg taaaaagtca aaatttatta tacatcagag gactcacaca ggagagaaac   1440
cttacgaatg taatcagtgt gggaaatcct tctgccagaa gggaaccctt actgtgcatc   1500
agagaacaca cacaggggag aagccctatg aatgtaatga atgtgggaag aacttttacc   1560
agaagttaca cctcattcag catcagagaa ctcactcagg agagaagccc tatgaatgta   1620
gttattgtgg aaaatccttt tgccagaaga cacacctcac acaacatcag agaacacatt   1680
caggagagag accttatgtt tgtcatgact gtgggaaaac cttctcgcag aagtcagcac   1740
ttaatgacca tcagaaaatt cacacaggtg tgaaactcta caagtgtagt gaatgtggga   1800
aatgcttctg ccgcaagtct actctcacga cccacctgag gacccacaca ggagagaaac   1860
cgtatgaatg taatgagtgt ggaaaattct tctctcggtt gtcatatctc actgtacatt   1920
atagaactca ttcaggagag aaaccctatg agtgtactga atgtggaaaa aaattctacc   1980
acaaatcagc attcaacagc catcagagaa ttcataggag aggcaatatg aatgtaatag   2040
atgtgggaag gcttctctga agtcagacct cattttatat cagagaaccc tttcagtata   2100
gtgaatcaga aactcctgcc tgaagtcaaa caccttgtac atcagagagt tcacacaggt   2160
tagtgtggac atccccttgt gtgttggact cataatctga agactcacag aatggaaacc   2220
atgattataa caagaccaca tggtataaca atactagact atagacaagt aaaaatttat   2280
aaatattaag aatgtatata catgtcacca tggattggaa ctgttttgca tatcagggaa   2340
atcatagcca aggggaaatc tatcagtata aggaatgtgg aagacataat cctttggaaa   2400
ctgttaatac taaaagatat gtttctgata caatagcaaa cttga                   2445
```

<210> SEQ ID NO 6
<211> LENGTH: 701

-continued

<212> TYPE: DNA
<213> ORGANISM: Human

<400> SEQUENCE: 6
taacggtccc catcttcttg gatcgcttaa cagctggccg gcggttcaca aagtgagtct 60
gctgtgctgt gtgacctgtg cgcggtctgt ggccggacct aaagatagac cgcaatggct 120
gaaaatggtg ataatgaaaa gatggctgcc ctggaggcca aaaatctgtc atcaaattga 180
gtattatttg gcgacttcaa tttgccacgg gacaagtttc taaaggaaca gataaaactg 240
gatgaaggct gggtaccttt ggagataatg ataaaattca acaggttgaa ccgtctaaca 300
acagacttta atgtaattgt ggaagcattg agcaaatcca aggcagaact catggaaatc 360
agtgaagata aaactaaaat cagaaggtct ccaagcaaac ccctacctga agtgactgat 420
gagtataaaa atgatgtaaa aaacagatct gttatattaa aggcttccca actgatgcaa 480
ctcttgatga cataaaagaa tggttagaag ataaaggtca agtactaaat attcagatga 540
gaagaacatt gcataaagca tttaagggat caatttttgt agtgttgata gcattgaatc 600
tgtaagaaat ttgtagagac ccctggcaga aagtacaaga aacagacctt gctattactt 660
tcaaggacga ttactttgcc aaaaaaaatt gacgatgaaa a 701

<210> SEQ ID NO 7
<211> LENGTH: 3364
<212> TYPE: DNA
<213> ORGANISM: Human

<400> SEQUENCE: 7
gattgttgcc gtgcgctgga gccgagtttc gctctgctgc ccaggctgga gtacagtgat 60
gtgatctcct gacgtcaagt gatccattcg cctcggcctc ccaaagttct gggattacaa 120
gtaatacaaa atacagttaa taaaatgtca acctcctgga gtgatcggtt acagaatgca 180
gcagatatgc ctgctaacat ggataagcat gccctgaaaa agtatcgtcg agaagcctat 240
catcgggtgt ttgtgaaccg aagtttagca atggaaaaga taaagtgttt tggttttgat 300
atggattata cccttgctgt gtacaagtcc ccagagtatg agtcccttgg ttttgagctt 360
actgtggaga gattagtttc tattggctat ccccaggagt tgctcagctt tgcttatgat 420
tctacattcc ctaccagggg acttgtcttt gacacactgt atggaaatct tttgaaagtc 480
gatgcctatg gaaacctctt ggtctgtgca catggattta actttataag gggaccagaa 540
actagagaac agtatccaaa taaatttatc cagcgagatg atactgaaag attttacatt 600
ctgaacacac tattcaacct accagagacc tacctgttgg cctgcctagt agattttttt 660
actaattgtc ccagatatac cagttgtgaa acaggattta aagatgggga cctcttcatg 720
tcctaccgga gtatgttcca ggatgtaaga gatgctgttg actgggttca ttacaagggc 780
tcccttaagg aaaagacagt tgaaaatctt gagaagtatg tagtcaaaga tggaaaactg 840
cctttgcttc tgagccggat gaaggaagta gggaaagtat ttcttgctac caacagtgac 900
tataaatata cagataaaat tatgacttac ctgtttgact tcccacatgg ccccaagcct 960
gggagctccc atcgaccatg gcagtcctac tttgacttga tcttggtgga tgcacggaaa 1020
ccactctttt ttggagaagg cacagtactg cgtcaggtgg atactaaaac tggcaagctg 1080
aaaattggta cctacacagg gcccctacag catggtatcg tctactcagg aggttcttct 1140
gatacgatct gtgacctgtt gggagccaag ggaaaagaca ttttgtatat tggagatcac 1200
atttttgggg acattttaaa atcaaagaaa cggcaagggt ggcgaacttt tttggtgatt 1260
cctgaactcg cacaggagct acatgtctgg actgacaaga gttcactttt cgaagaactt 1320

-continued cagagcttgg atattttctt ggctgaactc tacaagcatc ttgacagcag tagcaatgag 1380
cgtccagaca tcagttccat ccagagacgt attaagaaag taactcatga catggacatg 1440
tgctatggga tgatgggaag cctgtttcgc agtggctccc ggcagaccct tttgccagt 1500 caagtgatgc gttatgctga cctctatgca gcatctttca tcaacctgct gtattaccct 1560
ttcagctacc tcttcagggc tgcccatgtc ttgatgcctc atgaatcaac ggtggagcac 1620
acacacgtag atatcaatga gatggagtct cctcttgcca cccggaaccg cacatcagtg 1680
gatttcaaag acactgacta caagcggcac cagctgacac ggtcaattag tgagattaaa 1740
cctcccaacc tcttcccact ggccccccag gaaattacac actgccatga cgaagatgat 1800
gatgaagagg aggaggagga ggaagaataa ggaggaaaac caaaacccca agcacccatt 1860
aaacaagtcc tggcaggact cacaggaaca aacgaggtcc ctgttagggt tctactcggg 1920
ggagggaggg ggctccatga aaggtacgtc tgaaaagttt ctgaagattt tattatcata 1980
gatacttgtt ttggttttgt gtatctgtac tctctgcaga tggtccaaaa ttgtaatgga 2040
gtctgtatta gaagaaaata agggtaaaat caggctgaac tgcatgtata tggctccact 2100
gtggcttgtg acacttttaa aatcatccgt atgtcagtgt atctggatac acgaggaaaa 2160
ggaaagagtc tcagagtgga acaaagagtg ggaagaggtg atctgtaatg ttacaaattg 2220
tgctattact ccaaggtcca acttttccag tgcattacat ggtattgtat atcagtggag 2280
aaatgtatta tttccatgat caaatgtagt ctctgttaag gtcaagtttt cttttataag 2340
cctttaattc atcctcagtg actctggcaa ggctgcttct ctatcactgg ctttgcacag 2400
aagtatgctc tacttgcgtt gctttagggc aggattctat tttgagggaa aagacagtat 2460
ccttattacc ttttgtttgt ttaatagcac aaatgcttat ttgttatcca aaaacaacct 2520
ccttcttatc tgtgataaat ctatagaaag aatttagctg caagtggaca aaggaacaag 2580
cccccagaaa agaaagggaa gaactgcctt cttatactac agaacatgca ttagtgtggg 2640
ctatatagct gtggctcatg ctacccaatt ccagatttct ttgtcctcta agagttgatt 2700
gctgtatatt aaaattgaac atcagaggat gggaagaggg ctctgtaagc cagaacctta 2760
ctaaagtaga gggcacaatc agtgtgaata aattcacttc agaatctcaa gtcaaggcca 2820
ggcacggcgg ctcacgcctg taatcccagc actttgggag gccgagacag gcggatcacc 2880
tgaggtcggg agttcgagac cagccttacc aacatggaga aaccccatct ctactaaaaa 2940
tacaaaatta cctgggcgtg gtggtgcatg cctgtaatcc catcatctac tcaggaggct 3000
gaggcaggag aattgcttga acccaggagg cggaggttgc agtgagccag gattgtgcca 3060
ttgcactcca gcctgggcaa caagaacaaa actccatctc aaaaaataaa aatcccaatc 3120
ccaagtcgaa atcacctctt gttttaaaca agaatgaatc attactgtgt atgttagggt 3180
attaaaactg tttcaccagt acagtgaaag ttgtttcaac attttaaaca aacagtggtt 3240
atagactctt tctttaacca ttgtatattt tcttccattc ttgtcattgg tcaatagggg 3300
agggtagatt agctgctcca gaattcaata aagtgtaata tttctaaaaa aaaaaaaaaa 3360
aaaa 3364

<210> SEQ ID NO 8
<211> LENGTH: 3825
<212> TYPE: DNA
<213> ORGANISM: Human

<400> SEQUENCE: 8
aagacaactt gagctgaaag cgaaaaacta tgctgaccag attagcagac ttgaagaaag 60

-continued

```
agaagcagaa ctgaagaagg aatataatgc attacatcaa agacacactg agatgatcca    120
taattatatg gaacatttag aaagaacaaa acttcatcag ctctcaggga gtgatcaact    180
agaatccaca gctcatagta gaattagaaa agaacgccct atatcattag gaattttccc    240
attacctgct ggagatggat tgcttacacc tgatgctcag aaaggaggag agacccctgg    300
atctgagcaa tggaaatttc aggaattaag tcaaccacgt tctcatacca gcctgaagga    360
tgagctttct gatgttagcc aaggcggatc taaagctacc actccagcat caacagctaa    420
ttcagatgtg gcaacaattc ctactgatac tcccttaaag gaagaaaacg aaggatttgt    480
gaaggttaca gatgcgccaa ataaatcaga gataagcaaa cacattgaag tacaggtagc    540
ccaggaaact agaaatgtat ctactggctc tgctgaaaat gaagaaaagt cagaagttca    600
agcaatcatc gaatctactc ctgagctgga tatggacaaa gatctcagtg gatataaagg    660
ttcaagcact cccaccaaag gcatagagaa caaagctttt gatcgcaata cagaatctct    720
ctttgaagaa ctgtcttcag ctggctcagg cctaatagga gatgtggatg aaggagcaga    780
tttactagga atgggtcggg aagttgagaa tcttatatta gaaaatacac aactgttgga    840
aaccaaaaat gctttgaaca tagtgaagaa tgatttgata gcaaaagtgg atgaactgac    900
ctgtgagaaa gatgtgctgc aaggggaatt ggaggctgtg aagcaagcca aactgaaact    960
agaggaaaag aacagagaat tggaggaaga gcttaggaaa gctcgggcag aagctgaaga   1020
tgcaaggcaa aaagcaaaag atgacgatga tagtgatatt cccacagccc agaggaaacg   1080
gtttactaga gtagaaatgg cccgtgttct catggagcga aaccagtata aagagagatt   1140
gatggagctt caggaagctg ttcgatggac agagatgatt cgggcatcac gagaaaatcc   1200
agccatgcag gaaaaaaaaa ggtcaagcat ttggcagttt ttcagccgac ttttcagctc   1260
ctcaagtaac acgactaaga agcctgaacc acctgttaat ctgaagtaca atgcacccac   1320
gtctcatgtt actccgtccg tcaagaaaag aagcagcacc ttatctcagc tccctgggga   1380
taagtccaaa gcctttgatt tccttagtga agaaactgaa gctagtttag cctcacgcag   1440
agaacaaaag agagagcagt atcgtcaggt aaaagcacat gttcagaagg aagacggtag   1500
agtgcaggct tttggctgga gtctgcctca gaagtacaaa caggtaacca atggtcaagg   1560
tgaaaataag atgaaaaatt tacctgtgcc tgtctatctc agacctctgg atgaaaaaga   1620
tacatcaatg aagctgtggt gtgctgttgg agtcaattta tctggtggga agaccagaga   1680
tggtggttct gttgttggag caagtgtatt ttacaaggat gttgctggtt tggatacaga   1740
aggcagtaaa cagcgaagtg cctctcagag tagtttagat aagttagatc aggaacttaa   1800
ggaacagcag aaggagttaa aaaatcaaga agaattatcc agtctagttt ggatctgtac   1860
cagcactcat tcggctacaa aagttcttat tattgatgct gttcaacctg gcaacatcct   1920
agacagtttc actgtttgca actctcatgt tctgtgcatt gcaagtgtgc caggtgcacg   1980
agaaacagac taccctgcag gagaagatct ttcagaatct ggtcaggtag acaaagcatc   2040
tttatgtgga agtatgacaa gcaacagctc agcagagaca gacagcctgt taggaggcat   2100
cacagtggtt ggttgttctg cagaaggtgt gacgggagct gccacttccc ctagtacaaa   2160
tggtgcttct ccagtgatgg ataaaccacc agaaatggaa gcagaaaata gtgaggttga   2220
tgaaaatgtt ccaacagcag aagaagcaac tgaagctaca gaagggaatg cggggtcagc   2280
tgaagacaca gtggacatct cccaaactgg cgtctacaca gagcatgtct ttacagatcc   2340
tttgggagtt cagatcccag aagacctctc cccagtgtat cagtcgagca atgactcaga   2400
tgcatataaa gatcaaatat cagtactgcc aaatgaacaa gacttggtga gagaagaagc   2460
```

-continued

```
ccagaaaatg agtagtcttt taccaactat gtggcttgga gctcaaaatg gctgtttgta   2520

tgtccattca tctgtagccc agtggaggaa atgtctccat tccattaaac ttaaagattc   2580

gattctcagt attgtacacg tgaagggaat cgtgttagta gccctggctg acggcaccct   2640

tgcaatcttt cacagaggag tggatgggca gtgggatttg tcaaactatc acctcttaga   2700

ccttggacgg cctcatcatt ccatccgttg catgactgtg gtacatgaca aagtctggtg   2760

tggctatagg aacaaaatct atgtggtgca gccaaaggcc atgaaaatag agaaatcttt   2820

tgatgcacat cccaggaagg agagccaagt gcgacagctt gcgtgggtgg gggatggcgt   2880

gtgggtctcc attcgcttgg attctacgct ccgtctctat catgcacaca cttatcaaca   2940

tctacaggat gtggacattg agccttatgt aagcaaaatg ttaggtactg gaaaactggg   3000

cttctctttt gtgagaatta cagctcttat ggtgtcttgt aatcgtttgt gggtggggac   3060

aggaaatggt gtcattatct ccatcccatt gacagaaaca aataaaacct caggtgtacc   3120

aggaaatcgt cctggaagtg taatccgtgt atatggtgat gaaaacagtg ataaagtgac   3180

tccagggaca tttataccct attgttcaat ggcacatgca cagctttgct tccatgggca   3240

ccgggatgct gtgaaattct ttgtggcagt cccaggtcaa gtcatcagcc cacaaagtag   3300

cagtagtggc acggatctga cgggtgacaa agcagggcca tctgcacagg agcctggtag   3360

tcagacgccc ttgaagtcta tgcttgtcat cagtggagga gagggctaca tcgacttccg   3420

aatgggtgat gaaggtggag aatcagaact tcttggagag gatcttccac ttgaaccttc   3480

tgtcaccaaa gcagaaagga gtcacttgat agtgtggcaa gtgatgtatg gcaatgagtg   3540

agcccatggg aaacaggtgg agatggggaa gccgtctctt ctgcatggtt tattttccct   3600

ctatcctttt atttaatgct cttttgtgag ataagtttca ccacataatg tgtgagcatt   3660

ttttcctgtt aactttatat tacaaaatcc gttctaccat aacaatacag aggaactagc   3720

tgtgttactg caccagtgtt ataggtaact tcagtatatt atgaacaaat caaagaatgt   3780

ttacttcctg caaactggtg aattatagaa agcaatccag atgtg                   3825
```

<210> SEQ ID NO 9
<211> LENGTH: 471
<212> TYPE: DNA
<213> ORGANISM: Human
<220> FEATURE:
<221> NAME/KEY: misc_feature
<222> LOCATION: (468)..(468)
<223> OTHER INFORMATION: any kind of base

<400> SEQUENCE: 9

```
tttggtttgt ttgtttttta aagacagggt cttgctctgt cacctaggct ggagtgcagt     60

ggcatgatct tggctcactg caacctccac ctcctggact caagcaatcc tcccacctca    120

gcctcccaag tagctgggac taaaagtgcg gacccggcta atttttgtat tttttgtaga    180

gatggggtct ccctatgttg cccaggctgg tctcgaatgc ccgggctcaa gtgatctgcc    240

cgccttggct tcccaaagtg ctgcgattac aggcatgagg cactgtgcct ggccttcgtg    300

gaaatcctaa aaagcaacac cacatagtgc tgggctgtat ccaggccagt gggcaccttc    360

cgtgctggta atgaacagcc acaaaacttc tggaaaacca catggaagtt tctattttat    420

gtgaaatgtc gaactcacac accacttgcc cagtggtcct gaggagtnca c             471
```

<210> SEQ ID NO 10
<211> LENGTH: 565
<212> TYPE: DNA
<213> ORGANISM: Human

<220> FEATURE:
<221> NAME/KEY: misc_feature
<222> LOCATION: (476)..(476)
<223> OTHER INFORMATION: any kind of base
<220> FEATURE:
<221> NAME/KEY: misc_feature
<222> LOCATION: (482)..(482)
<223> OTHER INFORMATION: any kind of base

<400> SEQUENCE: 10

```
ggcaccatac tgttttattt aaacctgcaa acaatataaa gaggtaagga cttctgacgc     60

caaaccatgc aagtaataac aaaggaacag agaaaaatat taataacaaa aagaaaatca    120

ttaaaaataa aaaaacaaag tacttcacat ttcacagcag tgctttggca gtactggcaa    180

gcatttctgg tcaactgctt ccaacagcag gaatatgaag aaacccccag atcttagcaa    240

aagtgtaaca acattttctc cctgacagct tacattccaa gtcattccat accataccgc    300

tccactccac agttttataa acctgatctt aagatgtaac taggtactat gtgtgctcac    360

aataaaaact aactaaaaac aaatcagagg gtagcagaca agtaaacaaa gtttccagta    420

aggcatcagg agatcactgc tggtgggccc ctcactttac cagcttaaag aagttntgat    480

tnttatttct cagcaaactc aatattcaga agctttacca gcagactcaa gtcaaaggtt    540

ttaaatacag tttacctcat ttttt                                           565
```

<210> SEQ ID NO 11
<211> LENGTH: 3615
<212> TYPE: DNA
<213> ORGANISM: Human

<400> SEQUENCE: 11

```
ggactgtgtg tgtctggctg tagcagacgc gaggcggcga cgaggcgccg gggacccgcg     60

cgaggggcgg ccgggaggcg gcggcggcgg ccgccagaag tagcagcagg accggcggcg    120

gcgacggcag ccctgaaatg cattttcctc tccagcggcc atgttaacca ggaaaccttc    180

ggccgccgct cccgccgcct acccgaccgg ccgaggtggg gacagcgccg ttcgtcagct    240

tcaggcttcc ccggggctcg gtgcagggcc cacccggagc ggagtgggga ctggcccgcc    300

ctcccccatc gccctgccgc ctctccgggc cagcaacgct gccgccgcag cccacacgat    360

tggcggcagt aagcacacaa tgaatgatca cctgcatgtc ggcagccacg ctcacggaca    420

gatccaggtt caacagttgt ttgaggataa cagtaacaag cggacagtgc tcacgacaca    480

accaaatggg cttacaacag tgggcaaaac gggcttgcca gtggtgccag agcggcagct    540

ggacagcatt catagacggc aggggagctc cacctctcta aagtccatgg aaggcatggg    600

gaaggtgaaa gccacccccca tgacacctga acaagcaatg aagcaataca tgcaaaaact    660

cacagccttc gaacaccatg agattttcag ctaccctgaa atatatttct tgggtctaaa    720

tgctaagaag cgccagggca tgacaggtgg gcccaacaat ggtggctatg atgatgacca    780

gggatcatat gtgcaggtgc cccacgatca cgtggcttac aggtatgagg tcctcaaggt    840

cattgggaag gggagctttg ggcaggtggt caaggcctac gatcacaaag tccaccagca    900

cgtggcccta aagatggtgc ggaatgagaa gcgcttccac cggcaagcag cggaggagat    960

ccgaatcctg gaacacctgc ggaagcagga caaggataac acaatgaatg tcatccatat   1020

gctggagaat ttcaccttcc gcaaccacat ctgcatgacg tttgagctgc tgagcatgaa   1080

cctctatgag ctcatcaaga agaataaatt ccagggcttc agtctgcctt tggttcgcaa   1140

gtttgcccac tcgattctgc agtgcttgga tgctttgcac aaaaacagaa taattcactg   1200

tgaccttaag cccgagaaca ttttgttaaa gcagcagggt agaagcggta ttaaagtaat   1260
```

-continued

```
tgattttggc tccagttgtt acgagcatca gcgtgtctac acgtacatcc agtcgcgttt   1320
ttaccgggct ccagaagtga tccttggggc caggtatggc atgcccattg atatgtggag   1380
cctgggctgc attttagcag agctcctgac gggttacccc ctcttgcctg ggaagatga    1440
aggggaccag ctggcctgta tgattgaact gttgggcatg ccctcacaga aactgctgga   1500
tgcatccaaa cgagccaaaa attttgtgag ctccaagggt tatccccgtt actgcactgt   1560
cacgactctc tcagatggct ctgtggtcct aaacggaggc cgttcccgga gggggaaact   1620
gaggggccca ccggagagca gagagtgggg gaacgcgctg aaggggtgtg atgatcccct   1680
tttccttgac ttcttaaaac agtgtttaga gtgggatcct gcagtgcgca tgaccccagg   1740
ccaggctttg cggcacccct ggctgaggag gcggttgcca aagcctccca ccggggagaa   1800
aacgtcagtg aaaaggataa ctgagagcac cggtgctatc acatctatat ccaagttacc   1860
tccaccttct agctcagctt ccaaactgag gactaatttg gcgcagatga cagatgccaa   1920
tgggaatatt cagcagagga cagtgttgcc aaaacttgtt agctgagctc acgtcccctg   1980
atgctggtaa cctgaaagat acgacattgc tgagccttac tgggttgaaa aggagtagct   2040
cagacctgtt tttatttgct caataactct actcatttgt atcttttcag cacttaattt   2100
taatgtaaga aagttgttca ttttgttttt ataaaataca tgaggacaat gctttaagtt   2160
tttatacttt cagaaacttt ttgtgttcta aaagtacaat gagccttact gtatttagtg   2220
tggcagaata ataacatcag tggcaggcca ctgattactt catgactgcc acgcatttac   2280
agattggtgt caaagacatt cactatgttt ttatggttca tgttatatcc tccccagggt   2340
gacagcccct taaggccctc cttttccctc catgctccag gtccatgcac aggtgtagca   2400
tgtcctgctt ccgtttttca taaattaatc tgggtgttgg gggtagtggg aggagaacgg   2460
tcagaatcaa agtgacattc taagaaaaac tgtaccttag agattttcct ctagtgctca   2520
aacaaataca aaataagatc cccaaggttt aaactgccca gttagcattc tgacattcta   2580
aaagccggca aagcagcttt tagtggataa atgggaatgg aaacgtgtgt gttcctccaa   2640
attttctagt atgatcggtg agctgttttg taaagaagcc tcatattaca gagttgcttt   2700
tgcacctaaa tttagaattg tattccatga actgttcctc ccttttctct gcttttctcc   2760
tctctgttcc tcttttaata ccacacgtct gttgcttgca tttagtttgt cttcttcctt   2820
cagctgtgta tcccagactg ttaatacaga aaagagacat ttcagctgtg attatgacca   2880
ttgtttcata ttccaattaa aaaaagaaca gcagcctagc tacttaaggt ggggatttca   2940
tagttccaaa gaagatttag cagattagag tgagttcaca cttttcaggt gccactgtaa   3000
ggttctctca gcctgggaaa ctatcaactc tttctttaaa aagaaagagg gttgaaaatc   3060
ctctggacga acagaagtca ctttggctgt tcagtaaggc caatgttaac aacacgttta   3120
gaggaggaaa agttcaacct caagttaaat ggtttgactt attcttcgta tcattagaag   3180
aaccccagag atagcattcc tctattttat tttactttct tttggattgc actgattgtt   3240
tttgtgggaa tgacacttta tctggcaaag taactgagag tttggtaaaa gaatattttc   3300
ttctctgaat aataattatt ttcacagtga aaatttcagt attttatcac taatgtatga   3360
gcaatgatct atatcaattt caaggcacgt gaaaaaaatt ttttagtatg tgcaatttaa   3420
tatagaaaga tttctgcctg tttggacaat aggttttggg tagtacagat taggataagt   3480
aagcttatat atgcacagag attattgtat tacctgtaaa ttgatttaca agtacttaaa   3540
agcgtggtcc ccagtgaggc caagaaagtt tccggttaag ttctttaata ataatcctac   3600
agtttatctt aagaa                                                    3615
```

<210> SEQ ID NO 12
<211> LENGTH: 4908
<212> TYPE: DNA
<213> ORGANISM: Human

<400> SEQUENCE: 12
acctgcgtgc agtcggtcct ccaggccacg cagcgcccga gagtaccagg gagactccgg 60
cccctgtcgg cgccaagccc ctccgcccct cacagcgccc aggtccgcgg ccgggccttg 120
attttttggc ggggaccgtc atggcgtcgc agccaaattc gtctgcgaag aagaaagagg 180
agaaggggaa gaacatccag gtggtggtga gatgcagacc atttaatttg gcagagcgga 240
aagctagcgc ccattcaata gtagaatgtg atcctgtacg aaaagaagtt agtgtacgaa 300
ctggaggatt ggctgacaag agctcaagga aaacatacac ttttgatatg gtgtttggag 360
catctactaa acagattgat gtttaccgaa gtgttgtttg tccaattctg gatgaagtta 420
ttatgggcta taattgcact atctttgcgt atggccaaac tggcactgga aaaactttta 480
caatggaagg tgaaaggtca cctaatgaag agtatacctg ggaagaggat cccttggctg 540
gtataattcc acgtaccctt catcaaattt ttgagaaact tactgataat ggtactgaat 600
tttcagtcaa agtgtctctg ttggagatct ataatgaaga gctttttgat cttcttaatc 660
catcatctga tgtttctgag agactacaga tgtttgatga tccccgtaac aagagaggag 720
tgataattaa aggtttagaa gaaattacag tacacaacaa ggatgaagtc tatcaaattt 780
tagaaaaggg ggcagcaaaa aggacaactg cagctactct gatgaatgca tactctagtc 840
gttcccactc agttttctct gttacaatac atatgaaaga aactacgatt gatggagaag 900
agcttgttaa aatcggaaag ttgaacttgg ttgatcttgc aggaagtgaa aacattggcc 960
gttctggagc tgttgataag agagctcggg aagctggaaa tataaatcaa tccctgttga 1020
ctttgggaag ggtcattact gcccttgtag aaagaacacc tcatgttcct tatcgagaat 1080
ctaaactaac tagaatcctc caggattctc ttggagggcg tacaagaaca tctataattg 1140
caacaatttc tcctgcatct ctcaatcttg aggaaactct gagtacattg gaatatgctc 1200
atagagcaaa gaacatattg aataagcctg aagtgaatca gaaactcacc aaaaaagctc 1260
ttattaagga gtatacggag gagatagaac gtttaaaacg agatcttgct gcagcccgtg 1320
agaaaaatgg agtgtatatt tctgaagaaa attttagagt catgagtgga aaattaactg 1380
ttcaagaaga gcagattgta gaattgattg aaaaaattgg tgctgttgag gaggagctga 1440
atagggttac agagttgttt atggataata aaaatgaact tgaccagtgt aaatctgacc 1500
tgcaaaataa aacacaagaa cttgaaacca ctcaaaaaca tttgcaagaa actaaattac 1560
aacttgttaa agaagaatat atcacatcag ctttggaaag tactgaggag aaacttcatg 1620
atgctgccag caagctgctt aacacagttg aagaaactac aaaagatgta tctggtctcc 1680
attccaaact ggatcgtaag aaggcagttg accaacacaa tgcagaagct caggatattt 1740
ttggcaaaaa cctgaatagt ctgtttaata atatggaaga attaattaag gatggcagct 1800
caaagcaaaa ggccatgcta gaagtacata agaccttatt tggtaatctg ctgtcttcca 1860
gtgtctctgc attagatacc attactacag tagcacttgg atctctcaca tctattccag 1920
aaaatgtgtc tactcatgtt tctcagattt ttaatatgat actaaaagaa caatcattag 1980
cagcagaaag taaaactgta ctacaggaat tgattaatgt actcaagact gatcttctaa 2040
gttcactgga aatgatttta tccccaactg tggtgtctat actgaaaatc aatagtcaac 2100
taaagcatat tttcaagact tcattgacag tggccgataa gatagaagat caaaaaaagg 2160

-continued

```
aactagatgg ctttctcagt atactgtgta acaatctaca tgaactacaa gaaaatacca   2220
tttgttcctt ggttgagtca caaaagcaat gtggaaacct aactgaagac ctgaagacaa   2280
taaagcagac ccattcccag gaactttgca agttaatgaa tctttggaca gagagattct   2340
gtgctttgga ggaaaagtgt gaaaatatac agaaaccact tagtagtgtc caggaaaata   2400
tacagcagaa atctaaggat atagtcaaca aaatgacttt tcacagtcaa aaattttgtg   2460
ctgattctga tggcttctca caggaactca gaaattttaa ccaagaaggt acaaaaattgg   2520
ttgaagaatc tgtgaaacac tctgataaac tcaatggcaa cctggaaaaa atatctcaag   2580
agactgaaca gagatgtgaa tctctgaaca caagaacagt ttatttttct gaacagtggg   2640
tatcttcctt aaatgaaagg gaacaggaac ttcacaactt attggaggtt gtaagccaat   2700
gttgtgaggc ttcaagttca gacatcactg agaaatcaga tggacgtaag gcagctcatg   2760
agaaacagca taacattttt cttgatcaga tgactattga tgaagataaa ttgatagcac   2820
aaaatctaga acttaatgaa accataaaaa ttggtttgac taagcttaat tgctttctgg   2880
aacaggatct gaaactggat atcccaacag gtacgacacc acagaggaaa agttatttat   2940
acccatcaac actggtaaga actgaaccac gtgaacatct ccttgatcag ctgaaaagga   3000
aacagcctga gctgttaatg atgctaaact gttcagaaaa caacaaagaa gagacaattc   3060
cggatgtgga tgtagaagag gcagttctgg ggcagtatac tgaagaacct ctaagtcaag   3120
agccatctgt agatgctggt gtggattgtt catcaattgg cggggttcca tttttccagc   3180
ataaaaaatc acatggaaaa gacaaagaaa acagaggcat taacacactg gagaggtcta   3240
aagtggaaga aactacagag cacttggtta caaagagcag attacctctg cgagcccaga   3300
tcaaccttta attcacttgg gggttggcaa ttttattttt aaagaaaact taaaaataaa   3360
acctgaaacc ccagaacttg agccttgtgt atagatttta aaagaatata tatatcagcc   3420
gggcgcggtg gctcatgcct gtaatcccag cactttggga ggctgaggcg ggtggattgc   3480
ttgagcccag gagtttgaga ccagcctggc caacgtggca aaacctcgtc tctgttaaaa   3540
attagccggg cgtggtggca cactcctgta atcccagcta ctggggaggc tgaggcacga   3600
gaatcacttg aacccaggaa gcggggttgc agtgagccaa aggtacacca ctacactcca   3660
gcctgggcaa cagagcaaga ctcggtctca aaaacaaaat ttaaaaaaga tataaggcag   3720
tactgtaaat tcagttgaat tttgatatct acccattttt ctgtcatccc tatagttcac   3780
tttgtattaa attgggtttc atttgggatt tgcaatgtaa atacgtattt ctagttttca   3840
tataaagtag ttcttttata acaaatgaaa agtatttttc ttgtatatta ttaagtaatg   3900
aatatataag aactgtactc ttctcagctt gagcttaaca taggtaaata tcaccaacat   3960
ctgtccttag aaaggaccat ctcatgtttt ttttcttgct atgacttgtg tattttcttg   4020
catcctccct agacttccct atttcgcttt ctcctcggct cactttctcc ctttttattt   4080
ttcaccaaac catttgtaga gctacaaaac ctatcctttc ttattttcag tagtcagaat   4140
tttatctaga aatcttttaa caccttttta gtggttattt ctaaaatcac tgtcaacaat   4200
aaatctaacc ctagttgtat ccctccttta agtatttaaa acttgttgcc ccaaatgtga   4260
aagcatttaa ttcctttaag aggcctaact cattcaccct gacagagttc acaaaaagcc   4320
cactttagag tatacattgc tattatggga gaccacccag acatctgact aatggctctg   4380
tgccacactc caagacctgt gccttttaga gaagctcaca atgatttaag gactgtttga   4440
aacttccaat tatgtctata atttatattc ttttgtttac atgatgaaac tttttgttgt   4500
tgcttgtttg tatataatac aatgtgtaca tgtatctttt tctcgattca aatcttaacc   4560
```

-continued cttaggactc tggtattttt gatctggcaa ccatatttct ggaagttgag atgtttcagc 4620
ttgaagaacc aaaacagaag gaatatgtac aaagaataaa ttttctgctc acgatgagtt 4680
tagtgtgtaa agtttagaga catctgactt tgatagctaa attaaaccaa accctattga 4740
agaattgaat atatgctact tcaagaaact aaattgatct cgtagaatta tcttaataaa 4800
ataatggcta taatttctct gcaaaatcag atgtcagcat aagcgatgga taatacctaa 4860
taaactgccc tcagtaaatc catggttaat aaatgtggtt tctacatt 4908

<210> SEQ ID NO 13
<211> LENGTH: 3302
<212> TYPE: DNA
<213> ORGANISM: Human

<400> SEQUENCE: 13
ggcacgaggc ggcagtctct tcgcggcgtc caccacttag acgcaagttg ctgaagccgg 60
ccggggagaa ggtgttgttg ccggagctga gaccgggcgg ccacagtccg cagggatgaa 120
cctcgagttg ctggagtcct ttgggcagaa ctatccagag gaagctgatg gaactttgga 180
ttgtatcagc atggctttga cttgcacctt taacaggtgg ggcacactgc ttgcagttgg 240
ctgtaatgat ggccgaattg tcatctggga tttcttgaca agaggcattg ctaaaataat 300
tagtgcacac atccatccag tgtgttcttt atgctggagc cgagatggtc ataaactcgt 360
gagtgcttcc actgataaca tagtgtcaca gtgggatgtt ctttcaggcg actgtgacca 420
gaggtttcga ttcccttcac ccatcttaaa agtccaatat catccacgag atcagaacaa 480
ggttctcgtg tgtcccatga aatctgctcc tgtcatgttg accctttcag attccaaaca 540
tgttgttctg ccggtggacg atgactccga tttgaacgtt gtggcatctt ttgataggcg 600
aggggaatat atttatacgg gaaacgcaaa aggcaagatt ttggtcctaa aaacagattc 660
tcaggatctt gttgcttcct tcagagtgac aactggaaca agcaatacca cagccattaa 720
gtcaattgag tttgcccgga aggggagttg ctttttaatt aacacggcag atcgaataat 780
cagagtttat gatggcagag aaatcttaac atgtggaaga gatggagagc ctgaacctat 840
gcaggaattg caggatttgg tgaataggac cccatggaag aaatgttgtt tctctgggga 900
tggggaatac atcgtggcag gttctgcccg gcagcatgcc ctgtacatct gggagaagag 960
cattggcaac ctggtgaaga ttctccatgg gacgagagga gaactcctct tggatgtagc 1020
ttggcatcct gttcgaccca tcatagcatc catttccagt ggagtggtat ctatctgggc 1080
acagaatcaa gtagaaaact ggagtgcatt tgcaccagac ttcaaagaat tggatgaaaa 1140
tgtagaatac gaagaaaggg aatcagggtt tgatattgaa gatgaagata agagtgagcc 1200
tgagcagaca ggggctgatg ctgcagaaga tgaggaagtg gatgtcacca gcgtggaccc 1260
tattgctgcc ttctgtagca gtgatgaaga gctggaagat tcaaaggctc tattgtattt 1320
acccattgcc cctgaggtag aagacccaga agaaaatcct tacggccccc caccggatgc 1380
agtccaaacc tccttgatgg atgaaggggc tagttcagag aagaagaggc agtcctcagc 1440
agatgggtcc cagccaccta agaagaaacc caaaacaacc aatatagaac ttcaaggagt 1500
accaaatgat gaagtccatc cactactggg tgtgaagggg gatggcaaat ccaagaagaa 1560
gcaagcaggc cggcctaaag gatcaaaagg taaagagaaa gattctccat ttaaaccgaa 1620
actctacaaa ggggacagag gtttacctct ggaaggatca gcgaagggta aagtgcaggc 1680
ggaactcagc cagcccttga cagcaggagg agcaatctca gaactgttat gaagaccttc 1740
gaagttcttc attctttctc actttgccat catgtggcct ctggacactg tggtcagtca 1800
tttgaaaatt gactttaatt taaaacaaag gcctgtgctc cacccaggag gtgggaggtg 1860
aattttatgt ttaaatgaag aagtgaatta tggaagaagg tatacgacct tcccttcctt 1920
ttcaagcata agtccaaata gactctcagg aatgaagatt tgtgaagaca tcagatagga 1980
attttggact catttaaact ttgatgctta gttatgttgc tggagaaaag atacttatgt 2040
tttgctcatc taacttcatt gtacccagcg tcattttgac atgtcatttc ctatctccca 2100
tttgccttcg gtcctcaatg catgtctttg agtgacttct tatctgaaat tttgctactg 2160
gtatcctagg aaagcttttg ttggatactc tcattttaaa cttctcctct ccccagatac 2220
ctcctatatt tccatattgt gtgcaaagga tgggcagaaa agaaagtgct tgaaagattt 2280
caaattttca gaaagggaac aacgaaggcc ctctcttcct ctcataccac gttttgctca 2340
agaagctggg ctgtaacaat tcagggtttt cccttgtttt cctctcattg catgtttccc 2400
tccaatattg gttcattgtc atcaatcatg gtttttgaag atagctagtt ttatccatct 2460
ccagcaaaga atcatcaata gtttatattg ctttacctgt gctggcttcc agagatggaa 2520
acaaacccag gtgtctctca acaagctact tttttactgg ggtgggggaa tctatgcaag 2580
gagtaaagta aaaccatcca gaatcaaagc agcaaccaca tagttcaaat caaagatcaa 2640
ggtgaatttt ttgtatcact gcctgtggaa atctatcctc atcagtcatt gcatttttcc 2700
ctgcctatac ctgtgctcct ttttcttact gtgttttcag tcacttcctt tctgtgaaag 2760
gttgcttagc tttttttttg acatttgttg ttctttatat aaaaataaca gattggatag 2820
atgtgtacat ttggtgtttg aaattctctg aaaatcccat taggaaacca ggtgtgaaaa 2880
gggctcagta gcttctctga gtggcgtttt tagctgactg gaagtgctta atctggatcg 2940
tctttttttt tttttttttt ttcaatattt taaaaggaga atttaaatac tgtgcttact 3000
gtgaaatata tcagttggtg agccgggcgt ggtgggtcac gcctgtaatc ccagcacttt 3060
gggaggccaa ggcgggtgga tcacccgagg tcaggagttc aagaccagcc tggccaacgt 3120
ggtgaaagcc tgtatctatt aaaagacaaa aattagctgg gcgtggtggt acatgcctgt 3180
aatcccagct acactggagg ctgagtcagg agaatcactt gaacgtggga ggcagaggtt 3240
gcagtgagtg gagatcgcac cactgccctc cagcctaggt gacagaatga gactctatct 3300
ca 3302

<210> SEQ ID NO 14
<211> LENGTH: 1999
<212> TYPE: DNA
<213> ORGANISM: Human

<400> SEQUENCE: 14
acgcgctctt agaccatggc gacccaggcg aagcgtccac gggtggcggg gcccgtggac 60
ggcggcgacc tggatcctgt ggcctgcttc ctgagctggt gccggcgggt ggggctggag 120
ctgagtccca aggtggcggt cagccggcag ggcacggtgg ccggctacgg catggtggcc 180
cgggagagcg tgcaggccgg agagctgctg ttcgtggtgc cgcgggccgc gctcctgtcg 240
cagcacacct gctccatcgg cggcctgctg gagcgagagc gagttgcgct gcagggccag 300
tcgggctggg tgccactgct gctggcgctg ctccacgagc tgcaggcccc ggcctcacgc 360
tggaggccct actttgcgct ctggcccgag ctgggccgct tggagcaccc gatgttctgg 420
ccagaggagg agcgccggtg cctgctccag ggcacaggcg tacctgaggc cgtggagaag 480
gatttggcca acatccgcag cgagtaccag tccatcgtgc tgcccttcat ggaagcccac 540
cccgatctct tcagcctcag ggttcgctcc ctagaactct accaccagct ggtggccctt 600

-continued

```
gtgatggcct atagctttca ggtaccactg gaggaagaag aggatgaaaa ggagcccaac     660
tcccccgtga tggtgcctgc tgcagacata ctaaaccact tagccaatca caacgccaat     720
ctagaatact ctgcgaattg tcttcggatg gtagccactc agcccattcc taaaggccat     780
gagattttca acacttatgg gcaaatggct aactggcaac tgattcatat gtacggtttt     840
gttgaaccat atcctgacaa cacagatgac acagctgaca ttcagatggt gacagttcgt     900
gaggcagcat tacagggaac aaaaactgaa gctgaaaggc acctagtgta cgagcgctgg     960
gatttcctat gcaaactgga gatggtaggg gaagagggag cctttgtgat agggagggag    1020
gaggtgctga ctgaagagga gctgaccacc acactaaagg tactgtgcat gcctgctgag    1080
gagttcagag agcttaaaga ccaggatgga gggggagatg ataaaaggga agagggcagc    1140
ctgacgatca caaatattcc caagctcaaa gcatcgtgga gacagctgct tcaaaacagt    1200
gttctactga ctttgcagac ctatgccaca gacttaaaaa ctgaccaagg tttactcagt    1260
aataaggaag tctatgcgaa actcagctgg agggaacagc aagccttaca ggttcgctat    1320
ggtcagaaga tgatcttaca tcagttgttg gaactgacaa gttagcagtt tccctgttcc    1380
ctgaaggaac agcaataaga actttattct aagctaatac tcattgatgt ttgaaaaaga    1440
ggaaaatttg gatctttctt ttgcttacta aacaccaaga ggaaaagtag caaagttggt    1500
gtgctaggat taactcaggt aagggtgatg tgttttagga ttgagaacag cagacttggg    1560
aatcactgct aattgttact taaagcatgt tacagctgtt ttgttctcag ttttaaccaa    1620
agccagtgga catacggtag taataactaa gtcttgttgt gtttcagcat ttaataatag    1680
actttggagg tagacccctg gtttaaatct aagtctagtt tgaggaagtc acttaacctt    1740
tattgaaaag actctggatt taataagctg tgtaactggt actcgatagt tacccaaagt    1800
tcagtctaga tggcacaaac cacctctcag ggaataaacc ctaagacatc actcaaggag    1860
gacttcaatt atttaatttt gaactgtttt gtcctctctg gccataaaac ttgacagtca    1920
tgaaaggtaa ggcaaatttt aagtgggtta agtttttaaa tacgtatcta ctcattttct    1980
ttaaaaaaaa aaaaaaaaa                                                 1999
```

<210> SEQ ID NO 15
<211> LENGTH: 1503
<212> TYPE: DNA
<213> ORGANISM: Human

<400> SEQUENCE: 15

```
ggggctccac tttctttccc tctccgtttt ggtgggctgg ttggagatga aatccactga      60
ggagggaagt ccagcaccct gtgtgccagt cctgaactgg cccatctgta gacccccctga    120
aaatcatatg ggcttggatt tggatattct caacagaaag ggttaaaggc tgatggtacc     180
taaagcctgg tacttgaatt ttgatcaaga taagctgcct taagttctct tcattacaca     240
aatgatccta gataattgat agatcctgtg gttcaactgg atttctagat agaagctgga     300
ttcatgtgat gccagaggag taaaatttca agagactgaa accagatctg agtttcgctg     360
ttccagtctg gacctctttg gagctgtaaa tcctggatat actgtagatg agtactgcgt     420
ttttctttta tggactctct tcagcttctg gagacctcac tatcctatta tgtctttgtg     480
tgaagacatg ctgctttgta attatcgaaa gtgtcgcatc aaactctctg gctatgcatg     540
ggtcactgcc tgctctcaca tcttctgtga tcagcatggc agtggtgagt ttagtcgctc     600
accagctatc tgtcctgcct gcaacagtac cctttctgga aagctagata ttgtccgcac     660
agaactcagt ccatcagagg aatataaagc tatggtattg gcaggactgc gaccagagat     720
```

```
cgtgttggac attagctccc gagcgctggc cttctggaca tatcaggtac atcaggaacg    780

tctctatcaa gaatacaatt tcagcaaggc tgagggccat ctgaaacaga tggagaagat    840

atatactcag caaatacaaa gcaaggatgt agaattgacc tctatgaaag gggaggttac    900

ctccatgaag aaagtactag aagaatacaa gaaaaagttc agtgacatct ctgagaaact    960

tatggagcgc aatcgtcagt atcaaaagct ccaaggcctc tatgatagcc ttaggctacg   1020

aaacatcact attgctaacc atgaaggcac ccttgaacca tccatgattg cacagtctgg   1080

tgttcttggc ttcccattag gtaacaactc caagtttcct ttggataata cacctgttcg   1140

aaatcggggc gatggagatg gagattttca gttcagacca tttttgcgg gttctcccac   1200

agcacctgaa cccagcaaca gcttttttag ttttgtctct ccaagtcgtg aattagagca   1260

gcagcaagtt tctagcaggg ccttcaaagt aaaaagaatt tgagccacgc atagtgtcac   1320

gcacctgtga tcccagctac ttaggaggtt gaggctggga ggatcacttg agcccaggag   1380

tctgaggctt tagtgatcta agatcatgcc actgcactcc agcctgggca acagagtgag   1440

accctgtttc taaaaaaaaa taaagataat ttagctaact tcaaaaaaaa aaaaaaaaaa   1500

aac                                                                 1503
```

<210> SEQ ID NO 16
<211> LENGTH: 5776
<212> TYPE: DNA
<213> ORGANISM: Human

<400> SEQUENCE: 16

```
gctcacccag gaaaaatatg caatcgtccc attgatatac aggccactac aatggatgga     60

gttaacctca gcaccgaggt tgtctacaaa aaaggccagg attataggtt tgcttgctac    120

gaccggggca gagcctgccg gagctaccgt gtacggttcc tctgtgggaa gcctgtgagg    180

cccaaactca cagtcaccat tgacaccaat gtgaacagca ccattctgaa cttggaggat    240

aatgtacagt catggaaacc tggagatacc ctggtcattg ccagtactga ttactccatg    300

taccaggcag aagagttcca ggtgcttccc tgcagatcct gcgcccccaa ccaggtcaaa    360

gtggcaggga aaccaatgta cctgcacatc ggggaggaga tagacggcgt ggacatgcgg    420

gcggaggttg ggcttctgag ccggaacatc atagtgatgg gggagatgga ggacaaatgc    480

taccccctaca gaaaccacat ctgcaatttc tttgacttcg atacctttgg gggccacatc   540

aagtttgctc tgggatttaa ggcagcacac ttggagggca cggagctgaa gcatatggga    600

cagcagctgg tgggtcagta cccgattcac ttccacctgg ccggtgatgt agacgaaagg    660

ggaggttatg acccacccac atacatcagg gacctctcca tccatcatac attctctcgc    720

tgcgtcacag tccatggctc caatggcttg ttgatcaagg acgttgtggg ctataactct    780

ttgggccact gcttcttcac ggaagatggg ccggaggaac gcaacacttt tgaccactgt    840

cttggcctcc ttgtcaagtc tggaaccctc ctcccctcgg accgtgacag caagatgtgc    900

aagatgatca cagaggactc ctacccaggg tacatcccca agcccaggca agactgcaat    960

gctgtgtcca ccttctggat ggccaatccc aacaacaacc tcatcaactg tgccgctgca   1020

ggatctgagg aaactggatt ttggtttatt tttcaccacg taccaacggg cccctccgtg   1080

ggaatgtact ccccaggtta ttcagagcac attccactgg gaaaattcta taacaaccga   1140

gcacattcca actaccgggc tggcatgatc atagacaacg gagtcaaaac caccgaggcc   1200

tctgccaagg acaagcggcc gttcctctca atcatctctg ccagatacag ccctcaccag   1260

gacgccgacc cgctgaagcc ccgggagccg gccatcatca gacacttcat tgcctacaag   1320
```

-continued

```
aaccaggacc acggggcctg gctgcgcggc ggggatgtgt ggctggacag ctgccggttt   1380
gctgacaatg gcattggcct gaccctggcc agtggtggaa ccttcccgta tgacgacggc   1440
tccaagcaag agataaagaa cagcttgttt gttggcgaga gtggcaacgt ggggacggaa   1500
atgatggaca ataggatctg gggccctggc ggcttggacc atagcggaag gaccctccct   1560
ataggccaga attttccaat tagaggaatt cagttatatg atggccccat caacatccaa   1620
aactgcactt tccgaaagtt tgtggccctg gagggccggc acaccagcgc cctggccttc   1680
cgcctgaata atgcctggca gagctgcccc cataacaacg tgaccggcat tgcctttgag   1740
gacgttccga ttacttccag agtgttcttc ggagagcctg ggccctggtt caaccagctg   1800
gacatggatg gggataagac atctgtgttc catgacgtcg acggctccgt gtccgagtac   1860
cctggctcct acctcacgaa gaatgacaac tggctggtcc ggcacccaga ctgcatcaat   1920
gttcccgact ggagaggggc catttgcagt gggtgctatg cacagatgta cattcaagcc   1980
tacaagacca gtaacctgcg aatgaagatc atcaagaatg acttccccag ccaccctctt   2040
tacctggagg gggcgctcac caggagcacc cattaccagc aataccaacc ggttgtcacc   2100
ctgcagaagg gctacaccat ccactgggac cagacggccc ccgccgaact cgccatctgg   2160
ctcatcaact tcaacaaggg cgactggatc cgagtggggc tctgctaccc gcgaggcacc   2220
acattctcca tcctctcgga tgttcacaat cgcctgctga agcaaacgtc caagacgggc   2280
gtcttcgtga ggaccttgca gatggacaaa gtggagcaga gctaccctgg caggagccac   2340
tactactggg acgaggactc agggctgttg ttcctgaagc tgaaagctca gaacgagaga   2400
gagaagtttg ctttctgctc catgaaaggc tgtgagagga taaagattaa agctctgatt   2460
ccaaagaacg caggcgtcag tgactgcaca gccacagctt accccaagtt caccgagagg   2520
gctgtcgtag acgtgccgat gcccaagaag ctctttggtt ctcagctgaa aacaaaggac   2580
catttcttgg aggtgaagat ggagagttcc aagcagcact tcttccacct ctggaacgac   2640
ttcgcttaca ttgaagtgga tgggaagaag taccccagtt cggaggatgg catccaggtg   2700
gtggtgattg acgggaacca agggcgcgtg gtgagccaca cgagcttcag gaactccatt   2760
ctgcaaggca taccatggca gcttttcaac tatgtggcga ccatccctga caattccata   2820
gtgcttatgg catcaaaggg aagatacgtc tccagaggcc catggaccag agtgctggaa   2880
aagcttgggg cagacagggg tctcaagttg aaagagcaaa tggcattcgt tggcttcaaa   2940
ggcagcttcc ggcccatctg ggtgacactg gacactgagg atcacaaagc caaaatcttc   3000
caagttgtgc ccatccctgt ggtgaagaag aagaagttgt gaggacagct gccgcccggt   3060
gccacctcgt ggtagactat gacggtgact cttggcagca gaccagtggg ggatggctgg   3120
gtcccccagc ccctgccagc agctgcctgg gaaggccgtg tttcagccct gatgggccaa   3180
gggaaggcta tcagagaccc tggtgctgcc acctgcccct actcaagtgt ctacctggag   3240
cccctggggc ggtgctggcc aatgctggaa acattcactt tcctgcagcc tcttgggtgc   3300
ttctctccta tctgtgcctc ttcagtgggg gtttggggac catatcagga gacctgggtt   3360
gtgctgacag caaagatcca ctctggcagg agccctgacc cagctaggag gtagtctgga   3420
gggctggtca ttcacagatc cccatggtct tcagcagaca agtgagggtg gtaaatgtag   3480
gagaaagagc cttggcctta aggaaatctt tactcctgta agcaagagcc aacctcacag   3540
gattaggagc tggggtagaa ctggctatcc ttggggaaga ggcaagccct gcctctggcc   3600
gtgtccacct ttcaggagac tttgagtggc aggtttggac ttggactaga tgactctcaa   3660
aggccctttt agttctgaga ttccagaaat ctgctgcatt tcacatggta cctggaaccc   3720
```

```
aacagttcat ggatatccac tgatatccat gatgctgggt gccccagcgc acacgggatg   3780

gagaggtgag aactaatgcc tagcttgagg ggtctgcagt ccagtagggc aggcagtcag   3840

gtccatgtgc actgcaatgc caggtggaga aatcacagag aggtaaaatg gaggccagtg   3900

ccatttcaga ggggaggctc aggaaggctt cttgcttaca ggaatgaagg ctgggggcat   3960

tttgctgggg ggagatgagg cagcctctgg aatggctcag ggattcagcc ctccctgccg   4020

ctgcctgctg aagctggtga ctacggggtc gccctttgct cacgtctctc tggcccactc   4080

atgatggaga agtgtggtca gaggggagca atgggctttg ctgcttatga gcacagagga   4140

attcagtccc caggcagccc tgcctctgac tccaagaggg tgaagtccac agaagtgagc   4200

tcctgcctta gggcctcatt tgctcttcat ccagggaact gagcacaggg ggcctccagg   4260

agaccctaga tgtgctcgta ctccctcggc ctgggatttc agagctggaa atatagaaaa   4320

tatctagccc aaagccttca ttttaacaga tggggaaagt gagcccccaa gatgggaaag   4380

aaccacacag ctaagggagg gcctggggag ccccacccta gcccttgctg ccacaccaca   4440

ttgcctcaac aaccggcccc agagtgccca ggcactcctg aggtagcttc tggaaatggg   4500

gacaagtccc ctcgaaggaa aggaaatgac tagagtagaa tgacagctag cagatctctt   4560

ccctcctgct cccagcgcac acaaacccgc cctccccttg gtgttggcgg tccctgtggc   4620

cttcactttg ttcactacct gtcagcccag cctgggtgca cagtagctgc aactccccat   4680

tggtgctacc tggctctcct gtctctgcag ctctacaggt gaggcccagc agagggagta   4740

gggctcgcca tgtttctggt gagccaattt ggctgatctt gggtgtctga acagctattg   4800

ggtccacccc agtccctttc agctgctgct taatgccctg ctctctccct ggcccacctt   4860

atagagagcc caaagagctc ctgtaagagg gagaactcta tctgtggttt ataatcttgc   4920

acgaggcacc agagtctccc tgggtcttgt gatgaactac atttatcccc tttcctgccc   4980

caaccacaaa ctctttcctt caaagagggc ctgcctggct ccctccaccc aactgcaccc   5040

atgagactcg gtccaagagt ccattcccca ggtgggagcc aactgtcagg gaggtctttc   5100

ccaccaaaca tctttcagct gctgggaggt gaccataggg ctctgctttt aaagatatgg   5160

ctgcttcaaa ggccagagtc acaggaagga cttcttccag ggagattagt ggtgatggag   5220

aggagagtta aaatgacctc atgtccttct tgtccacggt tttgttgagt tttcactctt   5280

ctaatgcaag ggtctcacac tgtgaaccac ttaggatgtg atcactttca ggtggccagg   5340

aatgttgaat gtctttggct cagttcattt aaaaaagata tctatttgaa agttctcaga   5400

gttgtacata tgtttcacag tacaggatct gtacataaaa gtttctttcc taaaccattc   5460

accaagagcc aatatctagg cattttcttg gtagcacaaa ttttcttatt gcttagaaaa   5520

ttgtcctcct tgttatttct gtttgtaaga cttaagtgag ttaggtcttt aaggaaagca   5580

acgctcctct gaaatgcttg tctttttttct gttgccgaaa tagctggtcc tttttcggga   5640

gttagatgta tagagtgttt gtatgtaaac atttcttgta ggcatcacca tgaacaaaga   5700

tatattttct atttatttat tatatgtgca cttcaagaag tcactgtcag agaaataaag   5760

aattgtctta aatgtc                                                   5776
```

<210> SEQ ID NO 17
<211> LENGTH: 2695
<212> TYPE: DNA
<213> ORGANISM: Human

<400> SEQUENCE: 17

```
gcgggcttta gcgccttttc tggcggcggt agatttgaag cgcttcaaag gaccggaccc     60
```

-continued

```
agagaagagg aaaactctac cggtgcagga gcacagggat cagttgtcct tgtttttttt    120
tggtcttttc ttcatttgaa gattaagtat tggagccatg ggaataaagg ttcaacgtcc    180
tcgatgtttt tttgacattg ccattaacaa tcaacctgct ggaagagttg tctttgaatt    240
attttctgat gtgtgcccca aaacatgcga gaactttcgt tgtctttgta caggtgaaaa    300
ggggaccggg aaatcaactc agaaaccatt acattataag agttgtctct ttcacagagt    360
tgtcaaggat tttatggttc aaggtggtga cttcagtgaa ggaaatggac gaggagggga    420
atctatctat ggaggatttt ttgaagacga gagtttcgct gttaaacaca acaaagaatt    480
tctcttgtca atggccaaca gagggaagga tacaaatggt tcacagttct tcataacaac    540
gaaaccaact cctcatttag atgggcatca tgttgttttt ggacaagtaa tctctggtca    600
agaagttgta agagagattg aaaaccagaa aacagatgca gctagcaaac cgtttgcgga    660
ggtacggata ctcagttgtg gagagctgat tcccaaatct aaagttaaga aagaagaaaa    720
gaaaaggcat aaatcatcat catcttcctc ctcctcatct agtgactcag atagctcaag    780
tgattctcag tcctcttctg attcctctga ttccgaaagt gctactgaag agaaatcaaa    840
gaaaagaaaa aagaaacatc ggaaaaattc ccgaaaacac aagaaagaaa agaaaaagcg    900
aaagaaaagc aagaagagtg catctagtga gagtgaagct gaaaatcttg aagcacaacc    960
ccagtctact gtccgtccag aagagatccc tcctatacct gaaaatagat tcctaatgag   1020
aaaaagtcct cctaaagctg atgagaagga aaggaaaaac agagagagag aaagggaaag   1080
agagtgtaat ccacctaact cccagcctgc ttcataccag agacgacttt tagttactag   1140
atctggcagg aaaattaaag gaagaggacc aaggcgttat cgaactcctt ccagatccag   1200
atcaagggat cgtttcagac gtagtgagac tcctccacat tggaggcaag agatgcagag   1260
agctcaaaga atgagggtat caagtggtga aagatggatc aagggggata agagtgagtt   1320
gaatgaaata aaagaaaatc agagaagtcc agttagagta aaagagagaa aaataacaga   1380
tcacaggaat gtatctgaga gtccaaacag aaaaaatgaa aaggagaaga aagttaaaga   1440
ccataaatct aacagcaaag agagagacat cagaagaaat tcagaaaaag atgacaagta   1500
taaaaacaaa gtgaagaaaa gggccaaatc taaaagtagg agtaagagca aagagaaatc   1560
aaagagtaaa gaaagagatt caaaacataa tagaaatgaa gaaaagagga tgaggtcaag   1620
gagtaaagga agggatcatg aaaatgttaa agaaaaagaa aagcagtctg attctaaagg   1680
aaaagatcag gaaaggagta gaagtaaaga gaagtctaaa cagttagaat caaagagtaa   1740
tgagcatgat cacagtaaaa gtaaggaaaa ggatagacgc gcacaatcca ggagtagaga   1800
atgtgatata actaaaggta aacacagtta taatagcaga acaagagaac gaagcagaag   1860
tagggacaga agcagaagag tgcgatcaag aacccatgac agagatcgca gcagaagcaa   1920
ggagtaccat agatacagag aacaggaata caggagaaga ggacggtcac gaagccgaga   1980
gagaagaaca ccaccaggaa gatcaagaag taaagatagg aggagaagga ggagagactc   2040
acggagctca gagagagaag aaagtcaaag cagaaacaaa gacaaataca gaaaccaaga   2100
gagtaagagc tcacacagaa aagaaaattc tgagagtgag aaaagaatgt actctaaaag   2160
tcgtgatcat aatagctcaa ataacagcag ggaaaaaaag gctgatagag atcaaagtcc   2220
cttctcaaaa ataaaacaaa gcagtcagga cgatgaatta aagtcctcca tgttgaaaaa   2280
taaggaggat gagaagatca gatcctcagt ggaaaaagaa aaccaaaaat caaaaggtca   2340
agaaaatgac catgtacatg aaaaaaataa aaaatttgat catgaatcaa gccctggaac   2400
agatgaagac aaaagcggat gagtgagtta tataaactta cttccattct gtttcggatt   2460
```

ttaagtttga gagacttgct aatgaatctc ctttatgttg ttttcctttt cattgttttt 2520
ggattgtttt atgtttgtcc tttttttttct taatgtggat ttcattgagt tgattttttg 2580
ataatctgca atctggataa tttgtactgc taaagtttta ataaactcga catgagaaaa 2640
acaaaaaaaa aaaaaaaaaa aaaaaaaaaa aaaaaaaaaa aaaaaaaaaa aaaaa 2695

<210> SEQ ID NO 18
<211> LENGTH: 1635
<212> TYPE: DNA
<213> ORGANISM: Human

<400> SEQUENCE: 18
ggcacgagcg cggcgttcac gggaattgtt cgctttagtg ccggcgccat ggggtcggag 60
ctgatcgggc gcctagcccc gcgcctgggc ctcgccgagc ccgacatgct gaggaaagca 120
gaggagtact tgcgcctgtc ccgggtgaag tgtgtcggcc tctccgcacg caccacggag 180
accagcagtg cagtcatgtg cctggacctt gcagcttcct ggatgaagtg ccccttggac 240
agggcttatt taattaaact ttctggtttg aacaaggaga catatcagag ctgtcttaaa 300
tcttttgagt gtttactggg cctgaattca aatattggaa taagagacct agctgtacag 360
tttagctgta tagaagcagt gaacatggct tcaaagatac taaaaagcta tgagtccagt 420
cttccccaga cacagcaagt ggatcttgac ttatccaggc cacttttcac ttctgctgca 480
ctgctttcag catgcaagat tctaaagctg aaagtggata aaaacaaaat ggtagccaca 540
tccggtgtaa aaaaagctat atttgatcga ctgtgtaaac aactagagaa gattggacag 600
caggtcgaca gagaacctgg agatgtagct actccaccac ggaagagaaa gaagatagtg 660
gttgaagccc cagcaaagga aatggagaag gtagaggaga tgccacataa accacagaaa 720
gatgaagatc tgacacagga ttatgaagaa tggaaaagaa aaattttgga aaatgctgcc 780
agtgctcaaa aggctacagc agagtgattt cagcttccaa actggtatac attccaaact 840
gatagtacat tgccatctcc aggaagactt gacggctttg ggattttgtt taaactttta 900
taataaggat cctaagactg ttgcctttaa atagcaaagc agcctacctg gaggctaagt 960
ctgggcagtg ggctggcccc tggtgtgagc attagaccag ccacagtgcc tgattggtat 1020
agccttatgt gctttcctac aaaatggaat tggaggccgg gcgcagtggc tcacgcctgt 1080
aatcccagca ctttgggagg ccaaggtggg tggatcacct gaggtcagga gctcgagacc 1140
agcctggcca acatggtgaa accccatctc tactaaaaat acaaaaaatta gccaggtgtg 1200 atggtgcatg cctgtaatcc cagctcctca gtaggctgag acaggagcat cacttgaacg 1260
tgggaggcag aggttgcagt gagccgagat tgcaccaccg cactccagcc tgggtgacag 1320
agcgagactt atctcataaa taaatagata gatactccag cctgggtgac agagcgagac 1380
ttatagatag atagatagat agatggatag atagatagat agatagatag atagataaac 1440
ggaattggag ccattttgct ttaagtgaat ggcagtccct tgtcttattc agaatataaa 1500
attcagtctg aatggcatct tacagatttt acttcaattt ttgtgtacgg tattttttat 1560
ttgactaaat caatatattg tacagcctaa gttaataaat gttatttata tatgcaaaaa 1620
aaaaaaaaaa aaaaa 1635

<210> SEQ ID NO 19
<211> LENGTH: 3165
<212> TYPE: DNA
<213> ORGANISM: Human

<400> SEQUENCE: 19

-continued

```
ggggatttgg ctagaaggct gggccggcag cggttgtgag gagttagctc gcggcattgc      60
aggctctgag aggaggggac ccggttcccg ggtgagtgtc caggcatgcc agcggaacgg     120
cccgcgggca gcggcggctc ggaggctcca gcaatggttg aacaactgga cactgctgtg     180
attaccccgg ccatgctaga agaggaagaa cagcttgaag ctgctggact agagagagag     240
cggaagatgc tggaaaaggc tcgcatgtct tgggatagag agtcgacaga aattcggtac     300
cgtagacttc aacatttgct tgaaaaaagc aatatatact ccaaattttt attgacgaaa     360
atggaacagc aacaattaga ggaacagaag aagaaagaaa aattggagag aaaaaaggag     420
tctttaaaag ttaaaaaggg taaaaattca attgatgcaa gtgaagagaa gccagttatg     480
aggaaaaaaa gaggaagaga agatgaatca tacaatattt cagaggtcat gtcaaaagag     540
gaaattttgt ctgtggctaa aaaaaataaa aaggagaatg aggatgaaaa ctcctcctct     600
actaatctct gtgtggaaga tcttcagaaa aataaagatt cgaatagtat aattaaagat     660
agattgtctg aaacggttag gcagaatact aaattctttt ttgacccagt ccggaagtgt     720
aatggtcagc cagtaccttt tcaacaacca aagcacttca ctggaggagt gatgcgatgg     780
taccaagtag aaggcatgga atggcttagg atgctttggg aaaatggaat taatggcatt     840
ttagcagatg aaatgggatt gggtaagaca gttcagtgca ttgctactat tgcattgatg     900
attcagagag gagtaccagg accttttctt gtctgtggcc ctttgtctac acttcctaac     960
tggatggctg aattcaaaag atttacacca gatatcccta caatgttata tcatggaacc    1020
caggaggaac gtcaaaaatt ggtaagaaat atttacaaac ggaaagggac tttgcagatt    1080
catcctgtgg taatcacgtc atttgaaata gccatgagag accgaaatgc gttacagcat    1140
tgctattgga aatacttaat agtagatgaa ggacacagga ttaagaatat gaagtgccgt    1200
ctaatcaggg agttaaaacg attcaatgct gataacaaac ttcttttgac tggtactccc    1260
ttgcaaaaca atttatcaga actttggtca ttgctaaact ttttgttgcc agatgtattt    1320
gatgacttga aaagctttga gtcttggttt gacatcacta gtctttctga aactgctgaa    1380
gatattattg ctaaagaaag agaacagaat gtattgcata tgctgcacca gattttaaca    1440
cctttcttat tgagaagact gaagtctgat gttgctcttg aagttcctcc taaacgagaa    1500
gtagtcgttt atgctccact ttcaaagaag caggagatct tttatacagc cattgtgaac    1560
cgtacaattg caaacatgtt tggatccagt gagaaagaaa caattgagtt aagtcctact    1620
ggtcgaccaa aacgacgaac tagaaaatca ataaattaca gcaaaataga tgatttccct    1680
aatgaattgg aaaaactgat cagtcaaata cagccagagg tggaccgaga aagagctgtt    1740
gtggaagtga atatccctgt agaatctgaa gttaatctga agctgcagaa tataatgatg    1800
ctacttcgta aatgttgtaa tcatccatat ttgattgaat atcctataga ccctgttaca    1860
caagaattta agatcgatga agaattggta acaaattctg ggaagttctt gattttggat    1920
cgaatgctgc cagaactaaa aaaaagaggt cacaaggtgc tgcttttttc acaaatgaca    1980
agcatgttgg acattttgat ggattactgc catctcagag atttcaactt cagcaggctt    2040
gatgggtcca tgtcttactc agagagagaa aaaaacatgc acagcttcaa cacggatcca    2100
gaggtgttta tcttcttagt gagtacacga gctggtggcc tgggcattaa tctgactgca    2160
gcagatacag ttatcattta tgatagtgat tggaacccc  agtcggatct tcaggcccag    2220
gatagatgtc atagaattgg tcagacaaag ccagttgttg tttatcgcct tgttacagca    2280
aatactatcg atcagaaaat tgtggaaaga gcagctgcta aaaggaaact ggaaaagttg    2340
atcatccata aaaatcattt caaaggtggt cagtctggat taaatctgtc taagaatttc    2400
```

ttagatccta aggaattaat ggaattatta aaatctagag attatgaaag ggaaataaaa 2460
ggatcaagag agaaggtcat tagtgataaa gatctagagt tgttgttaga tcgaagtgat 2520
cttattgatc aaatgaatgc ttcaggacca attaaagaga agatggggat attcaagata 2580
ttagaaaatt ctgaagattc cagtcctgaa tgtttgtttt aaagtggagc tcaagaatag 2640
cttttaaaag ttcttattta catctagtga tttccctgta ttgggtttga aatactgatt 2700
gtccacttca ccttttttat tatatcagtt gacatgtaac tagtaccatg cgtacttaaa 2760
tagatggtaa ttttctgagc cttaccaaga acaaagaagt atccatatta agtttagatt 2820
ttcagttaat ttttgagact gagtagtatt cttggataca ggctgatgtg tacttaacca 2880
cttccagatt tatacagtct tcctgtggaa gtttagtaaa tgtctttttc cctcctttct 2940
tctagtaatg cagttcatgg gctttaggta cttcagttat gaagtaggct tttcatgggg 3000
agagattggg attatgctct ctgttgttta agaaactgtt tgattttaga gtctatttct 3060
atgagatagt ttaccaaata aatgttcctt ataagatgaa aaaaaaaaaa aaaaaaaaaa 3120
aaaaaaaaaa aaaaaaaaaa aaaaaaaaaa aaaaaaaaaa aaaaa 3165

<210> SEQ ID NO 20
<211> LENGTH: 526
<212> TYPE: DNA
<213> ORGANISM: Human

<400> SEQUENCE: 20
tggttcctgc cgtccggact ctttttcctc tactgagatt catctgtgtg aaatatgagt 60
tggcgaggaa gatcgaccta ttattggcct agaccaaggc gctatgtaca gcctcctgaa 120
atgattgggc ctatgcggcc cgagcagttc agtgatgaag tggaaccagc aacacctgaa 180
gaaggggaac cagcaactca acgtcaggat cctgcagctg ctcaggaggg agaggatgag 240
ggagcatctg caggtcaagg gccgaagcct gaagctcata gccaggaaca gggtcaccca 300
cagactgggt gtgagtgtga agatggtcct gatgggcagg agatggaccc gccaaatcca 360
gaggaggtga aaacgcctga agaaggtgaa aagcaatcac agtgttaaaa gaaggcacgt 420
tgaaatgatg caggctgctc ctatgttgga aatttgttca ttaaaattct cccaataaag 480
ctttacagcc ttctgcaaag aaaaaaaaaa aaaaaaaaaa aaaaaa 526

<210> SEQ ID NO 21
<211> LENGTH: 4834
<212> TYPE: DNA
<213> ORGANISM: Human

<400> SEQUENCE: 21
cgaggtcaga ggggaggagg actctggagc tgacagcgcg cacttcaccc gcagttgttc 60
tagcgactgc gaagatagct cgctgagctg gaaccccaca gatcaccaac aaaaatgaag 120
gcggcagatg agcctgccta cctgacagtg ggaaccgatg tcagtgccaa gtaccgaggt 180
gccttctgtg aggcaaagat taagactgtg aaaaggctgg tgaaagttaa ggtactcctg 240
aaacaggata ataccacaca attggtacaa gatgaccaag taaagggtcc tttaagagtt 300
ggagctattg ttgaaacaag gacatctgat ggatcttttc aggaagctat tatcagcaag 360
ttgacagatg ctagttggta taccgtggtg tttgatgatg gtgatgagcg aacattgaga 420
cgtacctcac tttgtctgaa aggagagaga cattttgcag agagtgagac acttgaccag 480
cttccattaa caaatccaga gcattttgga actccagtaa ttgcaaagaa gacgaacaga 540
ggaaggagat cttctcttcc tgttactgaa gatgaaaagg aagaagaaag cagtgaagag 600

-continued

```
gaagatgaag acaagcgccg tctcaatgat gaattactag gaaaagttgt aagtgtggtg    660
tctgcaacgg agaggactga atggtatcct gctttggtaa tatctcccag ctgtaatgat    720
gacatcacag tgaaaaagga tcagtgttta gttcgatcat ttattgattc taaattttac    780
tctatagcaa gaaaggacat taaggaagta gacattctca atctaccgga atctgagctc    840
tccactaaac cagggcttca gaaagcaagc atcttcttaa aaactagagt tgttcctgat    900
aattggaaaa tggatataag tgaaatcctt gagtcatcca gtagtgatga tgaagatggc    960
ccagctgaag aaaatgatga agagaaggaa aaggaggcca aaaagacaga agaagaggtg   1020
cctgaggaag aacttgatcc tgaagagagg gacaacttcc tccagcagct ttataagttt   1080
atggaagaca gaggtactcc aatcaacaaa ccacctgttt tgggctataa agatctcaat   1140
ctcttcaaac tcttcagact ggtttatcat cagggtggat gtgacaatat tgatagtggt   1200
gctgtatgga agcaaattta tatggacctt ggcattccta ttttgaattc agctgcttcc   1260
tacaatgtaa aaactgctta tagaaagtat ctctatggtt ttgaggagta ctgccgttcg   1320
gcaaatattc agttcagaac tgttcatcac catgaaccaa aagtaaaaga ggaaaaaaaa   1380
gacttagaag aatcaatgga agaggctctc aaattagatc aagaaatgcc tttaacagaa   1440
gtgaagagtg aacctgagga aaatatcgat tcaaacagtg aaagtgaaag agaagagata   1500
gaattaaaat ctccgagggg acgaaggaga attgctcgag atgtaaattc tattaaaaag   1560
gaaattgaag aagagaaaac agaagacaaa ttaaaagata atgatacaga aaataaggat   1620
gtagatgatg actatgaaac tgcagagaaa aaagaaaatg agctactact ggggagaaaa   1680
aatacaccaa agcaaaaaga gaagaaaatt aaaaaacagg aggattctga caaagactca   1740
gatgaagagg aagagaaaag ccaagagagg gaagaaactg aaagcaaatg tgactctgaa   1800
ggagaggaag atgaggaaga catggaaccc tgcctaacag gaaccaaagt gaaagtaaaa   1860
tatggacgag ggaagactca gaaaatttat gaagccagta ttaaaagcac tgaaattgat   1920
gacggagaag ttttatattt ggtacattac tatggatgga atgtcaggta tgatgagtgg   1980
gtgaaggctg acaggataat ctggcctttg gacaaaggtg gaccaaagaa aaaacagaag   2040
aaaaaagcta aaaataaaga agatagtgaa gtggacgaaa agagagatga ggagaggcag   2100
aagtcaaaac ggggacgacc tcctttaaaa tcaaccctct catcaaacat gccgtatggc   2160
ttatctaaga cagcaaacag tgaaggaaaa tcagactctt gttcatctga tagtgaaaca   2220
gaagatgctt tagaaaagaa tttaataaat gaagaacttt ctcttaaaga tgaactagaa   2280
aaaaatgaaa atttgaatga tgataagcta gatgaagaaa atccaaagat ttctgcacat   2340
atattaaaag aaaatgatag gactcaaatg cagcctttag aaaccctgaa gttagaagtt   2400
ggagagaatg aacaaatagt acagattttt gggaacaaaa tggaaaaaac agaagaagtt   2460
aagaaagaag ccgaaaaatc tccaaaagga aagggaagac gaagcaagac aaaagatctt   2520
tctttagaaa ttataaagat ttcatcattt ggccagaatg aagcaggaag tgaacctcat   2580
atagaagctc atagtcttga attgtcttca ttagacaata aaaacttttc ttctgctaca   2640
gaagatgaaa ttgaccaatg tgtgaaagaa aagaagttga aacggaaaat actaggacaa   2700
tcatcgccag agaaaaaaat aagaattgag aatggaatgg aaatgacaaa tactgtatct   2760
caagaaagga ccagtgattg tattggatct gagggaatga aaaacttaaa ttttgaacag   2820
cactttgaaa gagaaaatga aggaatgcca tcattgatag cagagtcaaa ccaatgcatc   2880
caacaactga ctagtgaaag atttgatagt ccagctgaag aaactgtaaa tattccacta   2940
aaagaagatg aggatgcaat gcctctgatc gggcctgaaa ccttggtttg ccatgaagta   3000
```

```
gatttggatg atttggatga aaaggataag accagcattg aggatgtagc agttgaaagc   3060
tctgagtcta actctcttgt ttctattcca cctgccctac ctcctgtagt ccaacataac   3120
ttttcagtag cttcaccact tactcttagt caagatgagt ctcgaagcgt aaaaagtgag   3180
agtgatataa cgattgaagt tgatagtatt gctgaagaat ctcaagaagg tctctgtgag   3240
agggaatcgg caaatggatt tgaaactaat gttgcctctg gtacctgtag tataattgta   3300
caagagagag agagcagaga gaagggtcag aagaggccaa gtgatggaaa tagtggatta   3360
atggcaaaaa agcaaaagcg taccccaaag cgaacaagtg ctgcagccaa aaatgaaaag   3420
aatggaacag gacaaagcag tgatagtgaa gatcttcctg tcctagacaa ttcaagtaaa   3480
tgtaccccag taaagcatct taatgtatct aagccacaga aacttgcacg atctcctgca   3540
agaatatccc cgcacatcaa agatggagag aaagataaac acagagaaaa acatccgaat   3600
tcatccccta ggacatataa atggagcttt cagctcaatg aattagataa tatgaacagt   3660
acagagagaa tctcatttct ccaagaaaaa ctacaggaaa tcagaaaata ttatatgtct   3720
ttgaagtctg aagttgcaac catagacagg aggagaaaaa gattaaaaaa gaaagacagg   3780
gaagtgtctc atgcgggagc ctccatgtca tctgcttcat cagacactgg aatgagtccc   3840
tcatcatcgt ctcccccaca aaatgtactt gctgtagaat gtaggtgata aacattttct   3900
ctaccttccc agcagtttgc tgccatggac ataaatcccc aaaccctgaa ttacaaccac   3960
agaaagcact caactggttt gacattgcta agtatatcct gtatactttt ccaggctgga   4020
ttgtatctat gcccctctct cttctttttt cttgttgcaa aaaataagct gattaataag   4080
tgaaggttaa gcagcctgcc atatttgtca taatttttcc tctttacttt tgtttttcgt   4140
ttgttgtgat atagaacaaa gggcacttag caaatttgaa tttgtataat aaagctttca   4200
ggtgttacag aaatcgtaga caagcaagtg cacatgataa acaatcaaaa tattacccag   4260
ctgaatagtt actgctgcac tttcactaag atgtatttga acacttggtg agtagggggt   4320
ttatgttgtg ttttttttca ttatcgtttt ttttattttt gtgaagcact tgctatttag   4380
aactgccaaa gtatatgttc agcagtgtgc ccaggattga aggtgtaaat gggacaaaat   4440
aaattgtgaa aggaagtgta gttgactgaa aactacagtt gtaataagtc ttccactttt   4500
tataggattt ttgagcacac aattatgcaa atattttaat gtttattaat gtttacagtg   4560
gaattgtgaa taagttttca gtggactatc ttatcccttg acaaaaatat tttgtctttt   4620
ttctatgtaa tttcagagtt tttattttgt tacaaaaaga caaaaatgaa atatataaca   4680
acaatgaagt tatttaacaa gatttctaaa gctgaaattt ttgtgtaaaa taaggtatta   4740
tcttgcaact tgttaaatat atttattcag acattggatg ttgtattttt atgtattttt   4800
taaaatatta ataaaattta aaaaaaaaaa aaaa                               4834
```

<210> SEQ ID NO 22
<211> LENGTH: 1713
<212> TYPE: DNA
<213> ORGANISM: Human

<400> SEQUENCE: 22

```
ggggggtgtg agccacgggc tgccgggggc ctggggctcg gcgtcggtcc ccgggggatg     60
tggagagctg gcagcatgtc ggccgagctg ggagtcgggt gcgcattgcg ggcggtgaac    120
gagcgcgtgc agcaggctgt ggcgcggcgg ccgcgggatc tcccagccat ccagccccgg    180
ctagtggcgg tcagcaaaac caaacctgca gacatggtga tcgaggccta tggacatggg    240
cagcgcactt ttggcgagaa ctacgttcag gaactgctag aaaaagcatc aaatcccaaa    300
```

```
attctgtctt tgtgtcctga gatcaaatgg cacttcattg gccacctaca gaaacaaaat    360
gtcaacaaat tgatggctgt ccccaatctc ttcatgctgg aaacagtgga ttctgtgaag    420
ttggcagaca aagtgaacag ttcctggcag agaaaaggtt ctcctgaaag gttaaaggtt    480
atggtccaga ttaacaccag cggagaagag agtaaacatg gccttccacc ttcagagacc    540
atagccatcg tggagcacat aaacgccaag tgtcctaacc tggagtttgt ggggctgatg    600
accataggaa gctttgggca tgatcttagt caaggaccaa atccagactt ccagctgtta    660
ttgtccctcc gggaggagct gtgtaaaaag ctgaacatcc ctgctgacca ggttgagctg    720
agcatgggca tgtccgcgga tttccagcat gcggttgaag taggatctac aaatgtccga    780
ataggaagca cgatttttgg agagcgggat tactcaaaga aacccacccc ggacaagtgc    840
gcagcagacg tgaaggcccc gctggaggtg gcacaggagc actgagccag ggaatactga    900
gagcactaac tatgcactaa cctagatttt catttcgata ttccctgtgt cccagcgcag    960
tcctgctctc ctgtgacctg tggagagcac taatgatcac gtgtgttgat ggaaaccatc   1020
tgtgcttagt ctctgacata ggaagcttgc ttcaggcaat ggctttggat tgagtttgag   1080
aaattcaaac atttctgcag aacagatacc aaatcaatag ctaggaatca tgttcaatat   1140
tgaattctgc ccaggagcat gaactgatcc atgaatgcct tttccaggtt aaaatttggt   1200
cactgatgcc tataatcgtg gaagtcagag ggattcccct ttttcatctc attttaatag   1260
gaaaattcct tatggttaac atctccctac aaactcctac tacgtcgtct aaattgctgc   1320
tctggaataa ggtgatttct gcccccagat tcttccctag ccggtagata cgtgaagata   1380
ttcccaactg tggaatggca gtgtaggtag cttcaggaaa tggctcaggt taattctcaa   1440
aacacaaatt gttgctggcc aggcatggtg actcatgcct gtaatcccag caatttggga   1500
gacagaggcg gaaggatcac ctgagcctag gagttcaaga ccagcctcag caacagcagg   1560
agccccaccc cccgtctcta caaaaaatatt taaaaattaa ctgggcatgg tggctgaggt   1620
ggaagaatgg aagaatcact tgagcccagg agtttgaggc tgcagtgagc tatgattgca   1680
ccactgtact cctgccttaa aaaaaaaaaa aaa                                1713
```

<210> SEQ ID NO 23
<211> LENGTH: 4344
<212> TYPE: DNA
<213> ORGANISM: Human

<400> SEQUENCE: 23

```
gggatctgct agaagttggt cttccgccag gactagagtt tcctcgcggt aacagcctcc     60
gtggcctccg gaggaccatg tcattagact ttggcagtgt ggcactacca gtgcaaaatg    120
aagatgaaga gtatgacgaa gaggactatg aaagagagaa agagttgcag cagttactca    180
cagaccttcc ccatgacatg ctggatgacg acctctcctc tccagagctc cagtattcgg    240
actgcagcga ggatggcaca gacggacaac cacatcatcc tgagcaattg gagatgagct    300
ggaatgagca aatgctgccc aaatctcaaa gtgtaaatgg tcccagttgt caaggtttgg    360
aaccgtataa taaagtgaca tataaacctt atcagtcttc tgcccagaat aatggctcac    420
cagcccagga gataacagga agtgacacat tcgaaggcct gcaacaacaa tttttaggag    480
ctaatgagaa ctctgcagaa aatatgcaga ttattcaact tcaggttctt aacaaagcaa    540
aagagagaca actggagaac ttaattgaaa agttaaatga aagtgaacgt caaattcgat    600
atctgaatca ccagcttgta ataataaaag atgaaaagga tggtttgact ctcagccttc    660
gagaatcaca gaaactcttt cagaatggaa aagaaagaga gatacagctt gaagctcaaa    720
```

-continued

```
taaaagcact ggagactcag atacaagcat taaaagtcaa tgaagaacag atgatcaaga    780
agtccagaac aactgaaatg gctctggaaa gcttgaagca gcagctggtg gaccttcatc    840
attctgaatc acttcaacga gctagagaac agcatgagag cattgttatg ggcctcacaa    900
agaagtacga agagcaagta ttgtccttac aaaagaattt ggatgccaca gtcaccgcac    960
ttaaagaaca ggaagacatt tgctctcgtc tgaaagatca cgtgaaacaa ctggaaagga   1020
atcaagaagc aatcaagtta gaaaagactg agatcattaa taagttgaca agaagtctag   1080
aggagagtca aaagcagtgt gcccacttgt tgcagtccgg gtcagtacaa gaggtggctc   1140
agctacagtt ccagctgcag caagcacaga aggcacatgc tatgagtgca aacatgaaca   1200
aggctttgca agaagaatta acagaactaa aagatgaaat ttctctctat gaatctgctg   1260
caaaactagg aatacatcca agtgactcag aaggagaatt aaatatagaa ctcactgaat   1320
cgtatgtgga tttgggtatt aaaaaggtca actggaaaaa atccaaagtt accagcattg   1380
tacaagaaga agacccaaat gaagagcttt caaaagatga gttcattctg aagttaaagg   1440
cagaagtaca gcgtttgctg ggtagcaact caatgaagcg tcatctggtg tctcagttac   1500
aaaatgacct caaagactgt cataagaaaa ttgaagatct ccaccaagtg aagaaggatg   1560
aaaaaagcat tgaggttgag actaaaacag atacctcaga aaaaccaaag aatcaattat   1620
ggcctgagtc ttctacttct gatgttgtca gagatgatat tctgctgctt aaaaatgaaa   1680
ttcaagtttt acaacaacaa aatcaggaac ttaaagaaac tgaaggaaaa ctgagaaata   1740
caaatcaaga cttatgtaat caaatgagac aaatggtaca agattttgac catgacaaac   1800
aagaagctgt ggataggtgt gaaaggactt atcagcagca ccatgaagcc atgaaaactc   1860
aaatacgtga aagcctatta gcaaagcatg ctttggagaa gcagcagctc tttgaggctt   1920
atgagagaac tcatttgcaa ctgaggtctg agttggataa gttgaataag gaggtgactg   1980
ctgtgcagga atgttaccta gaagtgtgca gagagaagga taatctagaa ttgactctca   2040
ggaagaccac tgaaaaggag caacagactc aggagaagat caaagaaaaa ctcattcaac   2100
agcttgaaaa ggagtggcag tctaagctgg atcaaactat aaaggcaatg aaaaagaaga   2160
ccttagattg tggcagccaa actgaccaag taaccaccag tgatgttatt tccaagaaag   2220
agatggcaat tatgatagaa gagcagaagt gcacaatcca gcaaaactta gaacaagaga   2280
aggacatagc catcaagggg gctatgaaga aactcgaaat tgaattggaa ctcaaacatt   2340
gtgaaaatat taccaaacag gtagaaatag ctgtgcaaaa tgctcatcag cgatggctgg   2400
gagaactacc agagctggca gagtatcaag cacttgtgaa ggcagaacag aaaaagtggg   2460
aagaacagca tgaggtctct gtgaacaaaa ggatatcatt tgctgtttct gaagctaaag   2520
agaaatggaa gagtgagctt gaaaatatga ggaaaaatat acttcctgga aaggaattgg   2580
aagagaagat tcattctctt cagaaggaac ttgagttaaa gaacgaagaa gtccctgtgg   2640
tcatcagggc tgagttagct aaggctcgga gtgaatggaa caaagaaaag caagaagaaa   2700
tccacagaat ccaagaacaa aatgagcaag attaccggca atttttagat gatcaccgaa   2760
ataaaattaa tgaggtgctt gcggcagcta aagaagactt tatgaaacaa aaaactgaac   2820
tacttcttca gaaggagaca gaattacaaa cttgtctaga ccagagtcgt agagaatgga   2880
ctatgcagga agccaagcgg atccaactgg aaatctatca gtatgaggaa gacatcctga   2940
ctgtacttgg ggttctttta agtgataccc aaaaggagca catcagtgat tctgaggaca   3000
agcagctttt ggaaatcatg tcgacttgtt cttcaaaatg gatgtctgtg caatattttg   3060
aaaaactaaa gggctgcata cagaaagcat ttcaagatac acttcctctg cttgtagaaa   3120
```

-continued acgctgaccc agaatggaaa aagagaaata tggccgagct ctctaaggat tctgccagcc 3180
agggcactgg ccaaggagac cctggacctg ctgctggaca ccatgctcag cccttggcct 3240
tacaagcaac agaagcagaa gctgataaga aaaaggtcct tgaaattaag gatttatgct 3300
gtggacactg cttccaagaa cttgaaaagg caaagcagga atgtcaagat ctgaaaggaa 3360
aactggagaa atgctgtagg catcttcagc atttagaaag gaagcacaaa gctgtagtgg 3420
aaaaaattgg agaagagaat aataaagttg ttgaagaatt aatagaagaa aacaacgaca 3480
tgaagaataa attggaagaa ttgcaaacac tttgtaaaac accaccaagg tcattgtcag 3540
caggggccat tgaaaatgct tgcctgccat gcagtggggg agccttggaa gaacttcgtg 3600
ggcagtacat taaagctgta aaaaaaatta aatgtgacat gcttcgttat attcaggaga 3660
gtaaggaacg agctgcagaa atggtaaaag cagaggtact gcgagaacgt caagaaaccg 3720
cccgaaagat gcgcaaatat tatttgattt gcctccaaca gattttgcag gatgatggaa 3780
aagaaggggc tgagaaaaag attatgaatg ctgctagcaa acttgctaca atggcaaaat 3840
tactggaaac acctatttct agtaagtccc aaagcaaaac tacacagtca ggtatgtcaa 3900
agtgagtcgc caaatggttt ttctatcttt tcttctttag ctatttaata ttttcagtat 3960
gaagaaggca gggaaggtaa ggagtgagag ttaatttgtg aagttttgta tgttttactt 4020
aaactagaag tttacgcaaa aagagtacac agtttccaat ttaagtaggc agactgagca 4080
tgcccatcag tttcctattg ctgcttccat ccctcgaaat gatagaaaag attttaaaca 4140
gcaaataaag aatgagaaaa agaagaaatt ataagtgggt tttaaaaagt tgcagtgggc 4200
caggcatcat ggctcacacc tgtaatccca gcactttggg aggctgaggt gggaggatcc 4260
cttgatccca ggaatttgag gttgcagtaa gctatgattg tgccactgta ctccagcctg 4320
ggtgacagag tgaggccctg tctc 4344

<210> SEQ ID NO 24
<211> LENGTH: 552
<212> TYPE: DNA
<213> ORGANISM: Human

<400> SEQUENCE: 24
ctcatatttc acacagatga gttggcgagg aagatcgacc tattattggt ctaggccaat 60
aataggtcga tcttcctcgc caactcatat ttcacacaga tgaatctcag tagaggaaaa 120
tcgacctatt attggcctag accaaggcgc tatgtacagc ctcctgaagt gattgggcct 180
atgcggcccg agcagttcag tgatgaagtg gaaccagcaa cacctgaaga aggggaacca 240
gcaactcaac gtcaggatcc tgcagctgct caggagggag aggatgaggg agcatctgca 300
ggtcaagggc cgaagcctga agctgatagc caggaacagg gtcacccaca gactgggtgt 360
gagtgtgaag atggtcctga tgggcaggag atggacccgc caaatccaga ggaggtgaaa 420
acgcctgaag aaggtgaaaa gcaatcacag tgttaaaaga aggcacgttg aaatgatgca 480
ggctgctcct atgttggaaa tttgttcatt aaaattctcc caataaagct ttacagcctt 540
ctgcaaagaa aa 552

<210> SEQ ID NO 25
<211> LENGTH: 2899
<212> TYPE: DNA
<213> ORGANISM: Human

<400> SEQUENCE: 25
aaaaaaaaaa gtacgcggac aagatggcgg cggcagcagt cgacagcgcg atggaggtgg 60

-continued

```
tgccggcgct ggcggaggag gccgcgccgg aggtagcggg cctcagctgc ctcgtcaacc    120
tgccgggtga ggtgctggag tacatcctgt gctgcggctc gctgacggcc gccgacatcg    180
gccgtgtctc cagcacctgc cggcggctgc gcgagctgtg ccagagcagc gggaaggtgt    240
ggaaggagca gttccgggtg aggtggcctt cccttatgaa acactacagc cccaccgact    300
acgtcaattg gttggaagag tataaagttc ggcaaaaagc tgggttagaa gcgcggaaga    360
ttgtagcctc gttctcaaag aggttctttt cagagcacgt tccttgtaat ggcttcagtg    420
acattgagaa ccttgaagga ccagagattt tttttgagga tgaactggtg tgtatcctaa    480
atatggaagg aagaaaagct ttgacctgga aatactacgc aaaaaaaatt ctttactacc    540
tgcggcaaca gaagatctta aataatctta aggcctttct tcagcagcca gatgactatg    600
agtcgtatct tgaaggtgct gtatatattg accagtactg caatcctctc tccgacatca    660
gcctcaaaga catccaggcc caaattgaca gcatcgtgga gcttgtttgc aaaacccttc    720
ggggcataaa cagtcgccac cccagcttgg ccttcaaggc aggtgaatca tccatgataa    780
tggaaataga actccagagc caggtgctgg atgccatgaa ctatgtcctt tacgaccaac    840
tgaagttcaa ggggaatcga atggattact ataatgccct caacttatat atgcatcagg    900
ttttgattcg cagaacagga atcccaatca gcatgtctct gctctatttg acaattgctc    960
ggcagttggg agtcccactg gagcctgtca acttcccaag tcacttctta ttaaggtggt   1020
gccaaggcgc agaaggggcg accctggaca tctttgacta catctacata gatgcttttg   1080
ggaaaggcaa gcagctgaca gtgaaagaat gcgagtactt gatcggccag cacgtgactg   1140
cagcactgta tggggtggtc aatgtcaaga aggtgttaca gagaatggtg ggaaacctgt   1200
taagcctggg gaagcgggaa ggcatcgacc agtcatacca gctcctgaga gactcgctgg   1260
atctctatct ggcaatgtac ccggaccagg tgcagcttct cctcctccaa gccaggcttt   1320
acttccacct gggaatctgg ccagagaagg tgcttgacat cctccagcac atccaaaccc   1380
tagacccggg gcagcacggg gcggtgggct acctggtgca gcacactcta gagcacattg   1440
agcgcaaaaa ggaggaggtg ggcgtagagg tgaagctgcg ctccgatgag aagcacagag   1500
atgtctgcta ctccatcggg ctcattatga agcataagag gtatggctat aactgtgtga   1560
tctacggctg ggaccccacc tgcatgatgg gacacgagtg gatccggaac atgaacgtcc   1620
acagcctgcc gcacggccac caccagcctt tctataacgt gctggtggag gacggctcct   1680
gtcgatacgc agcccaagaa aacttggaat ataacgtgga gcctcaagaa atctcacacc   1740
ctgacgtggg acgctatttc tcagagttta ctggcactca ctacatccca aacgcagagc   1800
tggagatccg gtatccagaa gatctggagt ttgtctatga aacggtgcag aatatttaca   1860
gtgcaaagaa agagaacata gatgagtaaa gtctagagag gacattgcac ctttgctgct   1920
gctgctatct tccaagagaa cgagactccg gaagaagacg tctccacgga gccctcggga   1980
cctgctgcac caggaaagcc actccaccag tagtgctggt tgcctcctac taagtttaaa   2040
taccgtgtgc tcttccccag ctgcaaagac aatgttgctc tccgcctaca ctagtgaatt   2100
aatctgaaag gcactgtgtc agtggcatgg cttgtatgct tgtcctgtgg tgacagtttg   2160
tgacattctg tcttcatgag gtctcacagt cgacgctcct gtaatcattc tttgtattca   2220
ctccattccc ctgtctgtct gcatttgtct cagaacattt ccttggctgg acagatgggg   2280
ttatgcattt gcaataattt ccttctgatt tctctgtgga acgtgttcgg tcccgagtga   2340
ggactgtgtg tctttttacc ctgaagttag ttgcatattc agaggtaaag ttgtgtgcta   2400
tcttggcagc atcttagaga tggagacatt aacaagctaa tggtaattag aatcatttga   2460
```

-continued atttattttt ttctaatatg tgaaacacag atttcaagtg ttttatcttt ttttttttaa 2520
atttaaatgg gaatataaca cagttttccc ttccatattc ctctcttgag tttatgcaca 2580
tctctataaa tcattagttt tctattttat tacataaaat tcttttagaa aatgcaaata 2640
gtgaactttg tgaatggatt tttccatact catctacaat tcctccattt taaatgacta 2700
cttttatttt ttaatttaaa aaatctactt cagtatcatg agtaggtctt acatcagtga 2760
tgggttcttt ttgtagtgag acatacaaat ctgatgttaa tgtttgctct tagaagtcat 2820
actccatggt cttcaaagac caaaaaaatg aggttttgct tttgtaatca ggaaaaaaaa 2880
aaattaatga accttaaag 2899

<210> SEQ ID NO 26
<211> LENGTH: 2289
<212> TYPE: DNA
<213> ORGANISM: Human

<400> SEQUENCE: 26
ttgtaccctt aaaattattt tttcctatgc agaattgact ttgattaaaa aatgtttttg 60
atgactattt tcctgattcg tcagtatatc taattgtgtt catattactc atgaaaaatc 120
ttgtctatga gggacgtatt tttagtaaca tttttatagc atataagaac ttttacagca 180
aaaacaggaa tcattaagtg tgtgtgcttt tatcataact tctcttttaa tggaacttaa 240
aatcttaact cgtgtttttg cagcactttt tttgcacatg gtaggttctt aatatttgaa 300
tggaattcag tgtgactgtt ctttgtgttc tcaaaagtct gatctttgta acaatttgtc 360
tttcacttga gacttttttt ttctttgcat atgtgcacgt ctcactcttg gttttcctta 420 atcttttta actaaacaca tctatgactc atatttccct atttatgaat aggagcaatt 480
taaaatttcc caacatggtg gtatgtgatg taacataacc aaaggctaca tgtttaccct 540
tgtttaatta cccttcattt gtggaaagat gacgtatgta tttatgatgt aaatgtcttt 600
cagaatgacc tttgggacta agcttttttt tttttttcc caccaaaaaa tggtcatgac 660
ctaggaagcc ttgttagtaa aatttaaaaa ggaaaagttg gctgggcatg gtggctcatg 720
cctgtaatct caacactctg ggaggccgag gtgggtgtat caattgaggt cagagttcga 780
gaccagcctg ggtaacatgg tgaaaccccg tctctactaa aaatacaaaa attagctggg 840
catggtggcc tgtgcctgtg atcccagcta ctcgggaagc agagacatga gaattgcttg 900
aacctaggag gtggaggttg cagtgagtgg agattgtgcc actgcacgcc aacctgggtg 960
acagagcgag acttcatctc aaaaataaaa taaaataaaa ataaacagga aaaatctggt 1020
caaatgcccc ttgttcttct tcaacagata catagtgagt tgtgtaaaaa aggagttgga 1080
aaaggaatat gtagattcaa agtgacttaa agaatagaaa aaaaatttgt tttaaaaaat 1140
ggccaagact aaatcatagt gtctagggag gtacacctga ataataaaac tataaagaaa 1200
tacaaaatat ggttactact aagaatagtc tgttgccagt agtacacaga atgagcactc 1260
aaattataac agaagcattt tggtattcat aaatgttctt tttttaaaaa agaacacaat 1320
cgaaattata ggctgtaagt actgatttta attgtagtga atgtgaaagt gttgttaatg 1380
aaaatataaa gaatatttgt taaagtgtgg acctagccag gaatactagg tagaaaaggt 1440
aactctttaa aaacattttt ttaattgtga agttaattta ttgtcacttt gtttgatatt 1500
tattattaga gtccctaggt taattctgtt tttattgctt ttcagaataa ttaagaccta 1560
aatcttctgc cgaattctgt ttggtttcct tatttctttt gccatgttct ttcattccac 1620
aaatgttatt gagcacttcc agtgtaccaa gccttgtgtt tactgctttg atgataaatg 1680

```
caataaggta atgctgcttt taaggatcct tcaggatagg ctcttgtagc agtaaggact   1740
tagtattttt gctatagaag tgtatggaga gctatctatg gtgcaataac tgtggaaata   1800
cagtttttat tctatttggt tcccatatac attgagtcct cctttggtgg gaatttgatc   1860
aggttggtct cagttgaatc ctggctgcat atgcctcagt aaggaagaag gcctagggga   1920
ctgtggaaag cctggtggtg gtcctggaag gcttgagaat acctggagct ggaagctcct   1980
tgctcattgg tgaccttttt catatgcagc agagctcttg gcattcctag catactacct   2040
tgaaaggact gtgtcttgcc tcctagaaat tctggacttg gtagaatcat ttgtttatgt   2100
tattttaaaa agaaaaaaaa ctctgaaatg tactttttgg aagaaaaatg aacttgtttt   2160
tggactttc tgtgtgttgt ttctttaatt gaaaattctg tctggagatt gattttcaac   2220
ccccttcctt tccctctagt tttaaattgt aacattgctt tccaagcatt tcaaaaaaaa   2280
aaaaaaaaa                                                           2289
```

<210> SEQ ID NO 27
<211> LENGTH: 1694
<212> TYPE: DNA
<213> ORGANISM: Human

<400> SEQUENCE: 27

```
atgccatggc tagtccaggg aaagataact atagaatgaa aagttataag aataaagccc     60
taaatcctca agagatgcgt agacgaagag aagaagaagg aatacagctt agaaaacaaa    120
aaagagaaga acagttgttc aaacgcagaa atgtctattt gcccagaaat gatgaatcta    180
tgcttgaaag tcctatacag gattcagata ttagttccac tgtacccatt ccagaggaag    240
gagttgttac tacagatatg gttcaaatga ttttttctaa taatgctgat caacagctaa    300
cagcaacaca gaaatttaga aagctgcttt ctaaagaacc taatccacca atagatcaag    360
ttatacagaa accaggagtt gtacagagat ttgtgaaatt tcttgaaaga aatgaaaatt    420
gcactttaca atttgaagct gcatgggcat taacaaatat agcatctgga actttctgc    480
ataccaaggt agtgattgaa actggggctg ttccgatttt tatcaaactt cttaattctg    540
aacatgaaga tgttcaggaa caggctgttt gggcacttgg taatattgct ggtgacaatg    600
cagaatgcag agattttgtt ttgaattgtg aaatacttcc acctctttta gagttattaa    660
caaattcaaa cagactcaca acaacaagaa atgccgtgtg ggccctctca aatttatgta    720
gaggcaaaaa ccctcctcca aactttagta aggtttcacc ttgcttaaat gtcctgtcac    780
gactgttgtt tagcagtgac ccagatgtgt tagcagacgt gtgttgggcc ctttcttatc    840
tttccgatgg acccaatgat aaaattcaag cagtcattga ttctggagtc tgtcgaagat    900
tggtggaact tttgatgcac aatgattata aagttgtatc acctgcatta agggcagttg    960
gtaatattgt gactggtgat gatattcaaa cacaggtaat tttgaattgt tctgcattac   1020
cctgtctctt acatttattg agtagcccaa aggagtcaat tagaaaagaa gcctgctgga   1080
ctgtttctaa catcactgct ggaaatagag ctcagattca ggctgttata gatgcaaata   1140
tttttcctgt tttgattgag attcttcaga aagcagagtt tcgtaccaga aaagaagcag   1200
cttgggctat aactaatgca acatcaggag gtactccaga gcaaataagg tatttggtag   1260
ctttaggctg cattaaacca ctttgtgatc ttttgactgt tatggactcc aaaatagtcc   1320
aagtggcttt aaatggactt gaaaatattt tacgtcttgg agaacaagaa tctaagcaga   1380
atggaatagg cattaatcca tactgtgctc tcattgaaga agcatatggt ctggataaaa   1440
ttgagttttt gcaaagccat gaaaatcagg aaatttacca gaaggcattt gatctgattg   1500
```

-continued aacattactt tggtgtagaa gaagatgacc ccagcattgt acctcaggtg gatgaaaacc 1560
aacaacagtt tatatttcag cagcaggaag caccaatgga tggatttcaa ctttaactta 1620
ctggaggaaa aaaaatttat ggctaaaaag ggtagcttca ggtaactcct ctttgttgcc 1680
aatgtaagga actg 1694

<210> SEQ ID NO 28
<211> LENGTH: 4756
<212> TYPE: DNA
<213> ORGANISM: Human

<400> SEQUENCE: 28
gcgacgctca cgaacgatca gagctgcggg cgacgcaacg aagcccggag gccgcaggct 60
gcgcgctccc tcgcagcagc cgggcgggca aaagccccca gtcctcggcc cccgcgcaag 120
cgacgccggg aaatgcccac atccgggaaa cctgcagcgg agtgcggcgg cggcgacact 180
gagtggaagg caaaatggcg gcggcggcgg cggtggcctg gtgttaaggg gagagccagg 240
tccttacgac ccctgggacg ggccgcgctg gcccgcggca gcccccccgt tcgtctcccc 300
gctctgcccc accagggata cttggggttg ctgggacgga ctctggccgc ctcagcgtcc 360
gccctcaggc ccgtggccgc tgtccaggag ctctgctctc ccctccagag ttaattattt 420
atattgtaaa gaattttaac agtcctgggg acttccttga aggatcattt tcacttttgc 480
tcagaagaaa gctctggatc tatcaaataa agaagtcctt cgtgtgggct acatatatag 540
atgttttcat gaagaggagt gaaaagccag aaggatatag acaaatgagg cctaagacct 600
ttcctgccag taactatact gtcagtagcc ggcaaatgtt acaagaaatt cgggaatccc 660
ttaggaattt atctaaacca tctgatgctg ctaaggctga gcataacatg agtaaaatgt 720
caaccgaaga tcctcgacaa gtcagaaatc cacccaaatt tgggacgcat cataaagcct 780
tgcaggaaat tcgaaactct ctgcttccat ttgcaaatga aacaaattct tctcggagta 840
cttcagaagt taatccacaa atgcttcaag acttgcaagc tgctggattt gatgaggata 900
tggttataca agctcttcag aaaactaaca acagaagtat agaagcagca attgaattca 960
ttagtaaaat gagttaccaa gatcctcgac gagagcagat ggctgcagca gctgccagac 1020
ctattaatgc cagcatgaaa ccagggaatg tgcagcaatc agttaaccgc aaacagagct 1080
ggaaaggttc taaagaatcc ttagttcctc agaggcatgg cccgccacta ggagaaagtg 1140
tggcctatca ttctgagagt cccaactcac agacagatgt aggaagacct ttgtctggat 1200
ctggtatatc agcatttgtt caagctcacc ctagcaacgg acagagagtg aacccccac 1260 caccacctca agtaaggagt gttactcctc caccacctcc aagaggccag actccccctc 1320
caagaggtac aactccacct ccccccttcat gggaaccaaa ctctcaaaca aagcgctatt 1380
ctggaaacat ggaatacgta atctcccgaa tctctcctgt cccacctggg gcatggcaag 1440
agggctatcc tccaccacct ctcaacactt cccccatgaa tcctcctaat caaggacaga 1500
gaggcattag ttctgttcct gttggcagac aaccaatcat catgcagagt tctagcaaat 1560
ttaactttcc atcagggaga cctggaatgc agaatggtac tggacaaact gatttcatga 1620
tacaccaaaa tgttgtccct gctggcactg tgaatcggca gccaccacct cccatatcctc 1680 tgacagcagc taatggacaa agcccttctg ctttacaaac agggggatct gctgctcctt 1740
cgtcatatac aaatggaagt attcctcagt ctatgatggt gccaaacaga aatagtcata 1800
acatggaact atataacatt agtgtacctg gactgcaaac aaattggcct cagtcatctt 1860
ctgctccagc ccagtcatcc ccgagcagtg ggcatgaaat ccctacatgg caacctaaca 1920

-continued

```
taccagtgag gtcaaattct tttaataacc cattaggaaa tagagcaagt cactctgcta   1980
attctcagcc ttctgctaca acagtcactg caattacacc agctcctatt caacagcctg   2040
tgaaaagtat gcgtgtatta aaaccagagc tacagactgc tttagcacct acacaccctt   2100
cttggatacc acagccaatt caaactgttc aacccagtcc ttttcctgag ggaaccgctt   2160
caaatgtgac tgtgatgcca cctgttgctg aagctccaaa ctatcaagga ccaccaccac   2220
cctacccaaa acatctgctg caccaaaacc catctgttcc tccatacgag tcaatcagta   2280
agcctagcaa agaggatcag ccaagcttgc ccaaggaaga tgagagtgaa aagagttatg   2340
aaaatgttga tagtggggat aaagaaaaga aacagattac aacttcacct attactgtta   2400
ggaaaaacaa gaaagatgaa gagcgaaggg aatctcgtat tcaaagttat tctcctcaag   2460
catttaaatt ctttatggag caacatgtag aaaatgtact caaatctcat cagcagcgtc   2520
tacatcgtaa aaaacaatta gagaatgaaa tgatgcgggt tggattatct caagatgccc   2580
aggatcaaat gagaaagatg ctttgccaaa aagaatctaa ttacatccgt cttaaaaggg   2640
ctaaaatgga caagtctatg tttgtgaaga taaagacact aggaatagga gcatttggtg   2700
aagtctgtct agcaagaaaa gtagatacta aggctttgta tgcaacaaaa actcttcgaa   2760
agaaagatgt tcttcttcga aatcaagtcg ctcatgttaa ggctgagaga gatatcctgg   2820
ctgaagctga caatgaatgg gtagttcgtc tatattattc attccaagat aaggacaatt   2880
tatactttgt aatggactac attcctgggg gtgatatgat gagcctatta attagaatgg   2940
gcatctttcc agaaagtctg gcacgattct acatagcaga acttacctgt gcagttgaaa   3000
gtgttcataa aatgggtttt attcatagag atattaaacc tgataatatt ttgattgatc   3060
gtgatggtca tattaaattg actgactttg gcctctgcac tggcttcaga tggacacacg   3120
attctaagta ctatcagagt ggtgaccatc cacggcaaga tagcatggat ttcagtaatg   3180
aatgggggga tccctcaagc tgtcgatgtg gagacagact gaagccatta gagcggagag   3240
ctgcacgcca gcaccagcga tgtctagcac attctttggt tgggactccc aattatattg   3300
cacctgaagt gttgctacga acaggataca cacagttgtg tgattggtgg agtgttggtg   3360
ttattctttt tgaaatgttg gtgggacaac ctcctttctt ggcacaaaca ccattagaaa   3420
cacaaatgaa ggttatcaac tggcaaacat ctcttcacat tccaccacaa gctaaactca   3480
gtcctgaagc ttctgatctt attattaaac tttgccgagg acccgaagat cgcttaggca   3540
agaatggtgc tgatgaaata aaagctcatc cattttttaa aacaattgac ttctccagtg   3600
acctgagaca gcagtctgct tcatacattc ctaaaatcac acacccaaca gatacatcaa   3660
attttgatcc tgttgatcct gataaattat ggagtgatga taacgaggaa gaaaatgtaa   3720
atgacactct caatggatgg tataaaaatg gaaagcatcc tgaacatgca ttctatgaat   3780
ttaccttccg aaggtttttt gatgacaatg gctacccata taattatccg aagcctattg   3840
aatatgaata cattaattca caaggctcag agcagcagtc ggatgaagat gatcaaaaca   3900
caggctcaga gattaaaaat cgcgatctag tatatgttta acacactagt aaataaatgt   3960
aatgaggatt tgtaaaaggg cctgaaatgc gaggtgtttt gaggttctga gagtaaaatt   4020
atgcaaatat gacagagcta tatatgtgtg ctctgtgtac aatattttat tttcctaaat   4080
tatgggaaat ccttttaaaa tgttaattta ttccagccgt ttaaatcagt atttagaaaa   4140
aaattgttat aaggaaagta aattatgaac tgaatattat agtcagttct tggtacttaa   4200
agtacttaaa ataagtagtg ctttgtttaa aaggagaaac ctggtatcta tttgtatata   4260
tgctaaataa ttttaaaata caagagtttt tgaaattttt ttgaaagaca gttttagttt   4320
```

```
tatcttgctt taaccaaata tgaaacatac cccctatttt acagagctct tttttcccct   4380

cataaccttg tttttggtag aaaataagct agagaaatta agccatcgtg ttggtgagtg   4440

ttcctaggct aatgataatc tgtataattc acatcctgaa actaaggaat acagggttga   4500

aaaaatatta atatgtttgt cagaaggaaa aataatgcat ttattttccc ccccaccccc   4560

cgccccatgg aatatttaat ctatttaatc ttcttgcatt tatttctcaa gaattactgg   4620

ctttaaaaga agccaaagca ctactagctt tttttccata ttggtatttt tgatgctgct   4680

tccaatttta aaagggaaca aagctgccat aaatcgaaat gttcaatact aaaagctaaa   4740

atatttctca ccatcg                                                   4756
```

<210> SEQ ID NO 29
<211> LENGTH: 2306
<212> TYPE: DNA
<213> ORGANISM: Human

<400> SEQUENCE: 29

```
ggaggcagga gaatcgcttg aaccctggag gcagaggttg cagtaagccg agatcgcgcc     60

acagcactcc agtctgggcg acaaagcgag actccgtctc aaaaaacaaa aacaaaaaca    120

aaaaacaaac aaaaaaccat aaattcacag ttcagtggca attttaaatg gaaagacacg    180

ccttattcac tatgatgctt ttattgctaa ttcattcagt gaagaggaat tatgcaaggt    240

ttaaaatggc ttgcctgtcc tggtatatcc aaaactctta attcagaaga ttcatctatt    300

tctccaagag aagaagctcg tggtggggct ggaggaggtt caggctcaag atcaaagtcc    360

aatttggtta ctgtagaatc gcttatagaa gataaagtaa ctcaccaaaa cagtaataga    420

aagtctgtat tttaaacagc tttaaaatta aagcaaacaa tttacttttt aagtaaacag    480

aacactactt tcaaaatact acttgggaaa aaagcaagac tcagtacacc tgctataatc    540

agtacgtaag aatgtcccaa taactttgta taagagatgc ttaaaatctc agacacatac    600

ctagctggag gtgctagttg agggatgcgt acatcaacca ctggcactgt agtaggcaca    660

ggagcttgag ggctgaaggt gccagaatga tttactgtag gaatagctct tcttactagc    720

cttccccaag tggcaatatt aatattcatt tgaggagctc tgagaaatgt tttgccttgt    780

tgctttgaaa aaattttctt ttgtctttga agttttggtc ttctttcaat aactggatta    840

aaaaaggtaa cctctgcaaa taaagtaccc tgtggttcca aatagagaca catgccatgc    900

cgttggttgt ctaaaaaatc ttctaacctc agaaaatttt acagcacaca gagaccgcca    960

atcacgccaa taaactgaaa tttccagttc acgtgacctg tccagttcca gtgtaaactt   1020

ctggtcccat gactgattgg aaatgggttt ccagctagtt tggccaacca cagtattatc   1080

gagcttcaaa acagcacaga catcattgga caagtcatcg gtttttagaa gatttcgact   1140

acttccgctt ttacttttac tcgttctgct catgaaagat gatctggttt cacttggact   1200

ccaaccaggc agtgcaactg atgttgcttt tgaccgtcca gggacattct ctaggatatc   1260

ttggcagccc ataagacgaa cttccaaagt acctgttagt gctgctggtt tggatagtgt   1320

actatattga ttttgcgtag atatcatact ttgacgtgga cttagtgttg gtgatgcagc   1380

aacaagtgaa agttcttcaa taataatcct gcttttggga tgattcttgg ggacttcgtt   1440

taatctttgc tctaatgaat actttaaaag gtccaacttc tgacttgatt cattaaatct   1500

tgcttgagct tctgaaagtg cttttctgtc tgttactttt cctgagccaa gtaatttcat   1560

tacattcttt gcaccttctg ctactgcaaa ctctatccta aaatgatgcc ttaattcttc   1620

catccgaagt tcaagaggac ttatcacagg ttttgcatta tcaaaagcca attcattagt   1680
```

```
ctggactgcc tgaagaatct gcattcgtat gacttctatt tttgtcttgc tgtcctggag   1740

cagttgctga gctgtaccat ggagtttccg atcctttgaa gatccatttg aatacatctg   1800

tatcatattc tctgcacctt gttttacttt aagttctata tccaattgtt tttgtagggc   1860

cttcaatcta ttggtgctag tagaacaacg agggtcatta tttggagtat ctggagtcct   1920

tgggcaatct gtaatatctt ctggatctga tacaacaata tgtgcattta attcctgcag   1980

cttgtgatgt agttcttcta atttttattt gattttttca aaatgttgtc tacataagcc   2040

aaactttttt tatctgttgt gactttcctc agattttcag ctccttcttt gattttcagt   2100

tctttcctta tttctctctt aattcgatcc ttgatatcat ccaatttctg ctgcaccatt   2160

gtatctgaaa agtctaattt ttgaacagca ctcacattct cagaaaacgg aagacttcgg   2220

gaatccccct gcagttccgt gagcagaatc tccccccgtt cggggttgga cgccattgcg   2280

ctccggtatg gactccgcac ctggac                                        2306
```

<210> SEQ ID NO 30
<211> LENGTH: 1842
<212> TYPE: DNA
<213> ORGANISM: Human

<400> SEQUENCE: 30

```
ccacagtggc gccggcagag caggagtggc tggaggagct gtggttggag caggaggtgg     60

cacggcaggg ctggagggct ccctatgagt ggcggagacg gcccaggagg cgctggagca    120

acagctccca caccgcacca agcggtggct gcaggagctc gcccatcgcc cctgcgctgc    180

tcggaccgcg gccacagccg gactggcggg tacggcggcg acagacggat tggccgagag    240

tcccagtccg cagagtagcc ccggcctcga ggcggtggcg tcccggtcct ctccgtccag    300

gagccaggac aggtgtcgcg cggcggggct ccagggaccg cgcctgaggc cggctgcccg    360

cccgtcccgc cccgccccgc cgcccgccgc ccgccgagcc cagcctcctt gccgtcgggg    420

cgtccccagg ccctgggtcg gccgcggagc cgatgcgcgc ccgctgagcg ccccagctga    480

gcgcccccgg cctgccatga ccgcgctccc cggcccgctc tggctcctgg gcctggcgct    540

atgcgcgctg ggcgggggcg gccccggcct gcgacccccg cccggctgtc cccagcgacg    600

tctgggcgcg cgcgagcgcc gggacgtgca gcgcgagatc ctggcggtgc tcgggctgcc    660

tgggcggccc cggccccgcg cgccacccgc cgcctcccgg ctgcccgcgt ccgcgccgct    720

cttcatgctg gacctgtacc acgccatggc cggcgacgac gacgaggacg gcgcgcccgc    780

ggagcggcgc ctgggccgcg ccgacctggt catgagcttc gttaacatgg tggagcgaga    840

ccgtgccctg ggccaccagg agccccattg gaaggagttc cgctttgacc tgacccagat    900

cccggctggg gaggcggtca cagctgcgga gttccggatt tacaaggtgc ccagcatcca    960

cctgctcaac aggaccctcc acgtcagcat gttccaggtg gtccaggagc agtccaacag   1020

ggagtctgac ttgttctttt tggatcttca gacgctccga gctggagacg agggctggct   1080

ggtgctggat gtcacagcag ccagtgactg ctggttgctg aagcgtcaca aggacctggg   1140

actccgcctc tatgtggaga ctgaggacgg gcacagcgtg gatcctggcc tggccggcct   1200

gctgggtcaa cgggccccac gctcccaaca gcctttcgtg gtcactttct tcagggccag   1260

tccgagtccc atccgcaccc ctcgggcagt gaggccactg aggaggaggc agccgaagaa   1320

aagcaacgag ctgccgcagg ccaaccgact cccagggatc tttgatgacg tccacggctc   1380

ccacggccgg caggtctgcc gtcggcacga gctctacgtc agcttccagg acctcggctg   1440

gctggactgg gtcatcgctc cccaaggcta ctcggcctat tactgtgagg gggagtgctc   1500
```

```
cttcccactg gactcctgca tgaatgccac caaccacgcc atcctgcagt ccctggtgca   1560
cctgatgaag ccaaacgcag tccccaaggc gtgctgtgca cccaccaagc tgagcgccac   1620
ctctgtgctc tactatgaca gcagcaacaa cgtcatcctg cgcaagcacc gcaacatggt   1680
ggtcaaggcc tgcggctgcc actgagtcag cccgcccagc cctactgcag ccacccttct   1740
catctggatc gggccctgca gaggcagaaa acccttaaat gctgtcacag ctcaagcagg   1800
agtgtcaggg gccctcactc tctgtgccta cttcctgtca gg                      1842
```

<210> SEQ ID NO 31
<211> LENGTH: 2524
<212> TYPE: DNA
<213> ORGANISM: Human

<400> SEQUENCE: 31

```
attggctgaa ggcacttccg ttgagcatct agacgtttcc ttggctcttc tggcgccaaa     60
atgtcgttcg tggcaggggt tattcggcgg ctggacgaga cagtggtgaa ccgcatcgcg    120
gcgggggaag ttatccagcg gccagctaat gctatcaaag agatgattga gaactgttta    180
gatgcaaaat ccacaagtat tcaagtgatt gttaaagagg gaggcctgaa gttgattcag    240
atccaagaca atggcaccgg gatcaggaaa gaagatctgg atattgtatg tgaaaggttc    300
actactagta aactgcagtc ctttgaggat ttagccagta tttctaccta tggctttcga    360
ggtgaggctt tggccagcat aagccatgtg gctcatgtta ctattacaac gaaaacagct    420
gatggaaagt gtgcatacag agcaagttac tcagatggaa aactgaaagc ccctcctaaa    480
ccatgtgctg gcaatcaagg gacccagatc acggtggagg accttttta caacatagcc     540
acgaggagaa aagctttaaa aaatccaagt gaagaatatg ggaaaatttt ggaagttgtt    600
ggcaggtatt cagtacacaa tgcaggcatt agtttctcag ttaaaaaaca aggagagaca    660
gtagctgatg ttaggacact acccaatgcc tcaaccgtgg acaatattcg ctccatcttt    720
ggaaatgctg ttagtcgaga actgatagaa attggatgtg aggataaaac cctagccttc    780
aaaatgaatg gttacatatc caatgcaaac tactcagtga agaagtgcat cttcttactc    840
ttcatcaacc atcgtctggt agaatcaact tccttgagaa aagccataga aacagtgtat    900
gcagcctatt tgcccaaaaa cacacaccca ttcctgtacc tcagtttaga aatcagtccc    960
cagaatgtgg atgttaatgt gcaccccaca aagcatgaag ttcacttcct gcacgaggag   1020
agcatcctgg agcgggtgca gcagcacatc gagagcaagc tcctgggctc caattcctcc   1080
aggatgtact tcacccagac tttgctacca ggacttgctg gcccctctgg ggagatggtt   1140
aaatccacaa caagtctgac ctcgtcttct acttctggaa gtagtgataa ggtctatgcc   1200
caccagatgg ttcgtacaga ttcccgggaa cagaagcttg atgcatttct gcagcctctg   1260
agcaaacccc tgtccagtca gccccaggcc attgtcacag aggataagac agatatttct   1320
agtggcaggg ctaggcagca agatgaggag atgcttgaac tcccagcccc tgctgaagtg   1380
gctgccaaaa atcagagctt ggagggggat acaacaaagg ggacttcaga aatgtcagag   1440
aagagaggac ctacttccag caaccccaga aagagacatc gggaagattc tgatgtggaa   1500
atggtggaag atgattcccg aaaggaaatg actgcagctt gtaccccccg gagaaggatc   1560
attaacctca ctagtgtttt gagtctccag gaagaaatta atgagcaggg acatgaggtt   1620
ctccgggaga tgttgcataa ccactccttc gtgggctgtg tgaatcctca gtgggccttg   1680
gcacagcatc aaaccaagtt ataccttctc aacaccacca agcttagtga agaactgttc   1740
taccagatac tcatttatga ttttgccaat tttggtgttc tcaggttatc ggagccagca   1800
```

```
ccgctctttg accttgccat gcttgcctta gatagtccag agagtggctg gacagaggaa   1860

gatggtccca aagaaggact tgctgaatac attgttgagt ttctgaagaa gaaggctgag   1920

atgcttgcag actatttctc tttggaaatt gatgaggaag ggaacctgat tggattaccc   1980

cttctgattg acaactatgt gcccccttg gagggactgc ctatcttcat tcttcgacta   2040

gccactgagg tgaattggga cgaagaaaag gaatgttttg aaagcctcag taaagaatgc   2100

gctatgttct attccatccg gaagcagtac atatctgagg agtcgaccct ctcaggccag   2160

cagagtgaag tgcctggctc cattccaaac tcctggaagt ggactgtgga acacattgtc   2220

tataaagcct tgcgctcaca cattctgcct cctaaacatt tcacagaaga tggaaatatc   2280

ctgcagcttg ctaacctgcc tgatctatac aaagtctttg agaggtgtta aatatggtta   2340

tttatgcact gtgggatgtg ttcttctttc tctgtattcc gatacaaagt gttgtatcaa   2400

agtgtgatat acaaagtgta ccaacataag tgttggtagc acttaagact tatacttgcc   2460

ttctgatagt attcctttat acacagtgga ttgattataa ataaatagat gtgtcttaac   2520

ataa                                                                2524
```

<210> SEQ ID NO 32
<211> LENGTH: 158980
<212> TYPE: DNA
<213> ORGANISM: Human

<400> SEQUENCE: 32

```
gatcagtcta aagagaattg gcaatatcta cacctgtaaa gtgtaaaatt aggaaaacaa     60

ctcaaaattg ttataaatgt acaataaata ctgctcattc aataacggct aacaacagac    120

tcattgttga aactgcaagt gttgaggatt ttagtaactt gattatgtaa atgagataaa    180

gccttgttta tagatataca aatttaacag gtaattatta atgttttgtt gtatatatga    240

gtgtgctcct gtgtgatgta aaaacagaga catgtttgag aaactatgaa taccttgtac    300

aaacaattta gttgctttat cttagaattt tttgttttac tgtgccttct ttcggctcaa    360

aaggaattat tgcctaagtc agtgattatc tgggcaacag aattaatgtt ctagctacag    420

cattgcacta tttcacagga tctattgatt actttttaaa aatttttctc atctgtcctg    480

ttctcattat tctactatta ttattttagt ttgggcctta tttaacaatt aactaaataa    540

ttacatttgc ccccaaatgg tatccctgcc atctatattc tctctctctc cctctccact    600

catcacctgt ctaccaatat atttattgtc tactactttc catgttcctc attaatttct    660

ggtattagta aactgatacc aaatgttgcc tcccttaaga aactgacagc ctagtccggt    720

ttactactgt tccgtagaac cttgcatctt tcttctttaa aaatctttaa cacctttcag    780

tggcttttag aaaagggttc acatttttca gagcttttga cactctttac cttttgacac    840

aatatattat tattatttgg gggaacagca ggaaccaggg atgattaatt tcctacaatg    900

tgcagggcag ttctatataa caaaattatt tgtcccacat tttacatgac tttcaaatgc    960

cccacaaaat gttcaaagac atgagaatct catctgaact cagagctcaa ctctgttttt   1020

ttataatgta caaagctttg attttattta ttttttggaa aagctttgat tttatttatt   1080

ttttggaatc attttaatat gcactgattt tgatgctaat ttcaacccac ctaattcctt   1140

gcccaactga tagatccatc ttctattttt aaactttagg aagtagaata ggtcagtgaa   1200

gagcattgtg ataaaaaccc agggtattcc cacactgttg ccctctgaac aattttttag   1260

gatgtgagtg tgtgtgtgtg tttgtgcatg tgtgtgtgtg aaggcgactt tcgcttggat   1320

aggatgccac tccataaaac agttagagaa taaaataaaa agagtacagt tggagtcctg   1380
```

-continued

```
ttcttgctct gcttacccccc attatcttgt gacacacagt acctgttcca aatccccact   1440
cagaattctt aacccagtat ctcaggagta aattctggca ctaaaggggt tctttccttc   1500
tgaggagcta agaaaaacag atggagaaaa tctgacctca agcagatgtg tctctgcccc   1560
tcattctcca aattcttggg agagtgttac tcagtcttac tgcacagtga cattatcaat   1620
ggaactttaa gaaatactaa tgcctaggtc tcattctaat ggcttctgat ttaattgctt   1680
tagggtatgc cctggtgatt ctgaaatggt tctctcacaa cctaggacta gggacttata   1740
atctaaggtg tatgtcctcc aaatgctgat tctacatagg gcagtaaaga gtggaaagtg   1800
aagacttgac ctgtgatttt ggtggtgggg aagagaaagg ctattttggt atttctggct   1860
ctttatctta agagtcatca atcctctact tgcactgtca gacacattgg gctgacacat   1920
tcgaaaatac acattgcctg accgtgtggc tgatactcct agagaagcgg tttctaaatt   1980
ttatagccca ttggaatcac ttggacatct ttaacaaaca ctgatacccg gctcctactc   2040
ctagacatgc cgatttaatt tctatggagt ggcacctggc tttaggattt ttaaaaagtt   2100
gtgcagcttg ttctaatgag cagcaaagat tgggacccag tcccagtgaa aaaaagctcg   2160
tagaacaata caacaggaca tttaaggagc acagccattt caaaacaata ttctgttaaa   2220
aattatagat gtccatatag ctgaaatagt aagacagatt gtgaatttaa aactagggaa   2280
gatatttgaa agattaaaaa aaggagtgga tagccaaatt cataccatat acacatatga   2340
aggtttccag gtcagaagac caacaaagaa tctaaagtaa gacagacatt aggtttttca   2400
acagtaaata ctatatgcaa gaagatgaca aagggatatt ttataagttc tgaaggaaaa   2460
taatttaaaa tatagaattt cccatcaagc caaacagtct tcaaatatgt cagcataagg   2520
aaaggttttg gaagcataga aagtcccaag aggtttgcca tgcagaaact cacatagaca   2580
acagttttgg ataaagtcag aggaaagaaa aatccaagag atgctgcaaa agatatctgt   2640
ataaaaggtg attgaatata ttggcaaagt ttgttcttgt cttggccatt tatttaaagt   2700
caaataaaaa gaggaaaaat attcataata atccacaatt aaaagtctgg aaaaaaaaag   2760
tcatggggat ttttgtggag aactaaggaa cttaagaatt ggccaatttc ttgccttaat   2820
agggagtaac ttttttttta ggagacagca ttaaaaagaa atagaaaagg taaacataaa   2880
caaaaaataa gttaaggttg gagaaacatg tccaagtata ccagtaataa tgattaatgt   2940
aagtagacta gattcaccaa tgtaaagtcc aatattgaaa aactgagtat taaaaaaagc   3000
cagatacata ttgtttaaaa agtatgtgga cttcacttgt gcccaacatg gagcaacaga   3060
aaccagattt acccttatat ctgaaacaac tgagaaactg ggtaaatata ggaaagaaca   3120
gctttcaagg cattggcatc aagcaacaca gaaccgtgat ccctggcaga cagcaaacaa   3180
atgaggtgag ccctctgatt ttactcaaga gaatttccag gccatcagaa ggggaaaccc   3240
aagtggagac cagtggactc cctgagtgaa ggagatgaag ctaagaatac aggaagaaga   3300
atgcagctaa ggttaacatg gcaactcaag caccaaagga gagagagcca cacagagata   3360
aaactctgga caactacaga aaaattgccc tttaatattc agcaaattac tgatcagtgc   3420
atgtatttga aggaaaaaac ctcaatcata attgagggat caattatcaa ctacccaaaa   3480
tgattaaagg aaacaggact cagcactcac ccagaatggg ggaaagtgct tgttccccac   3540
gaggcagact ggtaaaccat acaattcaca gggctttggg taagggatct tgtcttggca   3600
gtggggagta attaacccta gaccaaacat ggtgctgttc ttgcttaata agtcttaaaa   3660
gcaggacacc aaatggtcaa actgtttcaa gtaacttaac tgcatttcaa aaaaactcat   3720
gatactttta gaatacaaaa tattcaacat ccaacaaggt agaattaacg attcctggct   3780
```

-continued

```
tctaatagca tgaacccagg aggcagagct tgcagtgagc agagattgcg ccactgcact   3840
ccagcctgga caacagagtg agactccatc tcaaaaaaaa aaaaaaaatc agttcatcaa   3900
aattgatcaa tcaatcagaa ctgataaacc aatcagaatg gataaagatg tagtaattac   3960
cagacaagaa cattaaaata cttaaactct acatgctaaa aatagcagaa gaaagattga   4020
acattatatt aagagaactg gaaaatataa gagaaccaaa tagaactttt agggatgaaa   4080
actacagtgt cagagatgaa aaacacacaa agtagtatta acagcagacc aagcactgaa   4140
gaaaaaacca aaagtttagt gaatttatag gcttagcaat ataaattatc caaaatgaaa   4200
gaagtagaaa aaaagattta aaaagaaaat gaaccgtgtg ttagttagct ctgagacaat   4260
ttcaagtttc ctaatgcaca tgtaattgta gtctctgaag gagcaggagc agagaaatgg   4320
ttgaagaaac aatggcctaa aattttccaa atctaatgaa agctgcaaac ccacaagttc   4380
aaaggaaagc aatgaactcg aagtataaga gacataaacc tggccgggca cagtggctca   4440
cacctgtaat cccagcactt tgggaggctg aggggggtgg atcatttgag gtcaggagtt   4500
cgagaccagc ctcacaaaca tggtgaaact ttgtctctac taaaatacaa aaattagctg   4560
gacctggtgg cggtcacctg taatcccagc tactcgggac gctgaggcag gagaatcgct   4620
tgaacccggg aggcggaggt tgcagtgagc caagatcttg ccactgcact ccagcctggg   4680
tgacagagtg agactctatc tcaaaaaaaa aaaaaaaaaa aaaaaaaaaa aaaggcctaa   4740
acctacatat aattaacttg cttaaagtaa gtgataaaga gaaaatctta aaagaaatca   4800
gagcaaaaaa aagatatcac aactgagaaa caaagataag gatgctagga gactttgcac   4860
tggcaaatct gagaggatag tagagcagca tcattaaaga attatgggaa aaagaaacgt   4920
gtgcaccagg tgttctatga ttagcaaaaa tatatttcaa aaataatgtg aaaatacaga   4980
tttttcagat tatctagtca caagaatgaa gaaaaccaca aataacactg taggtacata   5040
taaaataatt tttcttctca tcagtatctc ttcaaaagat aattgatggt ttgaaaagtt   5100
ataccatgct tttgggggat ttataacata gccataatta aaatgcatgt catcaattgc   5160
ataaaggtag agagggaaca catggaaata taagagcata agagtgttat atgtgaagtg   5220
gtaaaatatt gctggaagta ggctctaata agatagaaaa aggctcagct aaaacataat   5280
aacaatcaaa ggttggatat aatgtcgact aagaaaagta ggtgtaggta tgttaggacc   5340
agataaaata acattgaatc attagagata aagaggagca caccataatg atataggctt   5400
ttaaaacatg cttatactta atacaagagt ttccaattat atgaagcaaa agtccgcaaa   5460
agtccattaa aatgctatag aaataaactg ataaatccaa catcaaaatg agaaatttta   5520
acacacccct ttaattttta gttggtcaaa gtgaagaaaa taaaagccag tatataaaag   5580
agatgaaaat aaaatcaaca aagatgactt aatcaacaca cgtagaattc tgcataccac   5640
aattgcagaa tacacattgt tctattgaag acacagaaag catataatag gcccttaaaa   5700
agccatgctc tttcacaaga caattaagtt aaaagttggt aacaaaaaca ataaattact   5760
agaaattaag aacatttcaa gaattttcta agcttgtagc ttcggtgcaa ataaagcata   5820
ttttgtttga aattttataa acagtgtttc accattttgg caaatgacat cacaatgtca   5880
cattaactat gttaacagtg catgaattag ggtgaggcaa gtgaggcaac caaggtgcaa   5940
aattcaagga atcaaccacc cgtggaatca tgtaaatacc tgtttacgta tttttgtccc   6000
aggagcttcc taggtttacc ccagttctgg ccctggtatt tgagtcatct caacaagtca   6060
cttgtgttgg tctacacttg tagctgttgc atataaatat gctaaatagg agattcgtgg   6120
ctcattttta acagatttag aacaccatta aattaacagt gaaacagcaa agtcagggat   6180
```

-continued

```
gctattacat ctcactagta aaggtaactt taaaaatatt tcatattttt taacctacgt   6240
atttttgatt tattctggaa tccattgata aattaatctg ctgtgaaaag agcagagtga   6300
aattatttat ataatttgga gttggcaatc tttttcaaac taactcagat aaatgtcctg   6360
caggataatt ttacaatttc tctacagatt cttattttat agttgggctg tttgtatatt   6420
ttatatttgc tcttaatcca tcctttcttc cccatcttca atagatatac ttcaagattt   6480
cagcaccaaa gcctaatata tgctttgaca agtagcaggc tttccagaga tgagatatgc   6540
cttctgtcat gatatgttac tgtctcattc catgcagtga cataaggaaa tattttgact   6600
ttataaagct cagctcattt gtgagggtat tatatttcat tttccgcccc tatgtcactt   6660
tgtcatttgt cttgacttat cacccctact tcaattaagg ttatgtccca ctttctttta   6720
tcacagaagt aatactagtc tgttttactt attgcatcaa ttctttttat tgctgctgta   6780
acaaatattc acaaacttgg cttgaaagag caaacattta tgacctgata gttctacagt   6840
tgagaagtct gacacaggtc tcactgggct aaaatcaagg ttttgacagg acaatgttcc   6900
tttctagagg ctctagggat gaatctgttt cctggtgttt cctctagagg ctgccagcat   6960
gccttaatgc gtggcctcct ccatccacaa agccagcaaa ggtaagcggt gcccttctct   7020
catctgcagc actctcacct ggcttctctc tccgcatttc tttctctggc tctgggtctc   7080
tcttccactt ttaatgatcc tcgtgattac atggggccca cccagacaat ccagaaaaat   7140
ctttcttttt aaggtcagcc aattaacaat cttaattcta cctgtgcaac cttaaattct   7200
ctttggcagg taacataata tattcacatg ttccaaggat tcagatgtgg atattttttg   7260
gtaggggcat tattctgcct gtaatatatt ttttcgaaca ccagttgttg ttctagtgtt   7320
catgcccatg tttgttgttt cattttccta ggcttctaca aaatgagttc acctcacttg   7380
tcacaaattg tatcttattc atttcctgta ggcacatgca tttgaaactt ttatacatct   7440
tctggtgtat acaagtcctt acatgatgaa atgtaaatta ttttaaatta ttttcctatt   7500
atggctctaa aattgtatgg ttggggcatc ctccctccct cctttccccc cttccttgct   7560
tcctcctttg aaattatgtg tgttggtagg ttgcattaat catcagtttt atttcagggt   7620
cataaaagga gtgtaacaaa ataagtataa taaaaaagga atgttggata tgttatgact   7680
gagaggcacc ttagcagaag ccaaaagttg actccttgga ctataagaga agcctcttca   7740
aggaaaattg tagtgctctg tccataaaga actgtgcaaa cactacctac ccccacctcg   7800
aaatactttg gatattcagg cagagccaga gctactgtca gtggaaatat tgaccttagt   7860
atgtcattta attacctgag ctctatcaag aaccttgtag acctgtgagc agaatatgaa   7920
atagagctta cctcctatag tttgataaga gctccacaga gccacagtgg aaaattaagc   7980
aaattcctag acaatttcaa taaaaatggt ctatttttaa agttattcta aataaaaatt   8040
aaaaatttgt gttaacctta ttttggttac taaatgataa tgaacatacc ttttcaaaat   8100
taaaataaag tttacattct tcttgtgggg acacttttaa tttctgctta gatgatttat   8160
aatggaattc atcaccaaaa gataatttaa ttatatgacg gtagtttaca tataaattag   8220
aaagttttag gctgggcaca gtggctcatg cctgtaatcc cagctctttg ggaggccaag   8280
gtgggtggat catttgaggt caggagtttg agatcagcct ggccaacatg atgaaacccc   8340
gcctctacta aaaatacaaa aattagccgg gtgtggtggc atgtgcctgt agtcccagct   8400
acttgaaggg aggctgaggc aggagaatca cttgagcaca ggaggtggag gctgcagtga   8460
gccgaaatca caccactacg ctccaacctg ggtgacaggg ggagactctt tctcaaaaaa   8520
aaaaaaaaga aagttttagg tttaaatttt tttttttctt cttggtgaga cggagtctct   8580
```

ctctaacgcc caggctggag tgcagtggca cgatctcggc tcactgcaag ctccgcctcc 8640
cgggttcacg ccattctcct gcctcagcct cccaagcagc tgggactaca ggcgccggcc 8700
accactccca gctaattttt tgtactttta gtagagaggg ggtttcaccg tgttaccatg 8760
gtctcgatct cctgacttcg tgatccacct gccttggcct ccgaaagtgc tgggattaca 8820
ggcgtgagcc accacgcctg gccttaattt ttttttaat tctttacatt ttccaatgga 8880
gtaattatat ccctgagtta caagtcaaat gcgagcctcc atcagatttc ttggctccct 8940
tcctaaagac aatagagcaa ctcattactc tgcttcagaa tctttctccc aacctttagg 9000
cttctctagc tatgtagtga tgggaggaaa ggtggtggta gggtggggtt gggcacaaat 9060
tcctattcct ttcatgactg ttttacagtt gcttccttgt agggacatgc cacagaaaga 9120
agacactaca ggatccagaa atacttaaat aagataattt gtggaaatct tatcccttaa 9180
atatcttcag ggagaagtat ccttagcaac ttcttctttc tataggcaaa tcatggctgg 9240
gtaggtggtg gtcttctgct tccaagaaac cggcaatcaa caactcaagt tgcctcactt 9300
ctcatataca agtcccagca agagcctaga tgaattcact aatgcacttc atcctcctgc 9360
cctcttcctg gttcaggcaa taataatcat agatcgccat tgtcaattct tttttgttag 9420
acatgatgct ttttaacatt atttcatcta atgctcacag aatctctatg tggttagaaa 9480
tactattact ttacaaatga aagaacgcaa aataattgag ggatgtagat aactctctcg 9540
agataatgca gtaaacaaag ggtgatatca ttttgctgtg tccccaccca aatctcatct 9600
tgaattgtag ctcccataat tccacgtgtt gtaggaggga cctggtagga gataattaga 9660
tcctgggggt ggtttcccct atactgttct tgtggtagtg aataagtctt aggagacctg 9720
attgttttat aggggtttc ctcttttgct tggctctcat tttctctctt gtctgctgcc 9780
atgtaagatg tgcctttcac ctttggccat gattgtgagg tctttccagc catgtggaac 9840
tgtgcatcca ttaagcctct ttttctttat aaattaccct gtctcgggta tgcctttatc 9900
agcaatgtga aaatggacta atataaatgg cagggcccat aaatgaactc tattctgttt 9960
aacaccagtg tgtatcgttc attcattcaa caaaacaatt cagttactta atatgtgcca 10020
agcagtgagt taggtattga aaaagcaatg attaaaaaga cagaaggtac ctttctcctg 10080
ggaggttaaa ttttactgaa ggaaatagag ggaaccaagg aaataaaatt aagtagttac 10140
aatatgtaat aattttgatg aagaaatcac atagggatcc ccaggagggc agaaaggtat 10200
ttcaagcaga aagttcaaga aaggtctctc tgagtaatga ccatttaagc taagtcttta 10260
ggaagacaaa gggtgtggcc tggaaaggct ggtgggggca gaaagagcat tccagagatg 10320
cacaccagcc agtgcagagg atgactcaca cgcagtttgg tgaagactga aggggtcata 10380
aaagtaaagc atttttggga gtgtaatttg gcaatagcca tccacatttt aagtacattt 10440
aaattttctt tgggtgcagc aatttctttt cttgtgggct ttaaaataag tgttgcatat 10500
gtgaactaag ccacacaatc aggtagacat tacactttcc taagggacag agagacatgg 10560
gatctcaggt ttttcttgct gttttctttt tttaatgttt tcttcctctt cttattttaa 10620
tcttctgggc tataagttat aatgctcctt ttagactttt tttttcctac cctgcaggca 10680
gtcacctgat agagaggttt cctggaatag taataggaaa ataatgcaca gcaaagctga 10740
cacaccacat gccgagctgt actgaaggca caatcataac ttttaataac gaaagtttct 10800
tttggtaaaa taatatcttt ccagctgtcc taacagatac taatgtgaaa tgctcccttg 10860
ggacaggacg gtggagagaa gtcacccccg ttccagaggg gcatgccctt ggctcagaac 10920
ctcagagcac taacataatg tagtactaag attgcagtga caccagtaaa acctgctctg 10980

-continued

```
taggactgca acaggctaca ttttttttat ttgtgctttt gttttcctgt aaatcacttt  11040
tgagtttctg tttctcaagt ctggaagcag caggtgtgta attttggcag aacttttccc  11100
agccattatc tagtggttta ttgtttattt agagtgtggg ggtgagttat aataaagaga  11160
ttggccctgt gggttaagac tgggcacatt tctatttaca gtcctaccag gtcttcacat  11220
tctaggcaaa atgaaaggct aagccagtta tccagatagt tcaggccaaa aggtaaacac  11280
aaagagagga tgatttagtg ctgtcccacc tccggcttac gcttctgagg taacaaccac  11340
agggttctgc tttggtttgg caatggaaat ctgagttctc ctagctgtga cttgtgttag  11400
gaacgtagac tctgtccagc tcagtaggct gtgacataga aaatacatga agttaacttg  11460
ggcatagaga tagacatgat ccaattcccg gttcaaaact tatcccctat tgccttgttt  11520
cttttccttt tatatgctct tacatctcta gtgaagtttg ccatcagtat atttagttgt  11580
attaaaaatt ctccaggttc agttaatgcg gtcattttgg gtagactgtg acatacattt  11640
gcatggattt ggtctccctc cctccctccc tcccttcttg ccccgcttca ttgctctctt  11700
atttcttttc ttcctttctt actcccttcc ctcatcactt ccttcctttc ttccacattt  11760
atttaatgtc tataaccaga acccatgcta catatttgag aaacaaagtc aaacaaagca  11820
tacatttatt ttctaataaa ctaacagtgt agttgttggg gaaaaagaaa agtaaatgaa  11880
aaattataat attttggtta aaatatacat tggaagctgc tggaaaagaa ttcatgaaca  11940
caacttagtt gtttttagtt ttacaggaag tgaacctgat atacaattat tggtggtcta  12000
gaaatacaga tgaactggat aaaataattt tgaaaaagag gtttaatctt tctcactgaa  12060
aatccattac agtatggaac atatttattt cttctttgaa ttatatacat ttcctaacac  12120
ataatagatg cttaattaaa atgtttgaaa gaaaggagat gtaaatgtca caattttaaa  12180
aagtaatgat ttggctgggc atagtggctc gtgcctgtaa tctcagcact ttgggaggct  12240
gagatgcaag gatcgcttga gcccaggaat ttgggaccag cctgggcaac aaagtgagac  12300
ctcgtgtcta caaaaaataa agaataaaaa taaaaagtac ccaggcacag tggcccattc  12360
ctgtagtccc aggtactcag gaaactgagg caggaggatt gctctagcct cggaattgga  12420
ggctgtggta agctatgatc atgccactgc aatccagcct gggtgacaga gcaaggccca  12480
atctttaaaa aaaaaaaaaa aaagaacaga aaaaaaaaga aatgattctt ttttgtagag  12540
agtatttaga aaacatttta tgccatgctt ttctgtatta gtgaggaaaa aactgaatat  12600
aatttacctt ttctttgaga actcaatcat cagtatgaac aatgattact taagtgaact  12660
ttaggtgttc aggcagagga agatgtaggg tatagggcca gtgggtagca acacgagcaa  12720
gtgcatcaca tattctttat tgaaatgatc tcatttgctg aatgcttgct tctagtttat  12780
ttttattgga tagtttcctt tctcacatat gtggaagaaa accaatgtat tgcttggccc  12840
ctagggaagt gtaatgtggc tattctttcc caatgtaaat catggaataa aaatccacag  12900
ccttctctca aattattttc ttaccctcca gaaaaattcc tttctctcct tgtcatttga  12960
tttctcaata acattcagat cattatctct ttttccaacc tgtcactatt aacatatcaa  13020
cttcaatata ttttctatat atttacacta tcatttattg aacaaatatt tattgaacac  13080
ctgctatgta tcagacattg ttctaagagt tgaaggtgca tcattaagca aaagtcagaa  13140
tccctaactt cacagagttt acaatacagt acatgtaact gaagtgtctc tctcactatc  13200
aagaatttgt gttcgtgtaa ttgggagggt tctttttctc tttctctttc tctctttctc  13260
gtttccttct tttcctttct ttctttcttt ctttgttttt ctttgtttct ctcttttttt  13320
tttttgatg gagttttgct cttgttgccc aggctggagt gcaatggcac catcttggct  13380
```

cactgcaacc tccaccttcc aggttcaagt gattctcctg cctcagcctc ctgagtagct 13440
gggattacag gtgcctgcca ccatgcgcag ctaacttttg tatttttagt agagacatgg 13500
tttcaccatg ttggtcaggc tggtcttgaa ttcctgacct caggcgatcc gcctgccttg 13560
gcctccgaaa atgctgggat tacaggcgtg agccaccgtg cccggcccca gggctttttc 13620
aaagtgtatt tcataataac aagaatgcct attcattaaa ggttttataa gattttacag 13680
ttgacaatgc tcttttagag aatacattct cattggaatt tcacagtaac ttttaagata 13740
cataggatag gcgttattat tgttttttg tactgtgcag atgcagaact tgggtttaga 13800
cagagtaaat tacttctcaa gatcccagag gtgtaagtag caaatacttg agtttagaat 13860
atttaaaaat tccaaaactg ccttagtact tttaaatttg gaaaatattt ttatatttat 13920
tattttattt gttcttcaaa atgatctgtg tggtaattac tgattcctct ctaatcttcg 13980
tgcccgatga tgtggaattg ttgcattatc tgcccagatt tatctagctg gtaatggtag 14040
aactgaaaat ccaactatgt tcattgaaaa aatcaactgt ggaagctgaa cacaaatatt 14100
ttctttaatc tttctatatt cttataggca aatggaattt taaaaattta ttataaatat 14160
aatagagatt tttaaatgct ttataaatta atttcccatg aagttaattt ttctcataac 14220
attatatatt ctaaataaca cccaggtata cagtttgaac aatgaagtga cagtggcagg 14280
cagtaaaatc ataaaacaat tacctgacac attctgcttt tcagagtatt ttctacaatt 14340
ttcttaagtc aacctgtcat tcagacaagg tttaaaaaag tacatttcag cttccaaaat 14400
aaggttaaaa caactagaaa aacaaaacaa aacagagctc tagcacccct ccttgtatgt 14460
ataatacata tcttgtaaat acagagctgg aaatgtacat tatttttgac agatagagct 14520
ttcaatagtg agggttttat tacataaaag acagcaggaa tggtatatgc aaaagccgtt 14580
aaggtctccc ttttcttctt aaactcagca gtttgtgatt attactattt ggcaagcagg 14640
agtaaattgg accacaattt caacagcctc atagaagtat tccaggagac agtgttgata 14700
aatgagtcct agaatgccat ataattttcc tgcagtttca ttgtttgatg acttactttt 14760
catggataca ctctgccctc aggtttcatg tcctgctgcc aaatgtgaaa gctgtttgtc 14820
agaaatcaat gggttcaagt ggcccatcaa aagcttctgc ctttttgttg ataggaaaca 14880
ctttgtatag gaatctgctt tctggagaac tcattgctat cccttttgta tatacctgaa 14940
ccttgtcctg gctattatta tggtttcctt tgccagggga ttccccagtg aagggtgctc 15000
tgcctagtac tgcttgggtt actctcaaga tgacaacccc tccaatacag caatgactgc 15060
aaagctccta aggacaatag gattcagagt gtcttcttcc accaaaagct gagctaaata 15120
tagcctaaat atagcttttt gtattttgtt ctagggggtc attgatgtat ttacaataag 15180
ggatagatag gaaattttca tatattgtga atctattatg tagcaggcac tgaggtgctt 15240
tccacatgct atcttcttaa attgtcatac gaaaactctc tataaattat gtattatccc 15300
cattttacag atgagcaatc tgctactcaa gaaagatagt atttgctgaa aggcaaataa 15360
cagaggtggg atttcaaatt cagttttatc ttactcccaa gatcatgctc tttctactta 15420
gcatttggtt aaccgggttt aatttgcact aagaccaaat gacagcaaaa gaatttctct 15480
tctgataggc aaactgacaa atcaaatcta tgcttttgaa aagtctgtta cttcccatga 15540
ctctgttttt tgtttgtttt ctattggtga gaatagagta catccagtca aaagtaagtc 15600
tggttaaggt gggattttga aagttgggtg gaagttaagt gtctgactag ttctgtccac 15660
tctttgtccc aaatctccat tgtgataggt aggatctcct cagtccaggt gtctgtatgt 15720
gacaataggt tagaaagatt cttgtacttg aggctttatg aagttgacca aaagacatta 15780

-continued

```
agaatgacta agtgggccag gtgtggtggc tcacacctgt aatcctggta ctttcagagg  15840
tcaaggtagg cggatcgctt gaggctagga gtttgagacc agcctggcca acatgaagaa  15900
atcctttctc tactaaaaaa tacaaaaatt agtcaggcgt ggtggcacat acctgtattc  15960
ccagctactc gggaggctga ggcatgagaa tcacttgaac ccgggaggtg gaggttgcag  16020
tgagctgaga ttgcaccaca gcactccaat ctgggtaaaa gagtgaggct ccatctaaaa  16080
aaaaaaaaag aacgactaac tgcacttagg aatggggact acattcattt tttctgtata  16140
gatactggag gtcttactag gggttgtgg gattagtttc catatgtaat tgttctaaat  16200
gctttgcaac ctcacagttt tgagtctttt gatccctttg gtggtttatc caggctttac  16260
tacctggaac tgctgatact tggttccaga actcttatta gcaagatctt ggttagtcct  16320
tgcatctaca aatagctcaa gttcacctta agtagaaagc ttatcaatag atttctgtgg  16380
agactgcgga tccctccaat acacttgttg cttgatttat ttactagctc tcctctcttc  16440
ttggctttat ctcttactgt ttaagtagga gtttgttttc tcttttgttt gttttatttt  16500
tggttaaagc agcagagaac ccagctcaaa ttggcttaaa aagtgaaagt gattaaagtt  16560
ttcgtggtat tgtgggcttc agcttttgat cagtgaagaa tctggctcta tttctctgct  16620
attcttttgg ctctggtttt gcagttgtag ctttgcccta agtctggctt gtcctatggt  16680
tataaaacgg ctgccagcaa cttctgaagt gacccgtttc tccattcagg tttatagaaa  16740
agaaagagag aattgcttct caagccattg aattgaagtt ctaaattttt ctctgaagga  16800
atcaatcatg gatgcttggg gtaaatgaga ttaacctgat ttattctaat caaggtgcac  16860
ccctggaaga ggtcaactct tccaacaaat gcacggtttc tatacaatga agagtgacaa  16920
agacttgttt ggaggtaatc aaaatgccca ccacatttca ctgaacctaa atattaaatt  16980
tgtctttact tttttgttgt ctgttttaca actagcaatg gagcagagaa agttggagga  17040
aggttattgg gatctttttg aagagcaaat cacattctca ttggtaacca tgatgaaaac  17100
atattttctt ccttgtgtgg gtctgagaca gtgtcataaa ctgctttcag caatagttag  17160
tatggtctaa ccgagtggtt ctcaatcagt tctaatcagt ggctccttct cccaggccag  17220
cagcatcagc atctcctgga aatgtttaga aatgcaaata ttgaaacaga aactctgggg  17280
atggggcaaa tctgagtttt aatgaacact gccattgatt ctgatcatgc tgaagtttag  17340
aaaccactgg tttgatgctt atttgcacta ttatactgtg gtttacatat gggcttgaca  17400
ggtccattta ctttcattta cttgctattt gagattttgt ctggccagac aactgagcct  17460
cagataaatt attttcttac taaattctgg taaataccaa taaaaccttg aatacaacca  17520
acataggaca gtcagttctg ctataatgat ttttaaaatg ggaatttgtt tcaatgcaat  17580
taatatattg ggaaacaaat ttagcataag gcaaattttg catttatttg tgcactactt  17640
catctgctag accaactagg tgaatgtagg aaccatacac agctgagctg agtctcatag  17700
gaacacataa aacacacaca cacctctcaa ggacaatcag tggcccagac ccatgcacat  17760
ctactattac aacttcttgt ccatttccac cacttcactg ttattaatac aagctgcaag  17820
tcttccacaa actaacttca ggtggttttc aagataaagt gccatattgc ttgcagtatt  17880
tatgtatttt ttaatcattt aatgaatgta aaactatgct accatttatt agctgcttct  17940
ttttaaaaat gttccactga caaatgtttt gagtattatg ccccgaggcc tatgattttt  18000
attgtgttct tttgcattgc acagagaatt ttagcaatcc ctatgttgca ctaaagcaga  18060
attgagacta atttgagcaa aacttagcaa cttataactg ttacaatcct tatttcaggg  18120
caaacttttc attttataat cataattatt ttgtttcctc ttgagtagca cacacacaca  18180
```

```
cacacacaaa tctaaggtgt tcactatcac agaataatag cctttaaaat gtttaccagt  18240
tttcatattg atatattttg tttgactctg tcattccggg ctttaagtac taaaatatat  18300
tagtcttttt cagaaaacat tccaagaaaa aagttgaatt cctacctagt ttcctctctc  18360
tttgataacc tattgtcata gtaatataca aatacctgaa aattgcccag attattcttt  18420
tcttcttgga acacagattt gttgataagt gccaaaggat tttttacaaa aacatgagaa  18480
gtttgacatc acagtaagat ttaaaaggaa aggctgttta ttgttattat catcattgct  18540
actactattt ccgttagtat atatttcttt gtcttatttg tccttttcca aaagattttt  18600
gttcttatat ttttaattag ctctttaaag aaatcaagaa ctgcttgttg attatagaca  18660
tccttattgt ataaagaggg agaagttctt tggtaattag ctgtgtatag gttctgttca  18720
aacaattggc tcaagtgagg ttgtacagaa agaactcttg tattttctta tttttcagta  18780
tattctccac tccatcacac ctctttttcc aaagatgcag tgcaaagaaa gtataatctc  18840
tggagtaatt aaagctcagt gaggaaatga tatcacctga tggccctatg aagcattcag  18900
caataaaagg tgagttgccc aaaatgcatt taccctgaac aggaatacaa tgaaactacc  18960
aagttttatc tttataatga ttcgtggctt attattttgt tgtttgtata tgttctgttt  19020
cccacatcag tgttgtctta cattattatc tgtcttaact tagactctgt tttctaaatt  19080
gctctgtgca attaaatgct ttgtgatcat aataaaaagc atcatgataa cttttagact  19140
agaggtttcc atacaaagct gtatcccatg gagagcagct actggcactg aacaatggct  19200
agagatactc tacataggga aggggctgac aattattcag tttaaatcaa tcacttgtgc  19260
atatatctcg atagaacact aggctagttc gttgtgtgtg tgtgtgtgcg tgtgtgtgtg  19320
tgcatgtgtg tgtgtgtgta tgtatgtaat tcactgctta ctctataaca gagagaatat  19380
caattaaatt gggccatata ggaagatcaa ttaatatatt tgttaattga ggaacttttg  19440
atggccttgt tgatccccta tggtttgatc tttaaatctg tagtgtttat tagactcact  19500
acagactctc tgtaaatcgt aagacattta catctataaa tgcattttaa aacatcaaat  19560
tttaaatttt gcagcactaa aatgtgtcag acaatattct caattaactt gcattaatat  19620
ttgcttagtg tctgataaaa tgtgtagtgt aggacaaaat gtcctacata atcaacaaaa  19680
cactcttcca aaattaaaca taatatttgt taagatggtc actgtttttt taaaaaaaga  19740
gcactactac acagatcaag ccaatgagcc ccagtcagtt gacagaagta catatttggg  19800
actccttctc taaatttttt ataaaaatac ctgaagaaga tgaatagtca tttgctttct  19860
tattttaaaa gatctgtccc cccaactaac tttttaatct tctacttgtt accaaatacg  19920
ataaaaagga gagggggaaa aaagcagaca ccagtttcat tcgtgaatgt aaactttggt  19980
tttttggttt tcttttcttt ttttttttga gacagggtct cactctgtca cctaagccgg  20040
agtgcagtgg aacgatctca gctcactcac tgcaacctcc acctcccagc tcaagccatc  20100
ctcttacctc aacctcccaa gtaattggga ttacaggcgc agccaccacg cctggctttt  20160
tttagtagag agagggtcca tgttgcccaa gctgacctct aactcctggg ctcaggtgat  20220
ccacccacct cagcctcccg aagtgctggg attacacatt gcacctggct gaacttctga  20280
aatgaatgaa gtgctcctaa atgaatgaac atcttgaatg gcaaattaag tttcaagtga  20340
catataagcc aacaagtatt tctaaatttc taaaataaat ttccaaattc gaagtcattc  20400
tttcttttct ttcttttttt ttttttgttg ttgttgtttg tttgtttttt tgtgtgtgtg  20460
tttttgccgg tctgttttta atcgtggcag cgcctcacac acacattcag ggttcagatc  20520
ttgttcaaag ctgcgatgtc gacactctgc acatgctcct caaacttggt gatctcctcc  20580
```

tccagcaagt ctgtccccac tttgtcgtcc tccaccacac actgaatctg catcttccgg 20640
ataccatagc ccacggacgc cagcttggag gccccgctca ctagcccatc cagctggata 20700
gagcgcacac atgcctccag ctgggtcatg tccgtcttat tgtcccaagg cttgatgtcc 20760
agcaggatgg aggacttggc caccagcgag ggattcttgg ccttcttggc gtacagccgc 20820
agccgctcct cccgcagccg ccttgcctcc ttgtcttcct ccttattgtc gctgccaaca 20880
gatcaatgtc atcgtcctcg ttatcctctg cttcttggcc ggggtcgtag taaggggggc 20940
gaggggaggg gcgctccact tggcgcatgg gagacacgtg ctgtgtctgc gggactgtgg 21000
accatggcca ggcgagctct tctctcttct ccggcatgtt cagccaggcc tccaggttgg 21060
agaccgcctg ctgcagctcc tgcaccacgc cgcgcaggct ctggttctcc acttccaggc 21120
tggcgatctg gaggacgagc tcgctgtggt cttccctggg gccgagctct ggcgggaggc 21180
gctggccaca ggcccattca tctgcttgta gaatttcctt tctgtatctt catatttgaa 21240
tttgtcgagc cagatcttct catgtgctag gaattttgta gccatttttc tgacgcctgc 21300
caagaatgcg gctaccagaa atgaggaatc ggtagacgca ggacgcctaa gggcgaagtt 21360
gctctttcat aatgtacaaa acccttaagt cttcaacaga aagcaccttt tttatttaaa 21420
agaaaatcct gcagtttgca aataaaagtt tgtatttcag agagttggtg aggaaataat 21480
ccattaaaga ctgcctttat aaacataaac tgctgggaat aaagtaagat ttttaaaaga 21540
caatgaaaac attctgacat ctcaacagga gttagcctga tgaatccatc tcataccaga 21600
agtctttgtt ttctatttct ggctccttca ggagctcaag gttttacctt ggacaggtca 21660
tttcatctgt cagagccttg tttctcttac atcaaaggaa gaggcttgtc tgtaaaatct 21720
ttaaagttct tctttttctc aaatataaaa ttatcattca gatactcttg gtataatatt 21780
taaaaattat ttaaatattt aaagaaaaat gttttgaata tttttctata tactgagctg 21840
ctatgttgag aaatcccaga ggtattattt cagtgtacta ttgctctgat gaccagctac 21900
cactggagag gggtactatt tcttccttaa aacttgtata ttcccctcaa atactgatgg 21960
aggaaagagt acatgaatct ttatagtaaa agatagacaa ttagatataa ttgatcttaa 22020
tagatctgta gataatatgg accattatct acatatcatt tgttaaatta atgccttcta 22080
gcactcagct aaactaattg tatcgtgtgt gtgtatttct taagcaaagt ttgtttcata 22140
gatcagtgcc cctgggctag acaggaaaat gtcaaagctc ttaaaccagt ccaccaaagt 22200
atgtcaacta aaagcctcag aactagtagt atttctcgtt aggttttcag ttgcagggta 22260
gagaaagaaa gcaaaatcac aaggcaggta tttttctaca gcagtttgat ttagcaaatg 22320
ttgaacaaat aaaccattaa ctaaataaaa tattgcatat atatatatat atatatatat 22380
gtatattgtg tttattttca tgttgtctga catcctgaca actaaaggga aaataatata 22440
gaagtatttc tacattattt tgtgtctctg agtttgtgtc tctgagtttc ctgggcaaac 22500
tttgtgtctc tgagtttcct gggcctgaaa taattggcag ggtgaatctg aaatgcagac 22560
acagaaagtc acccttggtt tgatgccctt tttttttcc ttttcatgtt tatattttgg 22620
tgcatttccc cccgatatca aatattacct tggtactaaa aaaatcaaga agggaaaatg 22680
caggcaggag aacgaggaga atcaccttgt tacttctctc ccatatatga ttgggctcat 22740
gtgattggtg cattagactt tgtagtgtca tttcactcct ttctctgtag acatcaatac 22800
taacaaatga actgcaaaat cctaaagtgt gaggataaac accaattatt tatgtatgca 22860
catcatttgt atggatttct aactattgat cttcaggtaa atgtctagac agaagtagat 22920
ttaaatgtat aggtagttgt gctatatttt tacatttata gtaattaaca tctagaaaag 22980
caagaaggaa gagacaaaat atcagttatt attttgccta cttgcctctg caaaaaagaa 23040
gaaataaaag gattgccttc tatctacctg agacagacat ttaaactata gtgaattcag 23100
aatctttagg cattctcctc aaagtttcct tcagtgaaaa ttgatttgaa tcaaaaattt 23160
atgttaaaaa aaatggcagg gccaatgttc ctagcagagt tatctgaatg atttgctagg 23220
tcaagcaatc ggtcaactat tttcctctag atcataggat tagcatatca ggccagatac 23280
ttatcctgtg caatgttgag cacagttatt tttggaatct aagagatcat atgatttgac 23340
actcctaaag gagaccttct aagactttac ttccaaaaaa ctgactggat attatagtaa 23400
aatataattc ctatactaaa atacagctgt aaaaaccaaa atgcagcttg aatacattta 23460
gagggagtct tcagtgcttt gtccattaga taaaaagatt gcaaattaaa agtactcaaa 23520
aattgcagtt gacattcaga aactcattag cttctttctt tcccaaaatc accatagcaa 23580
ttagtctaca ctttaattgg tcaaaattat tcatcattaa aacactgatt tctaaaagac 23640
catttttttt cccctctgtc ttggacttaa atttttagg aatttaaatc ttctttctct 23700
accagtttct gaaatgatta agcacatttg cattttatct gtctagagaa gatattcctt 23760
cccttgaact ctctcattct ggcctcttct gcttggtcaa ctgtctgtgg aaattctgtg 23820
ctgatcatct atagattaca tgctaatcta tatttcctaa gaaaaatagg aaaaatatgt 23880
acacagggtt cagtttacat ttagaaatct caggatcttc tgtcaattct tacccaattt 23940
tcatgataat ccctacattt ttttcttaat ttaacttatc cagtttaaga tgttgcttcc 24000
ttattaaaat atttatcacc ttaaaattgt ccactacaat ttaatatata gaagctttta 24060
tattccttcc ttccttcctt cacatgtcca gtcaattagt catttattca ttcagtatct 24120
tccagtgcca gcactgtgct agaaacatgg aatgaaaaga ggaaagaggt gtgttctatg 24180
atctaaaaat gttcctaaag gtcaggtaaa caaataagtg catttaaatg ttaagagaac 24240
aaagacaaga gaatatgcag gacatgccgg aggcccaatg gaaggtagga attttcccat 24300
ctgggaggca ggtggtgaac cagaaggttt ataggtgaag acgatgcttg aactgtgttc 24360
acaggtgctt tttgccagat agtctaacag attaaggtgc tctccctata gagggagaac 24420
cagagggctg gaaactgaag gatgaattca gggaaaatga caagtagtgc agtctggcta 24480
aagcagaaag gcatatcagt ggggcaggga ccagttaatg gataataaca agacagagag 24540
tttggatttc aaaccacaaa atatggtcaa gggaaaaatc agcagagtta agccagaaca 24600
ataaatatgat atatattttt tcatttagac agaatgcact ggatatttaa agaaatagaa 24660
ataaaacatt tcagaatcta gcttttgctt ctcattgaca aagtctttac taagatggaa 24720
taaaaatgga agcatggaac agagagagag aagttgtatt tcttcatggg atgacaagaa 24780
gggtagatga ggctcgccca agtacagtga tgtttacacc taattgatca caaccagtta 24840
cagatttctt agttctttct ctactcccat tgcttcactt gactagactt agaaatgaaa 24900
aaaagaaaag aaaaagggtg gattatagag cttaagatct gtgctttggt ccccatattt 24960
ccaatccttg tcaccaatgc ttggtaaata tgtgggtata taaaaaatta tatttaatta 25020
attaattaac tatttttttg agatggaatt tcgctctcat tgcccaggct agagtgcagt 25080
agtgcgatct cagctcactg caacctccac ctcccgggtt caagtgattc tcctgcctca 25140
gccttccaag tagctgggat tacaggcatc cgccaccatg cccagctaag tttttgtatt 25200
tttagtagag acggggcttc accatgttgc ccaggctggt cttgaacttc tgacctcagg 25260
tgatacaccc gcctcagcct cccaatgtgc tgggattaca ggtgtgagcc acaatgcccg 25320
gcccttaatt atgttttttt aaagctatat gacagtaacc aaaactatat gattgaggaa 25380
atatttgtag aaatgatata tatgacaaca gtagcaaaaa ggacaagggt aaataaacag 25440
aagtcatatt tttcaaaatt cttgcacttt attagaagta ttataaaatt aattgtaagt 25500
agattgtggt acttaataat gaatgttgta aaccctacag catacactaa aaataatgta 25560
aaaatgtata tttaaaaagc caatagagga attcaaagga atattttata acaacatcag 25620
ttaaccttaa agaagacaga aaataaggaa gacaggaaca aaaatacagg tgagacaaac 25680
agaaaagaca tagcaagtta tagttgggtc ttgattttca aaatctgggc taagaatttc 25740
catcttttaa tggggagaag taatctattt ataacaaata taattgtcaa ttaagttggg 25800
cttaagtcct attaaaatat atagattttt agcctggata aaaatgtatg gccccattat 25860
atcctgtcca taagagaaaa actttttgtt aagaaaatac agattgattg aagcaaaata 25920
atggaaaaaa ttataccatg cattcaataa acataggcaa tatggagtgc ctatattaat 25980
accagaaaaa aatagacttc aatgtaaaga gtattatcag atatgaagaa gaatattaca 26040
taataataaa ctgctgattc attaaggaaa tataacaatt atatatgtgg gaaggtggag 26100
caagatggca gaatagaagg ctctaccgat tgtccccact accctgcaag gacaccaaat 26160
taacacctat ctacacagaa aaaaatatct tcagaagaat caaaaatcag gtgagcaact 26220
cagtacctgg ttttaacttt attgctgaat gaggcactga agaaatagaa aaaaacagtc 26280
ctgaatccca atgccttcct ccctacccac agaaactgag tgtggtgtgg aaagcatctc 26340
tcagtgctga gggaggagaa tacagcaatt atgaggcatt gaactcagta ctgttctttt 26400
agagcagaaa ggaaaatcac atcaaactta gctgatgtcc acccacaaag ggagcattta 26460
aaccagcccc agccagaggg gaattgctga tcccaacagc tgaaacttga gttcctgcaa 26520
acctccacac cgagggatac aatactctat gtctccaagt aaacttgaaa ggcagtctag 26580
gccataagga ctgcaacttt taggcaagtc ctagtgctgg actaggccta gaatagtgga 26640
ctgggctggt gcagtacata ctgagacacc agctggggca gggctgcaca gggtagaggt 26700
aatgctagca ctccctgagc cagacaccac cacctctccc ttaagcctag gctgcacaag 26760
tctctccaaa agagacccct ttcttccact tgaaggagag gagaggacag aatggggagg 26820
actttgtctt gcaacttagg tattagctca gccacagcag gatagagcaa tggtcagagt 26880
caagaagccc ttgttctagg ccctaggtcc cagacatttc tagacatacc ttgggccaga 26940
agggaaccca ctgccttaaa ggaaaggacc cagtcctggt agcattcatt acttgctaac 27000
tgaagagtct ttgggccagg aatgaccatt agtgatacac aggtgctatg tcttgggcct 27060
tgggtgagtc tctgagactt tctgacttca ggtgaaactc atcatcttac tagcttggat 27120
ggctatgggt caaaactccc tctgcttgag aaaagcagag ggaaaagtaa agtcttgcac 27180
cttaggtaca agcactgcca ctggggggta gagcaccaag tggtctcttg ggtccctga 27240
ttctagcact tgactcttgg atggcatttc tgcacctgcc ctgggccaca gaggtgctca 27300
ctgccctgaa ggataagtcc caggcaaggc agcattcacc acaagctgac ttagagccct 27360
tgggttttaa gggaatattg gagatagtct ggcagtactc cttgtggcct ggggtggtgg 27420
tggcaatggg gtgaagctcc tctacctttg gaaaggggag gaaagtgtgg gaaggactgc 27480
atcttgtggt ttgagtgcca gctcagccac agtacaatag aacaccagaa gacttctaag 27540
atttttgact ctagtctctg aactaccaga ctgtagctct ggacccacgt ggggcctggg 27600
ggaccttgcc accctgaaga aaaggacaca ggcctggttg gctttgccac tggctgattg 27660
ggtagcccca gggccttgag tgaacatagg cagtagccag ggagtgacta cagcaggcct 27720
tgggcgaggc ccggtgctgc gctaacttta gatctgaccc agtgcagtca tagtagtggt 27780

-continued ggacacagag gtgcttgtgt tactccaaat ttaggtgact tggaacagag agactttgtt 27840
catttggaag aaattaagga aagagaacaa gagtctctgc ctggtaatcc agagaatgct 27900
cctggatctt atccaagacc atcaaggcag tacttctatg agtctgcaag aaccacagtg 27960
ttactgggct tgaagtgccc ctaaatcaga cacagcttag atcataacac ctaagccctt 28020
tgaaatatct ggaaagcctt ctgaagaagg acaggtacaa atatgcccag acagtgaaga 28080
ctacaataaa tactgagttc ttcaatgccc agacaccaaa gaacatctga cagcatcaac 28140
actatccagg aaaatatgac ctcaccaaat gaactaaata aagcaccagg gaccaatcct 28200
ggagaaacag agctatgtga cctttcagaa acagcattca aaatagctgt atagaggaaa 28260
ttaaaaagaa attcacaata agacagagaa ggaattcaga attctatcag ataaatttaa 28320
caaagagaat gaaataatta aaaagaatca agcagaaatt ctgaagctga aaaatgcagt 28380
tggcatactg aagaatacat cagagtcttt taatagcaga tgtgatcgag cagaagaaag 28440
aattagtgag cttgaagaca gggtattcaa aaatcaacag tcagaggaga taaaagaaaa 28500
aaagaataaa aaacaatgaa gcatgcttac aggatttaga aaatagcttc aaaaggataa 28560
atctaagagt tattggcctt aaagaggagg tagacaaaga gatagggggta gaaattttat 28620
tcaaaggaat aattacagag agttcccaaa cctagaaaaa tatataaata tccaagtaca 28680
caaaggttat agaacaccaa gcagatttaa tccaaagact acctcaaggc atttaataat 28740
gaaactctca aaggtcaagg ataaagaaag aaccctaaaa gcagcaagaa aaaaagaaac 28800
aaataacata tgatggagct ccaataagtc tggcagcaga cttttcagtg gaaattttcc 28860
aggagagagt ggtgtgccat atttaaagtg ctgaaggaaa aaaaacttgt accctagaat 28920
actatatctg gcgaaaatgt tcttcaaaca cgaaggagaa ataaatactt tctcagacaa 28980
acaaaacccg agggacttca tcaataccag acttgtccta caagaagtgc taaaaggagt 29040
acttcaatca aaagaagaca tcagtgatca ataagtaatc atctgaaggt ataacactca 29100
ctggtattaa taagtataca gaaaatcaga atattttaac gctgtaactg tggtgtgtaa 29160
gctactctta tcctaagtaa aaagactcaa tgaagaacca atcaaaaata ataactacgg 29220
caacttccca agacatagtc agtacaataa tatataaata gaaacaacaa aaagtttaaa 29280
agcagggtgg gcaatgaagt taaggcatag attttttatt tgttttcttc ttgcttgttt 29340
ctttgtttat gcaaacagtg gtaaattgtt atcagcttaa aataatgggt tataagatag 29400
catttgcaag cctcatggtt acctcaagcc aaaaaacata caatggagat gcaaaaaata 29460
aaaagcaaga aaccaagtca taacaccaaa gaaaatcacc ttcactaaag gaaggtggga 29520
aggaatgaaa gaaggaagac aagatcacaa aacaaccaga aaacaattaa caaaatggta 29580
ggagtaggtc cttacttatc agtaataaca ttgaatgtaa atggacttaa tgctccaatc 29640
aaaagacata gactggctga atggaagaaa caagacccat tggtcttttg cctccaagaa 29700
acacacatca cgtataaaaa catagactca aaataaaggg atggaaaaag atattccatg 29760
ttgatggaag ccataaaaaa gtaggagtca ttatacatat atcagacaaa atagatttca 29820
agaccaaaac tttgagaaga gacaaagaag atcactatat aatgatgaag ggtcaattc 29880
agcaagaaaa tataataatt taaaatatat atatgcaacc aacactggag cacccagata 29940
tataaggtaa atattagagc taaagagaga tatagaaccc atatacaata atagctggag 30000
acttcaacac cccactttca gcattggact tatcttctag acagaaattc aacaaagaaa 30060
catcagactt aatctgcact atagactaaa tgtatctagt ggatatttat agaacatgta 30120
atgcaatggc tgcagaatac acattctttt cctcagcaca tggattattc tcaaggatag 30180

-continued

```
accatgtgtt acatcacaaa agaagtctta aaatattaaa aaattgaaat aatatcaagc  30240
atcttctctg accataatgg aacaaaacta gaaattaata aaaagaagaa tttgggaaac  30300
tatactaata caaggaaatt aagcaatatg ctcctgaatg accagtgggt caataaagaa  30360
attaagaagg aaatttaaaa atgtcttgaa ataaattata atagaaacac aacataccat  30420
aacctatgag acacagcaaa agcagtacta agaggcaagt ttattgctat aagtgcctac  30480
atcaaaaaag aggaaaagct tcaaaaaaca atctaataat gcatcctaaa gaactagaga  30540
agcaagagca aaccaaaccc aaaattagtg gaaaaagaga aataataaag atcagagcag  30600
aaataaatga aattgaaatg aaaaaaaaat tcaaaggatc aatgaaacaa gaagttggtt  30660
ttttaaaaag ttaaacaaaa ttggcaagcc tttagtcaga ctaagaaaaa aaggagagaa  30720
gatctaaata aataaaatca gaattgaaaa agtagacatt acaactgata ctccagaaat  30780
tcaaaggatc attagtggct acaatgagca actatatgcc cataaatttg aagatttaga  30840
agaaatggac aaattcctag acacattcaa cctagcaaga ttgaaccatg aagaaatcca  30900
aaacctgaac agaccaataa caagtaatga aattaaagct gtaataaaaa ttttcccagt  30960
aaagagaagc ctcagacctg atggcttcat tactgaattc tatcaaacat ttaaagaact  31020
aataccaatt ctactcatac tcttattaat attctgaaaa atataggagg agggaccact  31080
tccaaattca ttctacaagg tcagtggtta ccctgacacc aaaatcagac aaaagcacat  31140
taaaaaaaag gaaactacag gtcaatatat ctgatgaata ttgatacaaa aatcctcaac  31200
aaaatactag caaacagaat tcaacaatac ataagaaaga tcattcatta tgtccaagtg  31260
agatttatcc ctgagatgca agaatggttc aacatatgca aaccaatcaa tatgatacat  31320
catatcaaca aatgaaggat aaaaaccata tgatcatttc aattgatgct gaaaaagcat  31380
ttaataaaat taaacatcac tgcatgataa aaactctaaa aaaaaaaact gggaatggaa  31440
ggaacatatg tcaacataat aaaagctatg tacatcagac ccacagctag tatcacactg  31500
aatggggaaa aactgaaaac ctttcttcta agatctggaa catgacaagg atgcccaatg  31560
tcaccactgt tactcaacat agtattggaa gtcctagcta gagcaatcag acaagagaaa  31620
gatataaaag gcatccaaat gggaaaggaa gaagtcaaat tattcttgtt tgaaatgata  31680
tgatcttata tttggaaaaa cctacagact ccacaagaaa actattaaaa ctgataagca  31740
aattcagtga tattgcagga tacaaaatca acaaacaaaa ataagtagca tttccatata  31800
taacagtgaa caatgtgaaa aagaaataaa aatgtaaccc catttgcaat agccacacat  31860
ataattaaat aactaggagt taattgagga agtgaaaggt ctctgaaaac tatgaaatgc  31920
tgataaaaga aatcgaagag aacacaaaaa atggaaaaat atttcacatt ggtggattag  31980
aagaattaat attgttaaaa tggccacgct atccaaatca gtctacagat taaatgcaat  32040
ccctatcaaa atactaatga cattctttac agaaatagaa aaaacaatcc taaaatttat  32100
atggaaccac agaacatgca gaatagccaa atctatccta agcaaaaaga ataaaactgg  32160
aggaatcaca ttgcctgact tcaaattatg ctatagagct atagtaatca aaacagcatg  32220
gtgctggcat aagaacagac acataaacca atggaacagg atagagaacc cagaaacaaa  32280
tccactcacc tacagtgaac tcatttttga caaaagtgtc aataacttac cctggggaaa  32340
ggaccgtgtc ttcaataaat ggtgctggga aagctagatc ttcacaggca gaaaattgaa  32400
actagacctc tatctctcac catatacaaa aatcaagtca atatggatta aacacttaaa  32460
tttaagacct caaactctga aagtactaca ggaaaacttt ggggaaaata tccaggacgt  32520
tggtctgggc aaaaatgtct tgaccaatac cccagaagca taggtaacca aagcaaaacg  32580
```

-continued

```
ggacaaatgg aatgacatca agttaaaaaa cttccacaca gctaagcata caatcaagaa  32640
agtgaagaaa caacccatgg aatgagagaa actatttgca cacttcccat ctgacaaagg  32700
attaacaacc agaatatata aggagctcaa acaactctac aggaaaaaaa tctaataatt  32760
caatttaaaa aatggtcaaa agatttgtat agacatttct caaatgaaga cataccaatg  32820
gcaaacaggc gtataaaaaa tgctcaacat cattgatcat cagagaaatg caaatcaaaa  32880
ctgcagtgag acatcatctc accccagtta aaatggcttt tatccaaaag acaggcaata  32940
acgaatgctg acgaggatgt ggagaaaagg gaacccttgt acactgttgg tgggaatgta  33000
aattaataca accactatag aggtcagttt ggaggttcct caaaaaaaaa aaaaaaaaaa  33060
atctgagctg ccatatcatc tggtaatccc actgctgagt acatagccaa aagaaaggat  33120
atcagtatac caaagatatt tacactcctg tgtttattgc agaactgttt acaataagta  33180
agatttggaa gcaacctaag tgtccaccaa caaatgaatg gataaagaaa atgtggtaca  33240
tatagacatt agagtattat tcagccataa aaagaatgag attcagtcat ttgtaacaac  33300
atggatacaa ctggagatca ttatgttaag tgaaatgaac caggcataga aagacaaaca  33360
tcacgttttc actaatttgt gggatataaa atcaaaacaa ctgaacttat taacatagag  33420
agtagaagaa tggttaccag aggctgggat gagtggtgca agcctgggaa aggaggtggg  33480
gatgaataat gggtataaaa attgtagtta gaatgaataa gacctgctat ttgatagcac  33540
aacagtgtga ctatagtcag tactaactta attgtgcatt ttaaaataaa aacagtgtaa  33600
ctgcatcatt tgtaactcaa aggataaatg cttcagggaa tggataacct attctccatg  33660
atgtgctaat ttcacgtttc atgcctgtat caaaacatct tctgtgctcc ataaatatgt  33720
acacctacta tgtacccaca actttttaa aaaattaaaa tatatatgtg tatgtactaa  33780
taacagagct tcaaattcaa tgaaaaaaaa aacacaaaat ttgacagaac cgaaaaaaga  33840
aataggcaat tccaataatt atatcacttt tctctcatta atgtagaaca actaggcaaa  33900
ggaatcagta actgtatgga atatcagaac aaaaatatca gatactttca gttaactaac  33960
atcaacagaa tacatccaat aactgcagaa tatacattct ttttaagtga acatagaaca  34020
ttcaccaatg tagctgatgt gctaaacatg tctaaataaa ttttaaaacc ttgcagtatt  34080
gctgactata atctctaacc acaatggatg taaattagaa aaaaatacga tgtctaggaa  34140
agtctggaat atttgaaaat taaataacca actctaaata atattaatat atgggccaaa  34200
ggtgaaatca caagaaatat taaacaacat tttgaagtga atgataatga aagtacaaca  34260
tataagaatt tgagaaatgg aatggcaaat tcatttgctt tcatgaggtg gtaactaata  34320
tagaattgcc ccctttctgt aaataattag aaaactggac caaatatgta aaacagttat  34380
ttttaaagat tggcctatag ataacaaagg actattattt tcttaacaaa tgagttaagc  34440
cctaccagct agaggaaaaa caggtatgta aggatgatca cagatttctc ttcatagttc  34500
aacactaact atgtgttgtc tgcatgagac acatttttaa tataatgacc cagaaatact  34560
taaaaataaa agaatgggaa tatatgtacc atgcatttaa aaactattat gatataccaa  34620
ggaggctgca gcaccacttc tgtggtattc ctgccaaaag tatgtatctt gaatctaatc  34680
atggggaaac atcagacaac ccaaggtgag ggaaacccca caaaatgact gacctgtcct  34740
ctgcaatagt gtcaaggtta taaaagtcaa ggaaaaaccg aagagttgtt ccagatgaag  34800
aaaactaaag agaccttcaa ggggtgattc tgaactggag cttttaaata taagtcttgt  34860
tggaacaacg ggtcaaactt gaataggatt caaagaggtg gcctaaagag ttaaaagact  34920
taagtgatag tattgcatca gtgttaatct tctgattttg atggctgcat ttcattatcg  34980
```

```
tgaaagaatg ttaaatgtct ttgttcatag gaaatacaca ctaaagtagt cagggtgttg  35040
aggctttagg ttgataattt attctcagat agttcaggaa aaattctttc tgctgtttgt  35100
gcaacttttg tgtacgttgg aaaattttta tacaaaaatc aacttcaaaa ttgaccatat  35160
aaatgaatac cattgaaata tcatttaaat tatcagtagt aacattagat gctagagata  35220
gtggagtaat gccttcaaaa ttctcggggc aactgctgtt catcactgaa tcatacgcag  35280
atcacctttc aatcaagtgt gagggtaaaa cagcaacatt ttcagatata tgagaactca  35340
gagtccccat tccctctatc aaaaactgga gaatcaacct tatgcaaatg aggcaataaa  35400
aaatgcacac agtggtggag agaaacaata aaatgacagt gttctgttgg cctaagaagt  35460
taaaaagagg ggccaaaaag tagcagaatg ggagagtgtg cagagatatg tctggaaatt  35520
actattttcc aatgtagata ttttaaaata ggtgcatgca tttctttact gattatttaa  35580
aaattatatt taatatgaat ttaaagaagt gagtggggaa atgaagacgg caagtaaagc  35640
ctaatttttt taacagcaaa taaaggagaa agcagagaag gtagttaaaa aggaatctat  35700
gtttgagaga ctgtttttcc tgctaaatta agagaaataa gcatggtact gtgatctgaa  35760
ggaaagccag aaactgggtg accaaataaa atgcactaga aaagagtgct tttttactaa  35820
ggttggtaga aaggaggtga tgtaccaagt agatagaaat aatttgtagt ctagtgtgct  35880
gcagagagcc tcacttttct ttatacaaag gcatattcta agaaaaaaaa aatagggcat  35940
agatggataa agaggattgc aaagctttgc aaaaagttga aataacatcc atgcctcata  36000
gttgagggag ctaaaagagg aacacacaga agaattgccc agcagcatgg atggtcctgc  36060
tgaggaggtg aacatgaatt tttaacagca ttagccacac atttgtatag tgctttttaa  36120
agcttttatt ctaatgtttt tggcagcctg ggtgtagcta ctaaatttag atttgggatt  36180
tgcccagtct tgcaaacaag taataaccca gggtatggcg taaactaaaa agaaaaagaa  36240
gagaaactat gcaagtatgt caggcagaat tcaactggag gtcaaaattt gctgaaatag  36300
caggtagagt gggattaaag gagcaaaaag aggggattct atgaagttgt ggtccatgaa  36360
agactgagag gaggagggga agaaattcag aattgaaatt gactactcaa aaggcttgct  36420
cgtgaaaaaa actgccaata aaaaatcaag catccttgtg tacaaagaag aaaatcaaag  36480
agagatgcct agggaccttc agttgttttt aggaagttaa gctggcctag agtttcttgc  36540
tgagtatcct tgcattcgtg gggatgacat ttctgggaca aagcaaactt ccaccacatc  36600
aaactacctg tggatgataa accaactatg atgaagttgg ccttttccag gtttctacct  36660
tggcaccaat ttaacacttg catcctttct agcaaggttg ttttttattt atgtttttta  36720
tttcctctgc atctcagtga tagttgtctt ggcacacagt cccagctgca gacagctttt  36780
atttttaggt ttccctattc agaaagagta gtccctgttt aggcatttca ctgtcattct  36840
aagctttcca ctgagctaca accctgcagc tttcttcaaa ttcaagtcac tggggagggc  36900
ttttgaaatg ctcaaagaac gagacaacat tttgtacaaa ggggaaaaag caaccataaa  36960
gatattccaa aaccaagtag ataccatgaa aacgaatgga aaagagaaga cagtgacagg  37020
aaccaaaagg acaaaagaca atatgttgaa tctgtaataa gccagccaga agccccaagg  37080
acaatggtag gaacctacag atagaggtct gcacataggg aaataaattc ttacttcgtg  37140
attcccaaaa gcaccaccca agttactaga ggtgacaaaa atacttcctc ttattaaaat  37200
aaggaagtta ttttgggacc acattattag tgaactggtt agttttagag agctcttcta  37260
gaaactcatt gaggtataga ttttcaaagt agttaagtac attatttgag taaaataaca  37320
ttatgttcaa cctaacttac aaaaggaata gtataattaa acagacttgt gcctggaact  37380
```

gaaaatatac tcagttaagc attgccatat tttataaagg atgttagaat ccctttaccc 37440
tgtatttagt aatcctagct gtgatgcaag atagattaat agataagcca caaagtaatt 37500
gtaatcaaac ataaaggtac aatttaggaa atgggtaatg tacctatagg tgcctaatcc 37560
aatatatact tcatatgatg cccaaatatg ccacattttt ggtctgttag aggagcatga 37620
aactagtgat ggtcaggaaa tgattcagaa agcaagtcct aaggcagttg caaagctgta 37680
gaaggaaagt cctggaaagc tttaatgttt tgggcttgca aatgggtctc tttgtcctca 37740
aatgttttaa gaataatttt tcagtcataa tttgtaaaaa ccaatggcat ttttgttgaa 37800
aatattttgg cctcttgagg tggacttgca gaaaatactg caacagcact tttgtacccc 37860
cactaaccat ttcgatgaac tcagctgtat catctcctgc cctcacccac tgtttcactc 37920
ctggttactg ccctctgttc ttagcatata tgataccctg ccatggctca ttcgttctca 37980
gcaaggggac aaggaactca agaactggca gcacgagagc aagttgcctc aggccagggg 38040
tcagacccgg ctataggtct tgccttgtct cctctccact ttctctattt ctttggctct 38100
cctgacaatt tctcatagct tccctgtttg agcacacatt ttgcttttcc ccttgcattt 38160
ctattgatca tccagaagct gtttgctggg gcctttgcaa ctcccagctt gcaatattta 38220
tgtccattct cttgatacct atgtgtatcc atttccctga cattttaaaa tgtgtttctc 38280
ctcagtttta gctcttctcc tgactactac tttgccctgt ccctagatat cctgccataa 38340
ttaatgttga atgaaagaat ctaatcaacc aagactggaa attcatacag actttgaaat 38400
ggggacaaaa tcttacattt gtttctagtg tgtccccata gatttgacta tcacactttg 38460
gggcatcagt ggcattaagt gacaaattac ttctgggagt tgtaggatga ttctatgtca 38520
agctctccac tcagatccaa tgagtcacta gttcctactt atgaacaggt attaacttgc 38580
ttcatttgca aaccccagca agaattttgg tcacaagcca cagttgccat aagaactggc 38640
tttggaataa gttaggcttt ggttcctatg ccagctctcc catgtcataa ctttgatcag 38700
gatagcaata ataataatat tttttctccc aagacttacc atagagtttg gtacatagaa 38760
agtacttaac tactatgatg aggcataaaa atgtttaatt aatcaccgag atttaaactg 38820
acttttagag gaactttctt agcaggtacc tggttcccca aagtttctca tgcccatgac 38880
acgcactata accttagcaa aggttatcag gatcttctgt tgactgtgct gttctttctg 38940
cacttttggc ttcttggaaa cactgtccct cccaacagtc catgctgaga gtttccaact 39000
gggtaatcac atctgtctag tcagatgcta actttctgct ccgcagaggt atgtccctca 39060
aagttcatac ctgaggaatc atttggaaag attccttcct tcaatatctc tggctgagtc 39120
atgcatacct cctcatcaaa gacaaataga aaacaaggtc aataggaaag cggtgctcac 39180
ctatcttact gtctgtacct tttcctatta tgactagcct cataatcttt aggttagaat 39240
gacttgcact aacctgttcc tagagtccct tccttgtccc ttgtggcact tgccagttgt 39300
gattgcaact ggtggtttta agcatgttac cacttcaaaa ctccaagctt tatgaaaacc 39360
aagaagatgt atgtaccatt tgactatttt tatatctccc atttctagcc caggggttgg 39420
cattatcaca tagcagttaa gagcttgtga tctggagcca gcctgcgtgg ttcagcttaa 39480
aactcaactc catattattt atgtgaattt aggcaagtca ctgaaattac tcctacttca 39540
gtttactttc ctaaaaacag gtattttcat aatagtgttt acctcttagg agagattaaa 39600
taagtcaata tgcataagca cttaggacaa tgcttggcac agagcaagta actattaaaa 39660
taggtactta gtaaatattt gctggattag caaatgccac aataggtcca gtcatcagca 39720
ttttgcagac atcatttaat caacccgaat agtccagtgg ctctagagtc tcttaatttc 39780 tttttttcatg attttttttc atttactgcc tctcaggctt tattgcattt gtgtcaaatc 39840
cacttgtcta aacatttaaa aaagcaaaac agtgttacat agttttaaaa accattataa 39900
tttgactcta tgagtttcaa aaacttcata tacaagtgct taattgtctc attcgaggtt 39960
ttacattgct gatgaaatcc actcatttaa gaggtaggta gtaatgcagt gtgtggggtg 40020
taaagtaaaa tgctaggggt gtgtgtgtgt aggtatgttt gtttatatgt gtgcttgtgt 40080
atatttttat gtgtgtatgt taggggtagc tggctgtgcc aaaggtgaat aagatgaagt 40140
tcctgctcta tagaatcttg aaatttaata aaagagataa ccatgcaaac aactaactaa 40200
atcacaaggc acaatcctct gtgagcctgt gagtatctgc atcctgctct gggaaagtgt 40260
aataatctct ttttgtgtct acgattgtac ccgggctggc atctgagtta gatcataggc 40320
tcctaacatt tcactttatc agttcgtaca atgccccaca tctctgtgag ctaaaaaaac 40380
atgttgctat cagcacaatg tgagaagaat ggtttttttt ccccgaaggg acaaaagtag 40440
tgccataaag ctatagaata ggcaagtctc tcagtaaaat gagtttccct aaaaggattt 40500
cctaaggaac atcttaaggt atttaaataa acaaacaaat aagacaactg agtagagttt 40560
aagtctgtgc cttttcctta ttctctagtc ctggttcttt tgacgtaaag tgaaacattt 40620
ttggggttat ttatttccac ccccactctg tcataatata aagagaattc tcagagggga 40680
gactatagaa gtctgtcagc agctgactct tttctggcag gaagactatt ttataaaaaa 40740
aagaagaaat ggatttcctc tccttgtagt tcaatatttt cttcctctac acattggtta 40800
aattcctcca tcctatttcc ttgaaaatgt cagggttggg ttgccccaat ctcagacagc 40860
tctcttcatt atgattatca gtgttaatgc catgtcatta atcctcacga gtatatggag 40920
gcctcacact gaatgaatgg ggaaggtcac catggaaaca tctgtctcca tagatgactc 40980
acggcaaccc ccataactgc tgaaccacat cctgtctccc aaatgcactg gatgaagcca 41040
caaatttggc atttcctaca ggaccatatt ctttttaaaa gctattaaaa atctatgcca 41100
gggaagcatt tttcagactc atggcaataa tactctttgc aatgtgttta agtgggtgat 41160
gctatgcaat tagttgttaa caccttttaa taaatgcaca cagtaaacat tacctgtggt 41220
ttttcagctc ccggtttctt tgcagtgctg tcatctctgg agacaggcgc tggcagagag 41280
aaaagtgccc atgtagaaaa taagcaaaac acctgcattc tcacatttca gaaatgatcc 41340
tccttagggg ttagtgtggt ctatcaactt gcatcacagt gaagtggagg ggaataaaat 41400
ggtctttgct ggatttattt ttttggctgc ctcaatgaaa aaagcaagca agataactca 41460
tgtagaaaaa ttacatttga ggactgcaga cttctcactt agccttatca tggaacggca 41520
ggatatcaac atttcctaga tggaaaatta ggtctatgtt gggagatatc aggcttaagt 41580
aaaatcacat gacaactact gtgtatatcc cagtcacctc ggcacagcta cgctgagcag 41640
tctttctagg gttgctatgt tcagagttgg ctgtaactat acacaccgta agcccagttg 41700
gaaaagcaaa caagggagtg aaaaagggaa cagactattt cccaggctgt acacatttgc 41760
tgaatcttca caaaggcagg ttgtcatttc ttgtttattt cttgaatcct agatggaaac 41820
ctggaacttg agtgataata atagtagacc tttgctaact gtacatatat tagctcattt 41880
gtttctgtaa atgatcatat aatgtgggta gtattcttta cttcatttga cagattaaga 41940
gactgaggca tggaaaaatt aagtgatgtt accatggtca ccaagctctt aagtagctga 42000
ggcgggacat gaacccaggc atctggcatc cagtttattt cctttaactt taagccacat 42060
atttacctct tgtagagtca tatttattcg ttttctctcc tcttgtttcc tctcctcttt 42120
ctctccctct ctctttctta ccatttttct actactcttt cacacctgcc cccaatcttt 42180

-continued cccctcaagc ccacacccac ttcctacttc tctcctctct cctctctctc tccctctcta 42240
ttgctggaag tgatgagccc catctgggtc caccagctgg ccccagacag gggattttgg 42300
cctctcccaa attaaatcat acttgtaaag caggaaaagc tactccctgc ttccagatct 42360
ccccttccca ctgaccctcc cttgtccctc tgtcgccttc cttcttttgc ataggcttcc 42420
agttctcttg tactcttctc ccacagtttt ctcaggaaag aatgggttgt cttaaagtca 42480
tctgatatgg tttggctctg tgtccccacc cagatctcaa cttcaattgt aatctccagg 42540
tgttgaggga gagggttgat tggatcatgg gagtggtttc ccccatgctg ttcttgtgat 42600
agtaagtgag ttctcacgag atctggtggt tttataagac agtttcccta cccttgcttg 42660
cttctctctc ctgccatgtg aagaaggttc ttgcttcccc ttgtcttctg ccatgattgt 42720
aagtttcctg aggcctcccg agccatgtgg aactgtgagt caattaaacc tcttttgttt 42780
ataaattatc agtcttaggt agtagcttta tagtagtgtg agaatggact aatgcattat 42840
catatagtaa attcagtctc ttcatttaca ttaaagttcc cactttatga acatttgctt 42900
tttaaaaaaa actttgttat tgaagtacag tttaccatat aaatggtgtc gtggactgaa 42960
ctctgtccca aaattcatat gttgatgcct taactcacta tgtgactata tttggagata 43020
gggcctttaa aaaggtaatt aaagttaatt aaggcctata gggtgggacc ttaatcgaag 43080
atgactggta cccttataag aaaaggaagt gacacaggga catgtataaa taaagaaaag 43140
gccatgtgag gacacagtga gaattgttga catgttgatc ttggaattcc agcttccaga 43200
attgtaagaa aattaatttg ttgttgaagc cacctagtct atgacatttt gttattccaa 43260
cgctagcagg ttaatacata tggggaaata cacaaaaata ctcaaatctt aagtattcag 43320
cttgatggat ttctatatat tcataaaccc atgaaatcac tgcagatcaa gaaacagaac 43380
atttccagta ccccagaaac ctccctcctg ccccttccca ctcacgttag cagtctgtgc 43440
ccgattttca gatctgcttc cctgcagaga gggttcactt aggcccttct ctctcatgtg 43500
gaagagcttt acttctgcaa gtgcccctgt gcctgggtct ggatatgaga gtcaattttg 43560
ggagtcaggg ttggcggggc cacttggcca aagagctaag gcaacatttt ccaagctgtt 43620
ttcacaagtg ataaagatga cacaataatc ttcatctgat ttctgcatct atttctcaat 43680
tgtttctgaa ctagggaggg gaaaagggta tcattatctc cttgatacct aacattttgg 43740
tggttggctg tgtttaagtt tggaattttt aaaaataacc tatttttatt ataaaacatt 43800
tcaaacattc aaaacatttc acacattcaa aaatgtatat actaatataa tgaactacca 43860
cctgatttca ataaataaag acgatttact atatttgcct ttgaaaaaca ttttaaacta 43920
ctttagtaaa taagagtttc ttctattatt cttgaaacct aaaggctctg ggtcttttga 43980
acaaataatg actctaataa tcaaataaaa atcacaacat gacacaaagc tctcacaatt 44040
aattctactt tttatctaat gcactttcca tcatgttgca taccatctgt taactaatga 44100
aatgccctaa ggctcaaatt gataaataca aaaatctccc tttctttgat atgtgattga 44160
ggattccacg ctgatttgga ttagatcttt gatgaagtag tagaggcaac tgaaagttta 44220
agcaaatttg gggttgtcct acatcactaa catcatcctc tgggcaggaa tgggtcttgg 44280
gatccattta ctttcccttc tctccaacca catatatagg aagagcacct ggtggatcac 44340
accttgatga tcaggcagct acaccaaatg gttacagaaa atatgaatag gtttgagagg 44400
ggaagagcgt cataaattct tcaaagaatt gctatatggg tttagaggtg acaaagctat 44460
tactggtgaa gagtcatcac ggaaagtcct gagttctgaa tgaaaatgct caaaaaatga 44520
gaaaactggg acttcaaaga taggcataaa caaatggaag catattacaa gtgaaccagg 44580
cagaacatca aattcaggcc agggttagtt attgttttgg aggaattatc tagggcagtg 44640
aatgtgaaca gctatgaatg attttgaaca taaagaactc attgacttca tgtgctcact 44700
ccagagatct aaatagcatg tttgaaaaac aaatggccaa gtcgggagag cgggagagcg 44760
ggagagcggg agagcgggag agcgggagag cgggagagcg ggagagcggg agagcgggag 44820
agcgggagag cgggagagcg ggagagcggg agagcgggag agcgggagag cgggagagcg 44880
ggagagcggg aactgaaagt ggtgagaacc ctacattagg ttgagaagaa acaagacata 44940
ttaagaaaca agttaaactg ttaatgggaa catgtcttga ttttcttgtg tgattccttc 45000
aattctttag aattatcaat atgaatgata aaccacatgc atccagtaat aaaaaatccc 45060
agtctacagc tgctgaggaa attcaaaacc catttgggtg tttgagtgag atacttctgc 45120
cagcattcag cagtagcttt gcaaggactt acattagggt cacatcctta gtctcaatcc 45180
agccctcata tccacctact cttaggagaa ggaggaactt acctgattgg tgggtttagg 45240
attagttaga tataatcaat gcagcccatt cctctctctt cttcttgagt ctgtgtgctg 45300
ggagaaggga tgtattgtgt gctctttacc acttgatacg accctgctac agtgtggtag 45360
gtctgccact ttctggctgt acttatggac agaagggaag gggtaaattt gttcatttca 45420
gaggtgaagt cttagcaagt tcgcactgcc agtgtctaag ccatagtctc caatcacttt 45480
tgttagtaat aaaagtgtat tttgttagta atataccttt tgtcactttt gttagtaata 45540
aaggtatatt ttgatgttat cccaaagttg aacatggagg aaagatatgt ttttcaacaa 45600
tactttcagc agtattctgc tctatttcct aaatgacagg atagaattaa aataaatttg 45660
caatgatgta ctaatataaa taaatgaagt atcagtaatg aatgtacgaa ttaagtcaga 45720
gcatgtagcc ttgaacaagc tggggaacag aatataaggt cttacataat catactaatg 45780
gctaatattt accaagtgtt tattctgtcc aattaatttt ggtaatattg tgagccccat 45840
tttttgtgag tcccaatatt gtgagatgac agccaaaaag acgtggagac tggattcata 45900
atcaagggct tgatctcaga gtgggttctt ttagaatata ctggaaattt attaagacaa 45960
atttgtctct gaacttcctt gaaaatagaa cttttgttat cagtgctaat agttctttcc 46020
tttttccttt ttatattgag atatattacc aggagaaaaa taaattatct gttaagacat 46080
cctgcaaaag tatactccaa aaagtttccc ccaatttatc ctgccagtaa ggggacataa 46140
gtgtgcacat tttaatccac cttggattaa gatttattta aattaaaatg tattttaaaa 46200
taggctattg tcacttttta tgtttaattt cagtcaggag agtctgtgga catccacagt 46260
atcaagcagc ctcagaactt tattgactta aaacaactta gatgtatatt ttgctcaaac 46320
tacataattt tttacaggct aggtgggtgc tctgtcctct atcctttctc tagaatccca 46380
cgcagaagag ctgtataggg ttttgcatgt gctattcaat gttcttttcc agaagtaaaa 46440
aatatcactt agttcacaat ccattagtca taacaagtca tctggcttca cccacttaca 46500
agttgcctag aagtgcaaat ctaccatgta ccaaaaagga agaaagctag acaacacttt 46560
gtgatcagca ctaggattgc tacatgtttt tacaagtttt atagctgaaa aatggcaact 46620
agccttcttt ggcatttaca ttacaagaga ggttatgcaa ttattttctc ttttgtgaat 46680
tgtttgtgca tgcccttttt ttgtctgaca tattaaaatg ggtatgttgg cagagtcccg 46740
tagaaaagtt ggtggaggaa tttaagttgt tctcaagtaa tcaacaaaga ttatccattt 46800
ctactccctg ccccttaccc gctgctgtct cccttatccc ttggaactaa gaagttgtat 46860
ataggaaaat attctggagg gtggtggtta cctcatcgta acacactata agcaacatgt 46920
cttagaatgg tttccatggg ggcattgatc atttagtgtt tcctaacctg tgattgattc 46980

-continued ataagtacat caatatcaca tgtcaggcta cttcaggtac tctgtaaaag atacctattt 47040
ttccaaggtg tatttcttag gcctctctca atttgaagtg aaataattcc aatctgaacc 47100
agttaaaaaa aacaaaacag tgtgtcctca agtaaaagtt atagggggttt cctaggttta 47160 ggcatggctg gatatgtgaa gtcaaataat aacatcagaa cttactcatt taccactaag 47220
accaaactgg gaagttaaat ttgagtcttc acttcctcat ctatgtatcg gggataatta 47280
ttatttttct cctgtgcttg ttgtgaggat tctttcatta attcatgcaa aactttattt 47340
ttgaggcgga gtttcactct tgttgcccag gctggagtgc aatggtgcaa tctcggctca 47400
ctgcaacctc tgcctcccgg gttcaagtga ttctcctgct tcatgctccc aagtagctgg 47460
gattgcaggc gtatgccacc atgcccggct aatgttttgt atttagtaga gatggggttt 47520
caccatgttg gttaggatag tcggaactcc tgacctcagg tgatccacct gcctcagcct 47580
cccaaaatgc aggattacag gtgtgagcta ctgcacccag cacatgcaaa acttttaata 47640
caatgcctta catagtaata gaaatagaag ataactgcct actattgttc ttactacatc 47700
tactattact gtttattctt atgtatagat tgttcaatac actgaaatga cctaattgca 47760
tctgtcattc tgagatttga atttagctta actattatct ttagacttta ttattgacaa 47820
aaagatgaag gtgacaggta tgaaagattt gaaatatgtt tttcaaatat atcctaaacc 47880
agatttcagg aagagactag aaactggact tgccagattc cacatatctc aatgctgtgt 47940
ggaatttttt ttaaattttt ttttacaatt tgagatggag tctagctctg tcatcaggct 48000
ggagtgcaat ggtgtgatct tggctcactg caacctccgc ctccccggtt caagcaattc 48060
tcctgcctca gcctcctgag tagctgggac tacaggtgca tgccaccaca cctggctaat 48120
ttttgtattt ttagtagaga tgggtttcac catgttggcc aggatagtct aaatctcctg 48180
acttcgtgat ccgcgtgcct ctgcctccca aagtgctggg attacaggcg tgagccaccg 48240
ctcctggtct gagtgtgtgg aatttgacgc acctatgtgg taacaaaatg gatatatcca 48300
gtttatagct ggaactctga ttctgtacag aggtcaggat aataaacaaa agaagagtca 48360
tttgtttatg tcagagattt gttatgtggt attaaatata tccataatgt taggcaaaaa 48420
tggattgtgt attttttttcc tcctaaatag atcttaataa atgggctact ttaaatatta 48480
catacaaaga aatttagttt taaagaataa atttgcttga catgacaaat atcaaaggga 48540
actgaggagc agctacttct ttggccatga ttccaattct tcattcagta tgtatgcaca 48600
cctattcctc atttgtttgg gtcacttgct tcccctctgg aggaatttga gcactgagtc 48660
tgatcaaggg taatagagtc cttgacaaag ttcatggcta aggccagaga cctaagtgag 48720
gttgccattt ggaaacagaa gaaaaggggg ccaattatgg aagtggggag aatagccatc 48780
caaagaaact gagaagaatc agtaagaaca gcaggagaga gcagtttcac ccaagtcaaa 48840
gtaggagata gtgctatctt tttatttaca ttattattat tttttaattt tagagatgaa 48900
attttgtcct gttgaccagc tggagtgcag tggtgggatc atagctcact gcagctgcaa 48960
tctcctgggc tcaagcaata ctcctgctcc agtcttgcta gcagctggga atataggccc 49020
tcaccacggt gcctggttag ttttttaagt ctctttatag agaagaatga tcagcgccat 49080
gttcccagat aaatctaata gacttagtga aaataatcta tgaatttcat caattagaag 49140
ataatgacat acaatgaaag cagtttcact cttgtgatag ggcagaaatg tacaatactt 49200
tctgtctcta tgattttgcc tattctaagt agctcatgta agtggaatca tatggtatat 49260
gtattattgt gactggttta cttcatttag cataacacct tcaaggttca tccatgttgt 49320
agcatatatc aatatttctt ttttaatttt tttaaatgtt tttagagatg aggtctcact 49380
atgttgccta gggtgacctt gaatttctgg gctcaagcag tcttcccacc tcagcctccc 49440
taggagttgg gactacaggc atgtaccaca ttttgctttt ccattcatcc cactggtgaa 49500
cacttgagtt acttctatgt tttagctatt gtgaataatg ctgttgtaac atgggtatat 49560
aaatatctct tcaagattct gttttcaatt ctttggggtg tataccaaga attggaactt 49620
ctggatcata tgataattgt atttttaatt tttgaggact tgccatactg ttttccacag 49680
tggctataac attttgcatt ccagcaacag tgcagaagag tttctatgtc tccacattct 49740
tgtcaacata ttattttcta tgtttttaaa aaagttttcc tgtaatccca gcactttgag 49800
aggccgagat gggtggatca cgaggtcagg cattcaagac cagcctggcc aacatagtga 49860
aaccccgtct ctactaaaaa taaaataaaa aaaaaagctg ggcatggtgg tggggcctgt 49920
aatcctagct acttgggagt cttgggcagg agaatcactt gaacctggga ggcggaagtt 49980
gcagtgagcc cagatcatgc cactgcactg cagcccaggt aacagtgcga gactccgtct 50040
caaaaaaaaa aaaaaaaaaa aatttatagt atccttaaca ggtgtggggt gttatctcat 50100
tgtaagtttt ggcttgcatt tccctaatga ttagtgatgc tgagcacctt tcatgtgctt 50160
attggccatt tatatatctt ctttagagaa gtgtctactc atgtcttttg cccactttta 50220
aatcaaattg ttcctttttc attgttgagt tttaggagct ctctttatat tagtatctta 50280
tcagatatgt gatttgcaaa tattttattc tgtaggttgc ctttttactc tgttgatatt 50340
gtctttaaaa atgtatatta aaaattctaa ccagcttaat atattattga caaataaaag 50400
ttatatatat ttgtggtatg caacatgata ttttgatgta tgcatacagt atgaaatgat 50460
taaatcatgt taattgacat atccattgcc tcacataatt attcacaaat ttttttcctt 50520
tccataaagt ttaatttgtc tgtttttttt cttttgtagc ctgtgccctt agaatcatat 50580
ccaagaaata attgccaaat ccaatgtcat aaagcttttg ctgtatgttt tttcttaaga 50640
gttttatagc ttcttaaggt tttaaatgta gttctttgat ccatttaaat aaatttttgt 50700
atatggtgtt aggcaagggt ccaacttcat tattttgcat gtggatatcc agttttccca 50760
gcacctgttg ttgcaaagac tcttttccat attgaatggt cttagctctc ttgtgaaaat 50820
catttaccgt atatatgagg gtttatttct gaattatcta ttctattcca ttggtctatg 50880
tcttccattg gtctatatct atgtttgtga ctgtactaca ctgttttgat tactgtagct 50940
ttgtggtaag ttttaaactc aggaactgtg actcttccag atttgttcct ttttcaagat 51000
tgttctggct attcagggaa ctttgatatt ccatatgaat tttaggatga atttttctat 51060
aaagagtatc attaggattt tgataggatt gtattgaatc tgtagatcac tttgggtagt 51120
attgctatcc taaaaatgtt gtcttctact ccataaacat aggatgagtt tctatttttt 51180
tatgccttta atttcttcca gcaatatttt gtagttttc ttgtacatgt ctttcatctc 51240
cttggttaat tcctatgtat tttattttta tttggaaata tttattaggt gcccactttg 51300
ttccccatat tatcccaggg agttattaca aaatgatgag caagacagac atgggctcat 51360
ggggcttcct catgcatgtc ttttggtatc accaatttat ctcctgtggc ctgtggcaaa 51420
tgtatggtgt aattctagtc catgagctta gtatacttat tttcaggtac tcactcagct 51480
gtacttgttt aaaaaaatgc ctgaaacttg atttgcttgt gtggatatta agagtaaatc 51540
aactattcca tacatgtaaa gtacgtttta ttctccctgt aaaactctca atgtttttct 51600
tcaaaatata ctttatgata tatatattaa ctattatttt aagatagttg ggaaaatgaa 51660
gggaccataa tttaaaagaa atggaatatt tgatacatga tgtggctgcc tgtttttatt 51720
cttgtcacct agtctcagtt tttcaggttt ttaaaaatat tataaatgca cacatgtaca 51780

-continued cacacttaat ttcttcttaa tctgtgatct ttcaggtttc tattacatag attaattcat 51840
gtaaatttc ctagtctttt gaaattaaag aaagtcaatg acaaaaggac catcacgtgg 51900
acaaccagtg ggaatgtttc attcactctt gtaagttact tgttcccagt gcaaaagttt 51960
aaaagaaagt ctttttattt attcaaaagt tgaaggtttt ttttttttt ctcttcagca 52020
ccggaaactg tcaggaaaag cagtatatac ccctaatgac tagttcagaa ataaatgtat 52080
cattgttttt aataatttga tacagtatat aaatgttgtt ttgtaaagtt taaattctac 52140
tattaactga acaaaatata aaccaggaaa ttaacatcaa agaaataacc acattcacct 52200
gttcctctcg tctctaacat tctgcttttc ctttgctccg cagggtaacc atggtgagaa 52260
agatgttgat ggcttggatg gagaacaggt actaaaattt ctcattctat gttccgcctc 52320
tactagtttg gcatttacac atgtcatgat taatctagaa atgtaaacat gcatatttaa 52380
tgtttaaagt ttatctatgt ttgttcttat cccaaatata caagaaccct agaagtctaa 52440
ctcgaatcaa cctctcccat attacatttc tttccatctt atttttgtta aatctatcac 52500
ttagacattg ttattgtttt atatagtcaa tgcttattta gccctaccat catatgtctc 52560
caatttctg gaagagttag agaaggatta gtattcattc tttaaatgtt tggtagaatt 52620
cactgaggaa gccatcaggt ccatggtttt cttcaagaga ttttttgatt attgattcaa 52680
tcttcttacc attgattcaa tcttcttacc agttgtaagt ctattcatat tttctatttc 52740
ttcaggattt agttttgcag gttttgtgtt tctggaaatt tttccatttt ataaagacta 52800
cctagttgtt ggcatacact tgttcttagt actatcttag aatgtttttt tattttttg 52860
agacggagtc ttgctctgtt gcccaggctg gagtgcagtg gtgtgatctt ggctcactgc 52920
aatttctgcc tcctgggttc aagcgattat tctgtctcag cctcctgaat agctgggatt 52980
gcaggcgtag gctaccatgc ccacccaatt tttgtatttt tagtagagac atggttttac 53040
catttttgcc aggttggtct caaactcttg acctcaagtg acctgcctgc cttggcctcc 53100
caaagtgcta gaattacagg catgagccac ctcacccagc ctattataat tctttttatt 53160
tatgtggact cattatttcc actttcattt ttgattttat taatttaaat ttttctcttt 53220
tttttttagt tcatctggct aaaatttcat cacttttgct aatcttgagg aatcaatttt 53280
tggttttatt gattttctct attatttctc tgttctctat tttatctttg ctctaatctt 53340
tatttccttc tttctccaag ttttgagttt agttcttctt tttctagttt cttaaggtat 53400
aaagcgaagt tgttgatttg agaccttttt tgttttttaa cgataagtgt ttacagctat 53460
agttttttcc tttagcacca cttttgctgt gtaccataag ttttcgtgtg atgtagtttc 53520
atttttcatt tgtctctaat tatattctaa tttcttttgt gatttctttg atccattggt 53580
tgttgaagac tgtgctgtat gatccttttg tagttcacaa gcctgatgat tgggttttca 53640
ttcacgtgga tgagatgcac ctccctcaaa cctggttgtt acagcatagg cacattactt 53700
gtctaacacg aaaaaaagga aaaaggagtg tgctgtgcaa tttccacaaa tttgtgaagt 53760
ttctaatttt acttgtgtta ctgagttcta atttcatcct gttgtgatca gagaagacaa 53820
tttgcataat atttatcttt tataatccat cgagaattgg tgacttaata tattgtgtct 53880
ggagttggtt cctcctggtg ggtttgtggt ctccctgact tcaagaatgg agctgcggac 53940
cttagcagtg agtgatacag ctcttaaaga tggcacggac ccaaagagtg agcagcagta 54000
atatttattg tgaagagcaa aataacaaac attccccagc acggaagggg acctgagcgg 54060
gttgccgctg ctggctgggg tgcccagctt ttattccctt atttgtcccc acccatatcc 54120
tgctgattgg tccattttac agagtgctga ttggttcact ttacagagca ctgattggtc 54180
cattttacag tgtgctgatt ggttttacaa aactctagct acagagcgct gattggtgtg 54240
tttttacaga gcattgatag gtgcatttta caaacctcta gctagctaca gagtgctgat 54300
tggtacattt ttacagagca ctgattggtg cattttacaa accccttgta agacagaaaa 54360
gtcctccaag tccccattcg acccaggaag tccagctggc ttcacctctc aatatgatat 54420
atcttgataa atattccatg tgtacttgag aagaatgtgt atgctgttga tgttgagtaa 54480
tgctctgtat gtgtctgcta gatctagttg gtttgtgttg tgttctattt cctttcttat 54540
catctgtctg attggtgtct tcattattga gaggggagta ctgaaatctt taactattat 54600
tgtagaacta tatttctccc ttcatttctg tcagcttttg cctcatatat tttgatggtc 54660
agttattaga tgcatgaatg tttatagttt ttatatcttc tttctgtatt gaacatttta 54720
atttataatg tccttcttta tgtctttttc actttttgga tttaaagtgt attttccctg 54780
atattggtat agccactgct gctctctttt ggttactatt tgcatggaat agcttatttc 54840
tttttttctt tctttttttt tttttaaata aacacatttt tttttttttt ttttgagaga 54900
cagtctccct cttgtccagt ctggaatgct gtggtgcaat ctcagctcac cgcaacctct 54960
gcctcctggg ttcaagcaat tcttatgcct cagtctccag agaagctggg actacaagtg 55020
cacaccacca cccccggcta atgttttgta ttttagtaga gacagggttt tatcatgttg 55080
cccaggctga tcttgaactc ctgacctcag gcaatctgcc caccttggcc tcccaaagtg 55140
ctgggattat aggtgtgagc cactgcaccc agccagaata gctttttcta tcattccatc 55200
tttttttttt ttttttgaga tggagttttg ctcttgttgc ccaggctgca gtgcaatggc 55260
acaatcttgg ctcactccaa cctccgcctc ccaggttcaa gtgattctcc cacctcagcc 55320
tcccgagtag ctgggattac aggcgtgcgc caccacctca gataattttt tgtattttta 55380
gtagagacag ggtttcacca tattggccag gctggtctca aactcctgaa ctcaggtgat 55440
ccacctgcct cagcctccca aagtgctggg attacaagca taagccacca tgcctggcct 55500
atcattccat cttttcactt tctatctgtt tgtatttcta aatctaaaat gagtctcttg 55560
tagacagcat ttagttggat catgtatttt taaatctatt ctgccagtat gtatctttca 55620
attggagagt ttactccaca tttatttaaa gtaattactg ataaggagga cttacttctg 55680
ccagtttgct atttgttttc tatatgcctt atactttatt atccctcagt tcctgcatta 55740
ctgtcatctt ttgtgtttag ttgatttttt gtagggaagt gtttaaattt atttctcatt 55800
tccttgtata tagtctgtag ttattttctt tatggttgtc atgaggatta catttaacat 55860
cttaaagtaa taacactgta atttaaattt aaaccagctt aactttaata ctatacaaaa 55920
agtttactct gttatagctt catccccact tatttcagtg gctgatgtca taaaattaca 55980
gctttatata ttatgcaccc caaaacataa actaataatt cttttaaata cattagcctt 56040
ttaaattata tagaaaatga aatgtgaagt taccaaccaa agttacaata ttaggttttt 56100
gagtaataat tctttaaatg tatttttctc ttaaatcatg tagaaaataa aaagtggagt 56160
tataaaccat tattacaata atacttgatt ttatgattgc acatgtattt acctttgctg 56220
agatagttat tttttcatat gtctttgaat tactgtccag tgtcttttca tttcatgcta 56280
caggcttccc ttgagcattt ctttcagggc agctctagtg gtaatgaact ccctcagttt 56340
ttttatttgg gaatatctct tttttttttt gacaagatct tggtctgtca ctcaggctgg 56400
agtgcagtgg cacaactgta acttactgca gcctcaaact cctgggctca agtgatcctc 56460
ccacttcagc ctcccaagta gccaggacta caggcatgca ccaccatgcc cagctaatct 56520
tttttaatta ttattttttg taaggatgag gtctcactgt gattcccatg ttggttttga 56580
atgcttggcc taagcaatcc tcctgcttca ggctcccaaa gtgccaggat tacaggtgtg 56640
aatcactatg cccagccatc tgggaatacg tcttaatttc ttattttaga aggacagttt 56700
ggccagagat agaattttg gttaatagat tttttctttt ttttttttt ttgcacttgg 56760
aatatattga cccaatgcct tttggcctcc aaagtttcaa atgagaaatc tgcttatgat 56820
cttattgaaa atctcttgta tgtagtaagt ctgtctttgt tcaatcaaag gtttgattat 56880
aatgtatctc agtgtgggtc tccttgagtt catcatattt ggattttctt gaatttcttg 56940
gatgtttata ttcatgtctg tcatccagtg tcagaagttt ttcagtcatt atttctccaa 57000
atattcactc taccccttc tctcttctcc ttctaaaact tctgcaatgt gtatgttggt 57060
ctgcttgatg atgtgctaca ggtcccttag gctctgttca cttttcttca acattttttt 57120
ctttctgttc cttagactca ataatttcca ttgtcttatc ttcaagtgtc actgattctt 57180
ttgcctctta aaacctgcct ttgaatctct ctagggaatt ttttgtttca gttatcatac 57240
ttatcatttc cagaatttat ttttggtttc tttttaggtt ttggtatctt tatatttcta 57300
ttttgttcat ttatcatttt cttgattttt ttaacatctt cctttagttt tgaaaatata 57360
tttaaggcag ttgtttcaaa gactttgtct agtggatctt ccatctgtgt tactcaggga 57420
cagttttggt tgatttattt ttgtttcctt tgagtgagcc atagtttcca tttctctgaa 57480
tgccctgtga ttttttttt tgaaaactgc atatttgaac ctaataaagt ggtaactcta 57540
gaagccagat tctcctccct ttccctgtgt ttgctgtttt ttggttacaa tttattgttt 57600
attgattttt tttttaattt gagtgtttta agctatctct gtgtcaagga tcagaatgag 57660
gtatatactt aaggtcttct caggtatttt ctgagtcagt gctttcccat gggcttgtgt 57720
ggtgataaaa gaaaaacttc agctgaatta aatttgaagg agtttaattg agcaatgagt 57780
attttgtaag ttgggcagcc cccagaagca cagctgattc acagagactc cagcacagct 57840
atgtagtgga agaagattta tagacaaaaa aggggaaatg acctacagaa attggtggtg 57900
aggtacagaa acagctggat tggttacagg ttggtgtttg ccttattgga acacagtttg 57960
aacacttagc agtctatgag tgcttggagt atggccgctg ggattgccca agacagttat 58020
tgttacaggt gcatactgtt aaattaggtt tttaatcttg tgtgactatt aagctaggtt 58080
acagttcatc cacaaggact caaatataga agtatggagt ccttctcacg ccatatttag 58140
ttttctttaa gtggtcactt tctaattttc ctcacatata ctgctgcttt tgaatgtccc 58200
agcctttaat gtctggctcc caaaaaggca aaaagaaaaa aataaagggg agagggagga 58260
ggcagtggcc cttaaaatcc cctggaagtc aattcatttg ggggtaggag ggagtagcag 58320
caatttgaga agatacaaaa caatagctgc ctgcttcttt gcacctccga gatcaaaaac 58380
aacaatcagt aatcaaagct cagatcttga tttgcaggac agagttcttt ttgtcacact 58440
gatttccaca agctgcattc aagctgctcc aggaacatgt gcattgctac ctgacaagga 58500
actgtgtgta gggtatgtgt agctcctcct gtgcaaacta aagttggcaa aagtaatagc 58560
aatacactaa acaagccttc ctttggaagg tgcaagcctt caataggatc cacagttcca 58620
aaatagttac atcagataaa ttctgtcagt acaattgtag tagggagata gattttatgt 58680
aggcagatag attttaggta gggagataga tttctggttc ttcctattct gccatcccat 58740
cttctaaaac tacacctcat gttattatca ttattactat tattattatt tatttttgag 58800
acaaagtctc gctctattgc ccaggctgga gtgcagtgat gcaatcttgg atcattacag 58860
ccttgacctc cacccacctc agcctcccaa gtagcaggga ccacaggcat gcaccactat 58920
gcctggctaa tttttatgtt tttgtagaga cagggtttca ccatgttgcc caggctggtc 58980

-continued

```
tcaaactcct gggctcaaca tatctgcctg acttggcctc ccaaattgct gggattacag  59040
acatgagcca ctgtggccag ccctgaattt attttttaaa tagaagattc ataaaaaaaa  59100
ttgacctcac gattataggt aactagattt tttgcaaatg aaattatctt attagaaagt  59160
atattagata taagcagtta tatttttacc cagaaccaca ggcagttctt tctattcaga  59220
gtaaagagcg atattgggta tatttccaaa ttcaaatgtc attctaaaat atatttgtat  59280
ttttatcagt gccaagtgca atggtagttt gtgcaaatta gtgctcgtag taggagtgtt  59340
ttagtactat tgaataataa cagtgtaatt tgaaaggtaa tttcattatg gcaagcttcc  59400
tgggaaaagc aagtggcctg ccttataaat ttggactcat tgttagaaat tacaagttca  59460
ttgaataatg aatacagtag tcactgggcc tttagaagtg aagttttaag ttggtgataa  59520
aaagaggtag cttcatagaa ttccttttgt acttgttttt tttttttttt ttttgtcaaa  59580
ttatcaaacc ttgctttgga tgtaagaatg agttgcgagg ggagcaaaag ggcaactgtt  59640
cttcatgcca aaagtaatca ctcatttagt tttttctaaa cattttcttt gttccagggt  59700
aaataagatt ttcaagccac tttaattata atgaatgatt gttaaaatca tactgaacaa  59760
aaaatgttat tgttattcag gattattcta ttgagtagga cactcaaaaa cttcagttaa  59820
atattaatac aagataagag cctaataaaa acagtagaac agttttatac atgttaaata  59880
gttaaaaaat acatcaatgg ttataataca tttgacaatt taccttgaaa tagtctacag  59940
tttgcttgtg aaaatgagag ttggaagaat tgcagcttgt gagttactac gtagtagtga  60000
aatgagggtt atcaaaattt gcagtctttt tgcagcctta aaaactggga catgtttgtt  60060
ttccctttga gatgcagctc cttggaagca tatgtttaca atagatacct atgtcataaa  60120
tatttaaaat ttgatccaat gcatagtctt ctccttcaat taacttcagt atccctgctg  60180
gaaatctgtg actttttcat ctacactcat agctttactg ataggaaggc tttacgaatt  60240
gcagtggtgt ttgaaaccac caaaccaccc tctagtagca ctgaaaggag caaattatgc  60300
aggatttggt gataacggtc tttgtataga gatagtgctt tctctttgat tatgttttct  60360
ctttgattgt gagaaaggtt gtttttgatc attgcactat ttggtcttca tatgctgaac  60420
aatatttcaa tttcttgtat ttctttctgc cttgttctta ttgacttcat agcacttgaa  60480
gtgatttaag atacagccat gtatttgtgc agagttgtct ctgatggtcc accatgtgga  60540
ttcctttatg cttgttgctc tggagatatc atattccctc ctttctttca aaacacttta  60600
gttcaagatg atcttcaata tcatcaatac ttaaagattt tcttttacat gcacggcttg  60660
ctggttttga acacagatgc ttggatatgt ttgagagatt aattaaaaga gtgctttttt  60720
tttgtattga aaagttcatg agttcaaaag aatggaaaaa cagaacaatg taggctaaca  60780
catgctgtgg actgaggtaa ctggtagatg gctcaggtct gagcgtgtac gtgttttgtg  60840
tactaattcc cacatggatc catctaacca tgcagttttc tgcctttatc tagtgtttct  60900
taacactagt agagatttag cagagataga aaatttgttt tatgctgaaa acattccctc  60960
gtatgtcaat catgttggaa caaattcatg ttttaaaaca agtgctatag cagaaatgac  61020
tgtgataaaa aagtttaaaa aggaataaaa acttaggtct gtcattatag taagtgttaa  61080
ttgactgaaa tctcacttta caagaccatc agattgaagt aaaaaagcac aactatgtac  61140
tgcctttaca ggaaatgcat aataacaaga gatgagcaga gatatatgcc aaatggaaac  61200
aaaataaagc aagtgtggta ttgtaaatat cagagaggct gaaatttaat gataatagca  61260
ataatcagga taaagaaaga cattatacaa taaaattact attaatgaag gagatacact  61320
gttataaact tttatgcacc aaatatagca actaagcata taaactaaaa tctatgagaa  61380
```

```
attaaaatct atttgaattt aatataatga aactttagaa taccacttta aatttcaaat  61440
atgtccagta gaaaaaaatt ttaagagatg cttttaataa aacaatatta gacaaacaca  61500
tatacaacac acatacatac atgaatatga acataaatat aatattttac agcccttaag  61560
agaaaatata gcttagtctt agattttaac atataggtaa aaaataaatt aaatattaga  61620
aaaaatctta gagtttatca aacaattgat atactatgat aaaggtttta ttttagaaat  61680
gaatggtggt tccttatcag gaagtttgtc accagaattt ttttttcatc aacttttaag  61740
ttctggggta catatgcagg atgtacaggt ttgttacata ggtaaatgtt tgccatggtg  61800
gtttgctgca cctattaacc aatcacctag gtattaaccc cagcatccat tagcttccgg  61860
atgctctccc tctccctact ccccccacag gcctcagtgt gtgttgttcc cccaccatgt  61920
gtccatgtgt tctcatcatt cagctcccac tgataagtga gaacatgcaa tgtgatcttc  61980
aacaaatctg acaaaaacaa gcaatgggga acagattcgc tatttaacaa atggtgctgg  62040
gagaactggc tagccatatg caaaaaaatt gaaactagac acctttctta caccttatac  62100
aaaaactaac tcaagatgga atgacgactt aaatgtaaca cccaaaacta taaaaacccc  62160
agaagaaaat ctagtcacca gaatttaata caaaatttaa tggtaaagag aataagcatg  62220
tggtcataat agcagatgat gaaaatgacg ttttaaaaat ttatcaggaa tttctaataa  62280
aacgaattac aaaaaacaaa aagaccattt accaaaagca cagctgaagt tttttttttc  62340
ttttgtaagt gatgaaatac taaaaatact taaaattcat tgagggtata gtttccaaat  62400
gaaaaaatag acaaaggaca tgaatgggca attcacagga cagcaaatcc aaaagggcaa  62460
caaatacata aattgatgtg caaataggcc tgatgcaggg cttatgcctg taattccagc  62520
attttgggag gctgaggtgg gcggatcact tgaggtcaag agtttgagac cagcctggcc  62580
aacatgggaa aaccccatct ctaataaaaa tccaacaatt agctagacat ggtagtgcgt  62640
gcctgtaatc ccagctacat gggaggctga agcaggagaa tcgcttgagc ccaggaggca  62700
gaggtttcag tgagccgaga tcgcaccact gcactccagc ctgggtgaca gagcgagact  62760
ctgcctctaa ataaataaat aaataaataa ataaataaat gtgcaaactc attatttata  62820
aataaataaa tagatgagtc agggaagagt gaacccggga ggcagaagtt gcagtgagct  62880
gagatcacac cactgcatac cagtctgggt gacagaatga aactccttct ctagataaat  62940
aaacaaacga ttaattaaat gatacacaaa ctcactggga gtcagaaatg tgaattaaat  63000
tgaaaatgac atattataca cctaattaga ttggccaaaa taataaaata cccatatctc  63060
cctaatattt gtggtggtgt agagaaaagt atttccaaat attgctagtg gatatgtgag  63120
gtactatatt ttttggacag aacatttagc aataaatatt aaaataaaaa atttttaaaa  63180
ccctcatata ccctttgatc cagaaatccc aaaccaggta tttaggctat agaattaaag  63240
taccagtatg tgagcataag tataaggatg tttaataact taattattgt tcatactagc  63300
aaaaaatgga ggaaaatgaa tatccattgt aatagttaac ttatggtacc tgcatataat  63360
gaattatttt gcagctatta aaacttgtca ctgtttgctg atgatatgat tgtataccta  63420
gaaaaccctg aagactcatc caaaaagctc ctagatctga taaataaatt cagtaatgtt  63480
tcaggataca aaatcaatgt acacaaatca gtagcactgc tatacaccaa caaatgacca  63540
agctgagaat caaatcaaga actcaatccc tttacaacag ctgcaaaaaa aaaaaagaaa  63600
ataaaatatt taggaatata cttaactaag caggtgaaag atctccacaa ggaaaactac  63660
aaaacactgc tgaaaaaaat cacagatgac acaaataaat ggaaacacat cccatgctca  63720
tggatgggta gaatcaatat tgtgaaaatg accatactgc caaaagcaat ctacagattt  63780
```

aatgtaattc catcaaaata ccatcattct tcacataact agaaaaaaca attctaaaat 63840
tcatatggag ccaaaaaaga gccttcataa ccaaagcaat attaagcaaa aagaacaaat 63900
cgggaggcat catattaccc aacttcaaac tatactacaa ggctacagtt accaaaacag 63960
catggtattg gtataatagg cacatagatc aatggaacag aatagagaac ccagaaataa 64020
agccaaatag tgagaaccaa ctgatcttcg aaaacgcata caaaaaccta aaatgaggaa 64080
aggacaccct attcaataaa tggtgctagg ttaactggca agccacatgt aggagaatga 64140
aactggatcc tcatctctca ccttatacaa aaagtcaact caagatggat caaaggctta 64200
aatctaagac ctgaaaccat aaaaatttta gaagataaca tcagaaaaac tcttctagac 64260
attggcttaa gcaaataatt catgactaaa aacccaaaag caaatgcaac aaaaccaaaa 64320
ataaacagga cttaattaaa gtgaaaagct tctacacggc aaaagaaata atcagcagaa 64380
taaatagaca acccacagag tgggagaaaa tattcacaaa ctatgcatct aacaaaagac 64440
tgataagcaa aaaagtatat ataagatttc atttttatgt tgcaaataat tgtaaaagta 64500
tatattttttg catgtatatg ccgaaaatat ggtggaatag ttactacatt ttaaaatgtt 64560
ggaacatatt aaatatgggg aggaaaaatc gaataaatgt tataaagtgg ggaggggggg 64620
aagtggaatc aagaatagag aaaaacaagc aagtgataat agaccacaaa agaaaaaaca 64680
aaatgtttgg gaggcctagg caggcacatc acttgagcca ggagtttgag accagcctgg 64740
gcaagatggc aaagccccat ctttacaaaa aatacaaaaa ttggcagggc atggtggtat 64800
gaacctgtag aacccagcta cttgggaggc tgaagtagga gtaatgcttc ttgaacccag 64860
gaagtggagg ttgcagtgag ctgagatcat gccaccgcac tccagcctag gcaacagagt 64920
gagacagtgt cttgaaacaa aaaacaaaat gtctaatata tggtggtctc atttatgcat 64980
ttatgtaaat tagtattctg ctagtcttgt gctttttaga agagaaaaat tgatatttaa 65040
caattaatag gcttaattat aaatgcatta aaagccctaa taatgaacaa ccttaatcta 65100
ccagaatgag ttccaaaaat ggacaattat atggaaaatt tgggctttaa aatggtgtat 65160
tttgttgagg ctacacttgt atcctgcaga ccagagaggg cataggcaag atgctgacct 65220
tgccttgtct aggaaatact agggatggct ggagggttgc cgatttcaaa aggaagcagc 65280
aggattatat ttaaatgagg ggtctcaaat gggtactcat gcctgtaatc ccagcacttt 65340
gggaggctga cacaggcgga tcacctgagg tcaggagttc tagactagtc aggccaacac 65400
ggtgaaactc tactaaaaat agaaaaatta gccaggcatg gtggtatgca cctgtaatcc 65460
cagcaactca ggaggctgag gcaggagaat ggcttgaacc tgggaggcgg aggttgcagt 65520
gagcttagat tgtgccactg caatccagcc tgggcgacag agtaagactc tgtttcaaaa 65580
aaaaaaaaaa aattaaatgg tggggggtct tattactctg ctttgccttc tccattgacc 65640
actggaacaa attgctttga aggttatggc aggtagccat ctctgtatag gaatatgaac 65700
aattcctacc taactgaagg tatcaatttc taaatttacc aaaaaattct gatgcccagg 65760
ttttcattcc agagattctg attgaattgg tataagaggt gtgtggctgg ttttctgaag 65820
cccagagaga gagagagaga gagagagaga gagagaaatt taccctctca ggtttgttca 65880
gctagaatta caattcattt caaatctatc taaaatgatt gtcattacaa atgattccac 65940
attgtgctta gtaaccagat gaaacaagag ccaacaaggg ctgcattatt taattctcat 66000
ctattagtaa actaggacaa aatagagtaa ttaagtaatt atgatatcta aggcactgaa 66060
agtagggata aaagggaatg tcatcaagtg aatatacatg aggtgagaca cacagactag 66120
tatagaataa aggaaccgcc cttgacagtg cattggaatc acctggggaa ctttaaaaaa 66180

-continued

```
tactgatccc cacccccacc caccactcaa attctgatgc aagttgtcct gggcatagtg  66240
attttaaaag ttacccatga gattctgtta ggtagtcaga gttgaaaacc aataacctaa  66300
aaggaaatag gatgaaaaaa agtgattcgt gtagaggttc aaagaccctt taagatgggt  66360
atcattcatt catttattta ttcagttcag gtattcagtt tagtcattct tttcattgca  66420
ttcaattaat tcaatattta tgaagtaccc actttgtatt tgtccctgaa ttagagtccc  66480
caacatcacc acttgatgga taaaatgcaa atttgttttg actaatttct ttgtgcctgg  66540
aaggcatctc ttattctgag tctggctcta ttagaaagag aggcaaattt tctcctcttt  66600
tctcttctct cttttctttt tctttctttc tttcctttc ttgtttggtt ttagtaaagt  66660
gggaagatta ggggattgag aaagaaagag cctaggaaac tttcatttgg tttctactgt  66720
gttagctacg gattcacatt tcacaggcag aatctcacaa atctgtgaca gaggcattat  66780
tcactccagt ttacaaatga ggattctgag actaaaaatg attaaggaac ttgtaataag  66840
taaagccact tattacaaaa ctaggatgta aactgcaaag ttacttcccc caacattttt  66900
tcttccagtt tctctaaagt caaaaagagt atagccacgt ccccttgcaa atcatatgtg  66960
tatgcacgta tttcaggaag ttgttctggc aatgttgttt ctttgaaatt tcttcttgta  67020
tctttaaaac tcacttgaat ttttatttca cccccatatg atgattaaaa tgcaaaaatt  67080
gggcttaatt tgccattagg aaaaaataat ctgtttctgc cttaagggat gcaactgcat  67140
tgagtttatc aatttcagaa aatcgtgttg actaaagaga actgactcaa catataaggc  67200
tcagcatcta ggaaattgct ctgctctgga ttgcaatcac tgaatttcat agatctgggg  67260
atacaaatgg taacagatct ttttctccgt gcttcttttt tttttttttt ttttaatcct  67320
tgagacggag tcttgctctg tcgcccaggc tggagtgcag tggcacgatc tcggctcact  67380
gcaagctccg cctcccggat tcactccatt ctcctgcctc agcctcctga gtagctggga  67440
ctacaggcgc ccgccagcac acctggctaa tttttgtat ttttagtaca gacggggttt  67500
caccatgtta gccaggatgg tctcaatctc ctgacctcgt gatctgcccg cctcggcctc  67560
ccaaagttct ccatgcttct taaaccctca aatgctgcct gaattaaaaa ggcctctgca  67620
ttcactgacc agtctcactt aactcactga tgctgatctt ccccccaccc ccatatggta  67680
taatgcttat gtcatgaatc aagaatctcg aggacaaggc aggtggatca cttgaagaca  67740
ggagttcaag accagtctgg ccaacatggt gaaaccccat ctctactaaa aatacaaaaa  67800
ttagcagagc gtgatggcgc aggccgtaat cccagctact ggggaggctg aggcaggaga  67860
atcacttgaa tacaggaggc agagattgca gtgagctgag atcgcaccac tgcactccgg  67920
ctgaggaaat agagtgagac tctatctcaa aataataata ataataataa taataataat  67980
aataataaca atagtaatct caagtgactc atagtcccta ttagtaactc tcttcatcca  68040
gtgaaatttt atttttttgg tagtgattct gtgtctattt caaacactca tttggcagca  68100
ctttttattt ttggcaatta tttattcaac tcttgtaagt atctgtttac tttgcatatt  68160
ttctgctggt ataagctcta ggaaggtaga aacttagtct gtgtttctaa ctaatatatc  68220
ctccacacct agcattttgc ctggtagtat atatattggg catttagtat ttgttgaatg  68280
atcgcagcat aggactttca cagataattt actcctaaaa tatgcttttg acatgtcaag  68340
cttcactgac cttgaagaaa gcctgaagta atttttagtt taattgattt tgcctttttta  68400
ttgtattgtt ctattcatga tttcatttca gttgcaaaac attctgaaaa cgttttgaga  68460
gatttgtttg aaatatagct ataagaatgg ttgtccaggg attttttttt tctttccttt  68520
ttttttttt ttttttttga tatagagtct cactctgttg cgcaggctgg agtgcagtgg  68580
```

```
tgcaatctcg gctcactgca acctccacct cctgggttca aacaattctc ctgcctaagc  68640
ctcccgagta gctgggacta ccagcatgcg ccactacgcc catctaattt ttgtgttttt  68700
tagtagagat atgaggtttc accatattga ccaggctggt ttcgaactcc tgacctcgtg  68760
atccacaggc cttagcctcc caaagtgctg ggattacagg tgtgagccac cgcgctaggc  68820
ctagggattt ttaaaaaaca aaatctcact caatattcag gattatttat atttttacaa  68880
taataaaatt taaaatacaa ataagcatca aaactcacca acatgtttag tatcgatagt  68940
ttctgtgtta ccaccaattc acaagattag gttaagaaaa tatcctttgg ttgtttcttc  69000
tgtcaagatc attttaggga catctgaagg gtaactgact ccataatatt agatttctat  69060
gcatttccat tgtcttgtat gttgttactg gtttcaagtc tattttcaaa ttactggttt  69120
ttaaatcaca ctcaatattg ccagttgaac atgtaattta aaacttattt cccctcttaa  69180
gttatataaa agataacaaa tttgcttacc tatctactgt tattagaatt ttcagccaag  69240
cgcggtggct cacgcctgta attccagcac tttgggaggc cgaggcaggt ggatcacgag  69300
gtcaggagat caagaccatc ttggctaaca cagtgaaacc ccgtctctac taaaaacaca  69360
aaaaaattag ccgggcgtgg tggcgggcgc ctgtggtccc agctactcgg gactctgagg  69420
caagagaatg gcgtgaactc gggaggcgga gcttgcagtg ggccaagatc gcgccactgc  69480
actccagcct gagggacaaa gtgagactcc gtctcaaaaa aaaaaaaaga aaagaaaaac  69540
tcatgtaatt ggggagctcg tgatattggg aattagatta gtctcaaacc tgccctgtgc  69600
atatcgagta ttgagatata tgcaactact atatttcatt catggtatta ttttacgtat  69660
attccttatc aatcacctgt caaattaggt aattttatta cacacacagg tatttatata  69720
atttttagtg acacaggaca attatatatt atttcatact atcctcacac tgacagagaa  69780
gatatttgtt gttccttaaa aaatcaaaca aacaatagaa agcagctgag aatattgaga  69840
ttcagtcttg cccaaggtca cgtatgctca cacacagcta gaaccagtca cagatctgct  69900
cttcgtctgg tgctgtctac tctgatttcc aaaatagtgg ctcctgttca ctctccccta  69960
ttttaatttc agagttctgg cagaatggta agaatgtaaa gaaaatggtt cactgctacc  70020
tctggtatac actttatctt gtaagaattt atggtagatg gtgttgggga acagtgcctg  70080
catggcaatt cttgcagcat ctctgctgct gtatatcatc ccattttctt atttgccaca  70140
ttgtaaatca gctttgcaaa tagccactca tacagggaag taacacttta ggctggatag  70200
tacagtactt tccaattttg tagatgtttt aggaagctat gtctgctgaa tatgccacat  70260
ttcttatcac tgtcatctca aaaccataat taatattaac cgagaaatga tgatcaaggt  70320
aatagtctca aaactctttg gcaaataaac aatgctattg cagcacaact ttgttaggca  70380
ggatgtatat aggtaattaa tacttttagg atatctaaat agctattctg tggggctgag  70440
gaagaaaaac ttcatcagga gagtggcaat aaaaaaaaat gatgcagtac agcaagatgc  70500
cgctgaaaaa taatctttgc agaaagcaga acaggcacaa agtacatatt tggagctcct  70560
tttaagaaaa gttttaagct gatccaactg agtataaagt ggagttgcat gctcagggta  70620
aggctctgca gaaagcattg accaggtgtg tgtttatggt tttcaaagct agaactagct  70680
actgtgccag tggcttttac agcatctggt gggtaggaac cagcatgagt catccgggga  70740
gcactggact agccggggca ccccagtacc cactaaagag ctgacctagc ctcttgcctg  70800
gggctgagaa gctgcatttg gtctagatca aggtcctagg gaggaactaa gcaggtggtt  70860
tgatctgaaa tacttgaact ggcacaacgt caagtaggcc agacaggtag ggcagaggca  70920
ggcatagcaa gagcaccatg aactggtgac ttagtagatg cctggcctca gttctttttg  70980
```

gctaagggct gctctgttgt tctttgcctt ttctgcttcc ctgtgggata gaatttgcag 71040
atctaagagg ttcaaaaagt tgagaaaagc cctgttacct ggaaaaaata tcatattctt 71100
agttccctag gaaaagtctt ctgattctga attagaactt gttattgacc tttgtcctca 71160
ctggtaaaat cattccctgg tgttagaaaa agtgaaattt gtgctaggaa aagaggagaa 71220
tcttaaaacc acggatgcat ctgtccttaa gcagtaaaat cctaacccga gagaatccat 71280
gaaatctgca gctctcctta ctttgccctt gactctgtca gctcgtttac ttaaaaaggc 71340
aatgtggggc agactgataa gatgggttcc ccagagtata tccactgcct cttcaacctg 71400
gctgcgggtt gacggtttat ataacactaa ctctgaatat gtggaactga cagttgtcaa 71460
attagtattt atacagaatt tgctccatat gtaaaaccag tcaggctcaa gttttaaaca 71520
atggacattg gttttatact ttctgatgct ttaaatgcca tcctagtata actgaacctt 71580
accttggcat agaattatgg taggataagc gccgggctac ttttagtgca cagtcattaa 71640
gtacctctca cgagataact ttatgattat ccctcaaggg aactgtgggt aagactattc 71700
ttccttttct ctcctgtcga gttccagtca caaattctca cagagaagag gcttaactaa 71760
aatttcattt tccccgtaag ttttgtacaa ctctgttaga gcttcagcat ttggaatagg 71820
ccccaaaacc ccctttaata cattcactga ccaaaagttt ctcttctctg catttacaaa 71880
atgaacaata agctaatggt atcatttctg ccagaaactg cacaagctga aaatatacat 71940
gtttaaaaaa acattttaga tacatctgag caatattgtc accatttgta aacatcatgg 72000
aagacaatta ttctcatagc aggtctcaat gacagtgaaa tggtcagagc cagtatacct 72060
gaaagttatg aagatgtttg agaaataagg ctttagtcaa tggcacctac tgaaagattt 72120
ctgagcgtgg aagtatatac aactaagagg aattaagaaa gatcatgtaa taaaatgagg 72180
aagaaaatcc tttatcactt ccccaccaga catttttatc attttatatg tttttccctt 72240
atgtagcact tggtaaattt agaattatat atatgtaagt gagtctttga agaatgcctt 72300
atttccgcaa ataaagtagg agatccacaa gggcaagaac attgcccatt ttcctcatct 72360
tgaatccccc atatactgtg tatgatgcat ggagcctgca caagatgagt gttcaattta 72420
tttttatgaa agaataaatg aattagtgaa agaatgaatg agtctagtag ataattagag 72480
gcttagacag tcaagaaagt aagtgcaagg gtgccacaga gagtcaaaag agttgacagt 72540
gaataatatg actgaagagt ttatgctctg tgccctgatt tatagcctgt tgagtaccaa 72600
tggccctgag tgcccaggta ttgaccatga ccagcaagca ttgtgagacc tgaaggtgac 72660
tcttttctct gattgtgttg gtagcagcaa gctgttatct tactctggat tctgattacg 72720
tactatgtat acagtaattg tgtaataggc caggtgagca ttaaacaaag gctgttttca 72780
tttcttaaac ttcttgtgca attctttagc ataagagatg acaaacaatt tggcagaaag 72840
tcaaatgctt taaaaatatt ttcgggatag tcattaagat atcattgttg taattcctta 72900
aagtttatgg taacttttaa ttgtatgttc aataggaaca aatccaagct ggcctatcga 72960
actggttggt tgtgtaatta atatacataa taaagacatt aaaggaccat cttagctaat 73020
aatagcaagc ttatcttcct taagtgggct attttttttcc aaaacaattt gcaacataat 73080
ttatttaggc tagtttatgt tcaccaaatt tctttatgta ctgtctacta gaagcaattt 73140
gtcttttctt cataggctta taaatttgag ttttaaagcc aattaaagaa aaaaatcaaa 73200
tgaactcagc ctaatttatt gaactaagag cttttacaga ataaaaaata tatggaattt 73260
tatgtcttac tttgtcttta atgactttcc ttttagtacc ttagacttca atgccccatt 73320
atataatttt tagaattgag ttaatacttt aactaataca tctatattta tcttctgtat 73380
ataatagatg tgttataagc tataagctcc tctaaacaat atcaaatatg aaatgttcaa 73440
cacaaacctg tattaaagaa tttgttttta cctcttgttt ggtaaagcat taaaaaaaag 73500
tctcaatagt tttagaaaac atttattcaa ataccaggct agatgttgag gatatagtgt 73560
tgaaaatgta atcttaagtt cactgtgtat tgggaataca gataaagaag ccaaggattt 73620
cattacagtg tgataagtaa tataacagag gaattcacac aatatttaaa gatgagagca 73680
gagaatagag gcatattttt taacctaaaa attgactttg ttgtcaaaga agattttcta 73740
taggcaacta aacttaatgc atttcttgaa ggaaaagaag ataccagcca ggaggaaact 73800
cgtgtgtgtg tgtgtgtgtg tgtgtgcatg agagagagag aggtagtact ttgggtattt 73860
cgagtatgtg caaagcatgt gcaaagatat tctggcatca aatagcaatg tctcactttt 73920
aattctgtgt ggtatttagg tttagtaacc attgatgaaa agttggggga gataaacagg 73980
agacagatca tgaagaaacc tttaaaacat gctaaacaaa tggctcttta ttttaagaat 74040
aatgtggatc cactaacaaa tcttacacag aatagtcctt tttttttag gctacatact 74100
gtccttcaat atatatataa aaataatacg gcctccttta aaaaatgttg aagtgcaaaa 74160
taatcatttt ttctaagcta aagcaattgt aatctctgat aagattttct gaattaatct 74220
atcatatgat ttgtttaatt aaagaagtct cctttctttc acctacccct tccccaaccc 74280
ttagatggga ttattatatt atttccttgc agtcactcag ttgagaataa cagatttagg 74340
atcagtgtgg aatgtggata aagaaatctc agaatgacct ggggagatct gttagcaggc 74400
tcttgggtat tgcaggtaag agtgatgtgt gcctgtgctg acatagcagt gataggaact 74460
gagagaatgg gattggtata agagatacta tggaggttgc atcagtgaga cttggtggta 74520
gattgaatgg gggatggaaa gacagaatgg ttgatgttga ctgcccagtt tcttgctcag 74580
cctattgggt agatggtgac acatatcaca gtattttgaa ggggtatgga aaagaggtag 74640
aaaagatggt gagttcagtt gggtatctat tgacttagag atagtaatgt gtaataggca 74700
tatgaagata tgggttggag ctcagaagag atgtctgcta agcaattatg aatctgaaac 74760
tcattgctga acagatagtt gaagttacag gtttggccat ggtgttccag gacagagagt 74820
tgactggaat cagaagagta taaatcaaga aactttgggg aaaattccca tatttataag 74880
gagaaagagg aagataaaac ctgaaaaaaa ctgagaaaga gcaaccatag acataggatt 74940
caaatcaaga cagcaaaatt ttggaagatg ctgcaagaag taatcacagt gtcaaaagtg 75000
actgagaggt caagtaagat gaggacctac aaatgtccat tcaatttgga gttaaaaagt 75060
ccttggcaga cagattgcct catttgtaaa aattcaggtg acattttaat aattttatta 75120
agcaaaataa tttatcttga agagatgaaa ccaagccaaa ccaaaaaata ctctgatagc 75180
ataaaagcat ttcctttaca tatttttcta aatgttacaa gacactttgg tcttttggtt 75240
gaagagaaag gagagggaga gggaacatta tatttatggc attaacatcc ttattattta 75300
agtcaattat agattttagt aaatccatat attcaacatg acaaaatgtg cccctccaat 75360
ctatttcttt ctttttcatg gcagtacttg tatttctttt tataaattta aataataatt 75420
ctgagtgtca ttttctagaa tagcattagc gattctaggt tcataatata gagattataa 75480
tgtgaaatct aacaccatat taatgctttt ggaagaaggt aagagataat ataacttaaa 75540
aaataaacaa ttatagcatc ccttatgcag agaggctata ggtttcttca aggaaattag 75600
taaatttaaa agcatcaagg aagatttatt cccagagcaa ggtttttctc tctgatgcag 75660
gttttccagt ttgatcctta aacatgggaa gaaacataca tgaagtttga atctggtgac 75720
aagacaggaa acagaaggga aatacagaga cttaccagtg ttatttaaca gtattgtgaa 75780
caacaggcca acttctattt caaagtagag cgatcacaaa agctcaaaat agccttgggc 75840
agtacaggag agcagatgaa gcactgaact ggatgccaag atgaaatcaa tgagagagaa 75900
caggtgaaaa attgtcagca agagttacat tttgggccta ggaaagaatg tgacgattcc 75960
aaagggctac ccactctctg aaacaggatt gtatgaatta tatttcctag atatatagca 76020
cctgcagtgt ggatggttag gaattttgga gaagttaaat tgattgctta tttcattgta 76080
cgtcaatgca aacatttttc aatgaataga acatatctac aattaacaga agaaagttct 76140
agaaaatgta gcactcccta agtcagtgtc ttcttggtga ataagtagat gtgttcttat 76200
atccttgatc agcaacaccc aagggacaga gacaggactg atgaagattt ctattctctc 76260
aataagttta gcagagctga ttggagtcgt ctgccgtaga acatccacag agcaacgatg 76320
tatatatatg tcagtatatc tcagatgtcc tctaattcag attgtgaggg atggaagagc 76380
ttttgtttct ttagagtcag agggcacgct agacagttat gtgcacaaaa acattccaga 76440
aatcccccat ggcgccgtgt ctggaaatag taatttcttt gcttattgat ttaaaaatgt 76500
ctcaatctgg aaaccaatta gaatttttac gtaaatattt cagtaatcta gcattgtgtg 76560
tctgattcaa gacacctttg aaaatcactg caaggctggg tgagatggct tacgcctgga 76620
atcccagcac tttgggaggc tgaggcaggc ggatcacttg agcccaggag ttccagacca 76680
gcctgggcaa catggtgaga cccccatttc tacaaaaaat acaaaaaatta gctgggtatg 76740
gtggaagggg cctctggtcc caccttctcg ggaggctgag acactcaggc atctcccagg 76800
atcacttgaa cctgggatgt tgaggctgca gtgagctgtg attgtgcccc tgcactccag 76860
cctaggtgac agagcgagac actgtgttta aaaaaaaaaa aaaaaaaagc aaatggatgt 76920
ggacacatac aagatttgga aatttgattg cgggcatgac tcagggaaat atgagattaa 76980
actctgctgt ggaaaatgtt caagtcctga tatttatgtc tataccataa tttccatctt 77040
gctaaacgtg agaatttttt aaagaactat ataaaagttg cttggaaaag cagcatactt 77100
ttctagaaag atgattaacc aaatgctaac caaacgttgt caatgaggaa taagtgattg 77160
ttcacatttc tgtgatcctt tgaaacatga taggaatatt taactactcc ataaaatttg 77220
tttcccattt tatatatgtg agagttgctg gaaacaaatg aaacaccatt ataaagtatc 77280
aaattctctc cttggaatga atcgattttc caccagagcc attgaggcaa ttccttagct 77340
cctggttgtc aaaacctggc ttcagagagt gacatctttc agaagtccaa ctcctacccc 77400
tcttgttaaa aaatattcac tgactgcata ttagttagta aataaccctc cctccatctc 77460
tcactgacaa aaaatcggac tcattttcaa attctttcca aaatgtcatc tccttcctga 77520
agtcttttct gaatcttttc aaccaaatat actctgtcct tcctctgacc tcacaaacta 77580
tctcactctt aactttgtga catttatttg tttaatttgt tcatttgcca cactattttg 77640
taacttcctt gaaggcagag tttcttcttc gggtttgtat tatctatctc attagatcag 77700
tattagattg atagattgat tgatagattg atacagagct agagagacag agagataaac 77760
aggtagataa ctcatgttcg aatatcttgt ttttagtgga attaaatttt agagaagaaa 77820
agcaggcaaa cataaaagga ttttgaaaga tagaagatac tttggccaaa aacatattta 77880
tcagcagcat acaaatgtgc ttacacatgg aggcattatg gcaacccaaa tacaaactag 77940
ttcttttttt gtcaacacat ttttcactat tgtcacagta gcttgtttac catatttttc 78000
tcttgactca cttgcctcct attattgggt cctagaatga tcatgttcct gctggataga 78060
gcaagacatg tttagaagtt ttgcttatgg aaatcaaagt tgttacaatt tcaaggtcat 78120
cttatctttg cactttaaat ctactattta gttcgtctta atctttagct tttgtctact 78180

-continued tccaacctct gaaagtaatt ttgcctttca ttttgagctc catccctgtg tagagtttca 78240
gatgtctctt ggctctccca gtcctccctc taaacaactc acaaccctgg catgatcttt 78300
agtaagattc ttcttaggtt tttttttttt tttttttttt tttttttttt attaaagggc 78360
aaggtgggta ggggaatggc atagaagaac acatttggtt gtttttcagg gtacctaagt 78420
ttatgtaatt atcatcaggt agctcttgct ctttacatgg tttgatggtc gtttctctgc 78480
caagtggtct tgaagtcttg tcagggacac ttctgcttca gcaatgattt ctataggaaa 78540
gtgaagccca taacattcaa acttgggttt tttatcttct tgattactaa ttagctctaa 78600
cttccaatat ccacaaataa aacttcagag tcaagttaaa agtctttaat tgattacttt 78660
aaatttgaag ggtatgcata cttatttcca tggaattgca agatcaaagg ggatgaaatt 78720
cctgaaagca gtactgtgtc cctcaaatcc tctgatatta actgctctta aggatatggg 78780
gaaatgggct agtttgggat ggtctgtatc atagctctta ggaaataaaa aataagaatg 78840
gaggccgggc gcggtggctc acgcctgtaa tcccagcact ttgggaggcc gaggcgggcg 78900
gatcatgagg tcaggagatc gagaccatcc tggctaacac ggtgaaaccc cacctctact 78960
aaaaaataca aaaaattagc tgggcgtggt ggcgggcgcc tgtagtccca gctactgggg 79020
aggctgaggc aggagaatgg cgtgaatccg ggaggcggag cttgcagtga gcccagatcg 79080
cgccactgca ctccagcctg ggtgacagcg agactccgtc tcaaaaaaaa aaaaaaaaaa 79140
aaaaaagaat ggaatagatg cttcaaaata cattaggacg aaggtaaatt acacatttaa 79200
aaacttagat gtgtgtgaga atgatgtttt taacaaattt taaaaggtga ataagtaaaa 79260
taaatttaat tttgaaatag ttctacattt ttttgtaaat tatttcttcc atgatgattt 79320
agagggacta tcaacaaacc agtacaaata tttcataaat aatatctgcc tgttttctaa 79380
ccaattgagt aatttgttgc acaataagcc acttcacatc tttctgcaag taaaacatta 79440
gctgtgaata gtaaagacat tacacaatga attagggcac aattaaaatt tgatttaaat 79500
atttctttag gggagggaac accacacttc cacttaatga aaagaaacat ttttagagtc 79560
cagaggtctt ttgcttcttt tacacctatt atgccctgac tgcatagggg acaggttcca 79620
gcagctcagg ctttggttct cacaaagtat gtttccctgg gtggagcagg ctggtgcttc 79680
agttgaaccc aggaaccttt ctctttggct tctttctctg accattttcc tttatgtgtt 79740
ttaggaagcc gtctcggcac ttagagtgct taatatgctc aatatgcaca tgaattccct 79800
tggcaagaat cttgtcctta acttgtttac aacactgcca acagcatgct gggtaacact 79860
gtagattctt ccaattttgc catggtaata cttgtgaggc attccttttt gaacaggact 79920
cattcccttg atgtctacag tatcaccttt cttctaagtt tgcatgtaca tggccaaatg 79980
aacaactccc tgttttccaa atagactgga gaacatgtat cagtgcctat cctctttccc 80040
tgtgtgttca tcattttggt gaattactga aagatggtgg ttctggctga aaggctaatt 80100
ttttaattta aaaatttcta atgattctac ttttaataat ttctaattaa tttctaaaaa 80160
tcaattgtat agtattaagt aaatttcact tttcagaaat gatctaaatt tgtttttgtc 80220
taaacatacc aatatcataa tttcagattc agattgattc tgtttagcaa gccatttaaa 80280
atttgcttgt agttcccggt aatagtatga gaaggcaact tcttcttatt tatttatcca 80340
aatttgcagt actattcaat tcatacagta tttactcata tcccatttta gttttggtta 80400
atttctcttt ggagaaatat gggagacaat gaaatctcac tttggaaaag aaaaagagaa 80460
actaattctt attcagtacc tattacatac caaccactgt gtcagatact ttaatctcac 80520
aactattctt tgaggttgca aaagttttgt gcatttttat acggtttaag aaataaagta 80580
tcaagaagtt aagtaactaa gttgcaaata acctaaatga ctcaaagcta atggattgag 80640
taaacttttg tacattcatg tgttacaatg caaaaaagca atgaaagatt agtaagtatg 80700
ttattatttg atatcataaa atgcctacta gatattgcca aatttaaaaa atagtacaca 80760
caaccattta tatgtatgta tatgggtgtg tatacacaca catctgtttt ttaaaaaata 80820
aagacctaca tacaacacaa gactcacaga atcacataaa ataaaaaaac cacattaaaa 80880
cagagaaaac tggtaaaagt tgctttagca cttatatcag ggtagtgagt tacagatgat 80940
tttcattctt ttgtttattc actctaaatt tctgacgatg agtatatctc agctttatat 81000
tttaaaaaag caacgtatca tttaaaaaat acgtattcca atgttacaca gttgtaaaca 81060
ttagagctca gctttgaaat ataaggttat attctttcct ctatgatcaa agatagacta 81120
ctcaggccta aagaaaaaca ctcagatact cccgtgtggg ggctggggga cagggagaga 81180
aagagagaga gggaagaaag agtcaaagac acacactcac acacacacac acgcacacac 81240
acacgggggg gcggggtgga catagagaaa agagctttca tttggctgtt cttgacgtta 81300
gaccaccttc actctaatta ctgactgtac agttgtaaaa gcccttccca attacatata 81360
aggatatttt tgagtcctac tggttgctgt tgcaaagcta taaagatctt cataattacc 81420
ttcaggcagt taaaaattta gagatccaga gaggtctagg tatagattct tttggaatag 81480
cgggccagct gaaattgtta ggtggttatt attcagtaca agggaatttg gctcttcctg 81540
tttaaatggc aaatttaacc aatgcacaga ttagaagact ccaaaccaaa tcaattgtat 81600
atagagaaga acctagaaaa aagaaaggaa tccatttaaa cagcagagga ggtatagtaa 81660
ttgggcctat agatcacagg cccaactagt aagattgtat tactaagcca aaatcatcaa 81720
taaaagaaaa taaagccagg tgactaagtt aaggtctagt atgacaatgg tcatgaatca 81780
acacaaataa tcttggcaca aaagtttcag gacaggctgt ccaaaagcag ctgagtagaa 81840
gattcaagta aggttttatg tatggtatgt tacgctgatc ttcctccctc gcttacttcc 81900
ttgctttctc tttccctcct tcttcctatt cctccctccc tcccttcctt cccttcctta 81960
acttccttct ctcattttcc ttcttttaca aaaataatct ctactgcata cattgtttga 82020
agcacttata atgatgaata agatgtgtct ctcacctaaa aagagtttac agaatatgtg 82080
tgttgaggtc ataggttaat atttgtgttt acttattata tcttgagtac tcatttgcag 82140
tgttttagtt gttcacaatc taacatatgg atttaatgct gaacatgtgg ctcctgctgt 82200
agaaagttat gggcctttgg gcagaaaccc tactcctgac cttcaaactg aaatggatgt 82260
cctaaatgat gtaatgtgta tagctaatga tgttatacag tagaactcat ttgtaatagt 82320
ggtattgaga aactgggcta atggccacat gtagacttag taatataatg agagaaattc 82380
atgatgaaac tttaagtaag aggacatgat ttttcttcca gtataactga atctttgcta 82440
ttatgagaaa tattagggtg aaatttaata gaattacaca aaacatattg aactactgtt 82500
ggaatagtat ggaatgtgat atcaaaatca tgcttcaata gaatacaagt ttaggcttga 82560
aatatattat atttcaagtt gaaattcatg acagctgaat aagggatatg gtattgcctt 82620
ttaatgagct aatttcttcc caattttaag agtgaccaaa ggtcagccct tttggattgc 82680
acagcacaca cttgtaagaa acccttataa atcatcctta tgttcaagtg caaggcaact 82740
ataacacaag cccatgtatt aaatcaaaag tgcctttcag aatatgagag agagacgcaa 82800
atgttcacag taacagtatg ctaagggctt tatgaaatag aaaattaacc ttggaagttt 82860
ctcagtggac aaggcttaga taaaataaaa aagttattcc tttggtatgc ttagaggata 82920
ccaaacaatg tagaacaatt tgtattttaa tgtggaagtt gttccgtctt gtttatttct 82980

```
gagtgtcagt ccttctgcct tatccccatt attttcaaaa ctgtaaacta catacagcat  83040
ggctctaatg aatcaggttg acagggattg ctaatgcatt ggaacatttc tgaatgttca  83100
gagaaatttg aatttagtaa gtgccatatc tgaaaccagt acagaacctg gggtggata   83160
gttggtattg gtgggtggtc agaatttgac acccatcccc aaacttcaaa agggatttag  83220
agaagtattt ctaataagac tgaagttaaa aggatatgac aatgggaata ccaattggtt  83280
taatcctttt gaatggcaaa ttattattaa gaattagcta gcattaattt agtactttct  83340
atatgccagg aactgtatta atttatttat atataattta ataactgaat tacttactat  83400
gtgtaaggat tcttaaaagt attaatgggg ccaggcacgg cggctcacac ctgtaatccc  83460
agcactttgg gaggctgaga tgggtggatc acaaggtcag gggatcgaga ccatcctggc  83520
taacacagtg aaaccctgtc tctactaaaa atacaaaaaa ttagccaggc gaggtggcag  83580
gtgcctgtag tcccagctac tcgggaggct gaggcaggag aatggcatga acctgggagt  83640
tggagcttgc agtgagctga gatcgtgcca ctgcactcca gcctgggtga cagagtgaga  83700
ttctgtctca aaaaaaaaaa aaaagtatta atggtcttga cctagtattt ctatatccag  83760
gaactcatag taataattaa tgacccatat aaagaattat gcactaaaat gtttgcttca  83820
gcattattta catagcataa agtctgaaac aaatgtccaa cactgaagaa tgcttaggaa  83880
aagttacata aaggatatta tacagtcatt gaaatcatgt ttgcagtgaa tgcttaatgg  83940
gaagatgatc tccatgcaat gttaagagaa aaacaaagta gcacgcaaaa tagtatatat  84000
aaaatacttc aaaatataat aaacaataaa cattggaact tttataaaaa gacttagagg  84060
agatacagca aaatatcaat tgtggttata tctgggtaat gagaattata aataatttta  84120
gtttttaaaa tttatttctg tattttccaa gtttttttaca aaaagtttac atcaagtata  84180
taatttgaaa aataagctta aacattttct gggtgaaaag aattcctggc ttctctacag  84240
gcagattccc ttcacacatc ttcctgccca actactgtgt cagtgggacc cctgctcatg  84300
tgaatatttc tttgtgccag tgtttgggtc tccaggctag agcaattttc ttctgggctt  84360
tggagcattt tgtttcctac ctcttagtaa tccaccccca acagttgact cctggttttg  84420
gcatccaccc tttcatgaag ccatcctcag gttgaggtgg ttaaaccatt ccattccacc  84480
attagttgct cactgccaca ctggctggct tcatgcttta gtgaagctag taaaacctca  84540
agggatgtat caagtatccc aaaatctact taaaaaattt tgggatgacc agggggcata  84600
tttagccatc tttagctctc agaatttcgg ctacatctct ctaccaataa tcctgtttat  84660
actgaggact ttactgataa gatgggttac aagaatgttt tcatgcaagt ccctaggact  84720
cctcggtaaa ttaagggtat gggactttgg gattaaaagt cagttgctct cagagacgtc  84780
ggagcattat agatactcaa gaagtatttg atgaaggaaa gaatactagg ggtgataaag  84840
gtagtcttta atatttttac taatcaaaag aataagtatt atttttcaga aaataggagg  84900
tgggaaagac atatggagga agcagggaaa tcattcagag gcagggaaaa ttgatggaat  84960
aagtgccgca ttttgggaca gatattcagg gttaataagg aaaattaaga gaatagtgtg  85020
atatgatatc aatggacatg cagataactg atatcagtcc tttaacaaag gaaattgcaa  85080
attgtttttt caagagtttc aaagaggtac aatttttatg gcctagacct tctgtggctg  85140
actgtcatag gtgaataatg gctgccccaa aatatcaagt ccaaatcgtt ggaatttata  85200
aacgttatct tctttgaaaa aaaggtcttt gcagatatta caaagttaag gatttgaaa   85260
tgaatagatt ctaccttgga tgacccagat gagctttaaa taccatcaaa agtgtcttca  85320
taaaatagag gccgagggag attccacgcc gacacacaga ggagacaaac agaagaggag  85380
```

ggtgcaatgt gaccatggag acaaaaattg gggtggcatg gccacaaaac aagaaacact 85440
cggagttgcc caaaggtgga agaggcaaga gcagatactt ccctggatcc tttggagaga 85500
ctgtagtcct actgatgcct taatttcaga ctttgggcct tcagagcagt gagggaacac 85560
attcctgttg ttttcggcta gcaaatctgt ggtaatttgt tatggcagcc ctagaaaaca 85620
cacacagtga ataaaataac tcttgtgtgg gaaaacagcc tcattctgat tggttgggga 85680
ggaaagtgat tgccaatagt gtacctgtaa gacggtagaa ggtgaaatca gctgtaaagc 85740
gtaggaaggc agtggtggta ggtgtctagg agtacggtgg ccacaatagc atctgctatt 85800
gtaagagcac tggggagtga aggtgggaga ataagagtgg aagggtcact ttcctgagtg 85860
ccctaatccc tcttttagtt gacacatcag acctagccat ccagatgaga tgacattgtt 85920
ctatttaaaa gactgggtgg gaactggagc caggatactc tgtggggtta tttatccaaa 85980
tccggggtta ttattcaaaa gtgcatggct gggcaaatag gtttatgcca tagtttatca 86040
agacggaaac caaaagaaag aaagttgcca aattaatttt tgggggcttg aagaacagtt 86100
gtttgtaaag aaatggttta aattacagat taaaaaaaaa acacacacaa aaatccgtgc 86160
tgcttcaaaa ctcaaactag actacctcca caagcattcc ttcctcaaag ccaccttgta 86220
gacaccagac ctagtaaatt tacatttgac agacaaatag gaaacttttt catgttacac 86280
aaaggcaaca ttataatcta gctgtcaggc cttagctcca ttgatgcact gagatgtggg 86340
ccagatgaag ataattcagg gaatctagct ccagcgagag tttcagggag ccctccctca 86400
gttagttgat atcccaaacg cttatcacaa aagcaagaga aacttgataa cgacctggca 86460
gtggtgacca gacttattct tcctagaaca agaaagtgat attcagagat tgacataccc 86520
ttaaaacgat caaaagggaa aagcaaggtt ttctttttag aggttcaagt catgctgagt 86580
ttggtcagat agtgtgaggg gcccagtcga gtcacttgtg agggtatata aaataaagtt 86640
gggaaacaaa ggaaacgagt gaaaagaatg aggtatttat tcactaaaag gaccaatgaa 86700
accgatcccc tctaagtgta aaaggaggag tagagattac tgtgcctgtt gtttaaaatg 86760
tgtggacaga agattatttc tagaggacac ttagtatata tttaccatgg tatgcatcaa 86820
aggcaacaga attttgttac gtcgcttacc ataaaatatt agaataaaaa atcaatattg 86880
atgtttctgt tttaaaaagt aatacatgtt cattatttaa aaaaataaac aagtgctgta 86940
ataaaagtat atagtatgga gggcgacatt ctcagagata cccacttctt ggtgtcagcc 87000
acaattaact gtttggtgta caaaatcaca gaaataaggg ctgataaatt tgtagatgct 87060
gtctaatcca attcccttat ttcatagtgg aggaagatga ggcacaaaca gggctacaag 87120
gctactgagt tactgaagat tgtccagtta gttagagaaa gatgctggtt tgctcttata 87180
ttacctacag atacagataa ttttattcac cttttttttt tctgttgagc tatcagggaa 87240
acacatccta gatattcaga acccccctact aggttgacta aaacaaagca aggaaggaaa 87300
ttttaaaaat agcagagggt ctctaaagac agctgcttga ggtaagcaaa tgaacaggtg 87360
tttatgattg aattattagc ctcaataaat tgaagaaaac accatttttt tttcaaactt 87420
gaggtaaaaa cacaataaca atagagaatt tatcactctc cagaactttc tgtgttgaat 87480
acaggagtat atttttagct ttttctctag gaaaacggct tccagtttct gaatcatttt 87540
ggctaatttt tatatgcttc cgatctatcc tctgcagcac tcccgcaagc tgcttatttt 87600
gtggcaaata gtagcaaaca actttttatt tttttcagag atatccagaa tttcgccaaa 87660
tggtgatgtt ttttcctcta aaagagtcct tgtgaaaatc ccttacttct gtctaataaa 87720
tgccatattc aatatttact ttctccaggg acgattgttt cagtactatg aaaatctcag 87780

-continued

```
aagagcaact agagtcattt aacctactct taatctgtcc taatgccatt tctctcttaa  87840
acgtgtctcc attttttca gaattgtatg cctcttagtt tttcaaagca gtgagtaggt  87900
tgagcagaga aagggccaat acagcatttg ttctcctcat actgctgagc atagtcatca  87960
aaatgtccta agatatgtgt atgaataatc atctaagaat atgtgtatat tctgtgttca  88020
tatagaacac atttatatac gtacatgttc tctgatacat atagggttct caatttttga  88080
ataggaaagg gacttggact ttgagatcta tagatttggg atcaaatatc aacttctact  88140
tcatggctat gtgatcttgg aaaagtcatt tagcttctga aatttagttt tctcacttac  88200
aaaatgagga taataatgac tatcttaagg tgatgttaca aggattatat atggtaatga  88260
cataaaaggt ctgtttgata aatgcttgat gtatcagtgt caacaaatgg caattattat  88320
tttctcatat aatcacatat attttcaaaa aactaaacaa tactgcctga aaatattcat  88380
catttgccct ttctgtcatc tagaaaatgc tacttctttt agatcatttg caaattgtag  88440
ctttgttcag tctttcccaa acttacactt tctcccctgc tccatatttg acagctatag  88500
ctgctctgct attatcactt tctggctcct cttgttcatg catcatttca gattggattg  88560
taacgtgctc tggaaccact tcaggtattc tgccctctgt gcaattgcct tagaatcaac  88620
ttctcccaca attagttgtc actggttaca tttttatcgg ttaaccaaaa tgcttagttg  88680
aacatagatt aggttgtcat gcctctggag agcctgcagt tcagaacttt tttactggac  88740
actttctctt gtcacttgat gctaagagga acatgtcaac agtgaaactt atctgaaagc  88800
tgaatatgaa gtaactgata gacttaggtg tcacattata tagtagacag tagtgttgct  88860
tgatagaata ttgtttgact ctatgccaaa aggcacactg ggttcactat agctgtctaa  88920
cttttcccat atcagtatgt catttagaag cttgctaaaa atgtagcaag aggccaggat  88980
tatttttagt tggaaaagct tcatttactt ctcacaaggt aaatagatct ttaataactt  89040
ctttaattta gtcttgtttt taacacatga aatgggaata aatattcagt gatttgaatg  89100
atggattctc tataacaatg aaatatttaa atgctcttac taggagcagt aatcgaccgt  89160
aacgtttctt tttgacactc acaagtattt tctgttaagt gggagtaatg tttttaaaac  89220
taaacataaa atcacaaaca tagagcattt tcaatttgaa cttttaatac ttagaagtga  89280
gcctttattc agaaggctca tagaagtatt ttccttaatt gttgcatgca taaggatctc  89340
ttctaaatta acattaattt tatgattaat tttgaaacag aaatctaatt tttactcact  89400
ggcatgaaat gtttcttgga acaggaaaga gaaatttatt tttgtttctt actaactcag  89460
tcatcattta atgccatctg atattaaata ccatattttc aacaatctaa aatgaataat  89520
ttacaaaata ttttaattat attgttatga tattaaatat ggtaggctat gtatagtaac  89580
acaagctcac caataatgaa tttgctgaga ttaactgtga aatctggttg agagatatgc  89640
ctgtggagga ttatcctccc atggtaagaa ccatgaaggt ggttcattca tttgactaaa  89700
gctttgagct catgcttatg tggtagacca cttttcctcc atttcttatc aaaaaaatgt  89760
gtagccagag gaaaacagta ttttcaaata tttcttatag tagattaaga caatagttgc  89820
tattgtttgg atgtttgttc tctgcaaata tcatgttgaa atttaattcc tagtgtggca  89880
atgctgggag gtgggtccta ggtcatggga cacatcctgc atgaacagat taatgttctc  89940
tcttggtgct gagtgaggtt tcactttatt atttcccata agagctggtt gttaaaaaga  90000
gcttagcacc tcctccttct ttgtcttggt tgctctctgt acatctgatc tctgcacact  90060
ctggctttcc ttcaccttcc agctagtgga agcagcctga ggccctcacc agatgctcaa  90120
tcttgaatgt tccagttcca gtcagcaaaa ctatgggcta cataaatttc ttttctttat  90180
```

-continued

```
aaattaccca gtctcagcta tttctttaga acaacactaa gcagactaag ccaatagctc  90240
ttctatttcc tgtatgtgta gtgcttgaga atagatcatt atgtagcaaa aattcctgat  90300
ctttgacttc accagaactg acggaggtgt attttgttgt tgctgttatt tttctccctt  90360
taaattgtct aaaggactat ttatcaatca atttctggcc atttcaaact tgtcgtattt  90420
tactgtatgg gtaggtttta gtcaggaaac cagaagccac tctggatatt cagataggaa  90480
gggtttcgat acagtaattg taggtataat cattgttagg gctgcagagt gaagatcagg  90540
aaagtctccc tgttgagtag acctacagag cattctcaaa agttcatctg gaagctgctg  90600
tgaatcttaa gaatcaacat tcctgctgcc tgagatactc aaagtggctg atttgaaagc  90660
tgtcatgcac agaagctcat gcctgcatgt gcatatttcc ttaattgttg atagaaaaga  90720
atgctttttt ctgctttgat acccttacta caagcttgct tgtcatttgc agagtaatct  90780
gtagccatcc agttaaatgg gtactgggaa gggagttttg ggtttctctt tgttgaagta  90840
gacaaaatga taaaacaggc acagtaatga tgtcaagttg aagacaaatc tggcatagcc  90900
atgttttgtc aacctagcat tcgtatatac tcttctaccc acattctaac ttcaaaaaca  90960
accatccaac ttcatgcttc cacatgatat gatctaacta tgtcttatcc agccatatat  91020
acatatacat atatgtatac actctctccc tacaggggta gacacaaagt tctataaatc  91080
actgtatgct attttggggt gatgttcatt ctttttctaa ctcagttcca attctccttt  91140
ggtatctttt aacttataga ctaaattata aggtaaatct ctattaatac acttcgcatt  91200
agataaaaga tgaggatggt ggcaaaaaac tggttaatat atgcaactat gtacatcata  91260
aatcagaaaa ggaaataggc ttagctttca catgcttcgt ttctacaagt gaataagagg  91320
ccataattgg tctttacgat tttgctttct ccctatccat ttgatttgtt ctcagtgggc  91380
gcgttatctg gtcatggttc ttcacttgat gggatgatgc aaaacctcat ttttgaaggg  91440
ctagagccac tagtagcctt gctttttttgg gttgctctac tcctttgcta accttttaca  91500
ctagatatac aagtactgag gggcaatcca gagaatcctt tgaatcctct ttgcctttat  91560
tatgcagcag caactctatt tctccttgac aatcaatatt attcactccg gttagtacag  91620
caagcccttc tttgactgtt gccttagtgg catgaagaat tcaaagtgat agtttaaatt  91680
tcacattcag tagaatcatt gttaggtcca ctagtgtaag cattcatttt ttagaaatta  91740
agtcctctaa acctgcagag ccaaaagtgg ttaagagaag tgatatggtt tggatcttta  91800
tacccaccca aatctcatct ggaattgtaa tccccaggtg ttgagggagg gacctggtgg  91860
gaggtgattg gatcatgggg atggttcccc catgctgttc ttatgaaagt gaatgagttc  91920
ccgcaacagc tgatggttat aaaagtgttt ggcagttccc cccactttct ctgtctcctg  91980
tcgccatgta agaggtgcct tacttcccct ttgccttctg ccataattgt aagtttcctg  92040
aggcctcccc aaccatgcag aactataagt caattaaacc tctctccttt gtaaattaca  92100
ttgtctcaag ttgtatcttt agagcagtgt gaaaatggac taatacaaaa agcaaatctt  92160
ttgtgattgg gtctttaaga ataacagaga gaggaaccac tcccattccc acttcttggc  92220
tcctttatcc atgtcttctg gccatgggaa aagatagtgt catgttgtca tattgtttgc  92280
tagttcagaa catatatgaa atctttcagg acagcacata gccaaacaag gtattattac  92340
ttagccagca cccaaaatga gtttttaata gggcattcca ctgttatgtc aggcaggcca  92400
acttgaggtg atgtggtaca ctgtaagacc aataaattct acagatgtga acatttccct  92460
cattctttgc tggtcaatgt gttctttggc caggagcaaa gttatatggg catcattaaa  92520
gagaatcagg ctttccatta gcctgtggat actggtactt tacaaaggca gagcagacag  92580
```

-continued

```
ggatggcaca ttcatatcta ctgtgtttat tctggtaaaa catgctgttc tttcttccat  92640
gatggaggta gtcaacatgg ctagcagatc ccctcaagaa tagtgccaca gaaggaaatc  92700
agcatcaaac tcagctgaca acatactatg tttttagcaa ctgtgatagc tagaatagtc  92760
ttattgaaga gaagaccctg cttttgagcc catgcatagt ctctatcact gacactttga  92820
ccattttatt tatgagccca ttggtcaagc tcaaatggct gggaagaggg tggctaatat  92880
tcacagaaag cgttatctcg actttattat tcgaaaaatg ccttgcagtt gaagcctgtt  92940
tgtgagcaat tacttggggc acaaaaaatt tcaaactctt accattccca gaggtttacc  93000
atttcttact cagacctttg tgttatcaat cccttatttt attttcttca aaatccggag  93060
aaatgagaaa accactttcc attgtccagt gtagatatgg catctctttc caaaaaagaa  93120
aaaaaaaatt gaatgcagtt ctgcccacta gaaagatttc ctttttcccc aatccttaac  93180
ggccattaca tagtgggact gaaatgctac atggtacaag actattgtgt ggacatatct  93240
acaaaccagg actgatttgt tttacctcag tcacttgatg atgaactccc cctgaggtcc  93300
caaatgtggt gtgtggtata gttgtcaatg caagcttttg atgccaaaag ttcaaatttt  93360
gccatcagtt caaattctac cccatatctc atgtttctac tctggctggt gtgaagggca  93420
acttatgcca aacttatgtg agcttgctga atttttctct atagcacaac acacctgtgc  93480
tttcaggact aattgagctc agttgcacat acgccacttc agtttgataa tggaatgctg  93540
ctatacactc tttaaaaaat taaatcaatg ttattgagat ttaatttaca taccaaaatg  93600
cattcatttt aagtgcagaa tttgatgagc tttggcaaat gttctccctg tatgaccttc  93660
acgaaaccga atatatagaa tatttccttc attcaaaaat tacccagtgc ctttttgcag  93720
tcagtacctg cacttattcc tgccccaaac aaacactgat ctgattttta tcactataga  93780
ttggttttgc ctattctgga tttttacata agtggaatca tacagtgtat agtcttttat  93840
gcctggtttt atttcactat ataaagattc tgagattcat ccatgctgtt gcgtatatca  93900
gtagttggtt ctgtttcact gctgagtagt atcccattgt ttgaatatat cacaatttgt  93960
ttacccatca ctgtgttgga tatacttgta caagttcttt tttttaaat cttttttttt  94020
attatttata ctttaagttt tagggtacat gtgcacaatg tgcaggttag ttacatatgt  94080
atacatgtgc catgctggtg cgctacaccg actaactcgt catctagcat ttggtatatc  94140
tcccaacgct atccctcccc tcccccaacc ccacaacagt ccccagagtg tgatgttccc  94200
cttcctgtgt ccatgtgttc tcattgttca attcccacct gtgagtgaga atatgtggtg  94260
tttggttttt tgttcttgcg atagtttact gagaatgatg atttccaatt tcatccatgt  94320
ccctacaaag gacatgaact catcattttt tatggctgca tagtattcca tggtgtatat  94380
gtgccacatt ttcttaatcc ggtctatcat tgttggacat ttgggttggt tccaagtctt  94440
tgctattgtg aatagtaccg caataaacat atgtgtgcat gtgtctttat agcagcatga  94500
tttatagtcc tttgggtata tacccagtaa tgggatgggt gggtcaaatg gtatttctag  94560
ttctagatcc ctcaggaatc gccacactga cttccacaat agttgaacta gtttacagtc  94620
ccaccaacag tgtaaaagtg ttcctatttc tccacatcct ctccagcacc tgttgtttcc  94680
tgacttttta atgattgcca ttctaactgg tgtgagatga tatctcattg tggttttgat  94740
ttgcatttct ctgatggcca gtgatggtga gcattttttt catgtgtttt tggctgcata  94800
aatgtcttct tctttctgta aacaagtatt actaatttc ttgggtaaat aagaattaaa  94860
tgactggttt gaatgttctg ttcatgtttc gctttacaag ggactcacaa aatgttttcc  94920
aaatgatggt tgattattcc caccaacatt atagtagagt tctaattgct ccacattttt  94980
```

-continued

```
gccagtattt tgtattgtca gacttttaac tttagcaatt tctaacgggc atttggtgga  95040
cttaattttg atttttctgt tgattaatga tgtttcatat gcccattagc aatttatata  95100
tctttctatg tgatgcatca gttcaactct ctgtccattt aaaatttgat tgtttttctt  95160
attatttagt tgtaagaggt ctttatatat tctggaaact aatcctttgt cagaaatttg  95220
tactgtaaat gtttactccc agactttatc ttgccttttt atttttgtca aagtgtcttt  95280
caaagggcag tcatttttaa tcttgatgga gtacaagcat cagtttttct tttacgttca  95340
tgctttctac atagtatgta aaaataacac aaaaaacaat ataaacagta tagcaaggtc  95400
acaaatattt tctactatat tttattctag aagttttaca gttttaactt tcacacttag  95460
ggctatgatt taagttaatt tttatgtatg atttgaatta agcattaaag cttattttta  95520
ctttgctatt ttttatctctg gtttgagtta ggtcttcttc atatcatcca tgtttctatt  95580
taaaatgctt aatatttcct ctattaagct taactatcct aacttaactt aactatccta  95640
acttaactta actatcctaa atatttaggc agccaacatt gggccacata aaacaaattc  95700
ttagagacct ataaagagac ttagataacc acacaataat tgtgggagac ttaacacctt  95760
actgacagtg ttagacacat cattaaggca gaaaactaac atagatatct gggacctatt  95820
ggttcttgaa cacctggata gagttgtaat aactgtttta atgtctttgt ttatatgttc  95880
tatcatcttc ataatttctg ggtcagtttt gatttaattt tttctcttcg ttatgagtct  95940
tattttcctg ctttttttatg tttgtatggc agactttgtg aaatttacct cattgagtga  96000
tggatatttt tgtattacta taaatgttgt tgagctttgt tctgggacat agttaagtta  96060
ctcggaaaca gatgggttct ttcaggtctt gaatttaatc tttgttaggt gggattagag  96120
cagctaattt tgtcacgcta ctgaagaaaa gccattatgc atatactact caatgcccca  96180
ttttccactc tgactagtgg gtagagaaac tattcttggc cctgtgaaaa ctctgtaaat  96240
tttctcctct aatccttttg ggttgttctt tttccatcct cagagagttt cctcacagaa  96300
ataccctgat taatactcag ccaaagcctt gagggaaggg agatcctgtg aagatttctg  96360
aatctctgtg taactttccc ctctggtact ctgaccagca aaatgtagct ttctccaaag  96420
agacctgagc agtttgtcag ggattagagt atactggctc ctgagtggtg ttagccaggg  96480
aaatgaaatg ttttgtggtg atgtcaatca attttaaggc atcatttcct cattgtcaga  96540
catatctctc acataggcaa ggaagctcat gtcagctgac tagacatcct ctctccagga  96600
caatggtgga gattccctgt gaatctagcc ctcttggtct ccgtttcctt ttgttgcatg  96660
ccaacatacc cctgcttgat aaaccctctt tcttttgtgg taagtttgta gctctctcag  96720
tcccagtgac attacaatct ttgctaatta gtcatctcac ttggggtttc caaaactctt  96780
tattcacaaa tactgatagt cctatgagtc attcttatat atgagtaatt cagtaatttt  96840
gtgttgattt ttaccagttt tatctcaaag atcaatttca ttgtaaatgt tgtgactata  96900
attactgtga attaagaatt tttgaacata ttcctattta aaaaaaaatc tttgctagga  96960
ccatctatct tatttgtatg agctccttta taatctagat ttttgggtat tatttatttg  97020
ttaatatctt ctagtttgac cttgccctta ttttggttct atttcattgt ccatagaatt  97080
aaaataattt tttttgtggt ggattggtcg gtgaggggag gcagtggcag acagggtctt  97140
gctcttttgc ccagggtgga gtgcagtggc tcaatcatag ctttgtaaca tcaaactcct  97200
gggactccat acatgcacta tgactggcta attaaaaaaa ttattttgta gcagtggaat  97260
cttgctatgt tgcccaggct ggaacagaat taaaattcta atatagtaaa aagtataaaa  97320
tctttacatt tattgtttct tctctttaat gtatacgaat gaattaatat ttaatctaga  97380
```

gacctgaaaa gcattaaatt ccattttctg gtagattttt gaatatatat tttatttttg 97440
tagacatatt agagtgttgt tccgtctctc atatttttct ccttcctgac tactcctctc 97500
atcacttggc taatccatag cagcatgggg gtgggtccat aatagccctg ttggcacaat 97560
ctgattcttc ctctttgatg atggtttatt ttaatccagt gaccatctga atcaagatgg 97620
cctaattagc attattttcc tgggacttta aatctgggct gtaaaattta aattgaaaac 97680
aaggagagtc acttgaatga ataagatgta atcttaggac actgtagaag agatatctta 97740
gttatgatat cactggggtg ttcagagaaa gaggtgaata aatgaactta atgctcagta 97800
agaagcagaa gtgagaggag gaagggaatt tcctgggatt tttatgtctt ctgcttccta 97860
gttccagtgt ttctctaaaa ccagcctgca tttctgttct tggtcattaa taaaatgtac 97920
ttatatcttt ataataaatt ctctctttca cttactttag ctaaatttag tttatagtac 97980
ttctaattca ggagttttaa ctaataaaga attcaagttt tttccctttt ttgtaataag 98040
tttggtgtaa gctgtcagat ggagtatcca acattcaccc taagagtagg aactagataa 98100
attatatacc accttctggg cagcatatga aggcagttca caaaagaaag aggctgaggt 98160
caaggcagaa gctagttttg tatattacta ccagatctta taatttctaa gacaaaagaa 98220
attaagcttg agctaggtta gaaaaccgtg ggagagactg gttaagtatc aatacctagc 98280
ctggagaagg ggcagacaca aaatggaaga gtaataagag aagactggaa ataacactta 98340
gttaaactag ataatccata cagaatcaat ctagaaagag tctcatgatt aataagttta 98400
gttaatcctt tatttttttc atttagaagc tatataggca tagggtactg gacaaaaccg 98460
gcatatacag cagaaaccaa ggcaaacaca gcccttccat tatggagctc acattcttgt 98520
gggatggaga aggaaggtat taaataatta agtatacatt tattcattca ttattactgt 98580
aatgagtact gttaaggaga accattaaag tttaagctga aggaacttga ccaggtctgg 98640
gtgacaagga atgattcttt aagaaagtga aataaagtat ctttgcatat attttctagg 98700
ccagatgttt aaaatagtag acttgttcca gtgggcatgt ggattttttt ttaaaatcac 98760
tttataatta cttgtaacaa aaactggtag aaatgcaaaa gtgtatggat ttaaatttct 98820
gtgttctttt ttttatgcct ttgacattaa ttttcttctt gaaataagtg ttagtcatgt 98880
gacttaaaat gcagaaaatg atacacattg tctagctttg tcagagggat gcagtgagtg 98940
caaagaatta tcttgcctaa gaaatctaac atcctaaatg gaaaggcttc aaatatcaaa 99000
taaacccgat gctactttat ttgatacctc cttacaccat ttcatttagg cttttctttt 99060
ttctgcttcc taactcacat gctcagactt ctcgaaacct tcaggcactg ggaaggaaaa 99120
gagaacaagg aaactagaag attttaagca tgagctatgc accaggtcca ataggaggtg 99180
cttggccatt ttgggctgca tctttagcat tagaaatcca ttcttttcct caatgatctc 99240
tttatgtaat tctccaacag aacagagctt tctcaccaag gccagggacg tttggagtta 99300
ttgtgtggat ttcagggggt cagtaaaaac ttggaaaata tatatattat atatttctac 99360
atttctataa tttacaatca tatttaattg ttcttataaa cttttatttg taaaaaatat 99420
gtttagctta atgaacaaga cacatagagt tagtttattt tgttattact tgctattact 99480
gtactattta gaaaaggagc ttgtaaatgt caatttcttt tcctattatg catagtttta 99540
aaatgttaag gttagtagag taaataatat tgtttaacta ctcagtatgt tgtaggcaga 99600
ataatggctg acaaagatat ctacctcctt atctctgaat ctgtgaagat gttgtcttgg 99660
cataacctca tggcaagggg gtgtgaggtt gcaggtggaa ttaaggttgc tgatcaattg 99720
acctcagaat aagaatattt tcctgtatta ttgagatggg tgtaatgtaa acacaaaggc 99780

-continued

```
ccttaaatat agaagaggaa ggcagaagga ctggagtcag agttattcaa tgtgagaaag  99840
acttgccagt ctgtcgctgg ctttgaagat gttgatgtta ggagaccaca aacaggtgtt  99900
ctctagcagc aaacaaaggc aagaaaacat tctcccctga agctttgagg aaagtataca  99960
gaaaacacct tgattttagt ctagcaggac ctattttgaa cttcttatct ctggaattat 100020
aaggtaacaa atctgttttg ttttaagcca ctgaatttga agtggcaaca agaaacttac 100080
taatactatc aggtaggaac attagattac ttttattgtc cacacattgt gggccaagta 100140
aataattaag tactttacac acatgtattt ttagttctat ctgactgcag aatatacagt 100200
cttaaccatt gtgctataca acctcttttt taaattaata attcaatgaa tgattgaaat 100260
acggaacatc aagtctgtgc tcatttggag cacatacgaa gtactcagca aatgcttata 100320
aatgcttatc tgaagagtgg ctttttggcc cataggaata ttcagcaagc cagagttatt 100380
ctacctccct ggatagaggc gtcatggctg gagcaacttt gagcttagca cattctatct 100440
gagctgttca ttacattcat catttaagat atactcaagc ctttgagagt ttgtttctta 100500
caattctgaa aatatgaaga tatatgaacc tcctagtaca ccctggtgaa tcatcttaat 100560
cagggtgttt ccctcaaggt attccaaaca gacatttttt ataatatgag aaagtgaaag 100620
catattgaac ctaaggccaa gttatagatt ccctaaaagt aagcatcata taaaacaacc 100680
gatccatttt ttcttcaact ttccaaactt gtttttatcc atttgcttga aatgtttttct 100740
ctcttgctct ataagtatgt tttgtgtagt gcctgattct ccctatggta tttgctttcc 100800
attaacttcc tattgatttt cagttgtgtg tacacagtac tgcaggaaca taaactgcaa 100860
acaccagact taaagaagtc cgaactctaa ctgttttatc ttggtgacac agtactacaa 100920
cgtgaatatt acctgtggcc tcttttaaaa aatgtattta aaggcagttg tgacaagtag 100980
ggtcaagtct gaataatgat gtatataaat tacagtggaa aaatatttgg cgtctcagga 101040
tgaaggatgt tcaagttgaa agggcaggtt ggaacagata aagagcagtt tttgaaaata 101100
tggcattaca gaaggtgaag caaagtataa gtcactgtaa aaagaaaggt accaaaagat 101160
gacaaaagtg aggaggagtg ggaaggaagt aacacacagc aagttgatat gacactcaaa 101220
aaggaatacc gtttttgaaa caagtgaaat ttaaagttat cttaacttaa tctgatgaat 101280
aatttctcta acatttaaga gcattcacgt ttttattgtt ttgctttata gtaagctcgt 101340
ccaactggca gcacacaaac cgcatgcagc ccaggacagc tttgaatgcg gcccaacaca 101400
aatttttaaa ctttcttaaa acattatgag ttttgccaaa agcaattgca acaaaacaca 101460
gaactgacaa atgggatcta attaaactaa acagatacag cacagcaaag aaactatcat 101520
cagagtgtac aggcaaccta cagaatggga gaaaattttt gcaatctacc atctgacaaa 101580
ggtctaatac ccagaattta caagtcagga aacaatagat gctagcgagg ctgtggagaa 101640
ataggaatgc ttttacactg ttggtgggaa tgtaaattag ttcaaccatt gtggaagaca 101700
gaatggcgat tcctcaagga tctagaacca gaaataccat ttgactcagc aatcccatta 101760
ctgggtatat acccaaaata ccaaaatagt attctactat aaggacacat gcatacgtat 101820
gtttattgca gcactattca caatagcaaa gacatggaac caacccaaat gcccatcaat 101880
gatagactgg ataaagaaaa tgtggtacat atgcaccatg gaatactatg cagccataaa 101940
aagaaatgag atcatgtcct ttgcagggac atagatgaag ctggaagcca tcattttcag 102000
caaactaaca caagaatgga aaaccaaaca ttgtgtgttc tcacttgtaa gtgggagttc 102060
aacattgaga acatagggac acagagaggg aacaacacac accagggcct gttgggggt 102120
ggggaggtga ggggagagaa cttagaggat gggttagtag gtgcagccaa tcaccaaggc 102180
```

acatgtatac ctatgtaaca aacctacatg ttctgcacat gtaccccatt ttttttgga 102240 agaaataaaa aattgtgatt ttttttttt ttttttttt ttttagctca tcagctatca 102300
ttagtgtttg tgtattttat gtgtggcaca agacagttct ccttccaatg tggcccaggg 102360
aaggcaaaag attgacacac ctgctttata atctcaaaca cagtagcaca ctttgaagat 102420
cagagagaaa acacctaact tcatcagtct tggttgtgtc acctgtaaga cagagataat 102480
acatattaac tcagagagtt actgaatggc ttatgtgtat gtagagaaac tagtaaaggg 102540
cctgtgtagc ttacatatat ttttagaggt gataaaaata accaataacc atatttataa 102600
tatattgaag ttaattgaaa tgaaaaacaa taaattaaca gaaaagatta gtcataaata 102660
aaatgagttg aactaatcaa gcaaaaaaca tgtgtttaat ttctttcaat tattttatag 102720
attttgactg aagtccacag tgctgattaa atttacatct ctattaagaa gcattaataa 102780
tacagaagaa atagacaagc caaggagatt gatggcagac ataggattac tttaagttgg 102840
tgttctatga aaacaatctt aaattaaaat attgaagtgg ggttccttta tattataatc 102900
tcatgtttca caaatttgtg agtgtatgat tgtactgagc taaaattgaa attgaacatt 102960
ttttctgttt tctatatcaa atcgataaca agcaattttc tagaattttg agattgtatt 103020
cctctttcat gagtattttt agaaatggaa ctaagttata aatataagaa aattttgtca 103080
cattagtgaa aaatgtttac ataaaagacc tgaatttcgt gaagaacctt taaacaatgt 103140
tcatctccat aaacacaatg tctgctctga aacttctttc ttattagagc caggaaataa 103200
agaaaggtgt atttttggag gaaagataaa ttgcctgtga tatcttagct ttatgccttt 103260
ttttcttata cttcatttat actaatgaga attttctatt tatcttttat gagttgattg 103320
tttgaaacac tattttgtta tttttaccat attttgtttg gggtattcaa gactcttaag 103380
caagaagttt agttactgaa tattttatat tgatctagtt tcttttcttt ccaacataaa 103440
gttattttta attttttaat ttttttattt ttattttttg agatggagtt tcactgttct 103500
tgcccaggct ggagtgcaat ggcacgatct cagctcactg caacctccac ctcctgggtt 103560
caaatgattg tcctgcctca gcctcccgag tagctgggat tacaggcatg caccaccatg 103620
cccaattaat tgtgtatttt tagtagagac ggggtttctc cgtgttggcc aggctggtct 103680
caaactcctg acctcaggtg atccacctgc tttggcctcc caaagtgctg ggattacagg 103740
tatgagcttc aagtacaagg aaataatgct cagttgagac tgagttgggc tgagtgggtt 103800
tttgattaac tgtggtctgc ctgaaacaga aacagtgctc tctgtagcaa atgtatcttg 103860
aaggactgac agctatacct cctgttgttc tgttcctatt cttacactag tttcataagt 103920
atctataaga taaatagaaa attatcatta gcataaatga tatataagtt ccatttctaa 103980
ataaacaaat tattttaaaa gaagaagttt ttttttattt tattgagtgc ctattttccc 104040
agtcttaccc tcttccagga atgtactcct agttgggaaa aacatcgcct cttgataggt 104100
tacttgatat tgctatagta ttgaggtctc cttctagatc atggttcagt atagcaggtc 104160
atcatttttt ctgactggtg aagagaaagt ctagattttc aagtaccttg gaagagaata 104220
gatatgctac cacctgtggt agtcctgtta tttgatcagg gcttagctct tttcaaagga 104280
actttcctta agaattctgt ctcttaatac cacttctctt gatgactggt tcaccttcca 104340
tgataccgtt acatcagagg agagcctgga agaattgggg tggattttgt gtgcatgtgt 104400
gtgtacgtga gcagtgcatg attcttattg gcttgtttcc tcataattca gctaaaggaa 104460
agcgtatggt ggcgttgatc taactggtgt ttattatcta ccttatattt ccaagaaatc 104520
agaatattct cttgagttcc atttaccaaa gtaagtttta aatcatccta atatagagcc 104580

-continued aaaacatagt tacttttcaa aattgcaatt ccataaattt tagctttatt ttccaagatg 104640
agagaaacaa tagaggaaaa ttctcactca caacctaact cagttatcaa cagaacattc 104700
aaggctggat ctcctaatca acattgaaaa agtatcccct acattaggaa aatactctgg 104760
ttctgtcttt acttcatact gggttattca cagattggaa aggtatataa gtatggcgat 104820
tgaatctatt cccttcccca catatccctc cctttgtagt gaggtcaagc ttggctcttt 104880
cactgtgttc atgtcagcat tttgtgttag aaatttacga tgggtgtggg ggcattacag 104940
tgcattcaac attttttca gtgccttcta tttggaaata tggtgacatg tgcagccagc 105000
actgagtaaa agttttaatg ggaggggaaa ctagtataag gataggaaca gagcaacagg 105060
aggtgtagcc gtcagtcctt caagacacat ttgctacaga cagcactttt tctgtctcag 105120
gcagacaaca gttaatctta agttagaaga agaaagaagc agagctgatg caaaaaaata 105180
tatatatatg gagaaagtta agctgaatgt tgtagagcta acactcaata agtatttgga 105240
atgttagcag tacaaccttt attagcagct acaaaaatca gactacatag tttttgata 105300
acaagatgac caattcaagg tgatacagag gcttgtgctt ggagaaggat gtcttgtaga 105360
ctattgacca atagggcaga atttcccttt gtacattcat ccctgttcag gtctaacttg 105420
catcctttta agcacggaca cctgacccat cacacccgca aaagtggata agatcaatct 105480
caagcagtga acttacactg accaagcaca caggaaatgc atataaaagt agattcctca 105540
aggccacatc tgaccagagt attcattatt tgttacagaa gactcgggaa agcattgaat 105600
ggctatctta taattgtttt ttcctcccca tctgaagctg cagacaccat ttgaaaagtg 105660
gctacatccc agcctatgat tgttctcagg tggcattttt gtttttattt tctaaatctt 105720
gatgggtacc tcactgttat tcccacatat cactcataat atttatatta tatactggta 105780
attgaatgtg ggttccatat tctacattca tttgctagac aaataattga gattctactg 105840
tatgccaagc actggagtaa tctgttaatt ggttaattca tttattagtt tctttaagac 105900
atactgtatt tactatgtat tggggactat gttagaagct tgaaatatca cagtgaacaa 105960
gttagaccat ggctactttc aaagtgtcta tagaagaatt gagaaatcaa gtgaacaatc 106020
acaatacttc tgataagaga taacacagag gaggtaatag ggttttattt ttaaagaaca 106080
atatataaat atagtggctt tggtcttgta aaatttagtg gcaatgtaat tgtataaaac 106140
aagggaaccc aagtggataa ggtaggaaat caaaatatta gctagtagta aaataattaa 106200
atgacattct ctggtctgga aattttgcca agtcttttca aataaacgaa gaaaacaaca 106260
aaaaaaactt actttggttt gtttcctaac aagtcaaaag gaaaaccaca atccaacaac 106320
aatgcaagca acagaaaatc tttaaataat gacgctgaaa ttatcttata actttaataa 106380
gtaaaagtaa aaatatggaa ataaacagaa gtttggcaga aagaacagat acaaaaattt 106440
caaaactcag gagaaaaagt cgagatcttc atgaaacaaa gctttaaaag agaaaagtta 106500
atgttagaaa accacacaaa agtctaaaag cttagaatgt tcagatccct aaagaaataa 106560
ggagagcatc atatagattt tatggggcat tttattttca caatagttga tactgaaagc 106620
aattttttt ccaaagagaa tgtgccacat aacaactagt aaaatagcaa aaacaacagg 106680
caaaattgga taaaatactc cactttctag cagtccagga gttggccctg taatctgtct 106740
tctagttttt aacttagccc atccctgact gtctcatata acaattggtt tgtagatgat 106800
cccatcattg agtagtttag cgtctctgaa tcataggcca ggtacagcat tcaaacttac 106860
ctaaaaacat cactcttttg gttcttaaaa aatattttgt gaaggagatg ccacaagctt 106920
tcccttagaa gccctgtgga aatcatctaa ctggtgggct attattagac acattatcaa 106980

-continued agtttctgct tttttacaag tctcttctta atacagtact agcacatgat gccaacagcc 107040
catgttatta tcatgtcatt ctagtgcttt aactaatagg tccctggaag gagaagaatt 107100
cgtttattcc tttgggatta tatatagatt ttctttctta attttatcta cagtgtaaac 107160
ttatacccag atcatgtctt ttattttgta ttttatgtag caccctcttt gcctttagaa 107220
aaggtttaga agagacaatg aggaaagata gtttaagggt ggtagaaata agttgaattt 107280
gagatttgag atggatgtga aagggtttgg agaggtagtt gctgaggaag gggcaaagct 107340
gggactttgc ctttggagca ggcttcttgg acatgcagaa cagtatcttt gtcagagaac 107400
attctggacc aggaaaactg ggaacattaa tctagattag tacaggactt tgaacatagc 107460
tgtgactacc tgacttgtaa attggcatat ctgtattttt ctgctgtcct gagttagtta 107520
acttcgtatt ttaaaatact catctgaata tatctgctac ttttgcccac ccagaaccca 107580
ttacctttc ttcagtgcag cactgttccc tccccacctt ctttggaaaa cgatgctgct 107640
ccaaccttta gggcttttgt tttggaaggg cagaccacca acctagatca agatgtagct 107700
gtcgtccagg cctacccaat gaccttattc aatttccata cctacaaagc atggttgaga 107760
agaggaaaaa aacccacact tttcagaggc aatcctaggt ttgaactttt gaaaaggagg 107820
agctctttcc actgtggtag ttgaaggtag agggctgcct ggagctgcca gtagccatct 107880
tgccactctc tgggataagc ctgaccgaat aaagtccaca cagaggaaag cagaactgag 107940
agaaagagag ggaccaagtc cctactgatc tcatttgaca cactcgatct actgccttct 108000
gaacatttct tgagcctata gattactcta cctcccttat ttcccataag tcaccatgac 108060
ttgccttttt ctgttacaac caaatcagtc ctaggaaata aaatgtttgt tttgcttcca 108120
cacccacagt ggggcttggg agcatctgta tttcaaagct gagaattctc cacagaatcc 108180
agttcccttc tatcttgttt taccttctga ggagaggacc atgaaggcag cgtcaggcac 108240
acgacacaaa tggcagctgt gtttcatctc ttctgtgcag atagcttaat aataaatacc 108300
tccttccctt tttagggaac aaaatagttt tattttacat agaaatttct tctgtagtga 108360
gtagcagtga aacgctaata tttattaaag agaaattgcc actgataccc tttggtgtag 108420
cccaagagga tgtaagaaaa aaaggaacaa atggcaccta cactctataa gctgcctaag 108480
tggaatctta atgtagaatt tgttgctttg tagtcttctt ttttttttta tctagcaaga 108540
ctagtgttac agaggatcac ggacattagt cacttgttct tgataacctc tgaagagttg 108600
gataaaagaa agaaactgcc cccagtgaaa agggatgatc tgcaatatct gaagaattat 108660
ttctgtggaa gacaatgtta ttacaagaca ctgggatatt atgactattt tggtagctta 108720
aagaaaaata aattcataat actagatatt aattatattc gatgatatac ataatttata 108780
atactaggat agaaaaaatc tttattaatt ttcaagtagt tacatcattc tctcctcact 108840
tcttagcatg aaggccattt atgtactggc aggtaaatgt caggttgaga aggctctaag 108900
tcatttcaca gtagggaaag ttggtttttc aacttggaag caaattttat tttattattt 108960
ttagaaaatt atatatatat ataacttaaa atggaaaatt gcacaaatca taagtggaca 109020
gctccgtaca ttctcaccaa gagaacatat caatgtaatg aacacccaaa ttaagaaaca 109080
ctacatgggc cgggcgcggt ggctcacgcc tgtaatccca gcactttggg aggccgaggc 109140
gggtggatca tgaggtcagg agatcgagac catcctggct aacaaggtga aaccccgtct 109200
ctactaaaaa tacaaaaaat tagccgggcg cggtggcggg cgcatgtagt cccagctact 109260
cgggaggctg aggcaggaga atggcgtgaa cccgggaagc ggagcttgca gtgagccgag 109320
attgcgccac tgcagtccgc agtccggcct gggcgacaga gcgagactcc gtctcaaaaa 109380
aaaaaaaaaa aaaaaaaaaa aaaaaaaaga aacactacat gattagctcc ccaatatcct 109440
ccattcggct actgtctagc caattcccta ccaagggcaa ctgctacact gacttctaac 109500
actgtaaagt agtcactggc agagattttg aaaggcagta tgtcctgctg aaatgtgagg 109560
gaaattccac tgatgatttt aaacctaaaa cgatatgaat atctttagca acaaaaccta 109620
ctttcctcca gaccacataa gaacccgccc atgcctatgt cctatttcct ctggagcatt 109680
tttaggttaa gttttagatc ttgtagtctg gtgatatagt acattttgac ataacatgga 109740
gtaaggatgc catgaggatg cccagctcat gtagggggtg cttggctggt ctgtgatagt 109800
cactgggaga aaggtttaag ggaagggctg gcatgtcatt tccttctccc tcttatcctg 109860
ctccataatg atcaccactg tttattcttt aaataagtga aaagggaaag aaataaatgt 109920
gtcatttaaa gggttccaat ttaagtctcc tgctttattc ttaagccctg cttaatcttt 109980
cttgattcta ccctaaggag tacaaatctc ttttggctga tccactttcc tttgaggaac 110040
caaaagtgaa cacgagcaaa cagattaaaa gatagcccaa gagcactggt caacatgtgc 110100
cctgtgtggt tggatcaagt agagggaaac catgatttgc tttaaaagaa taacggtcat 110160
tgcaatgtcc tgcttctgtt ctggggttca gaatgtgata ttctgcatcc agttaaagga 110220
atctcttggc catttaccac agctaatagt aattaacaga acctactgaa aatgcagatg 110280
caccctcttc aaactagtaa gtgttactca tcatgctggg atattgagag agatttgact 110340
ttgagaagca tggagaaatg atttggttta aaactagaaa ctctggatta tacagatact 110400
catggcacta agcaaattca gaattaaaag aatgtgcctt cagagagaca aatgccacag 110460
gatctctcta tatgtgaaat ccagaaaagc caaactcata gaagtagaga ttagaatggt 110520
ggttaccaga aactgagggt ggtgatggtg gatggagaaa ggggagatgt tggttaatgg 110580
gtacaaagtt tcagttaggc agtaggcata agttctggtg atctcttcca tagcacagtg 110640
actgtagtta ataataatgt attgtatatt tcaaaattgc taaaagagaa gattttaaat 110700
gatcctacca caagaaatgg taaatatttg aggtgataga tatgctaatt agcctatcag 110760
atcattctgt gatatataca tgtattgaaa caaccttata cctcacaagt agatgcagtt 110820
attatgtcag ttaaaaataa aactaaaaaa aatttttaaa agaatgtgcc ttaaaaaata 110880
ttttgttctt ttcattaaat aataatctta gtaacactga cagtgagaat ctataaattt 110940
agcaatttcc aaagcaatca ttttaattgg atttaaaagg gatattatag tggataaaac 111000
cctcagaata ttttatgtag tagtgccatg gtttattaaa cagaattcat ttaaagtaca 111060
catgcaacac atcccgatag tttcttacaa accttgaaat aagcaattat tgagaagagt 111120
tgagagggtg attttctgag tttaacgaag aaggccttac atctagaagc ttgcagtctt 111180
cttgaagata gagattctga gttggttttg gctcagtgtc acccttgcct gaaatagtat 111240
gtggaaagcc acaataatgg gaatgagcat agtgtatctg ggggaggagt agacaggtca 111300
gtccagctga atgccgtgta tgtatgtttg tgtttgtgtg tttatacacc aagtgtaaaa 111360
taaaataaag tacaagtcat aaaattggac atgttacgga tagttttgta ttgtcataaa 111420
cacatttaca ctcaataaat gtggaacgaa taaatcaaag gacaaaaagc tttgaatacc 111480
taatggaacc tgagggtgtt catcctgaag gtaactagaa gatataagtt atttctctct 111540
ttgtggccag aaaggctaga attcctttta tagacagagc aatgttacta gttttcagac 111600
agatgggaat tgaaacaact tttatcttta aagacaaaat cctacccaac attgtacata 111660
tttaaattta tgtgaagttg cccacaggca gtggaatgag ttaatcaaat gataaagaaa 111720
tgtcaaaaca tcttatactt gtatataaac ctggtagttc agtatcctat aaagtacaac 111780
caatccatct gtccgaaagc ctaataccac tatttttggt gacactaaat gctttaaatt 111840
ttgtcagcaa gatttgaggc aatgtcaaat gctagagtga tcaatatcaa atactagagt 111900
gataaaaccc caatattatt atatataatt atatgtgtgt atgtatataa atatatgcca 111960
aaatgctata caaatctata cacactttat ataagtacta tatgcacaca tacacacaca 112020
taattattaa ctaagtttaa aaaattccac gtgatgagat tttttttaa ctttaaaaag 112080
tattagctca ttagacttca cttttttttt ttttttttt tttgagactg ggtcttgctg 112140
tgtcgcccag gctggagtgc agtggcgtga tctcggctca ctgtagtctc tgcctcctag 112200
gttcaagaaa ttctcctgcc tcagcctcct gagtagtgag gattacaggc taatttttgt 112260
atttttagta gacacagggt ttcaccatgt tggccaggct ggtctcgaac ccctgacctc 112320
aagtgatccg cccacttcgg cctcccaaag tgctgggatt acaggcatga gtcactgcat 112380
ctggccagct cattagactt cctgataaga tttcaaattt tatgtctttg tccgaagtca 112440
gatctataac tttaaaaata taaactagtt attttacttt gttttcattt gtttttcttt 112500
ctgatttttt aagtaattaa ttctaacaaa atggtctact tggctgtgct catgtgtata 112560
gctgatgtca gcatattaat agccagatgt agatgacata tcttgatctc tggtctcatc 112620
gctctactgt taccgtcaac attgttacca agcatgagct gggcaatgca aggcaattat 112680
tttctgaccc ttgcagtctg tataatttgg ttatccccta gatacaatct ctataaatag 112740
tgtttgttgg gttctggaaa ctagagtgga cagatggcat gggggacata atcaccaatc 112800
ttacccaagt atgtaacaga tctgagtata taaagaaagc ttgggtattt cttgtagtca 112860
gcatgatatt ttgctcataa atttccaaca taatataaat tttgaaacaa aaaggtaagg 112920
aaaataaagc tttaggactg ttttcagcct gctatttttg aggaacaagt gacagagtct 112980
ggtcatcatt ccattctgta tctttggatt attttaatgg attatgtccc agatggatat 113040
tagcgtattg gtagggcatg ggcagctaag tggtcaaaat ttttaaaaag cagcagctac 113100
tggattggct tgaactgttt ccttaaaatg gcagattagt tttaccagtg gtgtttttaa 113160
tacagcttca catcaaagca gatttgtgta atttggccac ctgctataaa catcaatttt 113220
aatcaatcac atatatcttt gccaatatag tttatcagtg gtaaatgttt aaagattttg 113280
aaataaattt tatgataaaa ttaagcagcc atctggaatt gtaatatagg ttttttctaa 113340
atgatttgca agtcataaat tttaaacact atatatagag aatacacaca gtaagtgtac 113400
attcattttg tccctgttta caatattgtt tttgaggaca tttcattgtg aataatacag 113460
aaaatttacc ttctgaacag gacctatcaa cagtcttggg cagaaagaca tttgagctct 113520
gctggtctag acctgtgtgc ttagataatg agtccagcta ttcttgccag aactgcttgg 113580
tgattatgat tcaatctctg tagcttttca gtcagtgtga aattattgta aaaaacaaaa 113640
tctgctctct gatacattta tttcaagtgg tattgcttta ataatgtacc cccaatccaa 113700
gtataactta caagaaaaat gtatttagcc tgcatatgca agttagatat cctccccatt 113760
agagtagtaa cttcccaaac tgtttaggaa agatgcatcc aaagaatttg cataattatt 113820
atattgcaat ctggatttgt gaaatcaaag gtattggata tctaaattag taggaatatc 113880
tgcacacaac ccctcaatcc acttatttca ttacatggct tattttaggt tttcttttct 113940
taggcttatt tttgaataat tgatgtattc attaccagta gtaggggatg tgggggttgg 114000
tttttatctc ctctgtttta tccccctttt tatacttctt ttattgctca ttttaacatg 114060
ccacctgtgg gggtttctcc ttgacgtaac tagtattctt ctggctaagg ccatatttta 114120
ttagttttat ggcttgtctt tcctttttatt caaaatctca ggtcttgaaa aagactggat 114180
acgaatgtaa aatgtaagaa agaacaaaaa tacactttaa aaagactttg gattgccaat 114240
ataaagtcca ttattagcat tcataaaata aactacttta gagccaataa ggatgaaatg 114300
ctctactttt aatttctgtg gcactattaa aaatactgta tatgggatac atcctacttt 114360
atagggatta actttcaaca tgcaaataaa caagaatcgt ataaccagtc ttacgtattt 114420
aagatttaat ctaaaattaa aatattttat atatttgatg tgtatcctta ggttatcact 114480
ttatgtagat agatgtggaa gtccttaata cttaacaaaa cacatataat aggctgggta 114540
cgtacctata tcatctgata taaaactcct gtgaggtaac tagggctgac tctggataac 114600
aagctatcat caatatacca cagtacttct cacataagct atatttgtga cacagcttga 114660
tgtgtggtat aatattcata gttatgaata agcatatgtt tggataatac aggaggatgc 114720
aactcgctct tccttgaata gtaatgattt cacagagaaa ctaatattta tattgggaca 114780
cgaggaatgc ataggaattt atccagtcca atttaattat tgtacaacga aagttaaaaa 114840
gagaaaacgc cattgacttt ggaaagtagg aactccagct atgaaagttg gaggtgaaga 114900
gtattccaac aaaaagagta gtatgaaata atatagtcag ttaagggaaa gccaagaaat 114960
tgaagttcat aagattggga aggtaaacaa aatggtggag aagtagagta aggggcttcg 115020
aactcatcta aggtcaggtt atcaagggca ttattgccaa gataaggaat aattctgcag 115080
gcatagagag ctagccaata ttttaaagcg ataagactga catcagttta tgacttttat 115140
aaagagatta tcaacttata ttgtggagat tgtaccaaac aggaacagat tgatagcagg 115200
gccaattata caaaaatgat actgatctat tattttttta gcagaaaagg aagccatggg 115260
tttttctagg aagagctctc ttatatgtaa ctaattagca ttggttttac tgctagatta 115320
caataaaata tataaagatt agagaatatt gttcatactt aatttttttc atttttttatt 115380
ttcaacaaga cagtttatca agatagttta tataatgatt tgaatacatc ttcatttttt 115440
tcatactttt taaaataatt tttttcacat gttcaagtta ctgttcatcc atgtggttga 115500
cagaggccca tgaggttgat aaatgaactc cactgtaacc aaaacaactg tttttaaaaa 115560
taaatacatc tcctttacca agattttgaa gacatctgaa agcaaaagca attgatctgt 115620
tttaccttcc ttacctgaca cttcctgcaa agcaaacaca atgtaaattg ttagaaaaag 115680
attcaaaagg cagctgactg aaaagaaaag gtgaagaaag tacataaacg agcaacacac 115740
caaatgacaa tttaattctt gtacaatgaa agttgaaaag acaaaatatc attgactttg 115800
gaaagtagga actcttgcta tgaagattat tattactcat atataatgcc tttattattt 115860
attctgtctt atttatactg ttcaaaatct ctactgtgat agattatgaa acagagaata 115920
ttcttgtgcc tggaattgtt tgtccatgtc aagtattgtt tgatggtttt gacttgattt 115980
gacaagtcag gttaatcaaa acaatcaagg ctctatacca tatctagtct cattatactg 116040
tcaaaattta gatgttttgt aatagtaaag catattaatt gtttgctgca agaagttcag 116100
ggtccttagc tgtccttcta gcatggaaaa tgttgttcat tttagtgaat atgtaaagga 116160
atagttgggt taacttttgg gcaaagcaat ttattttctt acttaatgca agactagtac 116220
taatgattct tgtaacaatt gtcataaaga tgattcatat ttttctatgt ggctttataa 116280
atgcaccatc tatcataaga tagaagattc tagtttaatt gctaacattt atctttttgg 116340
gtctcatttt ccccctggag taacatttct agaaatgata aaaaaaatca ttacttaaaa 116400
gattgggctt taaaattgga attcaaggtt attagataca aatttctgtg ggggaggaaa 116460
gcacatgtat tatcctaagt tatatattat tttgtctgtt aagccattga tataattaag 116520
gggttaattg ttacaatcgt ctttggagat caaagtttag attgaatgag caattgaaac 116580

-continued ttgctatgtt ttaaatgtaa gaaaagtagg aatttgcttt acagttatcc ttttaaataa 116640
gaccttacag gagagttctt ttctgtcatt ctccctctct tgccctctgc cttctccaat 116700
ctccattact tccctttgc ctcttttccc tccacaaata tttattgaga gattactgaa 116760
tgagtacaaa atgtattaat gtagtgacaa atatattgct gtacaaacaa atgcaaaact 116820
ttcttagact aaaatactgt taaggttagt tttgagcaat atttgaagaa ggaaagggct 116880
gcagtgttgg agggaagata tcaagagtgg acagtaacta catcaggata aaactgacca 116940
tttaggagca agtccaaaag cccaattagg taaaaggagt cttagaggca tggtagcact 117000
ggcaggcaag aagtcatgtt caagctagca gagggggaag ttctattaga tgatgactca 117060
agtaaggaaa taataaacta cagttctagc aggctttcat gagggaaaat tgcatggtac 117120
agaaaggggc attggcaatg agaagggagg cacaagcagt gttgggctat caaagaggat 117180
agattcattt taagagaaac caggtcactt tggcttcaac agtaaacatt ggttggtcca 117240
tagagtggat aaacaaacag agtgaacctt tgtcaaaaat attaatttaa attgtttggt 117300
tacctgctac tgttgttgtt gttttgaggg gagattatgg ctatcatgca atcaaaatag 117360
tacctaaggg ggacaatttc agagagcata gtgattaaga gcatgtactt tggagtcgga 117420
ctgcctgaat tcaaatccta gtttcactat ttacaaactt tgtgactttg ggcaaattat 117480
ttaacctctt tgtacctcag tgttcttata tttaaaatgg ggagaatagt agcacatacc 117540
tcaaaagatt gccataaaca ttaattgaaa tatttgtaaa gtgcttagaa taatacctga 117600
ccaatagtaa atggttgtta agtgtatatg tatatgagtg tgtatatata tatgtgtgtg 117660
tgtgtgtgtg tgtttgtgta ataaaggctg tatgcttgag tagctcatga cagaaatggt 117720
aaacactacc atttaaggga gcaaaagaca aatgtatggt aatgtttgaa cttgaagtaa 117780
agcttgcagt atgtaaagga tggagtggat ctagagttta tttattctgg ttttaccagg 117840
ccaatctagc atgttcttgc ccaaacatgc taaattagcc tagatgtact gttagttcag 117900
ccaggtaagt attaaaaggt ctaaagtttc aaactcctgc tttagggaac aaggactatt 117960
gagattccaa actactctag agttagcaaa attggaccaa gcttctcttt ctaggagtct 118020
tgagaatatt cagggctaga aaccttggtg cttctgagaa caccatacca catagtctac 118080
ataaatccag actccaaaca aacatgtcaa atacaagacc ggaaaggatt ttagagctgg 118140
ttcagaggct gttacctgta ttttgctcat tcatgaattg ctggcccttg tgattttttg 118200
tgggtggcac ctgggacttt ttgacatttg aaagtctctt tcaatatttg catctatgat 118260
gcatccattt ggaaagtcct aaaaatatga agatattttg tagaaatttt aggatgatgc 118320
agattaagaa acggttaatt tatggaacca aaaaagagcc cacattgcca agtcaatcct 118380
aagccaaaag aacaaagctg gaggcatcat gctacctgac ttcaaactat atacaaggct 118440
acagtaacca aaacagcatg gtactggtac caaaacagag atatagacca atggaacaga 118500
acagagccct aagaaataat gccgcatatc tacagctatc tgatctttga caaacctgac 118560
aaaaccaaga aacagagaaa ggattcccta tttaacaaat ggtgttggga aaactggcta 118620
gccatatgga gaaagctgaa actgcatccc ttccttacac cttatacaaa aattaattcg 118680
agatggatta aagacttaaa tgttagacct aaaaccataa aaaccctaga agaaaaccta 118740
gacaatacca ttcaggacat aggcatgggc aaggacttca tgtctaaaac accaaaagca 118800
atggcaacaa aagccaaaat tgaccaatgg gatctaatta aactaaagag cttctgcaca 118860
gcagaagaaa ctaccatcag agtgagcagg caacatacag aatgggagaa aatttttgca 118920
atctacttat ctgacaaagg gctaatatcc agaatctaca atgaattcaa acaaatttac 118980

-continued aagaaaaaaa caaccccatc aacaagtggg cgaaagatat gaacagacac ttctcaaaag 119040
aagacattta tgcagccaac agacacatga aaaaatgccc atcatcactg gccatcagag 119100
aaatgcaaat caaaaccaca atgagatacc atctcacacc atttagaatg gcaatcatta 119160
aaaagtcagg aaacaacagg tgctggagag gatgtggaga aataggaaca cttttacact 119220
gttggtggga ctgtaaacta gttcaaccat tgtggaagtc agtgtggcga ttcctcaggg 119280
atctagaagt agaaatacca tttgacccag ccatcccatt actgggtata tacccaaagg 119340
attataaaac atgctgcaat aaagacacat gcgcacgtat gtttattgcg gcactattca 119400
caatagcaaa gacttggaac caacccaaat gtccaacagt gatagaccag attaagaaaa 119460
tgtggcacat atacaccatg gaatactatg cagccataaa aaggatgag ttcatgtcct 119520 ttgtagggac atggatgaag ctggaaacca tcattctcag caaactatcg caaggacaaa 119580
aaaccaaaca ccgcatgttc tcactcatag gtgggaattg aacaatgaga acacatggac 119640
acaggaaggg gaacatcaca caccggggac tgtcgtgggg tggggagagg ggggagggat 119700
agcattagga gatatatcta atgttaaatg atgagttaat gggtgcagca cacccacgtg 119760
gcacatgtat acatatgtaa caaacctgca cgttgtacac atgtacccta aaacttaaag 119820
tataaaaaaa aaaagtagga atcaggcaaa aaaaaaaaaa ggttaattgt cctgttgaga 119880
ggttgattca gattttctgt tattctaggg ggagagttct attgatgaca aaaatgtaaa 119940
tttctttcta tgtcattttg ttcagtctgg ggagtagcaa aggattattc tttacagtat 120000
gttttctaat gatttgtcca aactgatttt gtattccaga atcacatact gctcttgggt 120060
ttttctcccc acatttccct tcagtggatt atttatactt ttaacaaaat gatgaatggg 120120
tcgttgtata ttcaaaatgt gttcacttcc cctggagaat ctgagtgaaa caagtacatt 120180
cttgcagaag aatcctaata tggttaccta gtcctttgaa attggtttta tctttgattc 120240
tgagaattct ctacaaattc aatgctgtat attaaaaagt tacaatattt catattttta 120300
atagcagaga taaaattgta gaaacaagtt ataatagaga aaagatttta gtttcttctg 120360
gagagcagta tttcataaca taaaataaat ccacttaggg atttatagaa tattttctct 120420
acatattact atgaaacttt taagacataa tttttttttc tctttcctgg aaatcctttc 120480
tctctcttcc tctctgttgc ccttatctat cccccacccc attattgtac tttagcactt 120540
aagcatttaa ctacagtttt gaccaacaga tgtatctgtt tgtttccata tagtaatata 120600
tgtttatttt agagaagaaa aaataagaca aagtaaaaat atacagcaac tgaggcacaa 120660
aattctgcag tgacttgctt catttttccc ttcctattta atcaaagtac tatcaaaaat 120720
tctatttaaa tttctcaaat tagaatatag gaaatatcat tcagatattt taaaaaatgt 120780
aattatatac ataagcataa gtaatagtac agaatgttgc atgagatgaa aatgtatata 120840
agcttagctg tcattgatca tactgaaaat tatttctaag atggacttta ataggctaca 120900
gatttttaag atttttaaaa ttgtaagctc tgatcaaggc actgtgttac ttacaggggg 120960
atgtatgcat gtgcatgact tggtccatac tttccagaaa tttataattt agttgaagag 121020
aaaagaagta gacaccatga cgatacaatc tagtttgtga gtggcacaga ttttgctata 121080
gctcagaaga ataaaggcat ttttaaattt caatagtttt tggggaacaa gtggtgcttt 121140
atcacataga taagttcttt agtggtgatt tctgagattt tggtgcaccc atcacctgag 121200
cagtgtacac tgtacccaat gtgtaatctt ttctccctca ccccccctggc actcttcccc 121260 ctgagtcctc aaagtccatg gtggtattct tgtgatgcct atctcccact tataagtgag 121320
aacataagat gtttggtttt ccattcctga gttacttcac ttagaataat gatttccaac 121380
tccatccagg ctgctgcaaa tgccattatt ttgttccttt ttatggccga gtagtattcc 121440
atgatacaca aacacacaca cacacacaca cacacacaca ccacacacac acacacacac 121500
acaccacatt tcccttatcc acttgttgat tgatgggcat ttgggctggt tccatatttt 121560
tggaattaca aattgtgcta ctctaaacat gcatgtgcaa gtatcttttt catataatgg 121620
cttcttttcc tcttgggatt cctggatcaa atggtagact tacttttagt tccttaagga 121680
atcttcatac tgttttccat agtggctgta ctagtttaca tttgaccagc agtgtaaaag 121740
tggtcccttt tcaccacatc caagccaaca tctatttttt taattttttt aaattatggc 121800
caatttttgc atgagtaagt tggtatctca ttgtgatttg aatttgcatt tccctgatca 121860
ttagtgatgt tgaccatgac ctattttggg ttcaagtttg gctttgggaa gtgctttgga 121920
gcttcttctg agtccagcca ctgagctggt catcaacagt tgtataaaat ccacttttca 121980
ttgcatgtca caattcgatc tagaaatggt ttgtcgtttt tgtgttgaat aagagaatat 122040
gacacttcca aatgacattt ttttaaattt tcagtcagct catgaggcac tcacttactg 122100
agctttttca cctttccaat ttgcttcaaa tgccaaacga ccatagaatg gtcaatgttg 122160
agttcttctg caacttcttg tgtagttgta ggaggattag cttcaatgat ggctctcaat 122220
tagtcattgt caacttctga tggctggcca ctatgcttca catcttcaac actctcacct 122280
cctttgcaaa acttcttgaa ccaccactgc actgtatgtt cattagcagt tcctgggtca 122340
aatgcattgt tgatgttgtg agttatctcc actgctttat gacccatttt gaactcaaat 122400
aagaaaatcg cccgaatttg tgttttgtct aacatcattt ccatagtcta agataaatct 122460
aaaataaaca gcaagtaagt cattagcaaa acaacataaa gcaagaaatg cacattaaaa 122520
tgatgtataa cataacaaca cttatttaag actgtatttc aatatcaaac agcaaatttc 122580
aacaatgcaa aaaccgcagt tatgtttgca ccaacctaat aactgtgaaa tatactttgc 122640
tttaggctgt ttctgtcaat gaagctgact agttacaatc ttactaggtg ctgagaattg 122700
aaaggaaggt gctacagttg acacagatca ccagtcctac actattcaaa attttaaatt 122760
aaaaaatatt tattgagtag tttttatgtt caagggactg taaaagacaa tggaaataat 122820
tttctagaag agtaaaaaac agttttgtct ccaaaaattt caccatccac attcggaaac 122880
aatcaagcta aaaagtcaaa ccaaacaaat caagctttaa tgaaacatgg ttggaggaac 122940
tcagaaaaaa gggtgtctaa ttctgttttg gggtatctgg taagctatga ccagaggagt 123000
aaatctcagg ataagtccca aagatagacc aggtaggaaa gggcatttca ggcagaggaa 123060
actttatagg cagatacact gaagtgacgt gaagtagaga atcctaagga aattgcagac 123120
taaatagtag agtgctgatg gagttgtcaa agccatgacc ccggagtgtg gcaaagggca 123180
gctcgtgaaa tgtcttgcac attagcccga agtaaagtgt tttgaagtgc agtccttcga 123240
gtcctgtaat gttagaagaa ataatgctgt cataatccct aaacatatta tgacaagaca 123300
taacacaaat ctatgaagtg ttgtgaaaca ggatggtgca gtctaatgtg aaacaagtgg 123360
tcatttttca ggatgaatct agattccctg gggtgaagga gagtcagagc gtaaatagat 123420
acggaaagtt taatgagctt tgaaaggcaa tctttatcga gtcagaatgt aaaagagtca 123480
caaaatgaat aacacaaatg tattaattta tctaataaat attaactgcc tttaatgtat 123540
ccctgtggga gatgagagtc ttgttcttga gaatttcata acataccaca aacatcaaga 123600
tctttgagtc tgaagaacca aagtaataga attggctgga cgatgttgtg gctacttctg 123660
gccccccagg tgtcttgagt taataatatt gctgatctgg aaatagtagg aaggttaatg 123720
aacaattgca tttcttaatg ttcttgtacg tgtttctttt gtgaactgaa tgttagccta 123780
tttataagac atgccacaaa gtgatctagt aggaactttt taagctcatg ctacaaactt 123840
ggggttgtga aaactaaagc aaataagttg gtatttttag tatgtaatga aaggaggaaa 123900
gttgtggatg agtagaacaa agagataggt ttaacaatca taacacacaa agtcatttgg 123960
tggcctatat ccaaactttc attgattttg ttcatgtttt gtcctagaac cttgagaatc 124020
aggagaatct agtctcttcc ccaacctcag gggtgaagct tgattagtcc aggccagtta 124080
tggtaattcc ataccattgt caagtgactc attctgttat ggacacagga cgacagaatt 124140
ttggcaaata agatatgagg gaaaatcagt tgggtagctt ctgagactgt tttagtcatt 124200
cttatttagg atagaaagat gagaaaatgc ccttttgtgg cttttcagta gtactgcgtg 124260
aggatgtaat atttgaagct gttgcagcca tcttgctatc atgaagggcc agaggatata 124320
gttctacttt ctgatgttgg cagtatggaa gggatggaaa gaacaggagt tatttttttt 124380
ataatggact gaggaattaa ccagctaacc attcttgccc tgccatagct ctaaactctt 124440
acataacata gaaaatgtat ttacaaaatc caatcttgtt ttaattgttt ttcttttcct 124500
tgcagctgaa agcattcttg gggaggaacg catttcttct atcctcttat tttcagtatc 124560
tggaagcctg caaattaaac aaaccacaaa aaaaaaggca gatctatagg aggaagggca 124620
tatatttctt ttcttcttaa aattttattg gagtatgatt gacaaaaaat atgtacatat 124680
ttaatgtaca caactttatg atttcaaaga taagtataca tccatgaagc cagcaccaca 124740
gtctatgcca taaacctatt cattacctac aagagtttac tcctgacttc ttatctatta 124800
ttcttatttc atatgataca aaaaagagaa aataatttaa aaatattgcc acaaagaagc 124860
atcaaaacac aaagatagac aacatgagat ggagagagga acacaataac tgcaaaacat 124920
tcagaaaaac agttaacaaa atggcaatag taagtccttg cctatcaata attactttaa 124980
atgcaagtgg attaaactca ccaataaaaa gacacagagt ggcagaatgt gttaaaaaat 125040
aaaaccagaa tgcaactata tgcagtctcc tttctctttt ctgtatctgc tgcaagtttt 125100
ttctttgtgg ttacaatgag gcttgcataa aactctttat tactgtaaca gtccattttg 125160
actaatgaca acttcaattg catgcaaaaa ctatacttgc actcccctgc cccactttat 125220
taatgtcaga attaacttat ttttgtacta tgtattcatt atccaacttt ctgcagttat 125280
agtttctttc tatgttttgc cttttaagct ctatgctagg gttaagagtg atttacgcac 125340
cctcattact attttacgtt attatgtatt tgtgtatata tttaccttta ccattgagag 125400
ttatgctttc atatattttc atattactgt ttggtgttct ttaatttcaa tttgaagaac 125460
tccttttagc acttcttgca tggcagttct aatggtaata aacttcttag ttttggtttc 125520
tctgggaaag cctttgtatc ttcttcatta ttagaggaaa gattttccag gtatattatt 125580
attggttagc agtttctttc tttcagcact ttgaatatat tatcctattc tctcctagcc 125640
tggaaagttt ctgctgaaaa attcattaat agtttcatag ggatccttcc tatgtgatga 125700
gtcacatttt tcttacagct tttaaaattc tctctttgac ttttagcaat ttagtgataa 125760
tgtgtcttag tgtagacctc tagtctttaa gttccacctg gggttttggg ggcttcataa 125820
atctggatgt tcattttcct tttcagattt gggaaatttt cacccattat ttctttaaat 125880
aaggattttg cccctttctc ttttattttt tttcctgagg tacccataag gtaaatattg 125940
atttgcagga tgttgttctg taagtcctgt aggctttctt cactcttttt catttttat 126000
cttttcattc ctctgaagag ataattttaa attacctgta tttgagctaa taaattcatt 126060
tttctgcatg atattctgct gttgaaactc tctatagaaa ttttgaattc agttattttc 126120
tttggtggta gaatttctgt ttggttctct tttatgattt ctatctcttc gaggaacttc 126180
ttgttttgct cctgtatcat tttcctgatt tatttatttg tctatctgtg ttcgcttgta 126240
acttattgag tttaagatga ttattttgaa ttcttatcag gcagttcata gatctccatt 126300
tcttcatggc tggttactgc cattttattt tgttcctttg ttgatgtcat gtttccctga 126360
ttctttgtga attttaggac ttgtatttat gtccatgcat ttgaagacat catttttttcc 126420
agtctttaca gactaatcag tccagtcaga gattctgggt gagctggttg gtccgctggg 126480
ggcaggactg ctgttgatgt ctttgggaag gtagcctgta acctgggttt ctgggagcag 126540
gcctggttct ggtttccact gtggtaggtc tggttttggg gtcatgataa agtctaatat 126600
acacttttct ctccctttct tccacaggtg aactcctgag ccaataagat ctctttgggc 126660
agttcattaa gtgggctagg gaaatactaa tgtggaagtg aaaccatcct ttctactctg 126720
catattgtgc cttttctaat ttatgtgctc tatttatgtg ctgcagtctt tcacctggat 126780
tccagagttc ttatcaagat gttttgtcca tggatgtttg ttaaattaat ttctgtggga 126840
tgacaagggc tggaaccatc tattccacca tattgctggt gtcatttccc catatgttgc 126900
tttatttaca ttaatatttt atatgcttga ggtatcagaa aaagaagtgg aaaccccaaa 126960
aggcagttag accccgaggc atatgtacca ctttaatgaa gggcaataaa ttgcagagaa 127020
gaaatcagca aaaaaaaggg atttgggctc ctaggggcag taaattgtga aaatgtgact 127080
agtattgtag ataaaggctg tttagtatgg tttgtcatac agataagagt tgtttacctc 127140
ttccaggtac aggagaggag aacaccttta aaaatggaga cctatgtcac ttttacaaag 127200
gaaaatttat gctgtgattt taggcagaaa gttgacacca gagaattctt cctgctgctt 127260
ctcaatttcc ttcagctcaa aaatgatcct tatgccaata tggaatattt ttggggtggc 127320
atattctgct cctcttcagc atccttcctg gtatgtgaat tacccaactc ttgtgttctc 127380
agaagttggg cttgagcctt ttgttcaggc ttatgggtac attttgtact ctctaggagc 127440
taaagcagat gggaaggtag tttttagcta agatattttt acaaatcata atttttatgt 127500
ctatagtaaa accaaatttt aagcatcatt acagcaaatc tgaagtggat aaatgaactg 127560
ataaattttt aaaaaaatta agatagtatt aagaaattga catgtagatt ctaaactaag 127620
atttaatagc taacaatgaa gacatcttcc ttatttttat gactgctgag agcaaaaaca 127680
caaagaccta aagcaagtaa ttgaaataaa aaatgatgga ttgggctggc agctattctt 127740
tagatataaa actaaatgca gtctgtctgg aatttaaagg gagtgggtga tccttagccc 127800
ttccttcaga tagacatgca agaaatacaa agtttaaccc ttaataaata aagcctggga 127860
gtaaggaaat tcagaaattt gaatcatatg accaataaaa tgtctctttt tatatcacta 127920
ttgatatcat ttgtgtaagg gtttgaatgg catttaagaa cctcttggtt atatgaaatt 127980
gaatttcagt gaaactaggc tgttattttg tgaagtatct gacttagcat tttttaagga 128040
agatatcatt ttaattagtg tatttgaagg tcgagtggat acttttactc tttttaagta 128100
gtggttttct tcacaaactt cggttctgtg tcatatatta ctgatcttta caatgtctct 128160
gagttactgc tgttttccat tcttaaattg ggagaacttt attcctgatt gagaagcaag 128220
aactgaaaat gtcacttttc cctttgaggt gtggaggaaa tcttttggaa atgttcagtc 128280
tctagtttcg taatgtgtaa cttatacttg tatagaacgt taggtcaaaa ttttttttacc 128340
agtggcattt ctcacattca ggtgtaaggg ctcgatgctt gcgtagatac aggaaatcaa 128400
actcacaaaa agtctccact tgttttaggg aattcagtac ccagctgaga gcaattacag 128460
gcaatattaa tatgttggca agaaatgtca gagttcaaat ggccagtctg agtgttcact 128520
ttttccttta tttgctctgt gatcatggct ttagaaggtt ttcttgttaa gaatagttgt 128580

-continued gacctcacct gaattgaaag gtggaagtaa tgtttcttat catgtgtggc atggcctctg 128640
gtcaagtgaa aattattcac tcacttggaa aatgtctttg gtacaggaaa tgatatcctg 128700
aaattcatta agggtttacc attgggttgg attctctata tgaagtgatc acagaacttc 128760
aaacatcatt ctatgaataa cagcttccta gggtgcatgg agaaaaactt cattttctca 128820
aatatttatt gggtaccaac acaggagacg ggcctgtact aggttattga tgtctataga 128880
tagttaagga aacttaagaa gtttccttaa ctatctatag tttccttaac tgtacctcaa 128940
ctatatcact tgcagctcat tatgtgtagg tatctctgca tgtatgatct atttccttct 129000
actgctacag actagtagat atcacagttg gcaattctac caaaagaacc tatagtccca 129060
gctactcagg aggctgaggg aggagaatca cttgaacccg ggacacagat gttgcagtga 129120
gccaagatcg cactactgca ctccagcttg gcaacagagc aagattcagt ctcaaaaaag 129180
agagaaaaaa aatgctcctt ttggtttccg atctgtttcc ttagggagaa attgttcccc 129240
tcaagctctc tttctaagag agtggacaga aatgtcttat ctctccagtc ggtaattatg 129300
acttctctgt aagtctacta ctacagacta gtagaaggaa atagatgata catgcagaga 129360
tacctacatg taatgagctg caggtgatat agttgaggta cagttagatg cagataatac 129420
agttgaggta gttatagctg aggtgcaagg gacaaaaatt agacactgtg tgattaaaag 129480
aaaatcatcc atcatctgag caacaactat tcattgaaca cctctaatgt gccaggatca 129540
cgctttgtac aagagttatg atggtgaaca aaatagactt tcagagttta ttcttgaatg 129600
gtaatgtatt aattaaaagg tctcattaat gtttaattac aaactagatt aagtattgtg 129660
gttcaagtgg acagctgggt caggggtgga gtatatctag gatagagaat ttcagttcta 129720
tattttacta attaactggt aaccaggagg tatgttctat acttacattt agctctgtgg 129780
cctgttgtgc ttcaatttcg tcatcttcaa aaccaggaag agctatattc atcttatctc 129840
acaaagctga ttaacataaa tgaaggagcc ttggaaaatg gaaagcatta tacaaatgta 129900
agttgtatag agttccacgg taattgctaa aaatactgag gcaaagataa tcctttgtag 129960
acagaggttt tggttaactt gtgagaatag agttagtaga atgctagaca tagaaaacag 130020
atttcagtga tttcaggaga aaatcagagg gaaggaagaa acatgaggtg ggtccagaag 130080
tggaagtctt caattccttt agaaaaggca catgtagctg gaagcagtgg ctcacgcctg 130140
taatcccagc actttgggag gccgaggcgg gtggatcaca aagtcaagag atcgagatca 130200
tcctggccaa catggtgaaa ccccgtctct actaaaaata caagaattag ccaggcgtag 130260
tggtgggcgc ctgtagtccc agctactcgg gaggctgagg caggagaatc acttgaaccc 130320
aggaggcgga tgttgcagtg agccgagttt gcactactgc actccagcct gtcaacagag 130380
caagactccg tctcaaagaa aaaaaaaaaa aaaacagtcc ccggtgtgaa catggcacgt 130440
gtatacatat gtaacaagcc tgcacattgt gcacatgtac cctaaaactt aaagtataat 130500
aataataaaa taaaaaaaag aaaaagagaa aaaaaaaagc tccttttggg ttccgatctg 130560
tttcctcggg gagaaattat tctcctcaac ctctctttct aagagagtgg acagaaatgt 130620
cttatctctc cagtgggtaa ttataacttc tctgtaagct ataaataggc aaaaaaattc 130680
cctaaggatg tatgcctggg gtgttgtagg ttttagtcat acctgaaagg gttgctcctt 130740
cttccttttt cagagtactc tgtatcgtta tctattcctt tcattttttt tctgaatatt 130800
ttcctaactt attttgtcca catgttctac aggtaaacct taaagattaa attctgttga 130860
ccctgtgctt tcttcagtct aactccttgg cacactgaaa ccacatttga tattgaatgt 130920
tttaacataa tctatttcag gaagtaaaaa aaatcctaga gctctctctt attttccttt 130980

-continued atgttaaata atcaccctct ctgacattgt agctttttaa ggaacacatc atgtagaatt 131040
gataggttct tttggtagaa ttcccaactg tgatatttat ttcatgacta cacatcattc 131100
tcagcaggtc aaaaatcatt gtattatgaa catctaaatt ggttctttaa tatatttttg 131160
ttagcagcag cacatctcct gaaaagcaac actgaagtcg attctgcgga cataaggatg 131220
atttggcatt gacatctgtc agcctgttaa ttactaagga agatttggct gaattaattt 131280
gtttcctggt tagctccttt tctctgctcc attatgccct ttactatgtt gcaaacttga 131340
acaaattaaa gatacattcc aagatatgag aagaattttc atcaaatgta tgaaaatcaa 131400
gtacatgaga aattcagttt ccaaaatata gggcatcatt gtgcagacga acagcttttt 131460
gaacctttct gttgaggaac acttccagtt ctataacatt tcttcagaca tttaatgaca 131520
gtttcctctg tgccaggcac tctctgtaag gtgaaagctc aggctgggaa gaggggtggg 131580
agtagggtga atgggaagcg ggtggggaca aggaaattaa cataagtgga catgcacaac 131640
aaaaaggccc tttcgggcgt taattttgta tcacctgcct gtatttctat tcaaacatga 131700
aaaatttttg aaacaaattt gaagggggag tggtccttca ccaataaggc accaataagg 131760
caggttattt tctcctttgt actggcaacc atcttttctg tagtttatgc tctgctcaca 131820
ccctatgtgc ttgtttccca tctgagataa ccctgcccct tttctgtttt catgaccatt 131880
attcaatgga aaattggaat aaagtaaaac aggacaagcc tgaattactt tgggctcttt 131940
gttatatctc atcatttttt ttggtctctt ttctccacta catttaaaac aaaaaataac 132000
ctttgcctgt gcttttccct cacttctaaa tatgtttttt ttaacctttt ctttcttctc 132060
ttttgtgctt gctttcttag ttaacattac aaattttctg ttttttctaa agctaatttt 132120
aaaaggaggc ctataatatt tgtgtaaagt ttttcattcc tccagtcatc ccattttcta 132180
tatgacttta atgtgttatc tgccagaaca actagaatag atatctccat tatttctgca 132240
cagatggcag agtgaacaag actttgtcct tagaatttcc atcaacaaaa caaaaccaaa 132300
ccacttacta tatatgtatt gccattcatg tttaagtgct gaaaatggac ttggagactt 132360
atctcagcac tatcacttat gtactctaac tcttctttat ttgagtaggg aatccttctt 132420
gtgacttcct tcagggtgtg gacacattga aagattaatt attcacatat cagctggaaa 132480
aaagtgaggt gacaagtgtt gacatttgcg tttctgaaag aggcacattg ttacatcaaa 132540
aaaaggataa tgccaattag gatttcatat gtgttgtttt attttcacaa ttacaatgtt 132600
agaggaaagc tcaaaagtaa aggcttttgt gaaaatgatc agatgataaa tcttgatacc 132660
tgtgtaagaa gtgaaagcac cagagttttt ttagaagatg aaaaatgaaa aaaaaaaaaa 132720
aaagaaaaag aaacaatttg gcattgttag aaattcttta ttgggagtgg aaaaacatga 132780
aataaaggga aaatagcttt aatcaactcc aaattccttc tttggaagtg ctgtgtgtaa 132840
tctccaataa tggtggtgta catttccccc aactctatta aaaccatcat tatcattgtc 132900
atcttcatca acatggtcat catcattgaa cacacactcc atacaaagta agatgttatg 132960
tgtttgtatt ataagcagag attagacaat aactctaatc acaaggatgc tgtaactagt 133020
agtgtagatg gtagatgtgc acaacaatga agggatgttt gatggtatct aagttgtgta 133080
atcattaggc ttacttgaag agtttcccct aatttttcta tttttctttt tccttttttt 133140
ttttttttc aaacagggtc ttagtctgta cccaagctgg agtgcagtgg cacattcctc 133200
atggctcact ggaggtgcct cagcctcctg ggctcaagca atccccccaac ctcagcctcc 133260
ctagtagcta ggactatagg catgccccac accagctcat tatttatttt tttatttttt 133320
tgcagaaaca tagtctcact ctttttccca ggctggtctc aaactccagg gctcaagcag 133380
tcctctgtcc tcaacctccc aaagtgctgg gactacaggt atgagccact gtgcctgacc 133440
agaatttttc ttgaatgtga tattctcctt cattctatta cacataattt ctctaatctt 133500
cataatttaa ttatcattga atttcagtct atctgattca tgtaaagaca acctgtcatt 133560
ccaaacatga tttgtcctct ttacaaaact aatctgatat gaactgtatt tgattcacta 133620
gagaacagag tatagtgatg cctcaagtta ttgatacctg cattgatcag ggtaactaag 133680
gcttactact ggaacaagca gtgctgtaaa tctcatgggc ttaacatgaa gtctgatatg 133740
gatttgggtg ggggctttac tagggggctt acctctaagc agtgacaaaa ctatgtaggc 133800
tttattcaat tgtgtggctc tgtcatcttt aagtccatca cttcctgcct cagctacaga 133860
agagagaaag aatgaactac caaatgagac tttttaggac tatatcacat gtggcttcaa 133920
cttaagagca acggtagctg ggaaatatca tcttcctgtg tacctcccaa aaaataaaat 133980
gggtttgtga atacatagca ttttctttat tacactatag aatatccaaa tagagatcgg 134040
atatttata gtgtaataaa gaaattggga aattaggagt tagggctgaa tgataaatat 134100
agcctttgaa gacagtgaca atgatataca gttgattagt tggatattgg ataataaaac 134160
ccatcaccta aagaaagagc atagcaaatg attaaaaaca ggatttaaag aatggttttt 134220
acaatgaggg acaatggtag aagcttattg tggtgtggac ttgtaattac ctcttaattt 134280
ccattttttt cttcctttgt aacaaaactc tagtttttttg cctaactaaa agactgttgt 134340
gtacccttct ttatagtagg gtataaccac atgactaatg tcacatataa aaatggagaa 134400
cgggtgcaca ttaaagagta ggtaagtggt taatatactt tttctctctc aatcctccca 134460
acctgccctc tttaccttta tctctccaaa ataacatgtt tgttgtttaa tagagatgac 134520
atcgtcctaa tctaaggctt aagattcctg taactcttaa gtcacacttt gccaaatttt 134580
tattcaatca ctgaaggctc acattgcctc tgaaagaaaa aaaaaaagca agtgaaatat 134640
ttctgactgt gagtgttctt atattggcat cttagtgtga acttagggga tatgttagcg 134700
ttgactgttt tctgtatcac ctcaggtgta ttttgtcttt cccctcttga cttcacttac 134760
ccactcactc tgactaatgt cctagcagtg gcaagcatgt agatgtctaa aaatgtagaa 134820
attgtaagaa agaggctgtt tcagggcagc atttggaagt ggctattgtg tagggctaac 134880
catatctctc tcctgccaga ggtcatggcc ttgttgatgg tctctagtca agagcaatcc 134940
cattagtgaa aaaaaaaaaa aaaaagaaaa ccagcactga cagtgactgc ttccaaatat 135000
tctcctgtct gctactatag aatttcctag tgtttcccat cttgtcaatt cctttccctc 135060
accttttta cactgagtga acaactttta tttgaagtgt taggtactaa cccagttctc 135120
tcaccctta ctctgcttcc ttcctttctt aaatgcttcc tgctttgtaa ccctctgcag 135180
ctagtgatac attagtttat gtttgtgttt tctcaagaag tgaaactgtt gtaggttgac 135240
ctattatata gaagtacata ctcctcagta gaaggcaact tatgattgta gaaactgggt 135300
gtttcgtgag aagttgctac ttaactgacc aattaggaaa aggggtacag aaatgattga 135360
gacctccaag gagatacaga ttcatttaag ttgagtgtac tgctgcagac atcattttga 135420
atatctgtat tacgagtaaa tggtggaaat ttgaagacaa gtccatactt tatgaaagta 135480
agagaacaag aaatttgttt ccctaaatct gtgagcatac cctataattc atcagaaaca 135540
gcaaattcac aaacacaaaa ttgacagaaa tatgtaaaac ttttccagca gtttacttct 135600
gaatacatta gaaaatgtga cagaacatag taaatttctt gtcattttac ttcccaaggg 135660
aagtgctagg tttgtaaatc ctagaatatc atcaaattat attttgaaat ttatttcttt 135720
ttgagctaga attttaaaag attacatgtt ttttcacaga atacgttcat ccagttacta 135780
ataatgatgc tgaaggaatg gaaatgtaat ttctagaaat catcactttt caaagtttta 135840
tagtttgtga actggaatac tgaagatgga agtatgattt aatatttggt agaaacagga 135900
gagtttgtta tttgtagctc tgatattaga aattacttga ggtttctgtt accaaacttc 135960
acaaaatata tttcataaaa agcattctta actcaggtta tacatttttt aaaaattatt 136020
ctgaaaggaa ttagatattt aacattgtag ctgacctaaa taaattggag aaaattctta 136080
aacaattatc tttcattttc ccatcaataa atggagcaat aataatacct aattatttat 136140
tgcacaggag tcttgcaata attaattaaa gctttaaagt actttgaaga tgaaaacaat 136200
tttataggcc tcattattaa aggtaatttg ttatggtaac cagtcaaagt cattcatttg 136260
gtcttttaaa cttgttttta aatgctctat tcggatccag gtgttaatta aaaaatttta 136320
aaacaacact taggaaacat atgaaattct gctttctatc ttgatgctta acttgtgaaa 136380
taataggtaa gttttttttc cgaattttgt ttttttcatg tttatacgcc tctctcaaat 136440
cccattgagt gagcgagtat tgctcccagc tcattattac aaaaagaggt ttgccatgtt 136500
aaagccacta agatttttct ttttctgaag ctctttactt aatgcaaaga caaagtgtca 136560
tctatgataa caattctgca tatggaaaac acaaggttat tcatccattt aaacatttat 136620
tgagcaaatg ctatagttta aaaaagataa gccactcggt aaattggaaa atatagtaat 136680
atgtcacttg catgaaattt ttatccaatg aaataatcaa gtaattaaat ttaaggtgaa 136740
agtgattgat gtaatatagg ttaaaagcca gtatggcaaa ggctgaaaca ttacaaagag 136800
aggcatcaaa tgtggttttg ggaagcactc aatttttgtg tagataatat cctagatgta 136860
cctgtatttc ataggaaaga aggcagtagt ggtattctag aacagtggtt ctcaacaagg 136920
gcaatagtcc cctgtccccc attcctggga catttatcaa tttctggaaa tatttttggt 136980
tgtcacaact agggaagtgc tacttgcatc tagtgggaag ctactaaaca tcctacaaaa 137040
cacaggacgg cccaccacaa cagagaatta tccagcccta aatatcaaca aaactgagct 137100
tgaggaagtc tgctcttgtt ggaaaacaca gaactatcaa ggcaccagat ggagaaagta 137160
taagatgtat atcaggaata gcttggcagg agtagacgtt gaaggtaaca ttgaaaatgc 137220
tttaggatag ccttgattat tagattagac tacaaagctg actcattgaa tcactcacgc 137280
actgtgagtc attcaataaa catttatatc tcaggcaata cggacagaga gatagaagat 137340
atagatgctg ctgtaaagtt tacaatttag ttggagacag tcagataaac cacccactgt 137400
gtgaacaaag tgatatctgt caaacaccaa ttctactgtg tctttaaaaa aagttcaatt 137460
aaaaataaat tttggaaaga gtatgcacta catacttctc cacaacttgg gactatatac 137520
aatcttgttt tgtgtatcag tttgccttta tttcagccag catttctttt ggcagtgtac 137580
ttttaattcc cttttatata acaactatta gcaacccatg acgtattgga tagcttccct 137640
tccagactca ctctggaccc ttctctgtgc tattccaggc tcaagatact gatcttcggg 137700
aacttcatgc tgagtgtccc tgtgttcggt tcttgattgt gtttggccca agagggacat 137760
ttataggaga tgagagggtg agaggagaca ggggttgggg catttggtcc ctcaactccc 137820
tcctccaaat agccaggtca ccacagactt gctgcatccc tccactgaag gccacactcc 137880
tttcagatgc cctttcttat agagctaccc tgtctgggtc cttataactg tttcctctcc 137940
ttatcccttc tatctaaagc tggcaatgtt cctcatctgt tgtgagctgt atgctgcttc 138000
actatccctc tttaggaaac tgcctacaca tttgtaaaaa tcctttatta agcactcctc 138060
aaagtgccag tctaggattc tcattgttat atatggggaa catgacttgg gaactgcttg 138120
tatggtagtt gcttttaaaa agagttctgc ataggaagga gtccgaaaag tttaaatttc 138180

-continued atattatgac ttatgcacat ctattgaaga atgtatctgt tagcttattt attcctgcat 138240
gtatgtatgt atctgtatgt atgtatttat ttattttgag atggagtcta gctgtcgccc 138300
aggctggagt gcagtggtgt gatctcagct cagtgcaacc tccacctccc ggcttcaagc 138360
aattctcctg cctcagcctc ccgagtagct gggattatag gaacctgcca ccacacccag 138420
ctaatttgtg tgtggtgtgt gtatttagta gagacagggt ttcgtcatgt tgtccaggct 138480
ggtctcgaac tcctgacttc aagtgatcca cctgcctcgg cctcccaaag tgctgggatt 138540
acaggagtga gccaccatgc tcagcctctt ttatttattt ttaaatgtgg tttagctgtt 138600
ccgcaggacc attctgatgt tctccatata attccatttt tgctatattt ggtttcagtg 138660
aaaatgtaag gttttgaaaa agtgaagtgg ctcaagagtc atgctttatt ctggtagatg 138720
gatttcaaag acgggaagaa ggcatgaggc aaggagacaa acccagatgt acatttaata 138780
atgagtaatt aatactttat tgattatgtt ttcctttatt tttataattct aatgaactga 138840 cgccaatatt tttaaaaagc aagataatga tttgaagaga gttagccatg gcagggaaag 138900
catgaatgga aaagagattg tgctgttata gtgacagtgc ctggaaactc attgaacctg 138960
acagtgtaga aagatgatgt gagataggca gggaaagaca gtagtaaaaa tccaaaattt 139020
aacgtacgga aacaaccatg tctgtggcca ttccactctg aacacgccga tactgtctga 139080
tctcagaggc taagcaccgt ccagcttggt tagtatttgg atgggaagaa acatcttctt 139140
ccccaattcc tttttagtta ccaattatat ctattacttt tatgaatgtt aagagtctac 139200
attgagatta gattagcatg caggggtatg acaatctttt aatggagaag gtaacttctg 139260
gtatctataa actggagaaa aagtgattct tcttacaaga aataaactgc agatgcaggc 139320
actaatagac tgaagcaata actctatttc cctcttttga tctttgaagt atctatatca 139380
aaaaaatctt cttggtggtg gggatatact acatggagat gggccaaaga ctacaaagag 139440
agacttaggt aaaatcttgt ctttgtatga ggattctact tgaattcaat aggcctgtgt 139500
ccctaaagaa aaaaaaatgt atttattgca aaccaattta gcttaagtaa aggtacacat 139560
tttggggttt tattggttgt ggttgttcag ttaaattata cttactgtac tggacaccat 139620
atacgccaat cactgttatc aattctagga atgcacaaat gaataaaata tggtccctgt 139680
cttttctatt ttctgtgaac tttctactta cgtcacaatg gtgcaatggg aaaagaagaa 139740
atggatcatt tattcaaccc ttgataaaag aaagacccct cctagttagc atggtggtag 139800
cagggataat ctgtaaggaa acctaaatcc aatgtgaacc tctgaagaaa gtgaggatgg 139860
ttagagtaat ctagtcttgc ctccacatca ggacatactt gccatgacca gcctgggagt 139920
gtctattttt tttccccatt aaagagggta gcatttcctt ttagttaata ctgagattcc 139980
cccctagaaa ggttctaata attgtagtgt aacaaagtta gtatcaggtt aatatccact 140040
ttaatgggag aatttccaaa actaatatta tcagttttaa tgataccttt ttgatttacg 140100
aaatgtctgt tattcacata gtttttgtta gcagtcaaaa ccaacaaaaa tatttgatga 140160
acccagataa atatttgaga aacttgtatg ctataacact tcattttaaa agatatgtat 140220
tttgtcatct ccaagttttc tttttaaaat tgttattcca acccttcttc ccctcaattt 140280
accagcatca ctaaatgccc accttatttc ccagtagttt atgtgttctc tcatatttta 140340
aaaaggtttc ttgaggtata atttacatat tataaaatta tttatttatt tatttaattc 140400
atttttaaat gtggtttagc tgttccgcag gaccattctg atgttctcta tgtaattcca 140460
tttttgctat atttggtttc agtgaaaatt taaggttttg aaaaagtgaa gtggctcata 140520
aagagtcatg ctttattctg gtagtgtatt caggtgtaca cccattttaa gtgtacagtt 140580
caatgaaatt tagtaaattt ttataattgt gcaaccatca ccacaatcca gttatataac 140640
atttcagtta ccaagaagtt tccctcatgc ccctttgcag ttaattcttg ctcccgctgc 140700
agccctaaca acagccacta atttttctgt ctctataatt ttgccttttc tagaaatttt 140760
gtataaaagg aaccatacaa tatgtagtct tttgtgtcta attatatttg tatgtttttg 140820
aactattaac ttgccacatg tattagtact ttgttccttt tattgatgag tagcattcca 140880
catttggata tattttgttt attcagtcat cagttgatag atgtttggat tatttctagc 140940
atttgcctat tatgaattgt tctgaacaag cgattatgaa taatgatttc tcacacacaa 141000
gtgttatgta aacatatgtt tttatttctc ttgggtagat acctaggact aaaatttctg 141060
ggttatatga taagtatatt cttaactttt aaagaaacta ccaagctacc acttttccaa 141120
tgtgtacgta tcattgtgca ttgccaccag caatgtaaaa tggtttttct acactcttac 141180
caacacttga tattgttagt tgttttgatt ataatcactc tagttggtgt gttgtggtat 141240
catcttgttc aatatccatt ttcccaatgg ttacttatgt tgaacatatt tttatacgct 141300
tttgcatatc tttttcaatg aaatatccac atcttttgct catttttata ttgggttatt 141360
gtcctcttgg attgtaaaag ttcttttttt attccaaata caagcccttt cctagatatg 141420
attggcatat attttttccc agcctgaggc ttgtctttgc tttatcttaa tggtgtcctt 141480
aaaagccatg cttgtgtaaa catatgtatc cacaaacata aacactgtag gagttttatt 141540
ttgttttttt atcttattaa aatggaactg actctatata cttttcagca tcttgatttt 141600
ctcattcaac attacctcat agaaattcac ccattagttt caatttatta tttttaatga 141660
ctgcatacta tttcatggta tgcattcccc cactgatgag cattcaattt gtttctaggt 141720
ttattccaca cccccaacag ccagtaaaac aataaccaca tttgtaccca tttatagatc 141780
cttaagtacg ggtgcttttt atttctgtag tttcaagtcc aggagtaaaa tttttggctc 141840
aaaggcttat atggttttat tttgatttat gttgccagat ggctttctga aacgtatgtg 141900
ataattcact tttctcccaa atgtgtgggc atcctttctc ccatatccac ttaagtcagg 141960
gagctgtcca ttttcaaagg ttgttcagtt aaattgttca gttaaatgtg actgggcatt 142020
tgcattccta tcatgactag caaatttggg cattttcacg tgtttgctag ttgactgaat 142080
ttgctcaatt gttaacttca gtttaaccct ttataaattt ttcctttggg tgttttgtct 142140
ttttttttta gaatataaat atatttggaa ttgtagatat tgggttttgt catttgaatt 142200
gcaaatattt cttccagttg tattgtttga ctattggttt tgcttttgat ctcccttgct 142260
acaagaattt ttaaatttta ttattcctag tcttgaaata tttgtaatat cattactata 142320
tattttctaa ttctttaagg tgggtactag attcctttat ttttgtcttt ctcctttaat 142380
aaaggagtag tgtcctggaa gtgataacat cccagtatca aacacctaga gtccagatct 142440
tggtttctga aggtcattta cttctaaaaa gaaccaagag tgcttggaga aatggctgat 142500
tacaggttgt ggccaagaaa aaacaatcag atctgaatta ttttgtggcg ttagaaacaa 142560
ggaagtactc agagactaat ggagggagtc atgttaaaag gactcagaaa tcacattcaa 142620
ggagccactg ctggtctact ctggaaaaaa tttgaatacc aaaaatagag aataaataac 142680
aatgatggta aaggatcaca aaacatttga ataaacaaaa aaaaatcttg agtcagcaga 142740
gatattccaa aaaaatgaga gactaataaa tgtagggaaa acatgtatat ttaagaatca 142800
ctattgcagc tccagtataa catttgatta ggcaagaaca tggacagagg ctaaaatttt 142860
ggccattaga ttgttgggga acacggtagt ctcacaagga tacaatgttt gataaggttt 142920
ggctgtgtgc ccacccaaat ctcatcttga attgtaattc caaatgttgt gggagggact 142980
ggatgggggt aattgaatca tgggggcggt ttctcctatg ctgttcttgt gatagtgagt 143040
gagttcttat gagatctgat ggttttataa atatcttgca tttctcctgc tatcatttat 143100
tctctctcct gctgccctgt gaagaggtgc cttccaccat gactgtaagt ttcctgaggc 143160
ctctccagcc atgtggaact gtgagtcaat taaacctcta ttattgataa atcatccagt 143220
ctcaggtatt tcatcatagc agcatgagaa cagactaatg cagtaaattg gcaccacaga 143280
gagtgatgtg ctgctataag ggtactcgaa aatgtggaag tggctttgga actgagtagc 143340
aggcagaggt tgaaacagtt gggaggactc agaaaaagaa aggaaaatat gggaaagttt 143400
ggaacttcct ggagacttgg agggctcaga agacaggaat atgtgggaaa atttggaact 143460
tcctagagac ttgttgaatg gctttgacca aaatgctgat agtgatatgg acaatgaaga 143520
ccaggctgaa gtggtctcag atggagatga ggaacttatt gggaattgga gtaaaggtca 143580
ctcttgctat gctttagcaa agagactggc gacattttgc cctagaaatc tgtggaacat 143640
tgaacttgag agatggttta gggtatctga cagaaggaat ttctaagcag caaaccattc 143700
aagaagaagc agagcttaaa tgtttggaaa atttgcagac ttatgatgca atagaaaaga 143760
aaaacccatt ttctgggaat tcaagcctgc tgcagaaatt ttcataaata acaaggagcc 143820
aaatgttaat caccaagaca atgaggaaaa tgtcagagac cttcacagca gcccctcgct 143880
tcacagaccc agaggcctag gagagaaaaa gtgttttgtg ggccaggccc aagcgccccc 143940
cagccctgcc ccccggcagc cttgggacat ggtgcccagt atcccagctg cgtcagctcc 144000
agccttggtt aaaaggagcc aaggtacagc ttgggccatt tcttcagggg tactagcccc 144060
gtgacttggc agcttacatg tggtgttggg cctacgggtg cacagaagtc aagaattgag 144120
gtttaggaac ctccacctag atttcagagg atgtacagaa acccctggat gtgcaggcag 144180
aagtgtgctg cagcggtaga gccctcatgg agaacctctg ttggacaata cgaaagggaa 144240
atgtggggtt ggagcctcca cacagagtcc ccagtggggc actgcctagt ggagctatga 144300
gaattgggac acaattctcc agaccctaga atggtagatc tactggcagc ttgcaccatg 144360
tgcctggaaa agtcacagac actcaatgcc agcctgtgaa agcagccagg agggggcggt 144420
accctgcaaa gccacagggg cagagctgcc taaggctgtg ggaactcatc tcttgcatca 144480
gcgtgacctg gatatgagac atggagtcaa aggaaatcat tttggaactt taaggtttaa 144540
tgactgtcct attggatttg acttgcatgg ggcctctagc tctttggctt tggccaattt 144600
ctcatttgga atggatgtat ttacccaatg gctctacccc attgcatcta ggaagtaact 144660
aactttcttt ttattttgca ggctcatagg tggaagggat ttgccttgtc tcagatgaga 144720
ctttgaactt ggacttttgg gttaatgcta gaatgagtta aaactttggg gaacctttag 144780
gaaggcatgg ttgtgtttta aaacatgagg acatgtgatt tgggaggggc cagaagtgga 144840
atgatatggt ttgggtgtgt cctcacccaa atctaatctt gaattgtaat cccacgtgtc 144900
atgggaggga cccagtggga ggtaattgaa tcatgggggt ggtttcctcc atgctgttct 144960
tgtaagagtg agttctcatg agatctaatg gttttatgtg tctggcattt cccttgctgg 145020
cattctctct ctcctgccac cctgtgaaga ggtgccttcc tccatgattg taagtttcct 145080
gaggcctctc cagccataca gaagtacgag tcaattaaac catttttctt tataaattac 145140
gcagtttcag gtatttcttc atagcagtgt gagaacagac taatacagtg ttacttcata 145200
aattgcttac taatcgaaaa ggggaaaatg tattaatacc tttaagatag aaagatctgg 145260
caagtagaca aacttaacgt tgcaagtaat agaacataat attttgtttc tcctctgcta 145320
tgcagtataa agtacctaaa tcattaccaa caaactatgc ttaccaaaaa tgtttattct 145380
aaataaagca tctactgtgg ttctcattta tatagtaagt ataggaatta gagaaacaaa 145440
tgaagtagca ccattatgca tcaatcagac aaatccatga tttgggacat tctctaagtc 145500
aactaatttg gctcttttag aaagtgaaag tcaagagaaa ataaaaatgt aggaggcatg 145560
gcatggtggc tcacacctgt aatcccagca cttagggagg cagaggtggg tggatcactt 145620
aaggccggga gtttcagatc aacctgggca acatagtgag aactcgttct cttaaacaac 145680
aacaacaata aactcttgcc agcagaggtg tgctattaaa aaaaaaaaag taagagaact 145740
atcttgatta aaaatgattt cagagaaata atctttattg caatatgaga atttttcttt 145800
gaatactgaa gttgttttta aagatataaa atttattttg atgaaaattg aggaaacttt 145860
aatatggact gaattagatg acatgaaatt attattaatt tttaacaatt gtgataatgg 145920
tattgtactt atgtagaagc atgcccttat taggatatgt gtgctgaatg taggctttaa 145980
ttgctgcaaa agtcttcctc atgtaaagtc aaaatttttt aggtactaac tattggtctt 146040
cgttccgcca actggagtta aaagcatcag ttgatactgt cacaagaaaa ttatcttctt 146100
tgtattagta aaataattaa aattaaaatg tatatataca aggcagagaa ttacaaaatt 146160
tgggtatcaa tactactata ttaattttat gctactatag tatatgccct tttagatgtt 146220
taatatctgc taacagatat gtttaggtag aaatgatgta tatcaggtat ttctcaccat 146280
ttagatgcca tgaagttgct gtgaattaaa taaacatttg tttggtaaac tgcagtaacc 146340
tattttaaag tgttctttaa aaggtatgta taggccaggc gtgatggctc acacctataa 146400
tcccagcact ttgggaggct gaggtgggca gatgacgagg tcaggagatt gagaccatcc 146460
tggctaacac agtgaaactg cgtctctatt aaaaatacaa aaaattagct gggcgtggtg 146520
gtgggtgcct gtagtcctag ctactcggga ggctgaggca ggagaatggt gtgaacccag 146580
caggcggagc ttgcagtgag ctgagaccgc accactgccc tccagcctgg gcgacagaac 146640
aagactccgt cttaaaaaaa aaaggtatgt atatatacat acatgcacag acacatatat 146700
atttgtgtat ctttttaag attatatcta ttttatatga tgattatata ttatgtgata 146760
tattattata caataatata ttctataaaa ctatttttc ttcaatttat taaaatatta 146820
ttttcatgta atcctggcac tttggcaagc tgaggtggaa ggattgcttc agctcaggag 146880
tttgagacca gcctaggaaa cataaaaccc aactcataaa aattaaaaat atgtatactt 146940
ttcggtttta tacttgacag gctttacaag aatttcaagg agatataaaa ataatgcaaa 147000
ttgtctggaa gaactcgcct ctcctctcct tactccaccc tgctattggg aaaaagatta 147060
actgatggtg agtggtgagt ctataatacc atcactccat gttcctggat gttaaaagtc 147120
actcacacat gtgacttctg tctttacaac acatgaagta ggtaaggcca gaattctgct 147180
tccagctaac tgggagaggt agtctgttcc caaagactta aaatatcctc aggtcaggag 147240
tttcaaagtc tacacttaga gggaagaacc aggaagtccg taaagtcata ggtttcaacc 147300
gcatccttca atttagtatt tctaacaaca atgctggtat tttgatatcc atctctttaa 147360
tacctgcttc tatttccaac ttgtttagaa cttgaagagg gagataaggt ttaattttgt 147420
gccttcccca agcccagcat ttagggatgc agagatatta tgtattttaa gcatgtgctg 147480
tagtagccaa tgggaatcca gaatgttgtt gtttatttgc attttaattt actacagaat 147540
tgttgatttt aggccctttg atccaatgct aatttaaatc attttcaata gaacattgtt 147600
tatttccctt catgctttat aactctaaat aataaaaaat accatctttc actttaaagt 147660
ccatattctc caggcattat ttttgagctt cacataggct tagaagaaaa actgatcaac 147720
agtagtgatg tggtggttgt ggaagcagtt gcatagctta gatagctcag gttttaaatc 147780
tcacctttgc cttatgttaa ctgtgtgaac aggttaaaat tactttgatc tctctacacc 147840
tgtttccttg tatgtaaaat gagagtaaca aaagagtagc tgggaagatt agtgagctaa 147900
gacatgcaca gtgattacca tgtctcctgc catatacgcc tcaaaaattt agctcttatt 147960
atacttgttt ggttcatagt aggtgaagtg tttggtagaa aaattgggaa ttcattcctt 148020
tcttgattag agtgaatgac aatccatttg cagaaagctg cagaaagacc gctccagaaa 148080
tagaatgagg caaccgctct ggagaattga aaactaacgg gagctacgct ccacaaaaga 148140
taaggaaata aaaatgccag gaacaatatt ctgagaagaa gggaaaacaa aagaacagaa 148200
aaattatcag ttatatagcg gggaaaaatc tgaaaggaaa aaatctcaag agaaggggac 148260
taaagaagta taaagctgat tattctatat tgatcgaccc atcaatgtgc taatcaagca 148320
gtaagcagaa ggttgcagga tggaagtatg gattcttcct gaccattcgt tacgcagtag 148380
atgctttctc tacttaatga caacagcaat aggcaactgg aaaatgtcac ttagccagca 148440
tgtccaaatc catcttcctt gactttcctg gtgaaaccac atattttatt ctagatatca 148500
ggttgaccat agaggtaaga catgcagtgc tttggagttt gtattttctt tttttttccc 148560
tttctttttt tattttttat tttttttatt ttttgagact gagtcttgct ctgtcgccca 148620
ggctggagtg cagtggcacg atctcggctc actgcaagct ccgcctgctg ggttcacgcc 148680
attctcctgc ctcagcctcc cgggtagctg ggactacagg cgcccgccac cacgcccggc 148740
taattttttg tatatttagt agagacgggg tttcaccgtg ttagccagga tggtcttgat 148800
ctcctgacct catgatccgc ccaccttggc ttcccaaagt gctgggatta caggcgtgag 148860
ccaccgcgcc cggcctggag tttgtatttt cttaattctt ttggttggta ctttgcagat 148920
ttggggagca acaattggtg agaaaaacaa tagtattaac atatgtgaaa attcagctgc 148980
taccttttt atgtaaaaat aattcagctt ttcaattata tgctttcagg tataatctgt 149040
tgtttctata gcatcattag tggcagtatt taaaagtctc taagcctgac agttcacttc 149100
gacagatgca aagaacaata agcactgatt ttcaataagc taataagaag tagtttaaga 149160
aataaattgg cttaatttga gtttacaata atctaaaatt ttgcaaagat ttatttattt 149220
acatatcaca gtgtgctttt gaattagatg tttcttagac taatatgctt attttcagag 149280
gattacaagg atgcagtaga cagcattcca tttgatgtac atagctgcga atacatttaa 149340
cattgaaagt ttcaagcact ttcttttaga atttggattt ttcatttcag tctttctagc 149400
aagataactt agagatatgt atgagatata aagtaaatga caaaatagaa tgctatatgg 149460
aggaaaattt gatgaaaata taattgattg agagattttt gttgaacaaa tgaaaccaac 149520
gattttttcc ccatcagaaa ctaattgcat ttctttctta tttccttgga gacacatgtg 149580
gaataaaatg taataaatac tgtacttgtg tgtttactta ccagaatgtt ctcttcagaa 149640
aaagtaatga taccctttca ttgacatcat ccaagtgata atatactttt gtttctgtca 149700
ttggagtaat aataaccttt caaccacatc actgcacagt gcttctttct tttattgtac 149760
ataatgcata aaaataaaga gggtatatta tttcttaagg aaataggttg ttatttaaat 149820
aaattccaag catcagaaaa ctacagttct tgctgatgtg tactaaaatt tctatagata 149880
cttataactt tgtatagaaa tttaatttta atattctttc aattgtcaca tcatacttaa 149940
gtacggatct ccactatttc acatctcaaa aatatgactt aaaaccagtt atagttgttt 150000
ataccccgat gataagggat tagaattttt ttttgccaaa tactccttag gctaagtttc 150060
aaagtctggt ttgtataaaa tattactagc agataaatag tttgttaata aaacatccaa 150120
gcttgtgctg atgggtgaat ttgctataat gtaataaagg ctgacactac tcatagtgag 150180
aatttaacct tttcctcaga ataccttatt catttaaatg aactcacagg tttaatgtaa 150240
aatatttcat atatatttga tacgatcctg tacaaattgt ttcctagcat aataaattga 150300
atacagtgtg aaataaattg tgactttgtt ttttttactt agtatctcaa gtttgaagaa 150360
tataagttct ttatgttttt gcttaagttt gatttacttt atcattaatc ataataatag 150420
gatttgtgct ggatgatgga aatccaaacg gtgttactca gtataataag aaaagtgaac 150480
tacatatgga atgtttaaaa taaagaacta atcttaaacc aatcagattg tttcatgatg 150540
cagacaggaa tctcaggaaa taggcttagt ggaatttttct ggcaattaag tataaaattt 150600
tacatgcttt aagtaaatat ttcttaaaca agtgtctatt tctggtctca ttccactctc 150660
caaagagttt catctgagct taataatgtt ggtttgaagg catacttgca aatagagggc 150720
agaaatgtta actctatttc cagatttcta ctattgcaaa cagtctctaa gttaaagcca 150780
aagttgtttt ctattttatt ggagcaaggg aagcctgatt aaagcttttt ttagaataca 150840
tattcactca gcagagcaag aaaacaacct caagactgac atagctgttc taaaagtcat 150900
cttttggttt tattgttgga aagagggatt gctcatcaaa tcactgataa taagaatgct 150960
tagatgacgc tgttatgtag ttgatgttac ttagcatgcc aagtctcttt ctgtacatat 151020
taaaagtgat acgttgttct cagccaagac taataaattt ttttctggta acagctttat 151080
tgagatataa ttcacaaacc atacaattca cccactgaaa ttgtacagtt cgatggtttt 151140
tactatattc acagttaatg caaccatcac tgcaatcaat tttaggacat tttcgtcact 151200
ccaaaaagaa atctcgtatc tattagcaat cgctccttat ttcctcctaa ccacccctca 151260
cccaacctct cagctctagg caaccactaa tttactttct gtctgtatat atttgctatt 151320
gtagacattt aatataattg aaattatata gtatgtggtc tttcgtgact agcttctttc 151380
acttgtcata gtgttttcaa agctcatcca tgttgtagta tatatcagta gtatatcaat 151440
gtgttttatt gacaagtgat attccatcat gtgtatatac cacattttat ttagctcttc 151500
atcagttaaa ggacatttgg gttgtttcca ccctttggct attatgaata atgtcgctat 151560
gaacatttgt gtacacattt ttgagtggac atatgttttc acttctcttt ggtatatgcc 151620
aaggagtgga attgctggat tatatagtaa ctctatgatt acccctctga ggaactgctg 151680
gacagttttg caaagaggtt gtgccatttt tcattcccat aagtgttata tggggattcc 151740
attttctaca tgtcatcacc aacacttgat attatctgtc tttttttttat tatggccata 151800 ctgatggggg tgaagtagta tttcattgtg gttttgcctt acgtttcctt aatgatgttg 151860
acattcatct tttagtgctt tattggctgt tcgaatatct tctaagataa atgtctattc 151920
agatcctttg cctatctaaa aaattgtgtt gtctttttat tgttataata agagatcttt 151980
aaatattctt ttatcaattt tgctttgtgt ggtttactaa ggtaaaaacc ttgggtgtgc 152040
aattaataca ttcaattgtt agcaaaatta ttaaaacaat aacttataat ttttggtcca 152100
cctgaaatag ggaaactaat ttgactcaac ttttctttca attgttgtgg agtctggttg 152160
actgccaaat tttgtaaatt ttaatatttt acccagtaaa aagcttatta aataatagga 152220
tatactgatt agaggttact ttcaagaaat taaatatttt tgtgtcttca gaaagagttc 152280
tccttttgga aagatactat atggataaag aagtaaattt taagtacata tttttttaaa 152340
gtgcatcagt tattatttaa aggaacattt aaattttagc atttgagcag ctatctttcc 152400
tccttcaaag ttttctcatt atcctttcct tgtacgtatt attatttata ggctgcaaat 152460
gaaacctaaa agaacataaa tggttttcta tttcaacaaa agcaatcacc tccacgtctc 152520
actttcttat ctttaattaa ataagtaaga taaaaagtaa aaatcatggt tgccccttttg 152580 gttttgctgg tctgacccat tatcccagca cattgtggta gagatataat aagcctgctt 152640
tgcctagaag atcacttagg aacaaccaag gcttggggaa gaaatcagtt gccactaaaa 152700
tgtcaaagta tcaagtattt ctgcatgtgt aactagagga aaaggagaga agacagcagt 152760
gcttctgatg aggcccaaga tctctggcat ttgaaagaaa ggtgaaagct gttgatggtc 152820
actttctttg ggtctctttc cttgggtcag gattgtacat gaaagtcgct ttagatacat 152880
tggccagaaa gaatgtgtgt agcctaacac aaacgtgacc tactttttac gaaaggaaga 152940
aattcttggg aggtataact gaaaattatc gtcccaattt acaaactcac tggacagtat 153000
gaatttctct tagggctcct aatctatttc agtcagacag taagtcttcg ccatgaaaac 153060
aaaacgaaat ggactataaa actgaacagg ctgggcttag ttatagatct gattgtttgg 153120
ctatgtgcag ggaaccagca tttaaaaaat aattccagct ttaatctgaa ataaagcaaa 153180
gtctgaatgt atggcatagc ttagtgaaaa aataagctca taaatgtcta taaatgcatt 153240
tataaatata tttaaaaatt tttaaagcag atgcaattct ttgtcacaaa tacggatgtg 153300
attctaaata tcagcaagtt tctgctaaca aaaagatgca aatgaaagtc atgatccaaa 153360
acctgggcat agtaataatt ctggtatctg gtttgagttt tagctccttt cttagctgtc 153420
agcaaaatca tcctctgaac ttctcactct tatgcctgcc cgtctttatt ttaactcata 153480
gacaagcagt tggaattttg ccatttaaca gccaagccct gtggcaggat aataagtaac 153540
agtccactaa catgaatgca gagaaaagca tatgttaggc caggagggat gaaaattgtc 153600
cacatagaag aaaaaataga aaaagcaaga cagaaagaaa aagataaata aaaccttaag 153660
ggcaagaatt ttctgtttac aaatatgctc tcctttagcc tagcttttac aagtgggtga 153720
ctgcattttg cagtcttagt aaatcacgac tgcttaacca tgcatttaaa gctattaaat 153780
taagttacca acagccaatc ccccaaaact tatatgcatg aaaagacata aaaataaaat 153840
aaaacaataa agaaaatttc ttatttaaaa tttaatgttg atatgattaa aaacatatat 153900
caacatctta aaagcaatca gacttcataa tcaaggagta ggcatgttat aataaaaaca 153960
agctctagtt tcatttctgg tgcaggttta atttattatt attttttaa aagctgaaaa 154020 tggtaggagg tgattcattt gtttggattg aggactacat ctggttcaga gttaatagtc 154080
atctaaaagt aaagtatcat ttgagaaggc ttaggggtat gccggaagtt ttaactttta 154140
catcatttgc taatgtgcta gttatctgga agctattaaa ttagaatatc tgattttgct 154200
gagattaaaa agaaatatta gacccatagt taatttttg tgcagaacgc ttccattata 154260
ttctgccaag ttttaaacat ccaatgtaac agcctgtttt tgttttttt gctttaggaa 154320 atgttcttca atttgccata taggaaatta aaaagtataa catttgaagt aggataatgt 154380
tctgagctta tgttttacaa agctttgaac attaaaactg ttcatggttt aaataatttc 154440
atggttaata tttgtgatgt ataaattcac tggtttcctc tactatggca tgttaaattc 154500
caggtaacct atatctgaag aagaattagt tgtaacaaag attttttttt taatctttct 154560
cgaatgggaa gatccatata gtataggaaa ttgtgagaat actaatgaat tactcagaaa 154620
taaactaaaa ttgtgaaaaa agtaaagaag ttagagatga gagaatgtca tgaccaacga 154680
tggatttaga cttaattgcg tatttggcac attgaagtct aagtccattg ttggtcattt 154740
ataaattttt agactgcagt ttttaatatt tggttttctc ttcattttcc tttcctaaaa 154800
ttatttcctc ttcttccttt tcatctcttc ttttattcct tgtttcccag tgaaattatt 154860
ttctagcaca gcaagacatg gttccactct gaggcgaatt ttaagatgcc gatgttattc 154920
tatttggttt tgcaagctca gggcacacat atacgagtgt gtggagtgtg tgtacgtatc 154980
aaagaagttt ttattctaag aaaattttga atataagttt gaatttatta cttttctctt 155040
ttgcctagta tgttatacaa attctacata gttttagagc caaattacag caatcagttc 155100
acaatccctg tgatcatatt attttcttaa aatttcttgt ttatttgaaa tgactatatt 155160
gacttatttt agctgaaata tagtcacaaa cagatcctct tgtaatgctt ttctcaagat 155220
tccagctgag aaactgcaaa tatgaaaata ccacaactga tttcttcaac tacttattaa 155280
atatcatctt aagttacagt tcaagatcaa cttctttggg acaagcaact atttacttat 155340
gtatgagatt tttaaaaata tcgcttatga ttgttttggt gtatgaagga tcctgtcacc 155400
caggtagtaa gcatagtatc caaccaaagc tcaggaacat gcagtttacc catgtaacaa 155460
acctgcacat gtacccctg aactccaaag tcgaaaaata aaattaagtc ttccaatagc 155520
ttgttcttta aaaaaaagat tgtttttaaa ttttggaaat aattttctat tgcaacagta 155580
ttaaaagaat gggacttggt ccaagaataa ctcccaaact ggttgtttat ctcataataa 155640
agctgaattg tggaaatcta gaacctaact tcaatacatt gttttccgag aaaaaaaatg 155700
gaacactctt aatttatttc tgatttatca gaattttgct ctccatgtgc aatccaattc 155760
ttacctctgg atgcatgacc tcatagggga aaaaaattgt tcatttctgg ctcgccacaa 155820
tttcatgctc attttaactg agcccttacc agtgcccttc tattttaatt tatctgttgt 155880
tggttctcta acaaaatatc caaaggagta gctgccatga atattttatc tttccaattc 155940
catattccct tccttctcaa cttccatttg tattcctcat caaatgatta ttctccctgt 156000
tgatgtgaaa agatttagga cactttccct cctcctcagc ttgtcaactt gtgatttcct 156060
ttgatttcag agaaagagat gattcttcta taaaaccaac ctatctctct gtccttgacc 156120
cagcttctcc tgtttcataa gagatattac tcttatagat cttcttttct agtctttaca 156180
tacacatttg ttccctcatc cccctctggc tactgtcctc tttcctcttt tcctttagtg 156240
aaaaatgtct tccatgtccc ttgcatctgt atcaccctgg atgtaagttc atttaattgt 156300
tttctctttt tccctttcta cggagattgc cttctcaaaa tcaacttcgt gtcagctcta 156360
gcagtcacat attcactctc agtctggtta attctttagt gcatttcaca acttaaaact 156420
gtttttttct tgacttctgg gaaagcacat tatattgccc cataatactc agattcttct 156480
cttactacca cctaaatgct cagtcttttt catatattcc ttttcactcc tctgtgtgtt 156540
atctctacta aatatgaaat ctcagcgatc tcatctaccc cattactgca actctccctt 156600
ctatgtgaaa aagcccaaaa taataatcat ttcccatttt caaagagctt ttccttggat 156660
acttatattt aatctttaat aagaatttat gaggtagata cattcattac acagactacc 156720
aaattcacat tttcagtttc ctactatttg gtcattctcc ataagtcaac tagatattta 156780
ctgcacttag gcattcactg tggtgtagta atgtatcaaa aattaagtct attgtctttt 156840
tatgtcccat ccagtgtccc ttctcaacct tcctgttggt attaaattgg ccaggctact 156900
ggccaagtct gttagttcaa agtcttaaga gtaagcttca tttcaaacag tagaggcttc 156960
caatgggatg aacttggatt attatctgtt ggtgaccctc cccactgtca actcatcctt 157020
tagaagccca ctcaaatgcc agctccttca agagtcatca ccttatcgca atgctcctag 157080
gaacattttc acaactctgt tcctgtggca ctttttgtct ccatcctgat attgctaaat 157140
agtgtggctc tcagacctcg gggtgttggg tcagacaggc tcgtgctcca gtttttgtgc 157200
tgccacttac gaggtggatg acttgttgca agtcaccttt ttaaagcttc gtttttccat 157260
attggtacac agtgttcatg atcataatgc ctagtttgtg ggatgtttaa aaagattaca 157320
tcagataatc atacgcggaa ctggaacata ctaaatgctc aaaaaattgt tagctaactc 157380
actttctata atgtaatatt ctgaacacat gcagaacctg acttttaaga tccagttcct 157440
agttttgtgc ctgaggcttt acaatgctgt gatgctgtga tctggtcatg acttagaata 157500
ctttgattat ctctgctata caatggaatg tattataatt taaataagta tttgtggggc 157560
tggatgctat ggctcatgcc tgtaatccca gcattttggg aggctgaggc ggatggatca 157620
cttgagatca ggaattcgag accagcctgg ccaacatggc gaaaccctgt ctctactaaa 157680
aatacaaaat taagctgggt gttgtggcat gtgcctgtaa tcccagctac tcaggagagt 157740
gaggcaggag aatcacttga acccaggagg cagaggttgc agtgacccaa gatcgcacca 157800
ttgcattcta gcctgggtaa cagaaaggga ctccatctta aaaaaaaaaa aaaaaaaaaa 157860
aaaaaaaaag tatttgtggg atagatggaa aaatttctat aaagatgttc ataaactatt 157920
cttgctaaat tgtaaacaat gattaaaatc aagcatttga acagcagaat ctgattttgt 157980
acatctttgc attttgtata ttacatgagc aaaaccaggg tggattatat ttaaaaattt 158040
tagttatttg ttgattgaat ttactttgat gtcaatcctc catttcttat atatatgcac 158100
tttccaaatc ctattgatca aaaaaatgaa aaatctcatc ttcattaccc tgtaacccaa 158160
agccactcct ctaatcagac cccaactccc tttaagaata accataagtg tctcctactt 158220
ggccctcata cctccagctt ttaactctat taatccattt attacaatga tatacaatag 158280
ataatcttct gtaaacactc atttgaccat gcccttccct tgtttaagaa cttgcaatga 158340
cttgcttttt cctagcacag caaagctaaa tttctccctt gaattttaaa atcctccatc 158400
tgtttctact cttcctatgc aatattattt tccattattc cttaacaagc ttccaccatc 158460
ctactgagac aggtatattt tttgtctcta gtaaactagg ccctgaagat aaaaatttgc 158520
ataaaatatt cagtagcatg ttccttattt tgctctcacc ttctatgctt ttacacatgc 158580
tatttaagtc tcctggaatg ccttctccta aactccatga cccaatacac atttttttctc 158640 ccctgtcaac tatttcttca tgaatctccc ccctcttaat gttgttacat agtctctaaa 158700
aataatctaa aatagatgat ttagtcatgt ggaataagat tcagaaggta tcccaggcca 158760
tgtagttaaa gtctcttaac ctcagcaaca cgcctgccag attccctcct tctctgagag 158820
atgttctcta tataaacaaa tattatatat attcttccct tatttctctt tcgcccctct 158880
ttttaataca aatgatggag ggagtatcga agctgtccct aaagaggtca caattaagca 158940
gaaacctgaa agaaatgatt gagcatatca ggtaaggatc 158980

<210> SEQ ID NO 33
<211> LENGTH: 405
<212> TYPE: DNA
<213> ORGANISM: Human

<400> SEQUENCE: 33
cttgttgcta ttttagaagg tgtccagtgt gaggtacagc tggtggagtc tgggggaggc 60
ttggtccagc cggggggggtc cctgagactc tcctgtgcag cctcgggatt cgtttttaat 120
gtgtattgga tgagttgggt ccgccaggct ccagggaagg ggctggagtg ggtggccaat 180
ataaatcaag atggaagtca gaaatggtat ctggactctg tgaagggccg attcagtatc 240
tccagagaca acgccaagga ctcactttat ctgcaaatac acagcctgag agccgaggac 300
acggctctat attactgtgc gagaggagat tactacgact atagtggtaa ttacattgat 360
gcttttgatg cctggggcca agggacaatg gtcaccgtct cttca 405

<210> SEQ ID NO 34
<211> LENGTH: 1749

<212> TYPE: DNA
<213> ORGANISM: Human

<400> SEQUENCE: 34
gatttgctct gccagcagct gtcggtgccg cgctcgacac cgagtcctag ctaggcgctc 60
acagaatacg cgctccctcc ctcccccttc tctgtccccc gcctctcgct caccccggcc 120
cactccagcg gcgactttga gggattccct ctctggcggc ctctgcagca gcacagccgg 180
cctcattcgg ggcactgcga gtatggatct ccaaggaaga ggggtcccca gcatcgacag 240
acttcgagtt ctcctgatgt tgttccatac aatggctcaa atcatggcag aacaagaagt 300
ggaaaatctc tcaggccttt ccactaaccc tgaaaaagat atatttgtgg tgcgggaaaa 360
tgggacgacg tgtctcatgg cagagtttgc agccaaattt attgtacctt atgatgtgtg 420
ggccagcaac tacgtagatc tgatcacaga acaggccgat atcgcattga cccggggagc 480
tgaggtgaag ggccgctgtg gccacagcca gtcggagctg caagtgttct gggtggatcg 540
cgcatatgca ctcaaaatgc tctttgtaaa ggaaagccac aacatgtcca agggacctga 600
ggcgacttgg aggctgagca aagtgcagtt tgtctacgac tcctcggaga aaacccactt 660
caaagacgca gtcagtgctg ggaagcacac agccaactcg caccacctct ctgccttggt 720
cacccccgct gggaagtcct atgagtgtca agctcaacaa accatttcac tggcctctag 780
tgatccgcag aagacggtca ccatgatcct gtctgcggtc cacatccaac cttttgacat 840
tatctcagat tttgtcttca gtgaagagca taaatgccca gtggatgagc gggagcaact 900
ggaagaaacc ttgcccctga ttttggggct catcttgggc ctcgtcatca tggtaacact 960
cgcgatttac cacgtccacc acaaaatgac tgccaaccag gtgcagatcc ctcgggacag 1020
atcccagtat aagcacatgg gctagaggcc gttaggcagg caccccctat tcctgctccc 1080
ccaactggat caggtagaac aacaaaagca cttttccatc ttgtacacga gatacaccaa 1140
catagctaca atcaaacagg cctgggtatc tgaggcttgc ttggcttgtg tccatgctta 1200
aacccacgga agggggagac tctttcggat ttgtagggtg aaatggcaat tattctctcc 1260
atgctgggga ggaggggagg agggtctcag acagctttcg tgctcatggt ggcttggctt 1320
tgactctcca aagagcaata aatgccactt ggagctgtat ctggccccaa agtttaggga 1380
ttgaaaacat gcttctttga ggaggaaacc cctttaggtt cagaagaata tggggtgctt 1440
tgctcccttg gacacagctg gcttatccta tacagttgtc aatgcacaca gaatacaacc 1500
tcatgctccc tgcagcaaga cccctgaaag tgattcatgc ttctggctgg cattctgcat 1560
gtttagtgat tgtcttggga atgtttcact gctacccgca tccagcgact gcagcaccag 1620
aaaacgacta atgtaactat gcagagttgt ttggacttct tcctgtgcca ggtccaagtc 1680
gggggacctg aagaatcaat ctgtgtgagt ctgtttttca aaatgaaata aaacacacta 1740
ttctctggc 1749

<210> SEQ ID NO 35
<211> LENGTH: 2320
<212> TYPE: DNA
<213> ORGANISM: Human

<400> SEQUENCE: 35
ctcagctgca gttctctgat ggcttgcaca gggtggacca gcccccttcc tctatgtgtg 60
tgtctgctgc tgacctgtgg ctttgccgag gcagggaagc tactggtagt gcccatggat 120
gggagccact ggttcaccat gaggtcggtg gtggagaaac tcattctcag ggggcatgag 180
gtggttgtag tcatgccaga ggtgagttgg caactgggaa gatcactgaa ttgcacagtg 240
aagacttatt caacttcata taccctggag gatctggacc gggagttcaa ggcttttgcc 300
catgctcaat ggaaagcaca agtacgaagt atatattctc tattaatggg ttcatacaat 360
gacatttttg acttattttt ttcaaattgc aggagtttgt ttaaagacaa aaaattagta 420
gaatacttaa aggagagttc ttttgatgca gtgtttctcg atccttttga taactgtggc 480
ttaattgttg ccaaatattt ctccctcccc tccgtggtct tcgccagggg aatactttgc 540
cactatcttg aagaaggtgc acagtgccct gctcctcttt cctatgtccc cagaattctc 600
ttagggttct cagatgccat gactttcaag gagagagtac ggaaccacat catgcacttg 660
gaggaacatt tattatgcca ccgttttttc aaaaatgccc tagaaatagc ctctgaaatt 720
ctccaaacac ctgttacgga gtatgatctc tacagccaca catcaatttg gttgttgcga 780
acggactttg ttttggacta tcccaaaccc gtgatgccca acatgatctt cattggtggt 840
atcaactgcc atcagggaaa gccgttgcct atggaatttg aagcctacat taatgcttct 900
ggagaacatg gaattgtggt tttctctttg ggatcaatgg tctcagaaat tccagagaag 960
aaagctatgg caattgctga tgctttgggc aaaatccctc agacagtcct gtggcggtac 1020
actggaaccc gaccatcgaa tcttgcgaac aacacgatac ttgttaagtg gctaccccaa 1080
aacgatctgc ttggtcaccc gatgacccgt gcctttatca cccatgctgg ttcccatggt 1140
gtttatgaaa gcatatgcaa tggcgttccc atggtgatga tgcccttgtt tggtgatcag 1200
atggacaatg caaagcgcat ggagactaag ggagctggag tgaccctgaa tgttctggaa 1260
atgacttctg aagatttaga aaatgctcta aaagcagtca tcaatgacaa aagttacaag 1320
gagaacatca tgcgcctctc cagccttcac aaggaccgcc cggtggagcc gctggacctg 1380
gccgtgttct gggtggagtt tgtgatgagg cacaagggcg cgccacacct gcgccccgca 1440
gcccacgacc tcacctggta ccagtaccat tccttggacg tgattggttt cctcttggcc 1500
gtcgtgctga cagtggcctt catcaccttt aaatgttgtg cttatggcta ccggaaatgc 1560
ttggggaaaa aagggcgagt taagaaagcc cacaaatcca agacccattg agaagtgggt 1620
gggaaataag gtaaaatttt gaaccattcc ctagtcattt ccaaacttga aaacagaatc 1680
agtgttaaat tcattttatt cttattaagg aaatactttg cataaattaa tcagccccag 1740
agtgctttaa aaaattctct taaataaaaa taatagactc gctagtcagt aaagatattt 1800
gaatatgtat cgtgcccccct ccggtgtctt tgatcaggat gacatgtgcc atttttcaga 1860
ggacgtgcag acaggctggc attctagatt actttttctta ctctgaaaca tggcctgttt 1920
gggagtgcgg gattcaaagg tggtcccacc gctgccccta ctgcaaatgg cagttttaat 1980
cttatctttt ggcttctgca gatggttgca attgatcctt aaccaataat ggtcagtcct 2040
catctctgtc ctgcttcata ggtgccacct tgtgtgttta aagaagggaa gctttgtacc 2100
tttagagtgt aggtgaaatg aatgaatggc ttggagtgca ctgagaacag catatgattt 2160
cttgctttgg ggaaaaagaa tgatgctatg aaattggtgg gtggtgtatt tgagaagata 2220
atcattgctt atgtcaaatg gagctgaatt tgataaaaac ccaaaataca gctatgaagt 2280
gctgggcaag tttacttttt ttctgatgtt tcctacaact 2320

<210> SEQ ID NO 36
<211> LENGTH: 2722
<212> TYPE: DNA
<213> ORGANISM: Human

<400> SEQUENCE: 36
catagagcca gcgggcgcgg gcgggacggg cgccccgcgg ccggacccag ccagggcacc 60
acgctgcccg gccctgcgcc gccaggcact tctttccggg gctcctaggg acgccagaag 120
gaagtcaacc tctgctgctt ctccttggcc tgcgttggac cttccttttt ttgttgtttt 180
tttttgtttt tccccttttct tcctttttgaa ttaactggct tcttggctgg atgttttcaa 240
cttctttcct ggctgcgaac ttttccccaa ttgttttcct tttacaacag ggggagaaag 300
tgctctgtgg tccgaggcga gccgtgaagt tgcgtgtgcg tggcagtgtg cgtggcagga 360
tgtgcgtgcg tgtgtaaccc gagccgcccg atctgtttcg atctgcgccg cggagccctc 420
cctcaaggcc cgctccacct gctgcggtta cgcggcgctc gtgggtgttc gtgcctcgga 480
gcagctaacc ggcgggtgct gggcgacggt ggaggagtat cgtctcgctg ctgcccgagt 540
cagggctgag tcacccagct gatgtagaca gtggctgcct tccgaagagt gcgtgtttgc 600
atgtgtgtga ctctgcggct gctcaactcc caacaaacca gaggaccagc cacaaactta 660
accaacatcc ccaaacccga gttcacagat gtgggagagc tgtagaaccc tgagtgtcat 720
cgactgggcc ttcttatgat tgttgtttta agattagctg aagatctctg aaacgctgaa 780
ttttctgcac tgagcgtttt gacagaattc attgagagaa cagagaacat gacaagtact 840
tctagctcag cactgctcca actactgaag ctgattttca aggctactta aaaaaatctg 900
cagcgtacat taatggattt ctgttgtgtt taaattctcc acagattgta ttgtaaatat 960
tttatgaagt agagcatatg tatatattta tatatacgtg cacatacatt agtagcacta 1020
cctttggaag tctcagctct tgcttttcgg gactgaagcc agttttgcat gataaaagtg 1080
gccttgttac gggagataat tgtgttctgt tgggacttta gacaaaactc acctgcaaaa 1140
aactgacagg cattaactac tggaacttcc aaataatgtg tttgctgatc gttttactct 1200
tcgcataaat attttaggaa gtgtatgaga attttgcctt caggaacttt tctaacagcc 1260
aaagacagaa cttaacctct gcaagcaaga ttcgtggaag atagtctcca ctttttaatg 1320
cactaagcaa tcggttgcta ggagcccatc ctgggtcaga ggccgatccg cagaaccaga 1380
acgttttccc ctcctggact gttagtaact tagtctccct cctcccctaa ccacccccgc 1440
cccccccccac cccccgcagt aataaaggcc cctgaacgtg tatgttggtc tcccgggagc 1500
tgcttgctga agatccgcgc ccctgtcgcc gtctggtagg agctgtttgc agggtcctaa 1560
ctcaatcggc ttgttgtgat gcgtatcccc gtagatgcca gcacgagccg ccgcttcacg 1620
ccgccttcca ccgcgctgag cccaggcaag atgagcgagg cgttgccgct gggcgccccg 1680
gacgccggcg ctgccctggc cggcaagctg aggagcggcg accgcagcat ggtggaggtg 1740
ctggccgacc acccgggcga gctggtgcgc accgacagcc ccaacttcct ctgctccgtg 1800
ctgcctacgc actggcgctg caacaagacc ctgcccatcg ctttcaaggt ggtggcccta 1860
ggggatgttc cagatggcac tctggtcact gtgatggctg gcaatgatga aaactactcg 1920
gctgagctga gaaatgctac cgcagccatg aagaaccagg ttgcaagatt taatgacctc 1980
aggtttgtcg gtcgaagtgg aagagggaaa agcttcactc tgaccatcac tgtcttcaca 2040
aacccaccgc aagtcgccac ctaccacaga gccatcaaaa tcacagtgga tgggccccga 2100
gaacctcgaa gacatcggca gaaactagat gatcagacca agcccgggag cttgtccttt 2160
tccgagcggc tcagtgaact ggagcagctg cggcgcacag ccatgagggt cagcccacac 2220
cacccagccc ccacgcccaa ccctcgtgcc tccctgaacc actccactgc ctttaaccct 2280
cagcctcaga gtcagatgca ggaggaagac acagcaccct ggagatgtta aggcagaagt 2340
cagttcttct gtccatccct ctccccagcc aggatagagc tatcttttcc atctcatcct 2400
cagaagagac tcagaagaaa gatgacagcc ctcagaatgc acgttatgag gaaggcagaa 2460
tgtgggtctg taattcctcc gtgtcccttc tccccctctg caaaccgtcg taacaataat 2520
agttcctaac acatgggaca attgtgagga ttaaatgagt tagcctgcag aaatcacttg 2580
atgcacagca catgggaagc attgtgtgta tttattaatc cttcacaaag tctttgagat 2640
atatttttat caaatattta gcatggatcc cggtacactt tcaatactta ataaatggtc 2700
aatgttattc tttttcacta tt 2722

<210> SEQ ID NO 37
<211> LENGTH: 631
<212> TYPE: DNA
<213> ORGANISM: Human
<220> FEATURE:
<221> NAME/KEY: misc_feature
<222> LOCATION: (519)..(519)
<223> OTHER INFORMATION: any kind of base
<220> FEATURE:
<221> NAME/KEY: misc_feature
<222> LOCATION: (524)..(524)
<223> OTHER INFORMATION: any kind of base
<220> FEATURE:
<221> NAME/KEY: misc_feature
<222> LOCATION: (547)..(547)
<223> OTHER INFORMATION: any kind of base
<220> FEATURE:
<221> NAME/KEY: misc_feature
<222> LOCATION: (592)..(592)
<223> OTHER INFORMATION: any kind of base
<220> FEATURE:
<221> NAME/KEY: misc_feature
<222> LOCATION: (600)..(600)
<223> OTHER INFORMATION: any kind of base

<400> SEQUENCE: 37
ttattctcta ccttgttcca catctggcat tttttgtgca tcttccaact taagtacaca 60
gcagcaagtg ctctacatct ttgggtagct acacagaacc ccactgtggc tcactgtgga 120
cacaccattg aaaaccttgt atgtaggtca cttagtacaa ggaggaacac aactgttgaa 180
gaagtaccta aaaattgaat tacttgaaca aagtgtggga catttgctgt tttgatggat 240
tttaccacac tgtcttccca tttatgctta ccagcaatac ataggaacac ttgggtccct 300
gcagtcaggg tgtggaaatg gcagatgagt tcagccctaa ggtgcatttt tcttactagg 360
aggagatgga gtgtatttta tgggatataa gcattagcta catttcctgt cctgttcaca 420
tcctttgccc atgtgtctat gaggttattg atctttctta ctgatttatt ggtagctctt 480
acttaagagg taattagcct tttgcctgtg gagagtttnt tgtnttgcca tttgtccttt 540
tttaatnttt tttggttatt ggcccatttg tcttttggac tctgatgtgg tnttgctgan 600
ttcctttgat gtattctagt tatctgactt t 631

<210> SEQ ID NO 38
<211> LENGTH: 1761
<212> TYPE: DNA
<213> ORGANISM: Human

<400> SEQUENCE: 38
gtttagagta ctaggttatt tatgttttac aaagtttgaa tcttctataa actaagaaag 60
gggatgatcc ttagatttgc attaaaatat agaagtcttt taaagtaaat gtgaaccttg 120
tctaagtact gtaatccaca caacacatta taagaagcaa accagcatct taaggaatta 180
taaaattacc ctatttaaaa gccatgctat tgttctgcta ttaccagatt tattgtgcca 240
cacaaaagga tcatgtgtgt cagcaggggc cgtttggaac aaacctagtc attaatgagt 300
aagatactcc tgttagttca gggaccaagt tttatgaccc agaggcttaa tgatgtttgg 360
atatatttca aatcggcgtg cttacctcac tgatttaaat tattttctaa atagtggcca 420
ttgtagacct gactcaggct gaagctaaat agagaacaat ttagaaagtt aactaacaat 480
acagtgcatt ctacccgtag gcccaccatg cccttctgcc cctggctgat ttgatcctgt 540
gtctgatccc attgcaccct gactgggcag tccctacaga accagtgtta atttgaaggg 600
cctccactca ggctccaaat gtggcagcca aagagaacaa tccagggaac ctacatttat 660
ttttaaggac aaatatttcc tcctcagtgg tcctaatgtt cagggcttta gagggaaccc 720
aggtggtctc ttcaccctgt gtcctagaat gggagagtaa gtagacagtg gtgataaccc 780
cacactgctt ataagtgcat ctttatagta tttggggctt tcctacccct ttagccttct 840
gtacctagta ccatattcca gttttaaaga actggcagaa tgtgatggat aacagaggaa 900
gagctcaatt tatgtttatt ggaagaacat tttacttaaa tgatttgagg ggtgggaggg 960
agtgaactac tgagtttgcc agagtgaaaa tccatctgaa aaactcagct acctttagtt 1020
tttagtcctc atttttggtc ttgtctctgc ggactgtgaa gaatcacaat gctctatatg 1080
ccctggactg tgtggcaaat gcaggttgca gcgtgtgtgt tacatgagga tcttccacaa 1140
tttcagaatg cacgccagag ctgaaggggg aaacttggta acttgcccat tattctctgc 1200
ttttagccag agttaaacag actgatgggt ctggtagcca acaacttggc aacttccact 1260
ccttctcacc tcgtgagatt aagggctgtg aaaagaaatc tagtctaact ccaacagaaa 1320
tctgtctctg ttaagtgttt taccttctgt aagtagagat ggtagagcca agatttttct 1380
tttggtaatt tccctgtcta taaagtgaga ccaaagggat atctgttccc tgttaccttt 1440
ttggagaatt cataacattt gaagatcaaa aaattgaatg ataaatatga atggcttttc 1500
aattctgtgg actttgtacc atttggcttc accttgtact gcaagatgaa tttgtaaaca 1560
aaacaaaatt ggactgtctg gaaagctaaa gttctgaaat atggaatgta ctgcctctaa 1620
tttttctttg tcttcctctc actggcattt ttttctctcc caggtttctt aagaataatg 1680
ttttttaaag gaggcttttt gcccatcaag aataaaaaga aataaaacca aagggttacc 1740
ggaaaaaaaa aaaaaaaaaa a 1761

<210> SEQ ID NO 39
<211> LENGTH: 2414
<212> TYPE: DNA
<213> ORGANISM: Human

<400> SEQUENCE: 39
ggggtgaggg cagcagctcg ccacagctgc cagccatctg tccattcacc catctgtcca 60
tctggcagcc cgctgttcag acctgtctgt ctgtccgccc atctctgtaa gcccatctct 120
gtcccattgt ctatctgacc atctttctct tactgtcctc tttgtctagc tatctggcct 180
atctgtcgat ccatcttcgt gtctgtcttc agccccccacc tgtttttgtc catctgtcca 240
attacctgtg actctgtgca tcttcttgtc cattcatctg cccacccatc cgtccctccg 300
tctgcccacc agccgcccct ctcctcctgg gctgcagagc catggcccgg ggctacgggg 360
ccacggtcag cctagtcctg ctgggtctgg ggctggcgct ggctgtcatt gtgctggctg 420
tggtcctctc tcgacaccag gccccatgtg gcccccaggc ctttgcccac gctgctgttg 480
ccgccgactc caaggtctgc tcggatattg gacgagccat cctccagcag cagggctcac 540
ccgtggatgc caccatcgcg gctctggtct gcaccagcgt cgtcaaccct cagagcatgg 600
gcctgggcgg aggggtcatc ttcaccatct acaatgtgac aacagggaag gtggaggtca 660
tcaatgcccg ggagacggtg ccggccagcc acgccccgag cctgctggac cagtgtgcac 720
aggctctgcc actgggcaca ggggcccagt ggatcggggt gcccggggag ctccgtggct 780
atgccgaggc ccaccgccgc catggccgcc tgccctgggc gcagctgttc cagcccacca 840
tcgcgctgct ccgagggggg catgtggtgg cccctgtcct cagccgtttc ctgcacaaca 900
gcatcctgcg gccttccttg caggcgtcaa ccctgcgcca gctcttcttc aacgggacag 960
aacccctgag gcctcaggac ccactcccat ggcctgcact ggccaccacc ctggagaccg 1020
tggccacaga gggcgtggag gtcttctaca cggggaggct gggccagatg ctggtggagg 1080
acattgccaa ggaagggagc cagctgacgc tgcaggacct ggccaagttc cagcccgagg 1140
tggtggatgc cctggaggtg cccctggggg actataccct gtactcacca ccgccgcctg 1200 caggggggtgc cattctcagc tttatcctca acgtgctaag agggttcaac ttctcaacag 1260
agtctatggc caggcctgaa gggagggtga acgtgtacca ccaccttgta gagacgctca 1320
agtttgccag gggggcagagg tggaggctgg gggaccctcg aagccacccg aagctccaga 1380
atgcctcccg ggacctgctg gggggagaccc tggcccagct catccgccaa cagatcgatg 1440
gccgggggga ccaccagctc agccactaca gcttggccga ggcctggggc cacgggacag 1500
gcacgtccca tgtgtctgtg ctgggggagg atggcagcgc cgtggctgcc accagcacca 1560
tcaacacacc ctttggagcg atggtgtatt caccacggac aggcatcatc ctcaacaacg 1620
agctcctgga cttatgcgag cgatgcccct ggggttccgg caccaccccc tcacctgtga 1680
gtggagacag ggtgggtgga gctcccggaa ggtgctggcc cccagttcca ggcgagcgtt 1740
ccccatcctc catggtgccc tccatcttga tcaacaaagc ccaggggtcg aagctagtga 1800
ttggcggggc tggcggggag ctcatcatct ctgctgtggc ccaggccatc atgagcaagc 1860
tgtggcttgg ctttgacctg agagcggcca ttgcagcccc catcctgcat gtcaacagca 1920
agggctgtgt ggagtacgag cccaacttca gccaggaggt gcagagggga ctccaagacc 1980
gtggccagaa ccagacccag aggcccttct tcctgaacgt ggtccaggct gtgtcccagg 2040
agggggcctg tgtgtacgcc gtctcggacc tgaggaagag tggggaggcc gcaggctact 2100
aagacactgc tctgcccaga gctgaagtct ggccccacca tgagtcctgt gtccaggccg 2160
gacatggctg gggaccaac tactctggca ggatctggac ccctggcagg ggagtccagc 2220
tgagagtgga agaggtggcg gggaccagct gggcagatga gaggctgagc ctcatcccta 2280 acccccttc ccagagcccc tggtggtcct gaaccggccc ctctatccct ccgcaggcct 2340
cttacctggg gccactctcc caccctctcg atctgtatat cctccagtcc aagattaaag 2400
aagaggcgga ctgt 2414

<210> SEQ ID NO 40
<211> LENGTH: 2146
<212> TYPE: DNA
<213> ORGANISM: Human

<400> SEQUENCE: 40
cggggacggt gcgccagtgc cccctccgcg agccccaacc agtagacggt tccctgtctc 60
ccgcgcccca atttcgattt tcaaacgcaa ctcctacagg attctgagac cccgtcccat 120
ctcccatatc ccatttccag ctgcaaatta ctgcagaatc tgaacccagg aaagaaaccc 180
atttgccgac cccctcttcc ctctccagac aggtggagag cgggtgaggg tctcgctcgg 240 ctttcccccct gcacctttcc caccctcccg cccgtccctg gggtcctcc gtcaccgcgg 300 ccatggccca gaagccgaag gtggaccccc acgtcgggcg gctgggatac ctgcaggcgc 360
tggtcacgga attccaggag acccaaagcc aagacgccaa ggagcaagtc ctcgccaacc 420

```
tcgccaactt cgcttatgac cccagcaact acgagtatct gcggcagctg caggtcctgg    480

atttatttct cgattcgctg tcggaggaga atgagaccct ggtggagttt gctattggag    540

gcctgtgcaa cctgtgccca gacagggcca acaaggagca catcctgcac gcaggaggtg    600

tcccactcat catcaactgc ctatccagcc ccaatgagga gacggtgctg tctgccatca    660

ccacgctcat gcacctgagc ccgccgggcc gcagctttct cccagagctg accgccacgc    720

ccgtggtgca gtgcatgctt cgcttctccc tctcggccag cgccaggctc cggaacctgg    780

cacagatctt cctggaggac ttctgctccc cccgccaggt ggccgaggcc cgcagccggc    840

aggcgcactc tgccctgggt atcccactgc cgaggagcgt ggccccacgg cagcgctgat    900

ccatggagac tgcgagaccg tggcacccct actgctgggg accacagtcc tgatgtggac    960

gcagggaacg gggagcacat actgccccat tggtgccttt tcagccatct gaaaggcggg   1020

ttctttcagc aggacaggca tttacactga tgaaacgcca ctgggagtga ggaagccaga   1080

ctccagagac acggagaaga tcaaactgga gctgcgttca taggctggca ctctcaatcc   1140

tacatcaggt gccaccacca ccagactcag gccctggtgt aagaagcggc caagtgcctg   1200

gacccagagg ctttgcagga cagtgttctc aggagctggg cctgaggctt aggagagctg   1260

ccttcgctgc aggaaatcag ggattatccc ttaacagaag tgtctggagt agttttcagg   1320

tataggaatg agatgcctcg tggtgaaagg atctcaccct gggaagatgt ggtgcccccct   1380

ccagggctct ggaggatgga tgcctccccc aggggctctc caagctgggc atttgggcct   1440

ggtggatgcc aacctggata acctgtggcc cagcattgac tgtccaccca gccttgctgt   1500

taggcaccat gactccaaga tgaagatgtg gtccctgccc ttgagtgaca gcccagggac   1560

ttaatgtggc catcgggcat caagcacaag gccatgcagg tgatgatacg tcggaataga   1620

ggcaccagcc ctggtaactg catcttctcc ccttgccacc ccatggcccc ggctgaaagc   1680

ttcggccctc ctctgctgtc actcaatgat ggggagccct accccagaag tgtatcccac   1740

gagggcatca gggacgcagt gagtgttgct caagggagtc aggaagagac ggcaacgtaa   1800

aggatgtggc tccatgtcca tggtgccccc tggtcaacat aaggagcgtg ggatccgatg   1860

gaaaggtgga gctcagggaa aatgggggtc cttgcctctc gtgtaccccc tcaaggctga   1920

ccccttagat ggcccaggaa tggcaggtgc tacaaaaatg gtacccacgt gggcatggaa   1980

atggggcaga ttaggggacc actggactca gaggggaggg aagggctcat cagcacccgc   2040

tcagggagcc tgtcccttta tgttcccaaa taaagggtcc tagaagacta gaaagccaag   2100

gtcttttatt aaaggtcccg actggtaaaa aaaaaaaaaa aaaaaa                  2146
```

<210> SEQ ID NO 41
<211> LENGTH: 8789
<212> TYPE: DNA
<213> ORGANISM: Human

<400> SEQUENCE: 41

```
atgtctgaca aaatgtcgag tttcctacat attggagaca tttgttctct gtacgcggag     60

ggatcgacaa atggatttat tagcaccttg ggcctggttg atgatcgttg tgttgtacag    120

ccagaaaccg gggaccttaa caatccacct aagaaattca gagactgcct ctttaagcta    180

tgtcccatga accgctactc tgcccaaaag cagttctgga aagccgctaa gcctggggcc    240

aacagcacca cagacgcagt gctactcaac aaactgcacc acgctgcaga cttggaaaag    300

aagcagaatg agacagaaaa caggaaattg ctggggaccg taatccagta tggcaatgtg    360

atccagctcc tgcatttgaa aagtaataaa tacctaacag tgaataagag gcttcctgct    420
```

-continued

```
ctgttggaga agaatgccat gagagtcaca ttggacgagg ctggaaatga agggtcctgg    480
ttttatattc agccattcta caagctgcga tccattggag acagcgtggt catagtgac     540
aaggtggttc tgaaccccgt caatgctggt cagcccctac atgctagcag ccatcaactg    600
gtagataacc caggctgcaa tgaggtcaat tccgtcaact gcaatacaag ctggaaaata    660
gtccttttca tgaaatggag tgataacaaa gacgacatat taaagggggg tgacgtggtg    720
aggctgtttc atgctgagca ggagaagttt ctcacctgtg acgaacacag gaagaagcag    780
cacgtcttcc tgagaaccac gggccggcag tcggccacat ctgccaccag ttcaaaagcc    840
ctgtgggagg tggaggtggt ccagcatgac ccatgtcggg gcggagcagg gtattggaac    900
agccttttcc gtttcaagca tctggccacg ggcattact  tggcagcaga ggtggaccct    960
gatcaggacg cctctcgaag taggttgcgg aatgcccaag aaaagatggt atactccctg   1020
gtctctgtgc ctgaaggcaa tgacatctcc tccattttcg agctagatcc caccactctg   1080
cgtggaggtg acagccttgt cccaaggaac tcttatgttc ggctcagaca cctatgtact   1140
aatacctggg ttcacagcac aaatattcct attgacaagg aagaagaaaa gcccgtgatg   1200
ctgaaaattg gcacctctcc tgtgaaggag gataaggaag catttgccat agttccggtt   1260
tctcctgctg aagttcggga cctggacttc gccaatgatg ccagcaaggt gctgggctcc   1320
attgctggga agctagagaa gggcaccatc acccagaatg aaaggaggtc tgtaaccaag   1380
ctgctagaag atttggttta cttcgtcact ggtggaacta attctggtca agatgttctc   1440
gaagttgtct tctccaagcc caacagagaa cggcagaaac tgatgagaga acagaatatt   1500
ctcaagcaga tcttcaagtt gttacaagcc ccattcacag actgcggtga tggcccaatg   1560
cttcggctgg aagagctcgg ggaccagcgg cacgctcctt tcagacacat ctgccggctc   1620
tgctacaggg tgctgagaca ctcgcagcaa gactacagga agaaccagga gtatatagcc   1680
aagcagtttg gcttcatgca gaagcagatt ggctatgatg tgttggctga agacactatc   1740
actgccctgc tccacaataa tcggaaactc ctggaaaaac acattaccgc ggcagagatt   1800
gacacatttg tcagcctggt gcgaaagaac agggagccca gattcttaga ttacctctcc   1860
gacctctgtg tctccatgaa caaatcaatt ccagtgaccc aggaactgat atgtaaagct   1920
gtgctgaacc ccaccaacgc tgacatcctg attgagacca aattggttct ttctcgtttt   1980
gaatttgaag gtgtctcttc cactggagag aatgctctgg aggcaggaga agacgaggaa   2040
gaggtgtggc tgttttggag ggacagcaac aaagagattc gcagcaagag tgtgagggaa   2100
ttggctcagg atgctaaaga agggcagaag gaggaccgag acgttctcag ctactacaga   2160
tatcagctga acctctttgc gaggatgtgt ctggaccgcc aatacctggc catcaacgaa   2220
atctcaggcc agctggatgt cgatctcatt ctccgctgca tgtctgacga gaacctgccc   2280
tatgacctca gggcgtcctt ctgccgcctc atgcttcaca tgcatgtgga ccgagatccc   2340
caggaacaag tcacccccgt gaaatatgcc cgcctctggt cggagattcc ctcggagatc   2400
gccattgacg actatgatag tagtggagct tccaaagatg aaattaagga gagatttgct   2460
cagaccatgg agtttgtgga ggagtattta agagatgtgg tttgtcagag gttccctttc   2520
tctgataaag agaagaataa gcttacgttt gaggttgtaa atttagctag gaatctcata   2580
tactttggtt tctacaactt ctctgacctt ctacgattaa ctaagatcct tctggccata   2640
ttggactgtg tacatgtgac aacaatcttc cccattagca agatggcgaa aggagaagag   2700
aataaaggta acaatgatgt ggagaagctg aagagcagta acgtgatgag atctattcat   2760
ggcgtgggag agctgatgac ccaggtggtg ctccggggag gaggcttttt gcccatgact   2820
```

-continued

```
cccatggctg ctgcccctga aggcaatgtg aagcaggcag agcctgagaa ggaggacatc   2880
atggtcatgg acaccaagct gaagatcatt gagatactcc agtttatttt gaatgtgagg   2940
ttggattata ggatctcctg cctcctgtgt atatttaagc gagagtttga tgaaagcaat   3000
tcccagactt cagaaacatc ctccggaaac agcagccaag aagggccaag taatgtacca   3060
ggtgctcttg actttgaaca cattgaagaa caagcagaag gcatctttgg aggaagtgag   3120
gagaacaccc cactggactt ggatgaccac ggcggcagaa cctttctccg tgtcctgctc   3180
cacttgacga tgcatgacta cccacccctg gtgtcagggg ccctgcagct cctcttccgg   3240
cacttcagcc agaggcagga ggtgctccag gccttcaaac aggttcaact gctggttacc   3300
agccaagatg tggacaacta caaacagatc aaacaagact tggatcaact gaggtccatc   3360
gtggaaaagt cagagctttg ggtgtacaaa gggcagggcc ccgatgagac tatggatggt   3420
gcatctggag aaaatgaaca taagaaaacg gaggagggaa ataacaagcc acaaaagcat   3480
gaaagcacca gcagctacaa ctacagagtg gtcaaagaga ttttgattcg gcttagcaaa   3540
ctctgtgttc aagagagtgc ctcagtgaga aagagcagga agcagcaaca gcgtctgctc   3600
cggaacatgg gcgcgcacgc cgtggtgctg gagctgctgc agattcccta tgagaaggcc   3660
gaagatacca agatgcaaga gataatgagg ttggctcatg aatttttgca gaatttctgc   3720
gcaggcaacc agcagaatca agctttgcta cataaacaca taaacctgtt tctcaaccca   3780
gggatcctgg aggcagtaac catgcagcac atcttcatga acaatttcca gctttgcagt   3840
gagatcaacg agagagttgt tcagcacttc gttcactgca tagagactca cggtcggaat   3900
gtccagtata taaagttctt acagacaatt gtcaaggcag aagggaaatt tattaaaaaa   3960
tgccaagaca tggttatggc cgagctggtc aattcgggag aggatgtcct cgtgttctac   4020
aacgacagag cctctttcca gactctgatc cagatgatgc ggtcagaacg ggatcggatg   4080
gatgagaaca gccctctcat gtaccacatc cacttggtcg agctcctggc tgtgtgcacg   4140
gagggtaaga atgtctacac agagatcaag tgcaactccc tgctcccgct ggatgacatc   4200
gttcgcgtgg tgacccacga ggactgcatc cctgaggtta aaattgcata cattaacttc   4260
ctgaatcact gctatgtgga tacagaggtg gaaatgaagg agatttatac cagcaatcac   4320
atgtggaaat tgtttgagaa tttccttgta gacatctgca gggcctgtaa caacactagt   4380
gacaggaaac atgcagactc gattttggag aagtatgtca ccgaaatcgt catgagtatt   4440
gttactactt tcttcagctc tcccttctca gaccagagta cgactttgca gactcgccag   4500
cctgtctttg tgcaactgct gcaaggcgtg ttcagggttt accactgcaa ctggttaatg   4560
ccaagccaaa aagcctccgt ggagagctgt attcgggtgc tgtctgatgt agccaagagc   4620
cgggccattg ccattcccgt ggacctggac agccaagtca acaacctctt tctcaagtcc   4680
cacagcattg tgcagaaaac agccatgaac tggcggctct cagcccgcaa tgccgcacgc   4740
agggactctg ttctggcagc ttccagagac taccggaata tcattgagag attgcaggac   4800
atcgtctccg cgctggagga ccgtctcagg cccctggtgc aggcagagtt atctgtgctc   4860
gtggatgttc tccacagacc cgagctgctt ttcccagaga acacagacgc cagaaggaaa   4920
tgtgaaagtg gcggtttcat ttgcaagtta ataaagcata caaaacagct gctagaagaa   4980
aatgaagaga agctctgcat taaggtccta cagaccctga gggaaatgat gaccaaagat   5040
agaggctatg gagaaaagct aatttccatt gatgaattgg ataatgctga gcttcctcca   5100
gctccggatt ctgagaacgc cactgaggag cttgaaccaa gtccacccct gcggcagctg   5160
gaagaccata aaaggggtga ggcgctcagg caagttctgg tcaaccgtta ctatggaaac   5220
```

gtcagacctt cgggacgaag agagagcctt accagctttg gcaatggccc actgtcagca 5280
ggaggacccg gcaagcccgg gggaggaggg ggaggttccg gatccagctc tatgagcagg 5340
ggtgagatga gtctggccga ggttcagtgt caccttgaca aggagggggc ttccaatcta 5400
gttatcgacc tcatcatgaa cgcatccagt gaccgagtgt tccatgaaag cattctcctg 5460
gccattgccc ttctggaagg aggcaacacc accatccagc actccttttt ctgtcgcttg 5520
acagaagata agaagtcaga gaaattcttt aaggtgtttt atgaccggat gaaggtggcc 5580
cagcaagaaa tcaaagcaac agtgacagtg aacaccagtg acttgggaaa taaaaagaaa 5640
gacgatgagg tagacaggga tgccccatca cggaaaaaag ctaaagagcc cacaacacag 5700
ataacagaag aggtccggga tcagctcctg gaggcctccg ctgccaccag gaaagccttc 5760
accactttca ggagggaggc tgatcccgac gaccactacc agcctggaga gggcacccag 5820
gccactgccg acaaggccaa ggacgacctg gagatgagcg cggtcatcac catcatgcag 5880
cccatcctcc gcttccttca gctcctgtgt gaaaaccaca accgagacct gcagaacttc 5940
ctccgttgcc aaaataacaa gaccaactac aatttggtat gtgagaccct gcagtttctg 6000
gactgtattt gtggaagcac aactggaggc cttggtcttc tgggcttgta tataaatgaa 6060
aagaacgtag cgcttatcaa ccaaaccctg gaaagtctga ccgaatactg tcaaggacct 6120
tgccatgaga accagaactg catagccacc catgaatcca atggcattga catcatcaca 6180
gccctgatcc tcaatgatat caatcctttg ggaaagaaga ggatggacct tgtgttagaa 6240
ctgaagaaca atgcctcgaa gttgctcctg gccatcatgg aaagcaggca cgacagtgaa 6300
aacgcagaga ggatacttta taacatgagg cccaaggaac tggtggaagt gatcaagaaa 6360
gcctacatgc aaggtgaagt ggaatttgag gatggagaaa acggtgagga tggggcggcg 6420
tcccccagga acgtggggca caacatctac atattagccc atcagttggc tcggcataac 6480
aaagaacttc agagcatgct gaaacctggt ggccaagtgg acggagatga agccctggag 6540
ttttatgcca agcacacggc gcagatagag attgtcagat tagaccgaac aatggaacag 6600
atagtctttc ccgtgcccag catatgtgaa ttcctaacca aggagtcaaa actacgaatt 6660
tactatacta cggagagaga cgaacaaggc agcaaaatca atgatttctt tctgcggtct 6720
gaagacctct tcaatgaaat gaattggcag aagaaactga gagcccagcc cgtgttgtac 6780
tggtgtgccc gcaacatgtc tttctggagc agcatttcgt ttaacctggc cgtcctgatg 6840
aacctgctgg tggcgttttt ctacccgttt aagggagtcc gaggaggaac cctggagccc 6900
cactggtcgg gactcctgtg gacagccatg ctcatctctc tggccatcgt cattgccctc 6960
cccaagcccc atggcatccg ggccttaatt gcctccacaa ttctacgatt gatattttca 7020
gtcgggttac aacccacgtt gtttcttctg ggcgctttca atgtatgcaa taaaatcatc 7080
tttctaatga gctttgtggg caactgtggg acattcacaa gaggctaccg agccatggtt 7140
ctggatgttg agttcctcta tcacttgttg tatctggtga tctgtgccat ggggctcttt 7200
gtccatgaat tcttctacag tctgctgctt tttgatttag tgtacagaga agagactttg 7260
cttaatgtca ttaaaagtgt cactcgcaat ggacgggcca tcatcctgac agcagttctg 7320
gctctgatcc tcgtttacct gttctcaata gtgggctatc ttttcttcaa ggatgacttt 7380
atcttggaag tagataggct gcccaatgaa acagctgttc cagaaaccgg cgagagtttg 7440
gcaagcgagt tcctgttctc cgatgtgtgt agggtggaga gtggggagaa ctgctcctct 7500
cctgcaccca gagaagagct ggtccctgca gaagagacgg aacaggataa agagcacaca 7560
tgtgagacgc tgctgatgtg cattgtcact gtgctgagtc acgggctgcg gagcgggggt 7620

```
ggagtaggag atgtactcag gaagccgtcc aaagaggaac ccctgtttgc tgctagagtt   7680
atttatgacc tcttgttctt cttcatggtc atcatcattg ttcttaacct gatttttggg   7740
gttatcattg acacttttgc tgacctgagg agtgagaagc agaagaagga agagatcttg   7800
aagaccacgt gctttatctg tggcttggaa agagacaagt ttgacaacaa gactgtcacc   7860
tttgaagagc acatcaagga agaacacaac atgtggcact atctgtgctt catcgtcctg   7920
gtgaaagtaa aggactccac cgaatatact gggcctgaga gttacgtggc agaaatgatc   7980
aaggaaagaa accttgactg gttccccagg atgagagcca tgtcattggt cagcagtgat   8040
tctgaaggag aacagaatga gctgagaaac ctgcaggaga agctggagtc caccatgaaa   8100
cttgtcacga acctttctgg ccagctgtcg gaattaaagg atcagatgac agaacaaagg   8160
aagcagaaac aaagaattgg tcttctagga catcctcctc acatgaatgt caacccacaa   8220
caaccagcat aagcaaatga aagaaaggaa ttgtatttac cttttataat tattattagt   8280
gtgggaatgg ctaatgagtt ctgattcacc cacgaaggtt acatttatgc tgaatacatt   8340
tgtaaatact cagttttata ctgtatgtat atgattgcta ctctaaaggt ttggatatat   8400
gtattgtaat tagaattgtt ggcatgatga catttcattt gtgccaaaaa tattaaaaat   8460
gcctttttttg gaaggactaa cagaaagcac ctgatttgca cttgaaccag attatagatt   8520
taaaagtata tgacatgtat tttgtattta aaactagaat agccagtatt tatgtttttt   8580
ataaaactgt gcaatacgaa ttatgcaatc acaatacatt tgtagctccc gagtgtccta   8640
aagggagtgc acttctttga agctggtgtg ttaatactat gtaataaatg gttaactttc   8700
aaatgatgct gctgccaaaa ttatattaat agagagtttc aggcccctgg gaattcctgc   8760
agcccggggg atccccgggt accgagctc                                     8789
```

<210> SEQ ID NO 42
<211> LENGTH: 4394
<212> TYPE: DNA
<213> ORGANISM: Human

<400> SEQUENCE: 42

```
aaactcccag ggcccgccca ggacccccaa gccgccgcgg acgcagccca ggatggcggc     60
ccaggtgact ctggaggacg cgctgtccaa cgtggacctc ctggaggagc tgcccctgcc    120
cgaccagcag ccctgcatcg agcccccgcc atcctcgctg ctctaccagc caaatttcaa    180
cactaacttt gaagacagaa atgcatttgt tactggcatc gcaagataca ttgaacaagc    240
caccgtccac tctagcatga acgagatgct ggaggagggc caagaatatg ctgtcatgct    300
gtacacctgg aggagctgct cccgggccat cccacaggtg aaatgtaacg agcagcctaa    360
cagagtggaa atctacgaga aaaccgtgga ggttctggag cctgaggtca caaaactgat    420
gaatttcatg tacttccaga gaaatgccat tgagcgtttc tgcggggaag tgaggcgcct    480
gtgccatgcc gagaggagga aggacttcgt gtcagaagcc tacctgatca cactgggcaa    540
attcatcaac atgttcgctg tgctggacga gctgaagaac atgaagtgca gtgtgaagaa    600
cgaccactca gcgtacaaga gggccgctca gtttttacgt aaaatggcag atccacagtc    660
catccaggaa tcgcagaatc tgtccatgtt cctggccaat cataacaaga tcacacagtc    720
tctgcagcag cagctcgaag tgatttctgg ctacgaagag ctcctggcag atattgtgaa    780
tctgtgtgtg gattactacg agaacaggat gtatttgacg cccagtgaga aacacatgct    840
tctcaaagtc atgggatttg gtctgtacct gatggatggg agtgtcagta acatctataa    900
gttggatgcc aagaaaagaa taaacttatc caaaatcgac aagtacttca agcaactcca    960
```

```
ggtggttcca ctatttgggg acatgcaaat agaactggca agatatatca agaccagcgc   1020
ccactacgag gaaaataaat ctcgatggac gtgcacatcc tccggcagca gccctcagta   1080
caacatctgc gagcagatga tccagatccg cgaggaccac atgcgcttca tttcggagct   1140
ggcgcgctac agcaacagcg aggtggtcac gggctcgggc cgccaggagg cccagaagac   1200
ggacgcggag taccgcaagc tcttcgacct ggcgctgcag ggcctgcagc tgttgtcgca   1260
gtggagcgcg cacgtgatgg aagtgtattc ctggaagctt gtgcacccca ccgacaagta   1320
ctccaacaag gactgccccg acagcgctga agagtacgag cgtgccacgc gctacaacta   1380
caccagcgag gagaagtttg ccctagtgga ggtgatcgcc atgatcaaag gcctgcaggt   1440
gctgatgggc aggatggaga gcgtgttcaa ccacgccatc cggcacaccg tctatgccgc   1500
actgcaggac ttctcccagg tgacccttag ggagccgctg cggcaggcca tcaagaagaa   1560
gaagaacgtc atccagagtg tcctgcaggc catcaggaag accgtgtgtg actgggagac   1620
ggggcatgag cccttcaatg acccagcctt gcggggcgag aaggacccca agagcggctt   1680
cgacataaaa gtaccacgcc gcgccgtggg accctccagc actcagcttt acatggtgag   1740
aaccatgcta gagtccctca ttgcagacaa aagtggttcc aagaaaacct tgagaagtag   1800
ccttgagggg cccaccatat tggacataga aaaatttcat cgagagtcat tcttctacac   1860
tcacttgata aatttcagtg aaacgctgca gcagtgctgt gacctttcgc agctgtggtt   1920
ccgagagttc ttcctggagc tgaccatggg caggaggatc cagttcccca ttgagatgtc   1980
gatgccctgg atcctgacgg accacatcct ggagaccaag gaggcatcga tgatggagta   2040
cgtgctctac tccctggacc tgtacaatga cagcgcccac tacgcgctca ccaggttcaa   2100
caagcagttc ctgtacgacg aaattgaggc cgaggtgaat ctatgttttg accaatttgt   2160
ttacaagcta gcagaccaga tatttgccta ttataaggtt atggcaggaa gtttgcttct   2220
tgataaacgg ttacgatcag aatgcaagaa tcagggagcc acgatccacc tcccgccgtc   2280
taaccgctac gagacgctgc tgaagcagag gcatgtgcag ctcctcggca gatcaataga   2340
cctcaatcgt ctgatcaccc agcgcgtctc agcagccatg tataagtccc tagaactggc   2400
gattggacga tttgaaagtg aagatttgac ctccatagtt gagctggatg gcctgttgga   2460
aatcaaccgc atgacccaca agctgctgag ccggtacctg acgctggacg gcttcgacgc   2520
catgttccgg gaggccaacc acaacgtgtc agcgccctac gggaggatca ccctgcacgt   2580
cttctgggag ctcaactatg acttcctgcc caactactgc tacaacggct ctaccaaccg   2640
gtttgttcgg acagtgttac cattttctca ggaatttcaa agagataagc agcctaatgc   2700
acagcctcag tatctgcatg gatccaaggc tttgaacttg gcctactcca gcatttacgg   2760
cagctaccgg aacttcgtgg gacctccaca ctttcaagtc atctgccggc ttctcggcta   2820
ccagggtatc gccgtggtca tggaggagct gctgaaggtc gtcaagagcc tgctgcaagg   2880
cacaatcctg cagtacgtga agacgctgat ggaggtgatg cccaagatct gccgcctgcc   2940
ccggcacgag tacggctctc ctggtatcct ggagttcttc caccaccagc tgaaggacat   3000
cgtggagtac gcagagctga agacggtgtg cttccagaac ctgcgggagg tggggaacgc   3060
catcctcttc tgcctgctca tcgagcagag cctgtcttta gaagaagtgt gtgacctgct   3120
gcacgcggct cctttccaga acatcttgcc gcgagtccat gtgaaagagg gggagagact   3180
tgatgccaaa atgaaaagac tagaatcaaa gtacgccccg ctgcatcttg tcccactgat   3240
tgaaagactg gggacccctc agcaaattgc catcgcaaga gagggggacc tgctgacaaa   3300
ggagcgcctc tgctgcggcc tgtccatgtt tgaggtcatc ctgacacgga tccggagctt   3360
```

tctggatgac cccatctggc gcgggcctct gcccagcaat ggggtcatgc atgtggacga 3420
gtgtgtggag tttcacagac tgtggagtgc catgcagttt gtctactgca ttcccgtggg 3480
gacacacgag ttcacagtcg agcagtgctt tggtgatggg ctacactggg ctggctgtat 3540
gatcatcgta cttcttgggc agcagcggcg ttttgctgtg ctggatttct gctaccatct 3600
acttaaagtc cagaaacatg atggcaaaga tgagattatt aaaaatgtgc ctttgaagaa 3660
gatggtggag agaattcgca agttccagat tctcaatgat gagatcatca ccatcctgga 3720
taagtacctg aagtcaggcg acggggaggg cacgccagtg gagcatgtgc gctgcttcca 3780
gccgcccatc caccagtccc tcgccagcag ctgagggcac gcgctgcact ccgtaactca 3840
acatggcatg cctttctctc cgtaaactat ttagtgagat ttttagggac tatttttcag 3900
tatctctgta cctgttaaag gggtgcttt tcgatctaaa aacttaattt tataaaattg 3960
acttattttt ctagactaaa attgtatatg cttttggtaa ttaggaactc ttgagaatat 4020
tggctgctga ttgttgccat cacgttccta caaaattgtt tttctatggg atgttctggc 4080
agctgtgtca taaaatgctg ctgggttcat tcattcattc cataagaaac ttaataccag 4140
caaatgcatt aaatcccttg ccagttacca ttaactataa ctatttagct tttgtttagg 4200
gatctttctg atggtctttt atgagcaatc ttagttctaa gtcattgttc ccatcccttt 4260
tttgtgtgtt tcagaaaata gtgaacttga ttcccctgct tccactaaat ccagttgtga 4320
caaaatctaa cgtgacatca gatcgaaagg ttatagaaat aaaactaatg agatctaaaa 4380
aaaaaaaaaa aaaa 4394

<210> SEQ ID NO 43
<211> LENGTH: 1166
<212> TYPE: DNA
<213> ORGANISM: Human

<400> SEQUENCE: 43
gcaagaatgg tgcctgtcct gctgtctctg ctgctgcttc tgggtcctgc tgtcccccag 60
gagaaccaag atggtcgtta ctctctgacc tatatctaca ctgggctgtc caagcatgtt 120
gaagacgtcc ccgcgtttca ggcccttggc tcactcaatg acctccagtt ctttagatac 180
aacagtaaag acaggaagtc tcagcccatg ggactctgga gacaggtgga aggaatggag 240
gattggaagc aggacagcca acttcagaag gccagggagg acatctttat ggagaccctg 300
aaagacattg tggagtatta caacgacagt aacgggtctc acgtattgca gggaaggttt 360
ggttgtgaga tcgagaataa cagaagcagc ggagcattct ggaaatatta ctatgatgga 420
aaggactaca ttgaattcaa caaagaaatc ccagcctggg tccccttcga cccagcagcc 480
cagataacca agcagaagtg ggaggcagaa ccagtctacg tgcagcgggc caaggcttac 540
ctggaggagg agtgccctgc gactctgcgg aaatacctga aatacagcaa aaatatcctg 600
gaccggcaag atcctccctc tgtggtggtc accagccacc aggccccagg agaaaagaag 660
aaactgaagt gcctggccta cgacttctac ccagggaaaa ttgatgtgca ctggactcgg 720
gccggcgagg tgcaggagcc tgagttacgg ggagatgttc ttcacaatgg aaatggcact 780
taccagtcct gggtggtggt ggcagtgccc ccgcaggaca cagcccccta ctcctgccac 840
gtgcagcaca gcagcctggc ccagcccctc gtggtgccct gggaggccag ctaggaagca 900
agggttggag gcaatgtggg atctcagacc cagtagctgc ccttcctgcc tgatgtggga 960
gctgaaccac agaaatcaca gtcaatggat ccacaaggcc tgaggagcag tgtgggggga 1020
cagacaggag gtggatttgg agaccgaaga ctgggatgcc tgtcttgagt agacttggac 1080
ccaaaaaatc atctcacctt gagcccaccc ccaccccatt gtctaatctg tagaagctaa 1140
taaataatca tccctccttg cctagc 1166

<210> SEQ ID NO 44
<211> LENGTH: 5221
<212> TYPE: DNA
<213> ORGANISM: Human

<400> SEQUENCE: 44
cggccgcccg ggcaggtttt gtagactttc atagccaaag aaaccggctt cggcttcttt 60
aaaatccccg acgactcacc tgattaacct gctgcagttc tgaccctgcc aagagctgac 120
aatttactgg ttcatcaatg aaacaatatt aaattatgaa gatgtaagga aaaaatccta 180
cgctaacact gtcgcagttt gaaaggcttc tctgcagaat gtcaaacaaa gatcgacaca 240
ttgattccag ctgttcgtcc ttcatcaaga cggaaccttc cagcccagcc tccctgacgg 300
acagcgtcaa ccaccacagc cctggtggct cttcagacgc cagtgggagc tacagttcaa 360
ccatgaatgg ccatcagaac ggacttgact cgccacctct ctacccttct gctcctatcc 420
tgggaggtag tgggcctgtc aggaaactgt atgatgactg ctccagcacc attgttgaag 480
atccccagac caagtgtgaa tacatgctca actcgatgcc caagagactg tgtttagtgt 540
gtggtgacat cgcttctggg taccactatg ggtagcatc atgtgaagcc tgcaaggcat 600
ctttcaagag gaaaatacaa gccaatatag aatacagctg ccctgccacg aatgaatgtg 660
aaatcacaaa gcgcagacgt aaatcctgcc aggcttgccg cttcatgaag tgtttaaaag 720
tgggcatgct gaaagaaggg gtgcgtcttg acagagtacg tggaggtcgg cagaagtaca 780
agcgcaggat agatgcggag aacagcccat acctgaaccc tcagctggtt cagccagcca 840
aaaagccata taacaagatt gtctcacatt tgttggtggc tgaaccggag aagatctatg 900
ccatgcctga ccctactgtc cccgacagtg acatcaaagc cctcactaca ctgtgtgact 960
gtgccgaccg agagttggtg gttatcattg gatgggcgaa gcatatccca ggcttctcca 1020
cgctgtccct ggcggaccag atgagccttc tgcagagtgc ttggatggaa attttgatcc 1080
ttggtttcgt ataccggtct ctttcgtttg aggatgaact tgtctatgca gacgattata 1140
taatggacga agaccagtcc aaattagcag gccttcttga tctaaataat gctatcctgc 1200
agctggtaaa gaaatacaag agcatgaagc tggaaaaaga agaatttgtc accctcaaag 1260
ctatagctct tgctaattca gactccatgc acatagaaga tgttgaagcc gttcagaagc 1320
ttcaggatgt cttacatgaa gcgctgcagg attatgaagc tggccagcac atggaagacc 1380
ctcgtcgagc tggcaagatg ctgatgacac tgccactcct gaggcagacc tctaccaagg 1440
ccgtgcagca tttctacaac atcaaactag aaggcaaagt cccaatgcac aaactttttt 1500
tggaaatgtt ggaggccaag gtctgctaaa agctccctgg gccttccatc cttcattgtt 1560
gaaaagggga aataaaccca agagtgatgt cgaagaaact tagagtttag ttaacaacat 1620
caaaaatcaa cagactgcac tgataattta gcagcaagac tatgaagcag ctttcagatt 1680
cctccatagg ttcctgatga gtttctttct actttctcca tcatcttctt tcctctttct 1740
tcccacattt ctctttctct ttattttta tccttttctt ctttcacctc ccttatttct 1800
ttgcttcttt cattcctagt tcccattctc ctttatttc ttcccgtctg cctgccttct 1860
ttcttttctt tacctactct cattcctctc ttttctcatc cttcccttt tttctaaatt 1920 tgaaatagct ttagtttaaa aaaaaatcct cccttccccc tttcctttcc ctttctttcc 1980
tttttccctg tccttttccc tttcctttcc tttcctcttg accttctttc catctttctt 2040

-continued

```
tttcttcctt ctgctgctga acttttaaaa gaggtctcta actgaagaga gatggaagcc   2100
agccctgcca aaggatggag atccataata tggatgccag tgaacttatt gtgaaccata   2160
ccgtccccaa tgactaagga atcaaagaga gagaaccaac gttcctaaaa gtacagtgca   2220
catatacaaa ttgactgagt gcagtattag atttcatggg agcagcctct aattagacaa   2280
cttaagcaac gttgcatcgg ctgcttctta tcattgcttt tccatctaga gcagttacag   2340
ccatttgatc ccttaattgt tttttcaagt ctcccaggta tttgttagtt tagctactat   2400
gtaacttttt cagggaatag tttaagcttt attcagtcat gcaatactaa agagaaataa   2460
gaatactgca attttgtgct ggctttgaac aattacgaac aataatgaag gacaaatgaa   2520
tcctgaagga agatttttaa aaatgttttg tttcttctta caaatggaga tttttttgta   2580
ccagctttac cacttttcag ccatttatta atatgggaat ttaacttact caagcaatag   2640
ttgaagggaa ggtgcatatt atcacggttg caatttatgg ttgtgtgccc agtctggtcc   2700
ccaaacatca atttcttaac atgagctcca gtttacctaa atgttcactg acacaaagga   2760
tgagattaca cctacagtga ctctgagtag tcacatatat aagcactgca catgagatat   2820
agatccgtag aattgtcagg agtgcacctc tctacttggg aggtacaatt gccatatgat   2880
ttctagctgc catggtggtt aggaatgtga tacatgcctg tttgcaaagt cacagaccat   2940
tgcctcagaa ggagctgtga gccagtattc atttaagagg caataaggca aatgccagaa   3000
ttaaaaaaaa aaaatcatca aagacagaaa atgcctgacc aaattctaaa acctaatcca   3060
tataagttta ttcatttagg aatgttcgtt taaattaatc tgcagttttt accaagagct   3120
aagccaatat atgtgctttt caaccagtat tgtcacagca tgaaagtcac agtcaggttc   3180
cagactgtta agaggtgtaa tctaatgaag aaatcaatta gatgccccga aatctacagt   3240
cgctgaataa ccaataaaca gtaacctcca tcaaatgcta taccaatgga ccagtgttag   3300
tagctgctcc ctgtattatg tgaacagtct tattctatgt acacagatgt aattaaaatt   3360
gtaatcctaa caaacaaaag aaatgtagtt cagcttttca atgtttcatg tttgctgtgc   3420
ttttctgaat tttatgttgc attcaaagac tgttgtcttg ttcttgtggt gtttggattc   3480
ttgtggtgtg tgcttttaga cacagggtag aattagagac aatattggat gtacaattcc   3540
tcaggagact acagtagtat attctattcc ttaccagtaa taaggttctt cctaataata   3600
attaagagat tgagactcca aacaagtatt cattatgaac agatacacat caaaatcata   3660
ataatatttt cagaacaagg aataatttct ctaatggttt attatagaat accaatgtat   3720
agcttagaaa taaaactttg aatatttcaa gaatatagat aagtctaatt tttaaatgct   3780
gtatatatgg ctttcactca atcatctctc agatgttgtt attaactcgc tctgtgttgt   3840
tgcaaaactt tttggtgcag attcgtttcc aaaactattg ctactttgtg tgctttaaac   3900
aaaatacctt gggttgatga aacatcaacc cagtgctagg aatactgtgt atctatcatt   3960
agctatatgg gactatattg tagattgtgg tttctcagta gagaagtgac tgtagtgtga   4020
ttcttgataa atcatcatta gcaattcatt cagatggtca ataacttgaa atttatagct   4080
gtgataggag ttcagaaatt ggcacatccc tttaaaaata acaacagaaa atacaactcc   4140
tgggaaaaaa aggtgctgat tctataagat tatttatata tgtgagtgtt taaaaagatt   4200
attttccaga aagtttgtgc agggtttaag ttgctactat tcaactacac tatatataaa   4260
taagatatat acaatatata cattgttttc actgtatcac attaaagtac ttgggcttca   4320
gaagtaagaa gccaaccaac tgaaaacctg agatggagat atgttcaaag aatgagatac   4380
aattttttag ttttcagttt aagtaactct cagcattaca aaagagtaag tatctcacaa   4440
```

```
ataggaaata aaactaaaac gtagatttaa aaaagaactg cacgggcttt agggtaaatg   4500
ctcatcttaa acctcactag agggaagtct tctcaagttt caagcaagac catttactta   4560
atgtgaagtt ttggaaagtt ataaaggtgt atgttttagc catatgatcc taaatttaat   4620
tttgctcttt taggttcgtt cttatttaaa gcaatatgat tgtgtgactc cttgtagtta   4680
cacttgtgtt tcaatcagat cagattgttg tatttattcc actattttgc atttaaatga   4740
taacataaca gatataaaaa atttaaaact gctatttttc ttatagaaga gaaaatgggt   4800
gttggtgatt gtattttaat tatttaagcg tctctgttta cctgcctagg aaaacatttt   4860
atggcagtct tatgtgcaaa gatcgtaaaa ggacaaaaaa tttaaactgc ttataataat   4920
ccaggagttg cattatagcc agtagtaaaa aaaataataa taataataat aaaaccatgt   4980
ctatagctgt agatgggctt cacatctgta aagcaatcaa ttgtatattt ttgtgatgtg   5040
taccatactg tgtgctccag caaatgtcca tttgtgtaaa tgtatttatt ttatattgta   5100
tatattgtta aatgcaaaaa ggagatatga ttctgtaact ccaatcagtt cagatgtgta   5160
acccaaatat tatgcctttc aggatgatgg tagagcaata ttaaacaagc ttccactttt   5220
g                                                                   5221
```

<210> SEQ ID NO 45
<211> LENGTH: 1174
<212> TYPE: DNA
<213> ORGANISM: Human

<400> SEQUENCE: 45

```
ggcacgaggg ggccggagga gggacgcgcc ggagcgggac cgacgggacc gagcgagcga     60
ccgacgcgcc acccgccgac gcctcagccg cttggggccc gcacggaccc tctacttcag    120
tgtagaatga gccaaggaga ctcaaaccca gcagctattc cgcatgcagc agaagatatt    180
caaggagatg accgatggat gtctcagcac aacagatttg ttttggactg taaagacaaa    240
gagcctgatg tactgttcgt gggagactcc atggtgcagt taatgcagca atatgagata    300
tggcgagagc tttttcccc acttcatgca ctgaattttg gaattggggg agatacaaca    360
agacatgttt tgtggagact aaagaatgga gaactggaga atattaagcc taaggtcatt    420
gttgtctggg taggaacaaa taaccacgaa aatacagcag aagaagtagc aggtgggatc    480
gaggccattg tacaacttat caacacaagg cagccacagg ccaaaatcat tgtattgggt    540
ttgttacctc gaggtgagaa acccaatcct ttgaggcaaa agaacgccaa ggtgaaccaa    600
ctcctcaagg tttcgctgcc gaagcttgcc aacgtgcagc tcctggatac cgacgggggt    660
tttgtgcact cggacggtgc catctcctgc cacgacatgt ttgattttct gcatctgaca    720
ggagggggct atgcaaagat ctgcaaaccc ctgcatgaac tgatcatgca gttgttggag    780
gaaacacctg aggagaaaca aaccaccatt gcctgactgg ctcttatcag tgttaatagc    840
atctcagctt cctcagatca gttctatcac tggcactaca gaatccttct ctttcttaag    900
gcactttgca ttgtagaatg ttcctggatg ttcatatcta gtgtttgaag gggaggaggg    960
atttaaactg gtcctgtaca tagaaggttt gtttgacaga ggagaaaaat tagccaagga   1020
agattgttgt ttaaattcat ttgaaaccag aaggggactt tttagttgta tgtgtaacac   1080
attcattgaa ttattatcac tgttttcttg ggacaacatc aagcctaaat actgaacaat   1140
atgaagatta aaaaaaaaaa aaaaaaaaaa aaaa                               1174
```

<210> SEQ ID NO 46
<211> LENGTH: 1619

<212> TYPE: DNA
<213> ORGANISM: Human

<400> SEQUENCE: 46

```
ggggatatgg cggggccttt gtctctcgct gtcgccggag tcccaggtct gtcttcactg     60
ctctgtgtcc tctgctccta gaggcccagc ctctgtggcg ctgttaccag cagtattgga    120
gatccacagc taagatgcca ggacccccta gaagcctaga aatgggactg ttgacattta    180
gggatgtggc catagaattc tctctggagg agtggcaaca cctggacatt gcacagcaga    240
atttatatag aaatgtgatg ttagagaact acagaaacct ggccttcctg ggtattgctg    300
tctctaagcc agacctgatc acctgtctgg aacaagggaa agagccctgg aatatgaagc    360
gacatgagat ggtggatgaa cccccaggta tgtgtcctca ttttgctcaa gacctttggc    420
cagagcaggg catggaagat tcttttcaaa aagcaatact gagaagatat ggaaaatatg    480
gacatgagaa tttacagtta agaaaaggct gtaaaagtgt ggatgagtat aaggtgaaca    540
aagaaggtta taatggactt aaccagtgtt tcacaactgc ccagagcaaa gtatttcaat    600
gtgataaata tttgaaagtc ttctataaat ttttaaattc aaacagacct aagataagac    660
atactgaaaa gaaatctttc aaatgtaaaa aacgtgtcaa attattttgc atgctttcac    720
ataaaaccca acacaaaagc atttatcata gagagaagtc ctacaaatgt aaagaatgtg    780
gaaaaacctt taattggtcc tcaaccctta ctaatcatag gaaaatttat actgaagaga    840
aaccttacaa atgtgaagaa tataacaaat ctcctaagca actctcaacc cttactacac    900
atgaaataat tcatgctgga gagaaactct acaaatgtga agaatgtggc aaagctttta    960
atcggtcctc aacttttact aaacataagg taattcatac tggagtaaaa ccctacaaat   1020
gtgaagaatg tggcaaagca tttttctggt cctcaaccct aactaaacat aagagaattc   1080
atactggaga gcaaccctac aaatgggaaa aatttggcaa agcctttaat cggtcctcgc   1140
acctcaccac agataagata actcatactg gagagaaatc ttacaagtat gaataatgtg   1200
ccaaagccta agaaaaccct caattcttaa tagatataag attattccta ctggagagaa   1260
actacaaacc tgagagaggc gctaatgctt ttgacagtac ctaaaacttt aaagaaaatc   1320
attctgctga aaaatcctag aaatgtgaag aatgtgaaaa agcctttaaa tgattgtcac   1380
acttgattgt aggtaagata attcatactg gagaaaacta ccagtgtgaa caacgtggcc   1440
aagcttcgac aatgctcaca ccctattgca caggaaagca tttatacttg agaagaaatg   1500
tacaaatatt ggcaaagtaa aaaatccatt aacacctgct cacatcttac tcaaaattgt   1560
agagttcata gtaaataaaa gcattaaaat tcaaaaaaaa aaaaaaaaaa aaaaaaaaa    1619
```

<210> SEQ ID NO 47
<211> LENGTH: 534
<212> TYPE: DNA
<213> ORGANISM: Human

<400> SEQUENCE: 47

```
tttttacaac atatatcttt aattaaattt atattggtgg gtttaaaaaa cattaagtca     60
ggagatgata gctagggaaa taaggtatcc tgtgagtatt tataacaaaa tatttaaaat    120
ttaaaaagaa taagaaacat caattggctt tttgtaactt aaaagagact aaccaagtgt    180
tgtttcccag ttctgtacaa gcagaggcca caggaggatt cttacataag aagcacaggg    240
aaaagaattg ttaattctgc gtgtgtgttt ttgtttctca gaattgtttg gaagaacttt    300
gtccagtcag aaatgagtaa aaacaagatg taagaaacat taaaacaggg ggcatatggt    360
cttaagagat aatcttggag aatatagcaa aagacaaatt gctccattag atattataat    420
```

ttggtatgta acatgaacat ttaaaattct gattaaagtg actaaaaggg tttgtttttt 480
aaaaaaaatc aaaacagaac ttacgggata aaactcagaa taaatttact ctca 534

<210> SEQ ID NO 48
<211> LENGTH: 4763
<212> TYPE: DNA
<213> ORGANISM: Human
<220> FEATURE:
<221> NAME/KEY: misc_feature
<222> LOCATION: (3847)..(3847)
<223> OTHER INFORMATION: any kind of base

<400> SEQUENCE: 48
cccctcaccc cactcaactg ccccgggccc ccgcgcgcgc ggccgcccct ccactcaccc 60
tgtgtcggcc ccgctcccct ctcccccacc aggcgagcag gcgagcgggc agagcccgcg 120
gcggaggtcg gcgcggctcc ggggttcatg gtgacgaggc ggcggccgct cgagcccagc 180
ggcggcgggc ggcgggagct ggggcgcggg cccgggccgc ctctcccaga gcgcggggcc 240
gggcggcggg cgcgcccagg cagcggctgc gagcgccccc ccgcgccgcg cccccgcgcc 300
ccccgcgccg cgcccccgcg cgcttggctt gcggggggcc gggcctgcgg gcggccgccg 360
cgccgcgcac ccatggacgg cccggccatc atcacccagg tgaccaaccc caaggaggac 420
gagggccggt tgccgggcgc gggcgagaaa gcctcccagt gcaacgtcag cttaaagaag 480
cagaggagcc gcagcatcct tagctccttc ttctgctgct tccgtgatta caatgtggag 540
gcccctccac ccagcagccc cagtgtgctt ccgccactgg tggaggagaa tggtgggctt 600
cagaagccac cagctaagta ccttcttcca gaggtgacgg tgcttgacta tggaaagaaa 660
tgtgtggtca ttgatttaga tgaaacattg gtgcacagtt cgtttaagcc tattagtaat 720
gctgatttta ttgttccggt tgaaatcgat ggaactatac atcaggtgta tgtgctgaag 780
cggccacatg tggacgagtt cctccagagg atggggcagc tttttgaatg tgtgctcttt 840
actgccagct tggccaagta tgcagaccct gtggctgacc tcctagaccg ctggggtgtg 900
ttccgggccc ggctcttcag agaatcatgt gtttttcatc gtgggaacta cgtgaaggac 960
ctgagtcgcc ttgggcggga gctgagcaaa gtgatcattg ttgacaattc ccctgcctca 1020
tacatcttcc atcctgagaa tgcagtgcct gtgcagtcct ggttcgatga catgacggac 1080
acggagctgc tggacctcat ccccttcttt gagggcctga gccgggagga cgacgtgtac 1140
agcatgctgc acagactctg caataggtag ccctggcctc tgcctgcctc ccgcctgtgc 1200
actctggaac ctctggcctc aggggacctg cctgtcctca gctccctggg agctgaaagt 1260
gaggatactc cgtgctccag gccacagggt gaatgtggcc atgcctacct gttttgtttt 1320
tttaagaaca gaaacaacta ttttaaaaga actcttttaa gaaatttcat aaagggacat 1380
gcattttact gggtttgctt ttcttaaaac ataccaaaaa agaaaaaaat agaaaaaaaa 1440
aaaaaaaaag ctgatctcta tcagactctt caactgtcct ccctccaagc agaccacctg 1500
tccccttcta tcccagctca gagcagctga cccaactcag aatctctttc ctacaggatg 1560
aaagtgcctt ttgaatgtta tttttaagcc gagagttaat ttttctacac aacatatttc 1620
cagacatctt ttagtctttt attgtcttag atactataag aagatgaaca tgacaatttt 1680
ctagaacctg gtagcgtgtg tgtgtggttg gcggggggtg ctgagggagg ggagtgagtc 1740
acaggagcct gtcccccaac aggtgtgact gctctgacaa cctgtggcat gctgcagggt 1800
caggctcctg ataggaggat ttcatgacta tgtcattgtc tccactcatt tttgacccag 1860
tttggaatgt atctgcaatt gtgtggctca acactttagg aaacatagat tattttatat 1920

```
tattatttct gatggtgaca agtttgtctt gaggtcacat tttctccttg aaaagtgaca   1980
tcctgtcact tctgctctca cactactgcc atacatttgt gtttttttgt tgttattgtt   2040
tgggtagagc agttacaaga aaccctaaaa cccttggata taaaagaaat ctgtttattg   2100
atttttaaat ctttcctttc caaaagctgg atacacatgg agctgtttgg gaattttcct   2160
tgctgctacc gcgctgccac caaatggaat tgaccagcgg ctgttacact gttctttgcc   2220
actgtgccta tgctcagaat atgctcactg ctaagctaca aactcggaca gggtcagaaa   2280
cagaggtgtc ccatcccatt gcagcctcca ccacctgtaa ccccttcctg gcattggcca   2340
ctgaagggta caaaggcaaa aggaccacag caccacttag gtgtagcatg gattttaaac   2400
tgcagtcagt atcagatcct gtttgataaa taagctgact gttctctctt gagaacctgt   2460
ggcctcaacc agccaccaag ctgatgtggc ccaagctcca tctcttggtc ttctcctttg   2520
aagcacagcc tatttctgag ccaagggttg gggaagcctg tctagatgtg ggactcattg   2580
ccccaaacca gggagaggaa gagctcccac agggagagcc caggctctct ttgcagcctt   2640
tcccagtttg gtgtttaaag cagtgccatg ttccttgttt gacaacaaga cagtctgtaa   2700
agtattgctc ttaaaaacaa ttaaaaagaa ccctttcata ttggcaccat tgccttagtc   2760
ctctgtgggt tggtcttcag ccagcattct ggtgggagtg actggcatta acaagactgg   2820
aaatcggggg tcaaagtaaa atatctttgt tttgctttca ttcacaaagt aatgaagcca   2880
gctgccaatt acatcctccc aacagcactt tggtctgtga ctgctgtgtg atattcagaa   2940
gggaagtagt attcaggggg taaacaggtc tcccagcatt ctgagtgttc caaaccagta   3000
atccacatgc caattcaaat agaacagccc cttgctagat attaccacag ataatgacag   3060
tacatggtag aactgcccat gccacaaata tttatttgga aaagtagtca ttaaatgaac   3120
ccactgcctt aaatgtcttg aatgttgcag tcaagtgtct gtcatgtgtt gatatccaca   3180
cagaattagg ccctaatgag agccttagac cctcaaccat gccccccttcg ttggcatcac   3240
agggccttat ttggaagagc ggggcaaaga ggatggaaat cataaaatat ttcatgggaa   3300
tcgaacctag ggatagtgct ccacttctga cgatggagtg aagacacttg gcagacttga   3360
gccagacact tcacctagta gttcctgaaa ctgtgagcac cactgcacta agccagtgcg   3420
gagctgttag ggacgggccc agctcctgca cacggacaca gaatgtctgg agagggcagc   3480
aggcctctga gggttctgga atctgtgcca ccttatttga ccacactcca aaattctgtt   3540
tttattttaa cccttgaatc tgctttatgt acataatcaa aatatctata tctatatcta   3600
tatctatatc tatatatttt taatcatcta catgtaaatg aagcaataga attctaacat   3660
aaggccaaga aatgagacga atgtttgggg tttatgtttt ttaaggtaaa tacgggtatt   3720
gtttttaatt attaccatgt attaaattgt gggctttgaa acctaatgaa acctgttagc   3780
cacttctctg tgccatatac ttcccatgtt accaaaatac gcccaactct ttagccaaaa   3840
gagaacnctg acctcctgag tttccatgct cctttctgtc aggtttaaat gtagtcttct   3900
ggagaagtat ttttgacatt gagctctggg acaggacacc ttgggtttgt ggactgcagc   3960
ccactatgat gttattactt ctctggccag gcctccagtg gaagtgcaca ggcactccca   4020
atgttgttaa tgctctgtct tccatttgtt ctggaatcct acgtgttggt ctgtggttcc   4080
atgcattagc tgtttgtaaa taatgcattt gcatactgaa aaaggaatgc cacctgccac   4140
agttgatggt gagaagctcc tttgacgtgg tgcaattttg atgagatgtc tctggggaca   4200
cgaggatgcc ctaatgatgc tgacttgtca tggttgcagc atttgaactt ttggtgttaa   4260
aaaaaaaaac ctgtaagtct gtaacctggc aacattttac aaccctgtat ttttaaagat   4320
```

-continued ggctttctaa taaaaaatcc agaaccacac agccctatgg tcaaacaatc ctacgtttgt 4380
gcctctgctt ttaaaggtgc tgtgctggac agttggcatg ccagggttcg agaagagtga 4440
atggcttgac gtccttgcag ttaactgtgc aaaattggct ggctgcctct gttcctactg 4500
tactgtaact ttgatcatgt ctgttcctat tccattctcc caggagcttc tctgcagact 4560
gacacaccct cccccacccc gggtagtgga gatgctggtg tctgggtagt catggatttc 4620
tgctgacatt tgaatgtgat aaacaatcca gcattactta ggaaatgcta catgcggaat 4680
gtgcacgttt ccaggggcga gtattgtcaa tcaaaaggtt tgcaatgatt tccttcctgc 4740
caaaaataaa catgtgaaac tgc 4763

<210> SEQ ID NO 49
<211> LENGTH: 10300
<212> TYPE: DNA
<213> ORGANISM: Human

<400> SEQUENCE: 49
aactgctagt ggctgagtcc ctggcggggc gcggcggtgg aaggtgtcgc gtacgggctt 60
cccgagctga cgtggcttga attgggaggg gggcagctgg agcctcaggc ggcagcgctt 120
ctagaaatgc tgagccgatt atcaggatta gcaaatgttg ttttgcatga attatcagga 180
gatgatgaca ctgatcagaa tatgagggct cccctagacc ctgaattaca ccaagaatct 240
gacatggaat ttaataatac tacacaagaa gatgttcagg agcgcctggc ttatgcagag 300
caattggtgg tggagctaaa agatattatt agacagaagg atgttcaact gcagcagaaa 360
gatgaagctc tacaggaaga gagaaaagct gctgataaca aaattaaaaa actaaaactt 420
catgcgaagg ccaaattaac ttctttgaat aaatacatag aagaaatgaa agcacaagga 480
gggactgttc tgcctacaga acctcagtca gaggagcaac tttccaagca tgacaagagt 540
tctacagagg aagagatgga aatagaaaag ataaaacata agctccagga gaaggaggaa 600
ctaatcagca ctttgcaagc ccagcttact caggcacagg cagaacaacc tgcacagagt 660
tctacagaga tggaagaatt tgtaatgatg aagcaacagc tccaggagaa ggaagaattc 720
attagcactt tacaagccca gctcagccag acacaggcag agcaagctgc acagcaggtg 780
gtccgagaga aagatgcccg ctttgaaaca caagttcgtc ttcatgaaga tgagcttctt 840
cagttagtaa cccaggcaga tgtggaaaca gagatgcaac agaaattgag ggtgctgcaa 900
aggaagcttg aggaacacga agaatccttg gtgggccgtg ctcaggtcgt tgacttgctg 960
caacaggagc tgactgctgc tgagcagaga aaccagattc tctctcagca gttacagcag 1020
atggaagctg agcataatac tttgaggaac actgtggaaa cagaaagaga ggagtccaag 1080
attctactgg aaaagatgga acttgaagtg gcagagagaa aattatcctt ccataatctg 1140
caggaagaaa tgcatcatct tttagaacag tttgagcaag caggccaagc ccaggctgaa 1200
ctagagtctc ggtatagtgc tttggagcag aagcacaaag cagaaatgga agagaagacc 1260
tctcatattt tgagtcttca aaagactgga caagagctgc agtctgcctg tgatgctcta 1320
aaggatcaaa attcaaagct tctccaagat aagaatgaac aggcagttca gtcagcccag 1380
accattcagc aactggaaga tcagctccag caaaaatcca aagaaattag ccaatttcta 1440
aatagactgc ccttgcaaca acatgaaaca gcatctcaga cttctttccc agatgtttat 1500
aatgagggca cacaggcagt cactgaggag aatattgctt ctttgcagaa gagagtggta 1560
gaactagaga atgaaaaggg agccttgctc cttagttcta tagagctgga ggagctgaaa 1620
gctgagaatg aaaaactgtc ttctcagatt actctcctag aggctcagaa tagaactggg 1680

```
gaggcagaca gagaagtcag tgagatcagc attgttgata ttgccaacaa gaggagctct   1740
tctgctgagg aaagtggaca agatgttcta gaaaacacat tttctcagaa acataaagaa   1800
ttatcagttt tattgttgga aatgaaagaa gctcaagagg aaattgcatt tcttaaatta   1860
cagctccagg gaaaaagggc tgaggaagca gatcatgagg tccttgacca gaaagaaatg   1920
aaacagatgg agggtgaggg aatagctcca attaaaatga aagtatttct tgaagataca   1980
gggcaagatt ttcccttaat gccaaatgaa gagagcagtc ttccagcagt tgaaaaagaa   2040
caggcgagca ctgaacatca aagtagaaca tctgaggaaa tatctttaaa tgatgctgga   2100
gtagaattga aatcaacaaa gcaggatggt gataaatccc tttctgctgt accagatatt   2160
ggtcagtgtc atcaggatga gttggaaagg ttaaaaagtc aaattttgga gctcgagcta   2220
aactttcata aagcacaaga aatctatgag aaaaatttag atgagaaagc taaggaaatt   2280
agcaacctaa accagttgat tgaggagttt aagaaaaatg ctgacaacaa cagcagtgca   2340
ttcactgctt tgtctgaaga aagagaccag cttctctctc aggtgaagga acttagcatg   2400
gtaacagaat tgagggctca ggtaaagcaa ctggaaatga accttgcaga agcagaaagg   2460
caaagaagac ttgattatga aagccaaact gcccatgaca acctgctcac tgaacagatc   2520
catagtctca gcatagaagc caaatctaaa gatgtgaaaa ttgaagtttt acagaatgaa   2580
ctggatgatg tgcagcttca gttttctgag cagagtaccc tgataagaag cctgcaaagc   2640
cagctgcaaa ataaggaaag tgaagtgctt gagggggcag aacgtgtaag gcatatctca   2700
agtaaagtgg aagaactgtc ccaggctctt tcacagaagg aacttgaaat aacaaaaatg   2760
gatcagctct tactagagaa aaagagagat gtggaaaccc tccaacaaac catcgaggag   2820
aaggatcaac aagtgacaga aatcagcttt agtatgactg agaaaatggt tcagcttaat   2880
gaagagaagt tttctcttgg ggttgaaatt aagactctta aagaacagct aaatttatta   2940
tccagagctg aggaagcaaa aaaagagcag gtggaagaag ataatgaagt ttcttctggc   3000
cttaaacaaa attatgatga gatgagccca gcaggacaaa taagtaagga agaacttcag   3060
catgaatttg accttctgaa gaaagaaaat gagcagagaa agagaaagct ccaggcagct   3120
cttattaaca gaaaggagct tctgcaaaga gtcagtagat tggaagaaga attagccaac   3180
ttgaaagatg aatctaagaa agaaatccca ctcagtgaga ctgagagggg agaagtggaa   3240
gaagataaag aaaacaaaga atactcagaa aaatgtgtga cttctaagtg ccaagaaata   3300
gaaatttatt taaaacagac aatatctgag aaagaagtgg aactacagca tataaggaag   3360
gatttggaag aaaagctggc agctgaagag caattccagg ctctggtcaa acagatgaat   3420
cagaccttgc aagataaaac aaaccaaata gatttgctcc aagcagaaat cagtgaaaac   3480
caagcaatta tccagaagtt aatcacaagt aacacggatg caagtgatgg ggactccgta   3540
gcacttgtaa aggaaacagt ggtgataagt ccaccttgta caggtagtag tgaacactgg   3600
aaaccagaac tagaagaaaa gatactggcc cttgaaaaag aaaaggagca acttcaaaag   3660
aagctacagg aagccttaac ctcccgcaag gcaattctta aaaaggcaca ggagaaagaa   3720
agacatctca gggaggagct aaagcaacag aaagatgact ataatcgctt gcaagaacag   3780
tttgatgagc aaagcaagga aaatgagaat attggagacc agctaaggca actccagatt   3840
caagtaaggg aatccataga cggaaaactc ccaagcacag accagcagga atcgtgttct   3900
tccactccag gtttagaaga acctttattc aaagccacag aacagcatca cactcaacct   3960
gttttagagt ccaacttgtg cccagactgg ccttctcatt ctgaagatgc gagtgctctg   4020
cagggcggaa cttctgttgc ccagattaag gcccagctga aggaaataga ggctgagaaa   4080
```

```
gtagagttag aattgaaagt tagttctaca acaagtgagc ttactaaaaa atcagaagag   4140
gtatttcagt tacaagagca gataaataaa cagggtttag aaatcgagag tctaaagaca   4200
gtatcccatg aagctgaagt ccatgccgaa agcctgcagc agaaattgga aagcagccaa   4260
ctacaaattg ctggcctaga acatctaaga gaattgcaac ctaaactgga tgaactgcaa   4320
aaactcataa gcaaaaagga agaagacgtt agctaccttt ctggacaact tagtgagaaa   4380
gaagcagctc tcactaaaat acagacagag ataatagaac aagaagattt aattaaggct   4440
ctgcatacac agctagaaat gcaagccaaa gagcatgatg agaggataaa gcagctacag   4500
gtggaacttt gtgaaatgaa gcaaaaacca gaagagattg gagaagaaag tagagcaaag   4560
caacaaatac aaaggaaact gcaagctgcc cttatttccc gaaaagaagc actaaaagaa   4620
aacaaaagtc tccaagagga attgtctttg gccagaggta ccattgaacg tctcaccaag   4680
tctctggcag atgtggaaag ccaagtttct gctcaaaata aagaaaaaga tacggtctta   4740
ggaaggttag ctcttcttca agaagaaaga gacaaactca ttacagaaat ggacaggtct   4800
ttattggaaa atcagagtct cagcagctcc tgtgaaagtc taaaactagc tctagagggt   4860
cttactgaag acaaggaaaa gttagtgaag gaaattgaat ctttgaaatc ttctaagatt   4920
gcagaaagta ctgagtggca agagaaacac aaggagctac aaaaagagta tgaaattctt   4980
ctgcagtcct atgagaatgt tagtaatgaa gcagaaagga ttcagcatgt ggtggaagct   5040
gtgaggcaag agaaacaaga actgtatggc aagttaagaa gcacagaggc aaacaagaag   5100
gagacagaaa agcagttgca ggaagctgag caagaaatgg aggaaatgaa agaaaagatg   5160
agaaagtttg ctaaatctaa acagcagaaa atcctagagc tggaagaaga gaatgaccgg   5220
cttagggcag aggtgcaccc tgcaggagat acagctaaag agtgtatgga aacacttctt   5280
tcttccaatg ccagcatgaa ggaagaactt gaaagggtca aaatggagta tgaaaccctt   5340
tctaagaagt ttcagtcttt aatgtctgag aaagactctc taagtgaaga ggttcaagat   5400
ttaaagcatc agatagaaga taatgtatct aaacaagcta acctagaggc caccgagaaa   5460
catgataacc aaacgaatgt cactgaagag ggaacacagt ctataccagg tgagactgaa   5520
gagcaagact ctctgagtat gagcacaaga cctacatgtt cagaatcggt tccatcagcg   5580
aagagtgcca accctgctgt aagtaaggat ttcagctcac atgatgaaat taataactac   5640
ctacagcaga ttgatcagct caaagaaaga attgctggat tagaggagga gaagcagaaa   5700
aacaaggaat ttagccagac tttagaaaat gagaaaaata ccttactgag tcagatatca   5760
acaaaggatg gtgaactaaa aatgcttcag gaggaagtaa ccaaaatgaa cctgttaaat   5820
cagcaaatcc aagaagaact ctccagagtt accaaactaa aggagacagc agaagaagag   5880
aaagatgatt tggaagagag gcttatgaat caattagcag aacttaatgg aagcattggg   5940
aattactgtc aggatgttac agatgcccaa ataaaaaatg agctattgga atctgaaatg   6000
aagaacctta aaaagtgtgt gagtgaattg gaagaagaaa agcagcagtt agtcaaggaa   6060
aaaactaagg tggaatcaga aatacgaaag gaatatttgg agaaaataca aggtgctcag   6120
aaagaacccg gaaataaaag ccatgcaaag gaacttcagg aactgttaaa agaaaaacaa   6180
caagaagtaa agcagctaca gaaggactgc atcaggtatc aagagaaaat tagtgctctg   6240
gagagaactg ttaaagctct agaatttgtt caaactgaat ctcaaaaaga tttggaaata   6300
accaaagaaa atctggctca agcagttgaa caccgcaaaa aggcacaagc agaattagct   6360
agcttcaaag tcctgctaga tgacactcaa agtgaagcag caagggtcct agcagacaat   6420
ctcaagttga aaaaggaact tcagtcaaat aaagaatcag ttaaaagcca gatgaaacaa   6480
```

-continued

```
aaggatgaag atcttgagcg aagactggaa caggcagaag agaagcacct gaaagagaag   6540
aagaatatgc aagagaaact ggatgctttg cgcagagaaa aagtccactt ggaagagaca   6600
attggagaga ttcaggttac tttgaacaag aaagacaagg aagttcagca acttcaggaa   6660
aacttggaca gtactgtgac ccagcttgca gcctttacta agagcatgtc ttccctccag   6720
gatgatcgtg acagggtgat agatgaagct aagaaatggg agaggaagtt tagtgatgcg   6780
attcaaagca aagaagaaga aattagactc aaagaagata attgcagtgt tctaaaggat   6840
caacttagac agatgtccat ccatatggaa gaattaaaga ttaacatttc caggcttgaa   6900
catgacaagc agatttggga gtccaaggcc cagacagagg tccagcttca gcagaaggtc   6960
tgtgatactc tacaggggga aaacaaagaa cttttgtccc agctagaaga gacacgccac   7020
ctataccaca gttctcagaa tgaattagct aagttggaat cagaacttaa gagtctcaaa   7080
gaccagttga ctgatttaag taactcttta gaaaaatgta aggaacaaaa aggaaacttg   7140
gaagggatca taaggcagca agaggctgat attcaaaatt ctaagttcag ttatgaacaa   7200
ctggagactg atcttcaggc ctccagagaa ctgaccagta ggctgcatga agaaataaat   7260
atgaaagagc aaaagattat aagcctgctt tctggcaagg aagaggcaat ccaagtagct   7320
attgctgaac tgcgtcagca acatgataaa gaaattaaag agctggaaaa cctgctgtcc   7380
caggaggaag aggagaatat tgttttagaa gaggagaaca aaaaggctgt tgataaaacc   7440
aatcagctta tggaaacact gaaaaccatc aaaaaggaaa acattcagca aaaggcacag   7500
ttggattcct ttgttaaatc catgtcttct ctccaaaatg atcgagaccg catagtgggt   7560
gactatcaac agctggaaga gcgacatctc tctataatct tggaaaaaga ccaactcatc   7620
caagaggctg ctgcagagaa taataagctt aaagaagaaa tacgaggctt gagaagtcat   7680
atggatgatc tcaattctga gaatgccaag ctagatgcag aactgatcca atatagagaa   7740
gacctgaacc aagtgataac aataaaggac agccaacaaa agcagcttct tgaagttcaa   7800
cttcagcaaa ataaggagct ggaaaataaa tatgctaaat tagaagaaaa gctgaaggaa   7860
tctgaggaag caaatgagga tctgcggagg tcctttaatg ccctacaaga agagaaacaa   7920
gatttatcta aagagattga gagtttgaaa gtatctatat cccagctaac aagacaagta   7980
acagccttgc aagaagaagg tactttagga ctctatcatg cccagttaaa agtaaaagaa   8040
gaagaggtac acaggttaag tgctttgttt tcctcctctc aaaagagaat tgcagaactg   8100
gaagaagaat tggtttgtgt tcaaaaggaa gctgccaaga aggtaggtga aattgaagat   8160
aaactgaaga aagaattaaa gcatcttcat catgatgcag ggataatgag aaatgaaact   8220
gaaacagcag aagagagagt ggcagagcta gcaagagatt tggtggagat ggaacagaaa   8280
ttactcatgg tcaccaaaga aaataaaggt ctcacagcac aaattcagtc ttttggaagg   8340
tctatgagtt ccttgcaaaa tagtagagat catgccaatg aggaacttga tgaactgaaa   8400
aggaaatatg atgccagtct gaaggaattg gcacagttga aagaacaggg actcttaaac   8460
agagagagag atgctcttct ttctgaaacc gccttttcaa tgaactccac tgaggagaat   8520
agcttgtctc accttgagaa acttaaccaa cagctcctat ccaaagatga gcaattgctt   8580
cacttgtcct cacaactaga agattcttat aaccaagtgc agtccttttc caaggctatg   8640
gccagtctgc agaatgagag agatcacctg tggaatgagc tggagaaatt tcgaaagtca   8700
gaggaaggga agcagaggtc tgcagctcag ccttccacca gcccagctga agtacagagt   8760
ttaaaaaaag ctatgtcttc actccaaaat gacagagaca gactactgaa ggaattgaag   8820
aatctgcagc agcaatactt acagattaat caagagatca ctgagttaca tccactgaag   8880
```

```
gctcaacttc aggagtatca agataagaca aaagcatttc agattatgca agaagagctc   8940
aggcaggaaa acctctcctg gcagcatgag ctgcatcagc tcaggatgga gaagagttcc   9000
tgggaaatac atgagaggag aatgaaggaa cagtacctta tggctatctc agataaagat   9060
cagcagctca gtcatctgca gaatcttata agggaattga ggtcttcttc ctcccagact   9120
cagcctctca aagtgcaata ccaaagacag gcatccccag agacatcagc ttccccagat   9180
gggtcacaaa atctggttta tgagacagaa cttctcagga cccagctcaa tgacagctta   9240
aaggaaattc accaaaagga gttaagaatt cagcaactga acagcaactt ctctcagcta   9300
ctggaagaga aaaacaccct ttccattcag ctctgcgata ccagtcagag tcttcgtgag   9360
aaccagcagc actatggtga ccttttaaat cactgtgcag tcttggagaa gcaggttcaa   9420
gagctgcagg cggggccact aaatatagat gttgctccag gagctcccca ggaaaagaat   9480
ggagttcaca gaaagagtga ccctgaggaa ctaagggaac cgcagcaaag cttttctgaa   9540
gctcagcagc agctatgcaa caccagacag gaagtgaatg aattaaggaa gctgctggaa   9600
gaagaacgag accaaagagt ggctgctgag aatgctctct ctgtggccga ggagcagatc   9660
agacggttag agcacagtga atgggactct tcccggactc ctatcattgg ctcctgtggc   9720
actcaggagc aggcactgtt aatagatctt acaagcaaca gttgtcgaag gacccggagt   9780
ggcgttggat ggaagcgagt cctgcgttca ctctgtcatt cacggacccg agtgccactt   9840
ctagcagcca tctactttct aatgattcat gtcctgctca ttctgtgttt tacgggccat   9900
ctatagactt agttgttact ctttggacca ctcccttcaa aacttggaat tctctcacct   9960
ctaacatcag aacatcaatt ccagtggaac agtcttccca tttacaggtc ttctctccaa  10020
ctcttcacgg aaagtgcctg caaaaacaga ggtggatacg aggacaggtt ggagctgcag  10080
ggactggcga gtctgctttc ttctactgcc ctgagcctga acgcttctgc ttaatctgag  10140
aatcacattt ggtttgttga gcctaatatt tgttgagatt ttgcaggacc ctgatctttt  10200
gtggtcctgt aaaagatact gaggaatgtc tttcagccaa gccaagagga tggtttcaat  10260
aaacctaata atctgaagtt cagctttttt ttttttttt                          10300
```

<210> SEQ ID NO 50
<211> LENGTH: 2357
<212> TYPE: DNA
<213> ORGANISM: Human

<400> SEQUENCE: 50

```
gaggagacgc gctttgtgct gggcgccggc cgcgccagcc acggcctgcg gcgcccgcgg     60
caccatgatc tccaccaagg agaagaacaa gatcccgaag gacagcatga cgcttctgcc    120
ctgcttctac ttcgtggagc tgcccatagt ggcttcttcc atcgtatcct tgtacttcct    180
ggagctgacc gacctcttca agccggccaa ggtgggcttc cagtgctatg accgcactct    240
ctccatgccc tacgtggaga ccaacgagga gctcatcccg ctgctgatgc tgctcagctt    300
ggccttcgcg gcccctgccg cctcgatcat ggtggccgag ggcatgttgt actgtctgca    360
gtcccggctg tggggccgtg ccgggggggcc cgccggggcg gagggcagca tcaacgccgg    420
cggctgcaac ttcaactcct tcctgcggcg tacggtgcgg tttgtgggtg tccacgtgtt    480
cggcctgtgt gccacagccc tggtgacgga cgtgatccag ctggccacgg gttaccacac    540
tcccttcttc ctcaccgtct gcaagcccaa ctacactctc ctgggcacgt cctgcgaggt    600
caacccctac atcacgcagg acatctgctc cggccacgac atccacgcca tcctgtctgc    660
acggaagacc ttcccgtccc agcacgccac gctgtcagcc ttcgccgcgg tctatgtgtc    720
```

ggtgagtccg gcacctcact gcccttccca ggccctcttg ctgacccgtg gggagccctc 780
cctgacccca acccccatgc cccagatgta cttcaactcg gtcatctcgg acaccaccaa 840
gctgctgaag cccatcctgg tcttcgcctt tgccatcgcc gcgggcgtat gcgggctcac 900
gcagatcacg cagtaccgca gccaccctgt ggacgtgtat gccggcttcc tcatcggggc 960
gggcatcgct gcctacctgg cctgccacgc ggtgggcaac ttccaggccc cacctgcaga 1020
gaagcccgcg gccccggccc ccgccaagga cgcgctgcgg gccctgacgc agcggggcca 1080
cgactcggtt tatcagcaga ataagtcggt gagcaccgac gagctggggc ccccagggcg 1140
gctggagggc gcgccccggc ccgtggcccg cgagaagacc tcgctgggca gcctgaagcg 1200
cgccagcgtg gacgtggacc tgctggcccc gcgcagcccc atggccaagg agaacatggt 1260
gaccttcagc cacacgctgc ccagggccag cgcgccctcg ctggacgacc ccgcgcgccg 1320
ccacatgacc atccacgtgc cgctggacgc ctcgcgctcc aagcagctca tcagcgagtg 1380
gaagcagaag agcctggagg gccgcggcct ggggctgccc gacgacgcca gccccgggca 1440
cctgcgcgcg cccgccgaac ccatggcgga ggaggaggaa gaggaggagg acgaagagga 1500
agaggaggag gaggaagagg aggaggacga gggcccggcc ccgccctcgc tctaccccac 1560
cgtgcaggcg cggccggggc tggggcctcg ggtcatcctc ccaccgcgcg cggggccgcc 1620
gccgctggtg cacatcccgg aggagggcgc gcagacgggg gccggcctgt cccccaaaag 1680
cggcgccggg gtgcgcgcca agtggctcat gatggccgag aagagcgggg cggcagtggc 1740
caaccctccg cggctgctgc aggtcatcgc catgtccaag gctccgggcg cgccgggccc 1800
caaggcggcc gagacggcgt cgtcgtccag cgccagctcc gactcctcgc agtaccggtc 1860
gccgtcggac cgcgactccg ccagcatcgt gaccatcgac gcgcacgcgc cgcaccaccc 1920
cgtggtgcac ctgtcggccg gcggcgcgcc ctgggagtgg aaggcggcgg gcggcggggc 1980
caaggcggag gccgacggcg gctacgagct gggggacctg gcgcgcggct tccgcggcgg 2040
ggccaagccc ccgggcgtgt cccccggctc gtcggtcagc gacgtggacc aggaggagcc 2100
gcggttcggg gccgtggcca ccgtcaacct ggccacgggc gaggggctgc ccccgctggg 2160
cgcggccgat ggggcgctgg gcccgggcag ccgggagtcc acgctgcggc gccacgcggg 2220
cggcctgggg ctggcggagc gcgaggcgga ggcggaggcc gagggctact tccgcaagat 2280
gcaggcgcgc cgcttccccg actagcgcgg cggggccggg ggcgggcggg gggcgggccg 2340
agggcgcggg cggccgc 2357

<210> SEQ ID NO 51
<211> LENGTH: 3496
<212> TYPE: DNA
<213> ORGANISM: Human

<400> SEQUENCE: 51
aagattttac tgacaatttg gagctagatg aagaaggagc aggcgggttc acggctaaag 60
caatcgttca gagagacaga gtggatgaag aggccttgaa tttcccctac gaggatgact 120
ttgacaacga tgtggatgct ctgctggaag aaggcctttg tgcccccaaa aagaggcgaa 180
cagaggaaaa atatggcgga gacagcgacc atctgtccga tggagagaca agtgtgcagc 240
cgatgatgac caagattaaa acagtgctca aaagtcgtgg ccgcccacct acagagccgc 300
tgcccgacgg gtggatcatg acattccata actctggagt cccggtgtac ctacacagag 360
agtctcgggt ggtcacctgg tccaggccat acttcttggg aacgggaagc atacggaaat 420
acgaccctcc tctgagtagc atcccttgtc tgcattataa gaaaatgaag gacaacgagg 480

-continued

```
aacgggagca aagcagtgac ctcaccccta gtggggatgt gtcccccgtc aagcccctga    540
gccgatctgc agagctggag tttcccctgg atgagcctga ctctatgggt gctgacccgg    600
ggcccccgga cgagaaagac ccactagggg ctgaggcagc cctggggcc ctggggcagg    660
tgaaggccaa agtcgaggtg tgcaaagatg aatccgttga tctcgaggaa tttcgaagct    720
acctggagaa gcgttttgac tttgagcaag ttactgtgaa aaaattcagg acttgggctg    780
agcggcggca attcaatcgg gaaatgaagc ggaagcaggc ggagtccgag aggcccatct    840
tgccagccaa tcagaagctc attactttat cagtgcaaga tgcacccaca aagaaagagt    900
ttgttattaa ccccaacggg aaatccgagg tctgcatcct gcacgagtac atgcagcgtg    960
tcctcaaggt ccgccctgtc tataatttct ttgaatgtga gaacccaagt gagccttttg   1020
gtgcctcggt gaccattgat ggtgtgactt acggatctgg aactgcaagc agcaaaaaac   1080
ttgcgaagaa taaagctgcc cgagctacac tggaaatcct catccctgac tttgttaaac   1140
agacctctga agagaagccc aaagacagtg aagaactcga gtattttaac cacatcagca   1200
tcgaggactc gcgggtctac gagctgacca gcaaggctgg gctgttgtct ccatatcaga   1260
tcctccacga gtgccttaaa agaaaccatg ggatgggtga cacgtctatc aagtttgaag   1320
tggttcctgg gaaaaaccag aagagtgaat acgtcatggc gtgtggcaag cacacagtgc   1380
gcgggtggtg taagaacaag agagttggaa agcagttagc ctcacagaag atccttcagc   1440
tgctgcaccc acatgtcaag aactgggggt ctttactgcg catgtatggc cgtgagagca   1500
gcaagatggc caagcaggag acatcggaca agagtgtgat tgagctgcag cagtatgcca   1560
agaagaacaa gcccaacctg cacatcctca gcaagctcca agaggagatg aagaggctag   1620
ctgaggaaag ggaggagact cgaaagaagc ccaagatgtc cattgtggcg tccgcccagc   1680
ctggcggtga gcccctgtgc accgtggacg tgtgagggag gtggcacggg ccagggcgcg   1740
ggggccgcca gccgcacttc tgaggagacc agcagtcatg catcgtgcac cacagtgtca   1800
ggcctccaac ccacgctcct tccctgtggc caacctgtgg gcccggcctt agggtggaga   1860
ctttagtgta cagggacagc catggccaca cagcacacat gtggagcagc ggctctccct   1920
ggaaagctcc aggcctgaat ggatggactc agcgactgca ccagtggcag ctggtgactg   1980
tggacagtgg tggaccctgc ttctgtgcac ctgctgcagg ctctttttat gaaggctttc   2040
atgaatttta gtatgtaata cgcactgacg acacatgatg cttggatgac agatgagagg   2100
ggatggctga gtcctgtggc tggcccgtga tgccaggtgg cccatgtgcc cagggcgcct   2160
gcagggctgc tacagggacc tggtcaggag gtgcacatgg tgccctgccc tcacccaccc   2220
tctgtgtttc cccttctttg aaaaggtaga agagaaagga atattttaaa ccttttttggc   2280
ttaaacagaa ttttagcatc agaactagct ttctgggatt ggaggcaaac catcaaggtg   2340
gtccctctcc agtctggaca cgatgccagc aaggatgacg tcctgccacc tcctggagtt   2400
accctggcct cctagggtcc ctttttctga tgaagtctta attccctaaa agcgcctctt   2460
tggacactga ggccctctct gcctttcctg gcctccggca acagtttttt tacaaagatt   2520
ttttgcagtc gagtccatat gtccacccat tgatttttaa agcttttgtg atattttagc   2580
attttgaaag actttcacag tgagagtaga aggtagattt ggaatcatgc attttagcaa   2640
gtggacttgt tgaaacagga agcaagggcc ttcagtgtag cccattcttg atccagagct   2700
gttgcctgtg acagcggttt ctctggatgt caaaggcagc tgcctggtgc ccagcttgct   2760
tctcgactgg tggcccctat gggtgggtgt gcgatggaaa tgtgttcctg ccggagtctg   2820
aggcaccagg gtgtgctcaa aggctggccc tggtggtgga ctggcacctg tgcagagtgc   2880
```

cgtgtgcttg tggtgcgcca tctgaagcaa gagtccagcg ttctgccgtg tctgtccccc 2940
accatgcccc ctacaggcgg tactgatggc gcttttttt ttttttttct gtcaggaaaa 3000
caatgttggc ctgtgggccg cccacaacat atccttccct cactacctgt gtgaccaagg 3060
ttggcttctg ttgacctttt aaaaaagaaa ccctcaactc aaattgctat aattagacac 3120
ttgcttctgt cttgcctcct gtctgcagct gtgaatagtc atttgactgt gactgttgcc 3180
cttagccagc cagatgcgcc tgtgaaccaa agcttcgtgc acatgtgttc ccctaaaggt 3240
tggggagcct cgctgtgtct tgctgttccc aggcaccacc acagcaggtg ctgccatact 3300
cttgtggtct ctgtgcgccc cccccccccc cacccgtctg ccaagcatgg gtatgaatcg 3360
tgcacacagc catgcttcaa ggccggggca ggggagcctg tgctgatgcc atccagggca 3420
ctgggctgtg cctggaaggc gagccttgat tgtctgaaca cataaagcaa actgtccaga 3480
aaaaaaaaaa aaaaaa 3496

<210> SEQ ID NO 52
<211> LENGTH: 3508
<212> TYPE: DNA
<213> ORGANISM: Human

<400> SEQUENCE: 52
gcaacagccc agccctagct tgggagcgga cccacacgaa ctgctcaaag gcttggagcg 60
ggtctagtaa ggcgaacgga ctgcttccgg ccagaggtcc cgggcggagg aggaagctgt 120
ggctgccggc ggtgggacgc cccggccgct cagcccccgg gcactgctgt ggggcgttca 180
gctttccaca cttggggcaa agcaagccgc gaggaggaac cagacagtcc tgttagttgt 240
ggccagccct cattccctgg aaatggcaaa caaggggaac aagaagcgtc ggcagttctc 300
tctggaggag aaaatgaaag ttgtgggagc tgtagactca ggcaagagga aaggtgatgt 360
ggcaaaagaa tttggtatca ctccctctac tttatctaca ttcttaaagg atcgcaccaa 420
atttgaagaa aaggtgcggg aggcatccgt gggaccccag cggaaaagga tgaggagcgc 480
tctttatgat gacattgata aggctgtttt tgcttggttt caagaaatcc atgccaaaaa 540
cattcttgtg actggttctg tcattcggaa aaaagcacta aacttggcca acatgcttgg 600
ctatgacaat tttcaagcaa gtgtgggctg gctgaacaga tttagagatc gccacggaat 660
tgctttgaaa gcagtctgta gagaagatag tgacaggtta atgaatggtc taggaataga 720
taagattaat gagtggcatg caggggaaat tataaaactg attgctgact acagcccaga 780
tgatatcttt aatgctgatg agacaggagt gtttttccag ttgcttcccc agcacacact 840
tgctgctaaa ggagaccact gtagaggggg caagaaagca aagcagcggt tgacagcact 900
cttttgttgc aatgcctcgg ggactgaaaa aatgagacca ttgattgttg gtaggtcagc 960
cagcccacac tgcctcaaga acattcattc cctcccttgt gattaccgag ccaaccagtg 1020
ggcttggatg acaagggatc tgtttaatga gtggctgatg caagtggatg ccaggatgaa 1080
gagggcggaa cgccggatcc tcttgctcat agacaactgc tctgctcata acatgcttcc 1140
acacttggaa aggattcagg ttgggtatct gccctccaac tgtactgctg tcctgcagcc 1200
actgaatctt ggcataattc acaccatgaa agtactgtac cagagccacc ttctaaaaca 1260
gatcctcctc aagctcaaca gcagtgagga tcaagaagag gtggacatca agcaggccat 1320
cgacatgatt gctgcagcgt ggtggtcagt caagccatcc acagtggtga aatgttggca 1380
gaaggcaggc atcgtcccta tggaatttgc agaatgtgac acagaatcag cagccagtga 1440
accagacatt gccattgaaa agttgtggca cacagtggct attgccacct gtgtcccaaa 1500

```
tgaagtaaat ttccaggact ttgttactgc agatgatgat ctcattatct ctcaggacac   1560

agacatcatc caggacatgg tggctggcga aaataccagt gaagcaggaa gtgaagatga   1620

aggggaggta tctttaccag agcaaccaaa agtcaccatc acagaagcca tatcaagtgt   1680

acagaaactt agacagttcc tttccacttg tgtagacatt cctgatgcca tttttggaca   1740

attaaatggc atagatgaat atttaatgaa aagagtgaca caaaccctta ttgattccaa   1800

aattacagat ttcctccaaa caaaataatg caggaattta tttcagaaaa tgtagtttac   1860

aagaataaag atttctttag ataggttgtt gagccaattt aagtaaagca atgttattgt   1920

gacaacattc cagtactctg aaatagccag gaaacttctt tgaatggaat ttgactaata   1980

tgtgtgtttt cttttctttt gtttttggct gtctctggtc cttgattcaa gatgtatttt   2040

gattcatcca agggtttcca aacttgtctg caaattagga tcacttgaga atcctttaaa   2100

aattccaaag ctcaggccat atcccaggcc tattaaatca caatctttgg tgacgggtca   2160

caggcattgg tagttttgaa gctctccagg tgattccaat gtgcagacaa atttgaaaac   2220

tgaaccaacc acaggaacat caagtacact gtgggcctgg gtccagcttc tttccagtaa   2280

gtgtatctca ggggcttcca aatttagctt acatcagaat cacttggaag gcttgttaaa   2340

acccaaggct gctaggccca cccccagagt ttgatacagt agacctcagg tgggacccaa   2400

aaatttgcat ttctaacaca ttctcagctg atgcagtcca ggctccatgc tttgaaaacc   2460

actggtctag ctttagatag gatattgagc caatttaaat aaagcaatat actggtctag   2520

ctgagttcta gaacttctct ctttagctgg ccatctgaat actcccccat cactaattgt   2580

taaaaaaaga atcaactgtt cttactctag agctcttttt tcctttctgc tgatttgctg   2640

gaagcactac aagacttctg tttgttcgtt cgtttgtttg tttgtttgtt tttaaagatg   2700

gggtcttgtt atattgccta ggctggaatg cagtggttat tcacaggcat gattataaca   2760

cactactctc tctaactcct ggcctcaagc catcctccca aatagatggg actactgatg   2820

cacactgcca tgctggcctt acgaaatgtt ttaataggca tttcactaat agggatctgg   2880

agtacaagga aatacagtgc atttaagaca taggctgggc atggtggctc atgcctgtaa   2940

tcccagcaca ttgggaagat cacttgaggc aaggagtttg agaccagact ggccaacaca   3000

gcgagacccc catctctaaa aaaaaaaaaa ttaataagac atggatacaa ccagggaggg   3060

aggttataat aatagagcat cctgttaatc agaatcatgg gggagaacat acagcccagc   3120

gtgcctctca ctttccagaa agggtgagag gatcattaga gagttcatta gagagtattt   3180

attcctaata agtcagataa atgtcagttt catttttaga agtttcacac aatacctgct   3240

aatggtgtga tgtcattttt ccccctgctt caggttaatt ttttggatat ttcagaaacc   3300

catagcaatt cagtgatttt tctttttgta gtagctcagt caaaacaggt aacagcagat   3360

taatcataga aaatgttgct tccacattaa caaaacaatc actgaaaaac agcagatgtt   3420

taaatagatt attttatagc ttattttgga tattttttct tttaataaac taatatgatc   3480

atttgaatta aaaaaaaaaa aaaaaaaa                                     3508
```

<210> SEQ ID NO 53
<211> LENGTH: 1391
<212> TYPE: DNA
<213> ORGANISM: Human

<400> SEQUENCE: 53

```
tgcactcacc tcctagagac caggctgcca tcatgctctg gaagcttgtg gagaatgtca     60

agtacgaaga tatctatgag gaccggcacg atggtgtccc gagccacagc tcgcggctct    120
```

```
cccagctggg ctcggtgtcc caaggaccct actcgagcgc cccgccgctg tcccacaccc    180
cgtcgtcgga cttccagccg ccctacttcc cacccccta ccagccgctc ccctaccacc     240
agagccagga cccctactcc cacgtcaacg accccctactc cctgaaccca ctgcaccagc   300
cccagcaaca tccctggggg caacggcagc ggcaagaagt gggttcggaa gccggctctc    360
tcctgcccca gcctcgggcc gccttgcccc agctctcggg ccttgacccc cggagggact    420
accactcggt ccgccggccg gacgtgctgc tgcattcggc gcaccacggc ctggacgcgg    480
gcatgggtga cagcctctcg ctgcacggcc tcggccatcc cggaatggaa gacgtccagt    540
cagttgaaga tgccaataac agcggcatga atctattgga ccagtctgtc attaaaaaag    600
ttccagttcc tcccaaatcg gtgacttctc taatgatgaa taaagacggc ttcctgggag    660
gcatgtctgt caacaccggc gaggtgtttt gctccgtccc aggccgtttg tctctgctca    720
gttcaacttc gaagtacaaa gtaactgtgg gagaagttca gagacggctg tcgcccccctg   780
aatgcctcaa tgcatctctc ctcggcggag tcctcagaag agccaaatcg aaaaatgggg    840
ggagatcttt gcgagaaagg ctagaaaaaa tcggtttgaa tttacccgcg ggcaggcgca    900
aagcagcaaa tgtcacgtta ctcacctccc tggtggaagg agaagctgtt cacttagcta    960
gggattttgg gtacatttgc gaaacggagt ttcccgccaa agccgtctct gagtatttga   1020
accggcagca cacagacccg agtgacctgc actcccgaaa gaatatgctg ttggccacca   1080
agcaactttg taaagaattt acggatctac tggcgcagga ccggacaccg atagggaaca   1140
gccgacccag ccccatcctg gagccgggga tccagagctg cctcacgcac ttcagcctca   1200
tcacgcacgg cttcggcgcc ccggccattt gcgccgcgct cacggccctg cagaactatc   1260
tcaccgaggc gctcaaaggc atggacaaga tgttcttgaa caacaccacc actaacaggc   1320
acacgtctgg ggaaggccca ggtagtaaaa ctggcgacaa ggaggagaaa cacaggaaat   1380
gaaaaatttt t                                                        1391
```

<210> SEQ ID NO 54
<211> LENGTH: 4862
<212> TYPE: DNA
<213> ORGANISM: Human

<400> SEQUENCE: 54

```
acgcagctcc gccccgcgtc cgacccgcgg atcccgcggc gtccggcccg ggtggtctgg     60
atcgcggagg gaatgccccg gagggcggag aactgggacg aggccgaggt aggcgcggag    120
gaggcaggcg tcgaagagta cggccctgaa gaagacggcg gggaggagtc gggcgccgag    180
gagtccggcc cggaagagtc cggcccggag gaactgggcg ccgaggagga gatggaggcc    240
gggcggccgc ggcccgtgct gcgctcggtg aactcgcgcg agccctccca ggtcatcttc    300
tgcaatcgca gtccgcgcgt cgtgctgccc gtatggctca acttcgacgg cgagccgcag    360
ccctacccaa cgctgccgcc tggcacgggc cgccgcatcc acagctaccg aggtcacctt    420
tggctcttca gagatgcagg gacacacgat gggcttctgg ttaaccaaac tgaattattt    480
gtgccatctc tcaatgttga cggacagcct atttttgcca atatcacact gccagtgtat    540
actctgaaag agcgatgcct ccaggttgtc cggagcctag tcaagcctga gaattacagg    600
agactggaca tcgtcaggtc gctctacgaa gatctggaag accacccaaa tgtgcagaaa    660
gacctggagc ggctgacaca ggagcgcatt gcacatcaac ggatgggaga ttgaagattt    720
ctgttgaaac ttacactgtt tcatctcagc ttttgatggt actgatgagt cttgatctag    780
atacaggact ggttccttcc ttagtttcaa agtgtctcat tctcagagta aaataggcac    840
```

-continued cattgcttaa aagaaagtta actgacttca ctaggcattg tgatgtttag gggcaaacat 900
cacaaaatgt aatttaatgc ctgcccatta gagaagtatt tatcaggaga aggtggtggc 960
atttttgctt cctagtaagt caggacagct tgtatgtaag gaggtttata taagtaattc 1020
agtgggaatt gcagcatatc gtttaatttt aagaaggcat tggcatctgc ttttaatgga 1080
tgtataatac atccattcta catccgtagc ggttggtgac ttgtctgcct cctgctttgg 1140
gaagactgag gcatccgtga ggcagggaca agtctttctc ctctttgaga ccccagtgcc 1200
tgcacatcat gagccttcag tcagggtttg tcagaggaac aaaccagggg acactttgtt 1260
agaaagtgct tagaggttct gcctctattt ttgttggggg gtgggagagg ggaccttaaa 1320
atgtgtacag tgaacaaatg tcttaaaggg aatcattttt gtaggaagca tttttataa 1380
ttttctaagt cgtgcacttt ctcggtccac tcttgttgaa gtgctgtttt attactgttt 1440
ctaaactagg attgacattc tacagttgtg ataatagcat ttttgtaact tgccatccgc 1500
acagaaaata cgagaaaatc tgcatgtttg attatagtat taatggacaa ataagttttt 1560
gctaaatgtg agtatttctg ttcctttttg taaatatgtg acattcctga ttgatttggg 1620
tttttttgtt gttgttgttt tgttttgttt tgtttttttg ggatggagkc tcactcttgt 1680
cacccaggct ggagtgcagt ggcgccatct cggctcactg caacctctgc ctcctgagtt 1740
cacgtaatcc tcctgagtag ctgggattac aggtgcctgc caccacgctg gccaattttt 1800
gtacttttag tagagacagt gtttcgccat gttggccagg ctggtttcaa actcctgacc 1860
tcaggtgatc cgcccacctc agcctcccaa aatggtggga ttacaggtgt gtgggccacc 1920
gtgcctggct gattcagcat tttttatcag gcaggaccag gtggacttcc acctccagcc 1980
tctggtccta ccaatggatt catggagtag cctggactgt ttcatagttt tctaaatgta 2040
caaattctta taggctagac ttagattcat taactcaaat tcaatgcttc tatcagactc 2100
agtttttttgt aactaataga tttttttttc cacttttgtt ctactccttc cctaatagct 2160
ttttaaaaaa atctccccag tagagaaaca tttggaaaag acagaaaact aaaaaggaag 2220
aaaaaagatc cctattagat acacttctta aatacaatca cattaacatt ttgagctatt 2280
tccttccagc ctttttaggg cagattttgg ttggttttta catagttgag attgtactgt 2340
tcatacagtt ttataccctt tttcatttaa ctttataact taaatattgc tctatgttag 2400
tataagcttt tcacaaacat tagtatagtc tccctttttat aattaatgtt tgtgggtatt 2460
tcttggcatg catctttaat tccttatcct agcctttggg cacaattcct gtgctcaaaa 2520
atgagagtga cggctggcat ggtggctccc gcctgtaatc ccagtacttt gggaagccaa 2580
ggtaagagga ttgcttgagc ccagaacttc aagatgagcc tgggctcata gtgagaaccc 2640
gtctatacaa aaaattttta aaaattagca tggcggcaca catctgtaat cctagctact 2700
tggcaggctg aggtgagaag atcattggag tttaggaatt ggaggcggca gtgagtcatg 2760
agtatgccgc tgcactccag cctgggggac agagcaagac cctgcctcaa aaaaaaaaaa 2820
aaaaaaaatt caggccggga atggtggttc acgcctgtaa tcccagcact ttggggggtc 2880
gaggtgggca gatcacctga ggtcaggagt tcgagaccag cctggccaac atggtaaaac 2940
cccatttcta ctaaaaaata caagaattag ctgggtgtgg tggcgcatgc ctgtaatcct 3000
agctactcag gaggctgagg caggagaatc acttgacccc aggaggcgaa gattgcagtg 3060
agctgatatc gcaccattgt actccagcct gtgtgacaga gcaatactct tgtcccaaaa 3120
aaaaaaaaaa ttcaaatcag agtgaagtga atgagacact ccagttttcc ttctactccg 3180
aattttagct cctcctttca acattcaaca aatagtcttt tttttttttt ttttttttg 3240

```
gggatggagt ctccctctgt tgcccaggct ggagtgcaga ggtgcgatct ctgctcacta   3300

caagctctgc ctcccgagtt caagtgattc tcctggctca ccctcctgag ctgggattac   3360

aggcgcctgc caccatgcct ggctaatttt gtgtttttag tggagacggg gtttcaccat   3420

gttgtccagg atggtcttga tctcctgacc ttgtgatcca cccacctcag cctcccaaag   3480

tggtgggatt acaggtgtga gccaccgcgt ccagccagct ttattatttt ttttaagctg   3540

tctttgtgtc aaaatgatag ttcatgctcc tcttgttaaa acctgcaggc cgagcacagt   3600

ggctcatgcc tgtaatccca gcattttggg agaccaaggc ggatggatca cctgaggtca   3660

ggagctcaag accagcctgg ctaacatggt gaaacctcat ctccacttaa aatacaaaaa   3720

ttgccggccg cggcggctca tgcctgtaat cccagcactt tgggaggcct aggcgggtgg   3780

atcacgacgt caggaaatcg agaccatcct ggctaacacg ggtgaaaccc cgtctctatt   3840

aaaaaataga aaaaattagg cgggcgtggt ggtgagcgcc tgtagtccca gctactcgag   3900

agcctgaggc aggagaatgg catgaacctg gaaggtggag cttgcagtga gctgagatgg   3960

tgccactgca ctctaacctg ggcgacagag tgagactccg tctcaaaaaa aaaaacaaaa   4020

accaaaactt atccaggtgt ggcggtgggc gcctgtgagg caggcgaatc tcttgaaccc   4080

gggaggcgga ggttgcagtg agccaagatc acaccattgc actccagcct gggaaacaag   4140

agtgaaattc catctcaaaa ccaaattttc aaaaaaaaaa catgccgctt gagtactgtg   4200

tttttggtgt tgtccaagga aaattaaaac ctgtagcatg aataatgttt gttttcattt   4260

cgaatcttgt gaatgtatta aatatatcgc tcttaagaga cggtgaagtt cctatttcaa   4320

gtttttttg ttttgtttg tttttaagct gtttttaat acattaaatg gtgctgagta   4380

aaggaaatag gcagggtgtg ttgtgtggtg ttttaactag gcgcttctct ctcagagagt   4440

tttgaaacct gtttacataa aggcccaaga tgggaaggag atccaaacat aagccaccag   4500

cctcattcca agtctcttct ctttccaacc ctggattttt ttttttatt taacattgtt   4560

tcttttagct ttatttttct tataaaagaa atgtatcact ataaaaaatt acacactaca   4620

gaaaaatatt aagaagaaaa acattcacat cggaaacaaa gtttttccc atgaaaacag   4680

aacccaaaag ggtaagtggt tagtatttca ccagcaatta tgttgagaat aaggccaggc   4740

gaggtggctc acgcctgtaa tctcagcact ttgggaggcc agggcaggca gatcatctga   4800

ggtcaggagt ttgagaccag cctggccaac atggtgaaac cctatctcta ctaaaaatta   4860

aa                                                                  4862
```

<210> SEQ ID NO 55
<211> LENGTH: 3568
<212> TYPE: DNA
<213> ORGANISM: Human

<400> SEQUENCE: 55

```
atagttttca ggttaagaaa gccagaatct ttgttcagcc acactgactg aacagacttt     60

tagtggggtt acctggctaa cagcagcagc ggcaacggca gcagcagcag cagcagcagc    120

agcagcagca gcagggctcc tgggataact caggcatagt tcaacactat gggtcctcct    180

ctgaagctct tcaaaaacca gaaataccag gaactgaagc aggaatgcat caaagacagc    240

agacttttct gtgatccaac atttctgcct gagaatgatt ctcttttcta caaccgactg    300

cttcctggaa aggtggtgtg gaaacgtccc caggacatct gtgatgaccc ccatctgatt    360

gtgggcaaca ttagcaacca ccagctgacc caagggagac tggggcacaa gccaatggtt    420

tctgcatttt cctgtttggc tgttcaggag tctcattgga caaagacaat tcccaaccat    480
```

-continued

```
aaggaacagg aatgggaccc tcaaaaaaca gaaaaatacg ctgggatatt tcactttcgt    540
ttctggcatt ttggagaatg gactgaagtg gtgattgatg acttgttgcc caccattaac    600
ggagatctgg tcttctcttt ctccacttcc atgaatgagt tttggaatgc tctgctggaa    660
aaagcttatg caaagctgct aggctgttat gaggccctgg atggtttgac catcactgat    720
attattgtgg acttcacggg cacattggct gaaactgttg acatgcagaa aggaagatac    780
actgagcttg ttgaggagaa gtacaagcta ttcggagaac tgtacaaaac atttaccaaa    840
ggtggtctga tctgctgttc cattgagtct cccaatcagg aggagcaaga agttgaaact    900
gattggggtc tgctgaaggg ccatacctat accatgactg atattcgcaa aattcgtctt    960
ggagagagac ttgtggaagt cttcagtgct gagaaggtgt atatggttcg cctgagaaac   1020
cccttgggaa gacaggaatg gagtggcccc tggagtgaaa tttctgaaga gtggcagcaa   1080
ctgactgcat cagatcgcaa gaacctgggg cttgttatgt ctgatgatgg agagttttgg   1140
atgagcttgg aggacttttg ccgcaacttt cacaaactga atgtctgccg caatgtgaac   1200
aaccctattt ttggccgaaa ggagctggaa tcggtgttgg gatgctggac tgtggatgat   1260
gatcccctga tgaaccgctc aggaggctgc tataacaacc gtgatacctt cctgcagaat   1320
ccccagtaca tcttcactgt gcctgaggat gggcacaagg tcattatgtc actgcagcag   1380
aaggacctgc gcacttaccg ccgaatggga agacctgaca attacatcat tggctttgag   1440
ctcttcaagg tggagatgaa ccgcaaattc cgcctccacc acctctacat ccaggagcgt   1500
gctgggactt ccacctatat tgacacccgc acagtgtttc tgagcaagta cctgaagaag   1560
ggcaactatg tgcttgtccc aaccatgttc cagcatggtc gcaccagcga gtttctcctg   1620
agaatcttct ctgaagtgcc tgtccagctc agggaactga ctctggacat gcccaaaatg   1680
tcctgctgga acctggctcg tggctacccg aaagtagtta ctcagatcac tgttcacagt   1740
gctgaggacc tggagaagaa gtatgccaat gaaactgtaa acccatattt ggtcatcaaa   1800
tgtggaaagg aggaagtccg ttctcctgtc cagaagaata cagttcatgc catttttgac   1860
acccaggcca ttttctacag aaggaccact gacattccta ttatagtaca ggtctggaac   1920
agccgaaaat tctgtgatca gttcttgggg caggttactc tggatgctga ccccagcgac   1980
tgccgtgatc tgaagtctct gtacctgcgt aagaagggtg gtccaactgc caaagtcaag   2040
caaggccaca tcagcttcaa ggttatttcc agcgatgatc tcactgagct ctaaatctgc   2100
aatcccagag aatcctgaca aagcgtgcca cccttttatt ttccgtcagg tgccaggtct   2160
tagttaagat tcacaatctt tagaaagaat gagattcaca ataattaact cttcctctct   2220
tctgataaat tccccatacc tcccaatcca agtagcatct gtagctacat aacctatata   2280
cctccagcag ctggacatgg ggaggcgaca gtcctatcta gacatcatac acatttgcca   2340
agaaaggatc tctggggctt ccgggggtga gattcaagca ggacaataac aagaggctgg   2400
acaccctaca gatgtctttg atgttttcag ttgtttgata tatctcccct gtagggcatg   2460
ttgaggaagg aggagggctg atcaaggcca agctggtcta gcctgacatc ctagctcctg   2520
actgaacact atagacttcc cagcagcatt tcacccagca gccagagccg gctttaagtc   2580
cccaaccctt acagacacca ctgccaccac caccaaccac gaccaccacc accaccacca   2640
ctcaccacca tcatcacctc cggaaagtgt agtcctgccc taacccaagt cacccccgac   2700
agtaaatttt accttcatgt tgagaaagct tcctggtgct taatcaagag ctggagttca   2760
atgagtccta gacagtgaga ggggcctgag cttcagctca atggaagcct gctgtgtgcc   2820
acaagacgga aaagtggaag aagctgcagt gggagacaaa gcctcggtcc cccacccatc   2880
```

```
cacacacacc tacactcaca cacgcgcaca tgggcgcgca cgaactacca ttcaggcagt   2940

cagtgggcaa gaggaaagat aagtaagtac catacacacc taaaagatga gagaattcat   3000

ccagacatat tacagccagt ttggggcccc tgactgcaat gtgaaacctc tcgctgctgc   3060

taggtttaca aacaagccca ttgtcctgtg cctcctaata tcatttgtac tgaagacccc   3120

atctggggac ttgagacttt ggtcccagcc cagactcctc agacttttct ctcagttggg   3180

atgcttcact cgctgggggt gtttgtttgc cctctcattt ttcagtactt ctacagaatt   3240

ttctctagag tcagtcatta tgaaatgtac ttccctccat cttaacctat caactttctg   3300

cccctccttc aaggcccagt ataaatgcca cctcctccat gaagccttcc ctaattccac   3360

cccaaacccc caccttcaac aatatttcaa cgcttctgca atgatgaaaa agaaacatag   3420

ttgtagtact tagcctacct agaccagcaa gcattcattt ttagctcgct catttttttac   3480

catgttttcc agtctgttta acttctgcag tgccttcact acactgcctt acataaacca   3540

aatcacaata aagttcatat tcagtaca                                       3568
```

<210> SEQ ID NO 56
<211> LENGTH: 1955
<212> TYPE: DNA
<213> ORGANISM: Human

<400> SEQUENCE: 56

```
gaattcacca agcgttggat tgttcaccca ctaataggga acgtgagctg ggtttagacc     60

gtcgtgagac aggttagttt taccctactg atgatgtgtt gttgccatgg taatcctgct    120

cagtacgaga ggaaccgcag gttcagacat ttggtgtatg tgcttggctg aggagccaat    180

ggggcgaacg taccatctgt gggattatga ctgaacgcct ctaagtcaga atcccgccca    240

ggcgaacgat acggcagcgc cgcggagcct cggttggcct cggatagccg gtcccccgcc    300

tgtccccgcc ggcgggccgc ccccccctcc agcgccccgc gcgcgcggga gggcgcgtgc    360

cccgccgcgc gccgggaccg gggtccggtg cggagtgccc ttcgtcctgg gaaacggggc    420

gcggccggaa aggcggccgc cccctcgccc gtcacgcacc gcacgttcgt ggggaacctg    480

gcgctaaacc attcgtagac gacctgcttc tgggtcgggg tttcgtacgt agcagagcag    540

ctccctcgct gcgatctatt gaaagtcagc cctcgacaca agggtttgtc cgcgcgcgcg    600

gcggcgtgcg tgcgggggc ccggcggggc gtgcgcgtcc ggcgccgtcc gtccttccgt     660

tcgtcttcct ccctcccggc ctctccgccg accgcgggcg tggtgggggg gtgggggggg    720

gacgcgcgac cccggtcggc gcgccccgct tcttcggttc ccgcctcctc cccgttcacc    780

gcggggcggc tcgtccgctc cggccggga cggggtccgg ggagcgtggt ttgggagccg     840

cggaggcggc cgcgccgagc cgggcccgtg cgcggtcccc gtcccggggg ttggccgcgc    900

gggccccggt ggggccaccc ggggtcccgg ccctcgcgcg tccttcctct cgctcctccg    960

cacgggtcga ccagcagacc gcgggtggtg ggcggcgggc ggcgaggccg cacgggcgtc   1020

cccgcacccg gccgacctcc gctcgtgacc tctcctcggt cgggctccgg ggtcgaccgc   1080

ctgccccgcg ggcgtgagac tcagccgctg tctcgccgtg tcccgggtcg accggcgggc   1140

ttctccaccg agcggcgtgt aggagtgccc gtcgggacga accgcaaccg gagcgtcccc   1200

gtctcggtcg gcacctccgg ggtcgaccag ctgccgcccg cgagctccgg acttagccgg   1260

cgcctgcacg tgtcccgggt cgaccagcag gcggccgcga cgtgcggcgc accgacgaga   1320

gggcgtgcat tcccgttcgc gcgcccggac cctccaccgg cctgggcccg acggtggagc   1380

tgggaccacg cggaactccc tctcctacat ttttttcagc cccaccgcga gtttgcgtcc   1440
```

```
gcgggatttt aagagggagt cactgctgcc gtcagccagt aatgcttcct ccttttttgc    1500

ttttaggttt tgctcttgcc tttttttttt tttttttctt tctttctttc tttctttctt    1560

tctttctttc tttctttctt tctttctcgc tctcgcctct cgctctctcc ctcgctcgtt    1620

ttctttctct ttctctttct ctctctctct ctctctctct ctctgtct ctcgctctcg      1680

ccctctctct ctctctcttc tctctgtctc tctctgtctc tctctctctc tctctctctc    1740

tctctctctc tctctctctc tctctctccc tccccctccc tccctctctc cccttccttg    1800

gtgccttctc ggctcttgac acttagccgc tgtctcgccg tgtcccgggt cgaccggcgg    1860

gccttctcca ccgagcggcg tgtaagagtg cccgtcggga cgagccggac ccgccgcgtc    1920

cccgtctcgg tcggcactcc ggggtcgacc agctg                                1955
```